US007262045B2

(12) United States Patent
Schwartz et al.

(10) Patent No.: US 7,262,045 B2
(45) Date of Patent: Aug. 28, 2007

(54) METHODS OF PRODUCING INFLUENZA VACCINE COMPOSITIONS

(75) Inventors: Richard Schwartz, San Mateo, CA (US); John Michael Berry, Belmont, CA (US); Weidong Cui, San Jose, CA (US)

(73) Assignee: MedImmune Vaccines, Inc., Gaithersburg, MD (US)

( * ) Notice: Subject to any disclaimer, the term of this patent is extended or adjusted under 35 U.S.C. 154(b) by 0 days.

(21) Appl. No.: 10/788,236

(22) Filed: Feb. 25, 2004

(65) Prior Publication Data

US 2004/0265987 A1 Dec. 30, 2004

Related U.S. Application Data

(60) Provisional application No. 60/450,181, filed on Feb. 25, 2003.

(51) Int. Cl.
*C12N 7/00* (2006.01)
*A61K 39/145* (2006.01)

(52) U.S. Cl. ............................. 435/235.1; 424/204.1; 424/205.1; 424/209.1

(58) Field of Classification Search ............. 424/204.1, 424/205.1, 209.1; 435/125.1, 235.1
See application file for complete search history.

(56) References Cited

U.S. PATENT DOCUMENTS

| | | | | |
|---|---|---|---|---|
| 4,000,257 A | | 12/1976 | Cano | |
| 4,338,296 A | * | 7/1982 | Lobmann et al. | ......... 424/206.1 |
| 4,500,512 A | * | 2/1985 | Barme | ..................... 424/218.1 |
| 4,512,285 A | * | 4/1985 | McGehee | ................... 119/300 |
| 6,039,958 A | * | 3/2000 | Koyama et al. | ......... 424/230.1 |

FOREIGN PATENT DOCUMENTS

WO    WO 03/091401 A2    11/2003

OTHER PUBLICATIONS

Arora et. al., Concentration and Purification of Influenza Virus from Allantoic Fluid, *Analytical Biochemistry*, (1985) 144:189-192.
Cha et al., Genotypic Stability of Cold-Adapted Influenza Virus Vaccine in an Efficacy Clinical Trial, *J. Clin. Micro.*, (2000) 38(2):839-845.
Belshe et al., The Efficacy of Live Attenuated, Cold-Adapted, Trivalent, Intranasal Influenza Virus Vaccine in Children, *N. Engl. J. Med.*, (1998) 338:1405-12.
Boyce et al., Safety and Immunogenicity of Adjuvanted and Unadjuvanted Subunit Influenza Vaccines Administered Intranasally to Healthy Adults, *Vaccine*, (2001) 19:217-26.
Denizot et al., Rapid Colorimetric Assay for Cell Growth and Survival (Modifications to the Tetrazolium Dye Procedure Giving Improved Sensitivity and Reliability), *J. Immun. Methods* (1986) 89:271-277.
Edwards et al., A Randomized Controlled Trial of Cold-Adapted and Inactivated Vaccines for the Prevention of Influenza A Disease, *J. Infect. Dis.* (1994) 169:68-76.
Furminger, Vaccine Production, *Textbook of Influenza* pp. 324-332.
Gerlier et al., Use of MTT Colorimetric Assay to Measure Cell Activation, *J. Immuno. Methods*, (1986) 94:57-63.
Heeg et al., A Rapid Colorimetric Assay for the Determination of IL-2-Producing Helper T Cell Frequencies, *J. Immuno Methods*, (1985) 77:237-246.
Maassab, Adaptation and Growth Characteristics of Influenza Virus at 25 degrees C, *Nature* (1967) 213:612-614.
Maassab et al., Evaluation of a Cold-Recombinant Influenza Virus Vaccine in Ferrets *J. Infect. Dis.*, (1982) 146:780-790.
Merten et al., Production of Influenza Virus in Cell Cultures for Vaccine Preparation, *Novel Strategies in Design and Production of Vaccines*, (1996) pp. 141-151.
Mosmann, Rapid Colorimetric Assay for Cellular Growth and Survival: Application to Proliferation and Cytotoxicity Assays, *J. Immuno. Methods*, (1983) 65:55-63.
Murphy & Coelingh, Principles Underlying the Development and Use of Live Attenuated Cold-Adapted Influenza A and B Virus Vaccines, *Viral Immunol.*, (2002) 15:295-323.
Nichol et al., Effectiveness of Live, Attenuated Intranasal Influenza Virus Vaccine in Healthy, Working Adults: A Randomized Controlled Trial, *JAMA* (1999) 282:137-44.
Reimer, et al., Influenza Virus Purification with the Zonal Ultracentrifuge, *Science* (1966) 152:1379-1381.
Tada, et al., An Improved Colorimetric Assay for Interleukin 2, *J. Immuno. Methods*, (1986) 93:157-165.
Virus cultivation, Detection, and Genetics, S. J. Flint, L.W. Enquist, R.M. Krug, V.R. Racaniello and A.M. Skalka, "Principles of Virology," ASM Press, Washington, p. 27-62, (2000).
Vistica et al., Tetrazolium-Based Assays for Cellular Viability: A Critical Examination of Selected Parameters Affecting Formazan Production, *Cancer Research* (1991) 51: 2515-2520.
Wareing & Tannock, Preparation and Characterisation of Attenuated Cold-Adapted Influenza A Reassortants derived from the A/Leningrad/134/17/57 donor strain, *Vaccine*, (2002) 20:2082-2090.

* cited by examiner

*Primary Examiner*—Stacy B. Chen

(57) ABSTRACT

Methods and compositions for the optimization of production of influenza viruses suitable as influenza vaccines are provided.

27 Claims, 55 Drawing Sheets

Plaque assay shows the different titers of 5:3 and 6:2 at 33°C

| MOI | 5:3/33°C | 6:2/33°C | ratio | 5:3/25°C | 6:2/25°C | ratio |
|---|---|---|---|---|---|---|
| 0.01 | 1.50E+05 | 2.40E+03 | 62.50 | 1.50E+06 | 1.10E+06 | 1.36 |
| 0.001 | 2.40E+05 | 1.20E+03 | 200.00 | 1.50E+06 | 2.80E+05 | 5.36 |
| 0.0001 | 4.00E+04 | 3.00E+02 | 133.33 | 1.10E+05 | 2.50E+04 | 4.40 |

The M1 sequences of MDV-B and wild-type B viruses

```
                        1                                                           50
wt_B_Yamanashi_M1       ..........  ..........  ..........  ..........  ..........
wt_B_JHG_5_99_M1        MSLFGDTIAY  LLSLTEDGEG  KAELAEKLHC  WFGGKEFDLD  SALEWIKNKR
wt_B_Vic_504_2000_M1    MSLFGDTIAY  LLSLTEDGEG  KAELAEKLHC  WFGGKEFDLD  SALEWIKNKR
MDV-B-M1                MSLFGDTIAY  LLSLTEDGEG  KAELAEKLHC  WFGGKEFDLD  SALEWIKNKR
wt_B_HK_330_01_M1       MSLFGDTIAY  LLSLTEDGEG  KAELAEKLHC  WFGGKEFDLD  SALEWIKNKR 51                                                          100
wt_B_Yamanashi_M1       ..........  ..........  ..........  ....MGTTA   TKKKGLTLAE
wt_B_JHG_5_99_M1        CLTDIQKALI  GASICFLKPK  DQERKRRFIT  EPLSGMGTTA  TKKKGLILAE
wt_B_Vic_504_2000_M1    CLTDIQKALI  GASICFLKPK  DQERKRRFIT  EPLSGMGTTA  TKKKGLILAE
MDV-B-M1                CLTDIQKALI  GASICFLKPK  DQERKRRFIT  EPLSGMGTTA  TKKKGLILAE
wt_B_HK_330_01_M1       CLTDIQKALI  GASICFLKPK  DQERKRRFIT  EPLSGMGTTA  TKKKGLILAE 101                                                         150
wt_B_Yamanashi_M1       RKMRRCVSFH  EAFEIAEGHE  SSALLYCLMV  MYLNPGNYSM  QVKLGTLCAL
wt_B_JHG_5_99_M1        RKMRRCVSFH  EAFEIAEGHE  SSALLYCLMV  MYLNPGNYSM  QVKLGTLCAL
wt_B_Vic_504_2000_M1    RKMRRCVSFH  EAFEIAEGHE  SSALLYCLMV  MYLNPGNYSM  QVKLGTLCAL
MDV-B-M1                RKMRRCVSFH  EAFEIAEGHE  SSALLYCLMV  MYLNPGNYSM  QVKLGTLCAL
wt_B_HK_330_01_M1       RKMRRCVSFH  EAFEIAEGHE  SSALLYCLMV  MYLNPGNYSM  QVKLGTLCAL 151                                                         200
wt_B_Yamanashi_M1       CEKQASHSHR  AHSRAARSSV  PGVRREMQMV  SAMNTAKTMN  GMGKGEDVQK
wt_B_JHG_5_99_M1        CEKQASHSHR  AHSRAARSSV  PGVRREMQMV  SAMNTAKTMN  GMGKGEDVQK
wt_B_Vic_504_2000_M1    CEKQASHSHR  AHSRAARSSV  PGVRREMQMV  SAMNTAKTMN  GMGKGEDVQK
MDV-B-M1                CEKQASHSQR  AHSRAARSSV  PGVRREMQMV  SAVNTAKTMN  GMGKGEDVQK
wt_B_HK_330_01_M1       CEKQASHSHR  AHSRAARSSV  PGVRREMQMV  SAMNTAKTMN  GMGKGEDVQK 201                                         249      SEQ ID NO.
wt_B_Yamanashi_M1       LAEELQSNIG  VLRSLGASQK  NGEGIAKDVM  EVLKQSSMGN  SALVKKYL.   1
wt_B_JHG_5_99_M1        LAEELQSNIG  VLRSLGASQK  NGEGIAKDVM  EVLKQSSMGN  SALVKKYL.   2
wt_B_Vic_504_2000_M1    LAEELQSNIG  VLRSLGASQK  NGEGIAKDVM  EVLKQSSMGN  SALVKKYL.   3
MDV-B-M1                LAEELQSNIG  VLRSLGASQK  NGEGIAKDVM  EVLKQSSMGN  SALVKKYL.   4
wt_B_HK_330_01_M1       LAEELQSNIG  VLRSLGASQK  NGEGIAKDVM  EVLKQSSMGN  SALVKKYL.   5
```

Fig. 4

The M2 sequences of MDV-B and wild-type B viruses

```
                          1                                                                    50
MDV-B-M2               MLEPFQILSI CSFILSALHF MAWTIGHLNQ IKRGVNLKIR IRNPNKETIN
wt_B_HK_330_01_M2      MLEPFQILSI CSFILSALHF MAWTIGHLSQ IKRGVNMKIR IKGPNKETIN
wt_B_JHG_5_99_M2       MLEPFQILSI CSFILSALHF MAWTIGHLNQ IKRGVNMKIR IKGPNKETIN
wt_B_Yamanashi_M2      MLEPFQILSI CSFILSALHF MAWTIGHLNQ IKRGVNMKIR IKGPNKETIN
wt_B_Vic_504_2000_M2   MLEPFQILSI CSFILSALHF MAWTIGHLNQ IKRGVNMKIR IKSPNKETIN 51                                                                   100
MDV-B-M2               REVSILRHSY QKEIQAKETM KEVLSDNMEI LSDHIVIEGL SAEEIIKMGE
wt_B_HK_330_01_M2      REVSILRHSY QKEIQAKETM KEVLSDNMEA LSDHIVIEGL SAEEIIKMGE
wt_B_JHG_5_99_M2       REVSILRHSY QKEIQAKETM KEVLSDNMEV LSDHIVIEGL SAEEIIKMGE
wt_B_Yamanashi_M2      REVSILRHSY QKEIQAKETM KEVLSDNMEV LNDHIVIEGL SAEEIIKMGE
wt_B_Vic_504_2000_M2   REVSILRHSY QKEIQAKETM KEVLSDNMEV LSDHIVIEGL SAEEIIKMGE 101    109    SEQ ID NO.
MDV-B-M2               TVLEVEELQ           6
wt_B_HK_330_01_M2      TVLEVEELH           7
wt_B_JHG_5_99_M2       TVLEIEELH           8
wt_B_Yamanashi_M2      TVLEIEELH           9
wt_B_Vic_504_2000_M2   TVLEIEELH          10
```

Fig. 5

Mutations on the two conservative sites in MDVB-M1

| Virus name | M gene | HA,NA | Other genes |
|---|---|---|---|
| 6:2 | MDVB | B/HK | MDVB |
| 6:2M1 H | MDVB-His | B/HK | MDVB |
| 6:2M1 M | MDVB-Met | B/HK | MDVB |
| 6:2M1 HM | MDVB-His+Met | B/HK | MDVB |

Fig. 6

The growth curves of the B/HK 6:2 M1 mutations

A/New Caledonia/20/99 - Comparison of the 5th wash with NAF proteins

N/New Caledonia/20/99 1-X-Neat Sample, before concentration

A/New Caledonia/20/99, 10X Concentrated Sample

A/New Caledonia/20/99 – Comparison of 1X and 10X

A/New Caledonia/20/99 – 1X-W, sample after 5 washes

A/New Caledonia/20/99 – 1X and 1X-W Comparison

A/New Caledonia/20/99 – 10X and 10X-W Comparison

A/New Caledonia/20/99 – Permeate

A/New Caledonia/20/99 – 5 Washes

Analysis by SEC, Washings vs. Impurities Removed

A/New Caledonia/20/99 – 1XW and 10X-W, Comparison

A/New Caledonia/20/99
A/New Caledonia/20/99, Chicken RBC-HA Assay, 1X: Lane A1 to A12, 1X-W: Lane B1 to B12, 10X: Lane C1 to D12, 10X-W: Lane E1 to E12, Permeate: G1 to G12, Blank: H1 to H12

RHPLC of Control, 10X, 10X-W, and 1X-W

Bar Graph of Control, 10X, 1X-w and 10X-w samples

RHPLC of permeate, Wash 1 to wash 6

RHPLC ovomucoid removal (peak area)

RHPLC Lysozyme removal (peak area)

RHPLC Conalbumin removal (peak area)

RHPLC – Removal of Ovalbumin (by Peak Area)

A/New Caledonia/20/99 –10X-W, Sample after 5 washes

RNA analysis by RTPCR

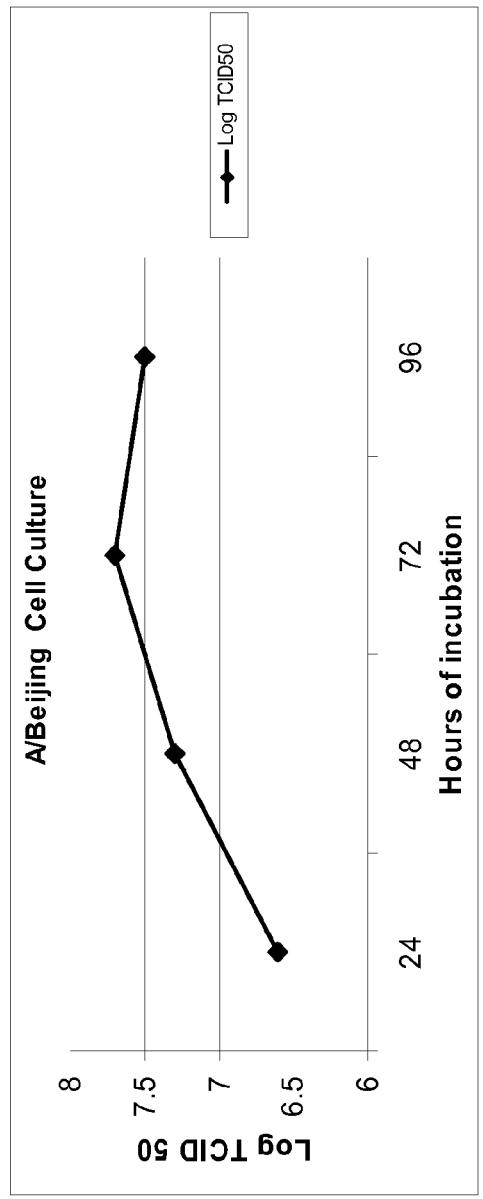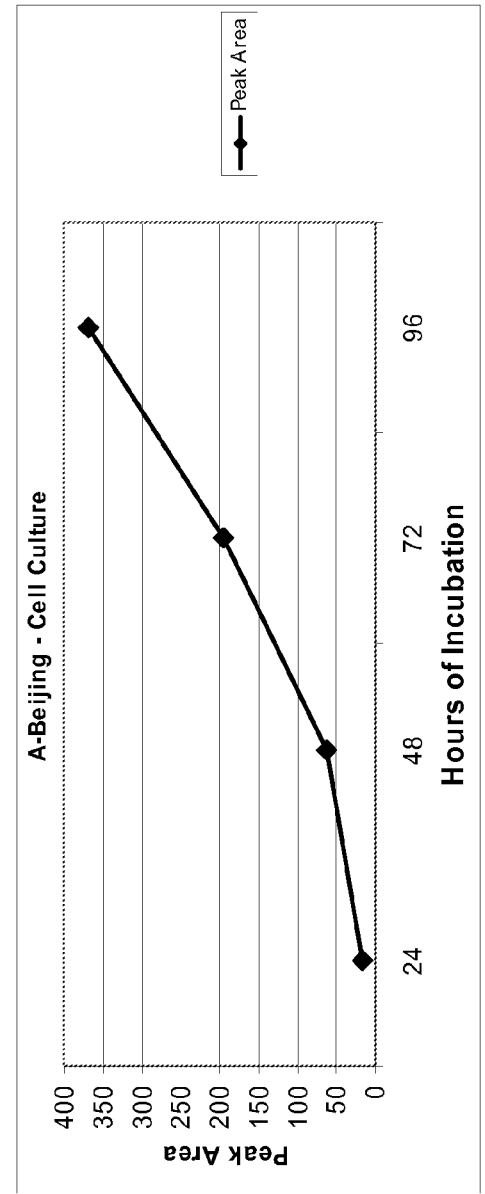
Fig. 35

Base Formulation: 60% NAF, 10% Sucrose, 1% Gelatin 2% Arginine
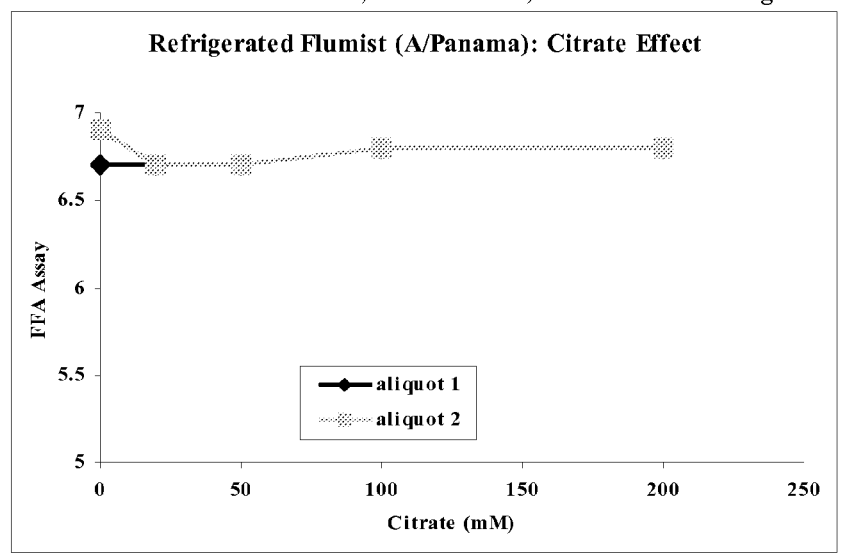
41a
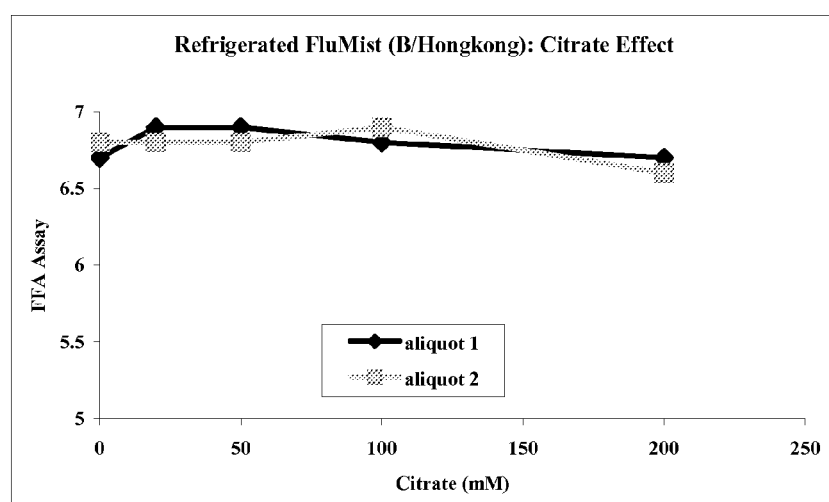
41b
41c
|  | FFA Assay (A/Panama) | | FFA Assay (B/Hongkong) | |
|---|---|---|---|---|
| Citrate (mM) | Aliq. 1 | Aliq. 2 | Aliq. 1 | Aliq. 2 |
| 0 | 6.7 | 6.9 | 6.7 | 6.8 |
| 20 | 6.7 | 6.7 | 6.9 | 6.8 |
| 50 | 6.7 | 6.7 | 6.9 | 6.8 |
| 100 | 6.8 | 6.8 | 6.8 | 6.9 |
| 200 | 6.8 | 6.8 | 6.7 | 6.6 |
Fig. 41

Base Formulation: 100 mM KPO4, 60% NAF, 10% Sucrose, 1% Gelatin 2% Arginine
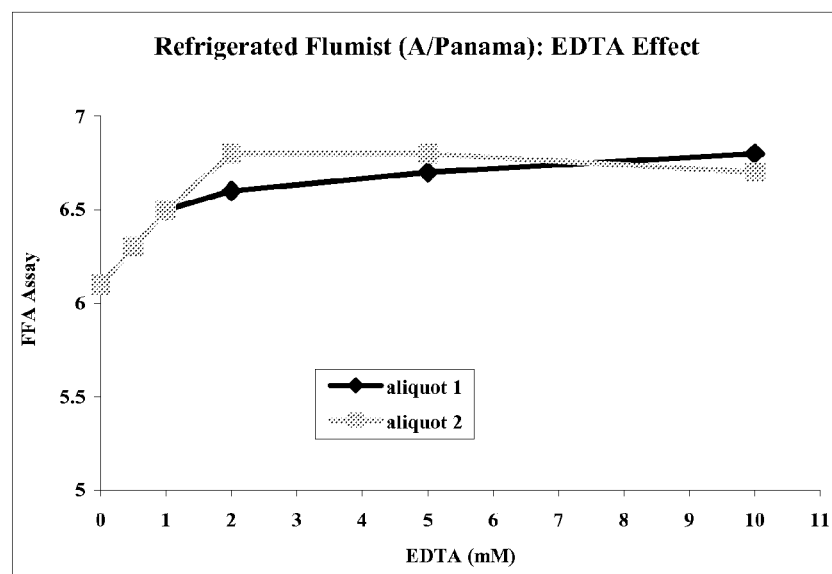
42a
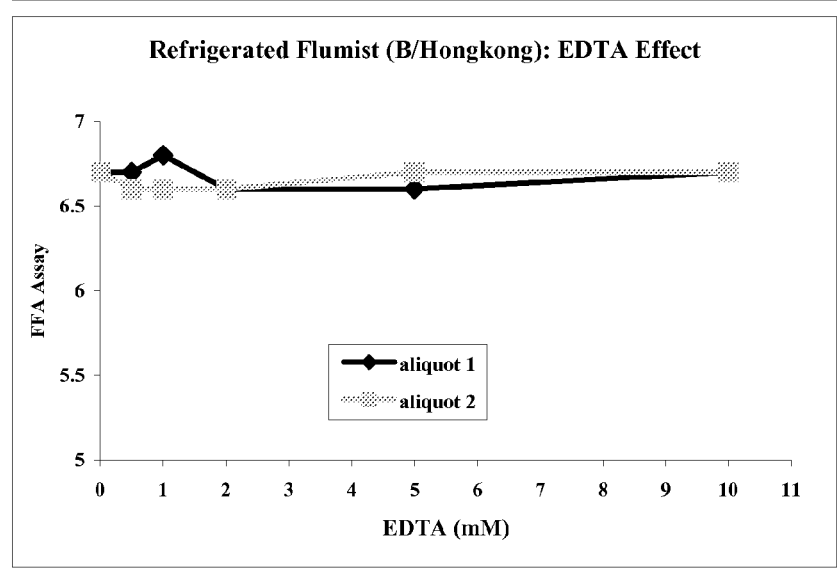
42b
42c
|  | FFA Assay (A/Panama) | | FFA Assay (B/Hongkong) | |
| --- | --- | --- | --- | --- |
| EDTA (mM) | Aliq. 1 | Aliq. 2 | Aliq. 1 | Aliq. 2 |
| 0 | 6.1 | 6.1 | 6.7 | 6.7 |
| 0.5 | 6.3 | 6.3 | 6.7 | 6.6 |
| 1 | 6.5 | 6.5 | 6.8 | 6.6 |
| 2 | 6.6 | 6.8 | 6.6 | 6.6 |
| 5 | 6.7 | 6.8 | 6.6 | 6.7 |
| 10 | 6.8 | 6.7 | 6.7 | 6.7 |
Fig. 42

Histogram of Absorbance at 570 nm Versus the Frequency of Occurrence

SEQUENCE LISTING

<160> NUMBER OF SEQ ID NOS: 10

<210> SEQ ID NO 1
<211> LENGTH: 163
<212> TYPE: PRT
<213> ORGANISM: Influenza B virus

<400> SEQUENCE: 1

```
Met Gly Thr Thr Ala Thr Lys Lys Gly Leu Thr Leu Ala Glu Arg
1               5                   10                  15

Lys Met Arg Arg Cys Val Ser Phe His Glu Ala Phe Glu Ile Ala Glu
                20                  25                  30

Gly His Glu Ser Ser Ala Leu Leu Tyr Cys Leu Met Val Met Tyr Leu
                35                  40                  45

Asn Pro Gly Asn Tyr Ser Met Gln Val Lys Leu Gly Thr Leu Cys Ala
        50                  55                  60

Leu Cys Glu Lys Gln Ala Ser His Ser His Arg Ala His Ser Arg Ala
65                  70                  75                  80

Ala Arg Ser Ser Val Pro Gly Val Arg Arg Glu Met Gln Met Val Ser
                85                  90                  95

Ala Met Asn Thr Ala Lys Thr Met Asn Gly Met Gly Lys Gly Glu Asp
                100                 105                 110

Val Gln Lys Leu Ala Glu Glu Leu Gln Ser Asn Ile Gly Val Leu Arg
            115                 120                 125

Ser Leu Gly Ala Ser Gln Lys Asn Gly Glu Gly Ile Ala Lys Asp Val
            130                 135                 140

Met Glu Val Leu Lys Gln Ser Ser Met Gly Asn Ser Ala Leu Val Lys
145                 150                 155                 160

Lys Tyr Leu
```

<210> SEQ ID NO 2
<211> LENGTH: 248
<212> TYPE: PRT
<213> ORGANISM: Influenza B virus

<400> SEQUENCE: 2

```
Met Ser Leu Phe Gly Asp Thr Ile Ala Tyr Leu Leu Ser Leu Thr Glu
1               5                   10                  15

Asp Gly Glu Gly Lys Ala Glu Leu Ala Glu Lys Leu His Cys Trp Phe
            20                  25                  30

Gly Gly Lys Glu Phe Asp Leu Asp Ser Ala Leu Glu Trp Ile Lys Asn
        35                  40                  45

Lys Arg Cys Leu Thr Asp Ile Gln Lys Ala Leu Ile Gly Ala Ser Ile
    50                  55                  60

Cys Phe Leu Lys Pro Lys Asp Gln Glu Arg Lys Arg Arg Phe Ile Thr
65                  70                  75                  80

Glu Pro Leu Ser Gly Met Gly Thr Thr Ala Thr Lys Lys Lys Gly Leu
                85                  90                  95

Ile Leu Ala Glu Arg Lys Met Arg Arg Cys Val Ser Phe His Glu Ala
            100                 105                 110

Phe Glu Ile Ala Glu Gly His Glu Ser Ser Ala Leu Leu Tyr Cys Leu
        115                 120                 125

Met Val Met Tyr Leu Asn Pro Gly Asn Tyr Ser Met Gln Val Lys Leu
130                 135                 140

Gly Thr Leu Cys Ala Leu Cys Glu Lys Gln Ala Ser His Ser His Arg
145                 150                 155                 160

Ala His Ser Arg Ala Ala Arg Ser Ser Val Pro Gly Val Arg Arg Glu
                165                 170                 175

Met Gln Met Val Ser Ala Met Asn Thr Ala Lys Thr Met Asn Gly Met
            180                 185                 190

Gly Lys Gly Glu Asp Val Gln Lys Leu Ala Glu Glu Leu Gln Ser Asn
        195                 200                 205

Ile Gly Val Leu Arg Ser Leu Gly Ala Ser Gln Lys Asn Gly Glu Gly
    210                 215                 220

Ile Ala Lys Asp Val Met Glu Val Leu Lys Gln Ser Ser Met Gly Asn
225                 230                 235                 240

Ser Ala Leu Val Lys Lys Tyr Leu
                245
```

<210> SEQ ID NO 3
<211> LENGTH: 248
<212> TYPE: PRT
<213> ORGANISM: Influenza B virus

<400> SEQUENCE: 3

```
Met Ser Leu Phe Gly Asp Thr Ile Ala Tyr Leu Leu Ser Leu Thr Glu
1               5                   10                  15

Asp Gly Glu Gly Lys Ala Glu Leu Ala Glu Lys Leu His Cys Trp Phe
            20                  25                  30

Gly Gly Lys Glu Phe Asp Leu Asp Ser Ala Leu Glu Trp Ile Lys Asn
        35                  40                  45

Lys Arg Cys Leu Thr Asp Ile Gln Lys Ala Leu Ile Gly Ala Ser Ile
    50                  55                  60

Cys Phe Leu Lys Pro Lys Asp Gln Glu Arg Lys Arg Arg Phe Ile Thr
65                  70                  75                  80
```

```
Glu Pro Leu Ser Gly Met Gly Thr Thr Ala Thr Lys Lys Gly Leu
                 85                  90                  95
Ile Leu Ala Glu Arg Lys Met Arg Arg Cys Val Ser Phe His Glu Ala
            100                 105                 110
Phe Glu Ile Ala Glu Gly His Glu Ser Ser Ala Leu Leu Tyr Cys Leu
            115                 120                 125
Met Val Met Tyr Leu Asn Pro Gly Asn Tyr Ser Met Gln Val Lys Leu
        130                 135                 140
Gly Thr Leu Cys Ala Leu Cys Glu Lys Gln Ala Ser His Ser His Arg
145                 150                 155                 160
Ala His Ser Arg Ala Ala Arg Ser Ser Val Pro Gly Val Arg Arg Glu
                165                 170                 175
Met Gln Met Val Ser Ala Met Asn Thr Ala Lys Thr Met Asn Gly Met
            180                 185                 190
Gly Lys Gly Glu Asp Val Gln Lys Leu Ala Glu Glu Leu Gln Ser Asn
        195                 200                 205
Ile Gly Val Leu Arg Ser Leu Gly Ala Ser Gln Lys Asn Gly Glu Gly
        210                 215                 220
Ile Ala Lys Asp Val Met Glu Val Leu Lys Gln Ser Ser Met Gly Asn
225                 230                 235                 240
Ser Ala Leu Val Lys Lys Tyr Leu
                245

<210> SEQ ID NO 4
<211> LENGTH: 248
<212> TYPE: PRT
<213> ORGANISM: Influenza B virus

<400> SEQUENCE: 4

Met Ser Leu Phe Gly Asp Thr Ile Ala Tyr Leu Leu Ser Leu Thr Glu
1               5                   10                  15
Asp Gly Glu Gly Lys Ala Glu Leu Ala Glu Lys Leu His Cys Trp Phe
            20                  25                  30
Gly Gly Lys Glu Phe Asp Leu Asp Ser Ala Leu Glu Trp Ile Lys Asn
        35                  40                  45
Lys Arg Cys Leu Thr Asp Ile Gln Lys Ala Leu Ile Gly Ala Ser Ile
    50                  55                  60
Cys Phe Leu Lys Pro Lys Asp Gln Glu Arg Lys Arg Arg Phe Ile Thr
65                  70                  75                  80
Glu Pro Leu Ser Gly Met Gly Thr Thr Ala Thr Lys Lys Gly Leu
                85                  90                  95
Ile Leu Ala Glu Arg Lys Met Arg Arg Cys Val Ser Phe His Glu Ala
            100                 105                 110
Phe Glu Ile Ala Glu Gly His Glu Ser Ser Ala Leu Leu Tyr Cys Leu
            115                 120                 125
Met Val Met Tyr Leu Asn Pro Gly Asn Tyr Ser Met Gln Val Lys Leu
        130                 135                 140
Gly Thr Leu Cys Ala Leu Cys Glu Lys Gln Ala Ser His Ser Gln Arg
145                 150                 155                 160
Ala His Ser Arg Ala Ala Arg Ser Ser Val Pro Gly Val Arg Arg Glu
                165                 170                 175
Met Gln Met Val Ser Ala Val Asn Thr Ala Lys Thr Met Asn Gly Met
            180                 185                 190
Gly Lys Gly Glu Asp Val Gln Lys Leu Ala Glu Glu Leu Gln Ser Asn
```

```
            195                 200                 205
Ile Gly Val Leu Arg Ser Leu Gly Ala Ser Gln Lys Asn Gly Glu Gly
    210                 215                 220

Ile Ala Lys Asp Val Met Glu Val Leu Lys Gln Ser Ser Met Gly Asn
225                 230                 235                 240

Ser Ala Leu Val Lys Lys Tyr Leu
                245

<210> SEQ ID NO 5
<211> LENGTH: 248
<212> TYPE: PRT
<213> ORGANISM: Influenza B virus

<400> SEQUENCE: 5

Met Ser Leu Phe Gly Asp Thr Ile Ala Tyr Leu Leu Ser Leu Thr Glu
1               5                   10                  15

Asp Gly Glu Gly Lys Ala Glu Leu Ala Glu Lys Leu His Cys Trp Phe
            20                  25                  30

Gly Gly Lys Glu Phe Asp Leu Asp Ser Ala Leu Glu Trp Ile Lys Asn
        35                  40                  45

Lys Arg Cys Leu Thr Asp Ile Gln Lys Ala Leu Ile Gly Ala Ser Ile
    50                  55                  60

Cys Phe Leu Lys Pro Lys Asp Gln Glu Arg Lys Arg Arg Phe Ile Thr
65                  70                  75                  80

Glu Pro Leu Ser Gly Met Gly Thr Thr Ala Thr Lys Lys Lys Gly Leu
                85                  90                  95

Ile Leu Ala Glu Arg Lys Met Arg Arg Cys Val Ser Phe His Glu Ala
            100                 105                 110

Phe Glu Ile Ala Glu Gly His Glu Ser Ser Ala Leu Leu Tyr Cys Leu
        115                 120                 125

Met Val Met Tyr Leu Asn Pro Gly Asn Tyr Ser Met Gln Val Lys Leu
    130                 135                 140

Gly Thr Leu Cys Ala Leu Cys Glu Lys Gln Ala Ser His Ser His Arg
145                 150                 155                 160

Ala His Ser Arg Ala Ala Arg Ser Ser Val Pro Gly Val Arg Arg Glu
                165                 170                 175

Met Gln Met Val Ser Ala Met Asn Thr Ala Lys Thr Met Asn Gly Met
            180                 185                 190

Gly Lys Gly Glu Asp Val Gln Lys Leu Ala Glu Glu Leu Gln Ser Asn
        195                 200                 205

Ile Gly Val Leu Arg Ser Leu Gly Ala Ser Gln Lys Asn Gly Glu Gly
    210                 215                 220

Ile Ala Lys Asp Val Met Glu Val Leu Lys Gln Ser Ser Met Gly Asn
225                 230                 235                 240

Ser Ala Leu Val Lys Lys Tyr Leu
                245

<210> SEQ ID NO 6
<211> LENGTH: 109
<212> TYPE: PRT
<213> ORGANISM: Influenza B virus

<400> SEQUENCE: 6

Met Leu Glu Pro Phe Gln

```
                20                  25                  30
Arg Gly Val Asn Leu Lys Ile Arg Ile Arg Asn Pro Asn Lys Glu Thr
            35                  40                  45

Ile Asn Arg Glu Val Ser Ile Leu Arg His Ser Tyr Gln Lys Glu Ile
 50                  55                  60

Gln Ala Lys Glu Thr Met Lys Glu Val Leu Ser Asp Asn Met Glu Ile
 65                  70                  75                  80

Leu Ser Asp His Ile Val Ile Glu Gly Leu Ser Ala Glu Glu Ile Ile
                85                  90                  95

Lys Met Gly Glu Thr Val Leu Glu Val Glu Glu Leu Gln
            100                 105

<210> SEQ ID NO 7
<211> LENGTH: 109
<212> TYPE: PRT
<213> ORGANISM: Influenza B virus

<400> SEQUENCE: 7

Met Leu Glu Pro Phe Gln Ile Leu Ser Ile Cys Ser Phe Ile Leu Ser
 1               5                  10                  15

Ala Leu His Phe Met Ala Trp Thr Ile Gly His Leu Ser Gln Ile Lys
                20                  25                  30

Arg Gly Val Asn Met Lys Ile Arg Ile Lys Gly Pro Asn Lys Glu Thr
            35                  40                  45

Ile Asn Arg Glu Val Ser Ile Leu Arg His Ser Tyr Gln Lys Glu Ile
 50                  55                  60

Gln Ala Lys Glu Thr Met Lys Glu Val Leu Ser Asp Asn Met Glu Ala
 65                  70                  75                  80

Leu Ser Asp His Ile Val Ile Glu Gly Leu Ser Ala Glu Glu Ile Ile
                85                  90                  95

Lys Met Gly Glu Thr Val Leu Glu Val Glu Glu Leu His
            100                 105

<210> SEQ ID NO 8
<211> LENGTH: 109
<212> TYPE: PRT
<213> ORGANISM: Influenza B virus

<400> SEQUENCE: 8

Met Leu Glu Pro Phe Gln Ile Leu Ser Ile Cys Ser Phe Ile Leu Ser
 1               5                  10                  15

Ala Leu His Phe Met Ala Trp Thr Ile Gly His Leu Asn Gln Ile Lys
                20                  25                  30

Arg Gly Val Asn Met Lys Ile Arg Ile Lys Gly Pro Asn Lys Glu Thr
            35                  40                  45

Ile Asn Arg Glu Val Ser Ile Leu Arg His Ser Tyr Gln Lys Glu Ile
 50                  55                  60

Gln Ala Lys Glu Thr Met Lys Glu Val Leu Ser Asp Asn Met Glu Val
 65                  70                  75                  80

Leu Ser Asp His Ile Val Ile Glu Gly Leu Ser Ala Glu Glu Ile Ile
                85                  90                  95

Lys Met Gly Glu Thr Val Leu Glu Ile Glu Glu Leu His
            100                 105

<210> SEQ ID NO 9
<211> LENGTH: 109
<212> TYPE: PRT
```

```
<213> ORGANISM: Influenza B virus

<400> SEQUENCE: 9

Met Leu Glu Pro Phe Gln Ile Leu Ser Ile Cys Ser Phe Ile Leu Ser
1               5                   10                  15

Ala Leu His Phe Met Ala Trp Thr Ile Gly His Leu Asn Gln Ile Lys
            20                  25                  30

Arg Gly Val Asn Met Lys Ile Arg Ile Lys Gly Pro Asn Lys Glu Thr
        35                  40                  45

Ile Asn Arg Glu Val Ser Ile Leu Arg His Ser Tyr Gln Lys Glu Ile
    50                  55                  60

Gln Ala Lys Glu Thr Met Lys Glu Val Leu Ser Asp Asn Met Glu Val
65                  70                  75                  80

Leu Asn Asp His Ile Val Ile Glu Gly Leu Ser Ala Glu Glu Ile Ile
                85                  90                  95

Lys Met Gly Glu Thr Val Leu Gly Ile Glu Glu Leu His
            100                 105

<210> SEQ ID NO 10
<211> LENGTH: 109
<212> TYPE: PRT
<213> ORGANISM: Influenza B virus

<400> SEQUENCE: 10

Met Leu Glu Pro Phe Gln Ile Leu Ser Ile Cys Ser Phe Ile Leu Ser
1               5                   10                  15

Ala Leu His Phe Met Ala Trp Thr Ile Gly His Leu Asn Gln Ile Lys
            20                  25                  30

Arg Gly Val Asn Met Lys Ile Arg Ile Lys Ser Pro Asn Lys Glu Thr
        35                  40                  45

Ile Asn Arg Glu Val Ser Ile Leu Arg His Ser Tyr Gln Lys Glu Ile
    50                  55                  60

Gln Ala Lys Glu Thr Met Lys Glu Val Leu Ser Asp Asn Met Glu Val
65                  70                  75                  80

Leu Ser Asp His Ile Val Ile Glu Gly Leu Ser Ala Glu Glu Ile Ile
                85                  90                  95

Lys Met Gly Glu Thr Val Leu Gly Ile Glu Glu Leu His
            100                 105
```

METHODS OF PRODUCING INFLUENZA VACCINE COMPOSITIONS

CROSS-REFERENCE TO RELATED APPLICATIONS

This application claims the benefit of U.S. Provisional Application No. 60/450,181 filed Feb. 25, 2003, entitled "METHODS OF PRODUCING INFLUENZA VACCINE COMPOSITIONS." This prior application is hereby incorporated by reference in its entirety for all purposes.

BACKGROUND OF THE INVENTION

Vaccines against various and evolving strains of influenza are important not only from a community health stand point, but also commercially, since each year numerous individuals are infected with different strains and types of influenza virus. Infants, the elderly, those without adequate health care and immuno-compromised persons are at special risk of death from such infections. Compounding the problem of influenza infections is that novel influenza strains evolve readily, thereby necessitating the continuous production of new vaccines.

Numerous vaccines capable of producing a protective immune response specific for such different influenza viruses have been produced for over 50 years and include, e.g., whole virus vaccines, split virus vaccines, surface antigen vaccines and live attenuated virus vaccines. However, while appropriate formulations of any of these vaccine types is capable of producing a systemic immune response, live attenuated virus vaccines have the advantage of being also able to stimulate local mucosal immunity in the respiratory tract. A vaccine comprising a live attenuated virus that is also capable of being quickly and economically produced and that is capable of easy storage/transport is thus quite desirable.

To date, all commercially available influenza vaccines have been propagated in embryonated hen eggs. Although influenza virus grows well in hen eggs, the production of vaccine is dependent on the availability of such eggs. Because the supply of eggs must be organized, and strains for vaccine production selected months in advance of the next flu season, the flexibility of this approach can be limited, and often results in delays and shortages in production and distribution. Therefore, any methods to increase throughput and/or increase output of vaccine production in hen eggs is greatly desirable.

Systems for producing influenza viruses in cell culture have also been developed in recent years (See, e.g., Furminger. Vaccine Production, in Nicholson et al. (eds.) *Textbook of Influenza* pp. 324–332; Merten et al. (1996) Production of influenza virus in cell cultures for vaccine preparation, in Cohen & Shafferman (eds.) *Novel Strategies in Design and Production of Vaccines* pp. 141–151). While eliminating many of the difficulties related to vaccine production in hen eggs, not all pathogenic strains of influenza grow well in cell culture, or can be produced according to established tissue culture methods. In addition, many strains with desirable characteristics, e.g., attenuation, temperature sensitivity and cold adaptation, suitable for production of live attenuated vaccines, have not been successfully grown in tissue culture using established methods. Therefore, any methods to increase throughput and/or increase output of vaccine production in cell culture is also greatly desirable.

Considerable work in the production of influenza virus for production of vaccines has been done by the present inventors and co-workers; see, e.g., Multi-Plasmid System for the Production of Influenza Virus, U.S. Ser. No. 60/375,675 filed Apr. 26, 2002, PCT/US03/12728 filed Apr. 25, 2003 and U.S. Ser. No. 10/423,828 filed Apr. 25, 2003, etc. The present invention provides methods of increasing/optimizing production (in both quantity/quality and speed) of such viruses, as well as for other influenza viruses, for production of vaccine compositions. Aspects of the current invention are applicable to traditional hen egg and new cell culture vaccine production styles (and also combined systems) and comprise numerous other benefits that will become apparent upon review of the following.

SUMMARY OF THE INVENTION

The invention provides embodiments of methods of making one or more influenza virus compositions by passaging an influenza virus (e.g., an A virus strain or a B virus strain, etc.) through eggs, heating the virus and filtering the virus through a membrane. In some such embodiments, the filtering comprises passage of the composition through a microfilter of a pore size ranging from 0.2 micrometers to about 0.45 micrometers. Furthermore, in various embodiments, the temperature of heating in such embodiments optionally comprises from about 28° C. to about 40° C. or more, while in some embodiments, the temperature comprises 31° C. or from about 30° C. to about 32° C. The heating in such embodiments optionally occurs before or during or before and during the filtration and optionally comprises from about 50 minutes to about 100 minutes, from about 60 minutes to about 90 minutes, or about 60 minutes. The invention also provides an influenza virus composition produced by such methods (including wherein the composition is a vaccine composition).

In other aspects, the invention comprises a method of making one or more influenza virus composition by passaging an influenza virus through eggs, heating the virus, and purifying the virus. Such embodiments also optionally include filtering the composition through a membrane and wherein the compositions comprises a vaccine composition as well as the actual vaccine composition produced by such embodiment.

In related aspects, the invention comprises a method of making one or more influenza virus composition, by passaging an influenza virus through eggs which are rocked during the passage. The rocking optionally comprises tilting the eggs at a rate of about 1 cycle per minute optionally for about 12 hours. Such embodiments optionally use influenza A virus strains and/or influenza B virus strains and also optionally comprise wherein a $TCID_{50}$ of such rocked eggs is 0.4 log greater than a $TCID_{50}$ of the same virus passaged through non-rocked eggs. Virus compositions produced by such embodiments are also features of the invention, including wherein the compositions are vaccine compositions.

The invention also comprises methods of making one or more influenza virus composition (e.g., biasing the reassortment of such) by introducing a plurality of vectors comprising an influenza virus genome into a population of host eggs (which are capable of supporting replication of the virus), culturing the population of eggs at a temperature less than or equal to 35° C., and recovering a plurality of influenza viruses. Such viruses optionally comprise, e.g., an attenuated virus, a cold adapted virus, a temperature sensitive virus or an attenuated cold adapted temperature sensitive virus, and can also comprise, e.g., an influenza B virus. A virus composition produced by such an embodiment is also a feature of the invention (including vaccine compositions).

Such aspects also optionally include further selecting for influenza viruses containing wild-type HA and NA genes (e.g., by incubating the plurality of viruses with one or more antibodies specific for non-wild-type HA and NA genes (e.g., done within the one or more egg). Virus compositions produced thusly are also features of the invention, including vaccine compositions.

Other aspects of the invention include making one or more influenza virus composition by introducing a plurality of vectors comprising an influenza virus genome into a population of host eggs (which is capable of supporting replication of influenza virus), culturing the population of eggs at a temperature less than or equal to 35° C., recovering a plurality of viruses, incubating the plurality of viruses with one or more antibodies specific for non-wild-types HA and NA genes, passaging the virus through eggs (which are rocked) and heating the virus and filtering the virus through a membrane. Viruses produced by such methods are also features of the invention (including vaccine compositions).

In the various methods embodied herein, the influenza virus composition is optionally assayed through use of a fluorescence focus assay. Such virus compositions optionally comprise from about 10% to about 60% unfractionated normal allantoic fluid (and optionally from about 1% to about 5% arginine). The compositions are optionally diluted with a buffer which is optionally substantially free of normal allantoic fluid. The compositions herein are optionally substantially free of gelatin. These compositions are stable from about 2° C. to about 8° C., or are stable at 4° C. In some compositions and methods herein, the viruses are influenza viruses, while in yet other compositions and methods herein (e.g., those involving microfiltration and/or ultrafiltration and/or heating and/or rocking) the viruses optionally comprise, e.g., non-influenza viruses (e.g., viruses that are produced through culture in eggs, e.g., myxoviruses, paramyxovirus, RSV, mumps virus, measles virus, Sendi virus, yellow fever virus, pIV, etc.). Thus, the methods and compositions of the invention are also applicable to such other viruses and/or to non-influenza viruses.

In yet other aspects, the invention comprises an influenza virus composition, wherein the composition is made by: passaging the influenza virus through eggs, heating the virus, and filtering the virus through a membrane, which composition has a first $TCID_{50}$, which first $TCID_{50}$ is greater than a second $TCID_{50}$, which second $TCID_{50}$ results from an influenza virus not made by: passaging the virus through eggs, heating the virus, and filtering the virus through a membrane.

Other aspects of the invention include an influenza virus composition, wherein the composition is made by: passaging the influenza virus through eggs, wherein the eggs are rocked during said passage, which composition has a first $TCID_{50}$, which first $TCID_{50}$ is greater than a second $TCID_{50}$, which second $TCID_{50}$ results from an influenza virus not made by: passaging the influenza virus through eggs, wherein the eggs are rocked during said passage.

Still other embodiments herein include an influenza virus composition, wherein the composition is made by: introducing a plurality of vectors comprising an influenza virus genome into a population of host eggs, which population of host eggs is capable of supporting replication of influenza virus, culturing the population of host eggs at a temperature less than or equal to 35° C., and recovering a plurality of influenza viruses, which composition has a first $TCID_{50}$, which first $TCID_{50}$ is greater than a second $TCID_{50}$, which second $TCID_{50}$ results from an influenza virus not made by: introducing a plurality vectors comprising an influenza virus genome into a population of host eggs, which population of host eggs is capable of supporting replication of influenza virus, culturing the population of host eggs at a temperature less than or equal to 35° C., and recovering a plurality of influenza viruses.

These and other objects and features of the invention will become more fully apparent when the following detailed description is read in conjunction with the accompanying figures appendix.

BRIEF DESCRIPTION OF THE DRAWINGS

FIG. 4: Displays the M1 sequences of MDV-B and wild-type B viruses (wt_B_Yamanashi_M1, SEQ ID NO:1; wt_B_JHG_5_99_M1, SEQ ID NO:2; wt_B_Vic_504_2000_M1, SEQ ID NO:3; MDV-B-M1, SEQ ID NO:4; and wt_B_HK_330_01_M1, SEQ ID NO:5).

FIG. 5: Displays the M2 sequences of MDV-B and wild-type B viruses (MDV-B-M2, SEQ ID NO:6; wt_B_HK_330_01_M2, SEQ ID NO:7; wt_B_JHG_5_99_M2, SEQ ID NO:8; wt_B_Yamanashi_M2, SEQ ID NO:9; and wt_B_Vic_504_2000_M2, SEQ ID NO:10).

FIG. 6: Displays mutations on the two conservative sites in MDV B-M1.

FIG. 7: Displays the growth curves of the B/HK 6:2 M1 mutations.

FIG. 8: Shows various CEK cell infections at different MOIs.

FIG. 35: Shows cell culture harvest of A/Beijing in Vero cells.

FIG. 41, Panels A–C: Show stability of exemplary virus storage formulations with differing citrate concentrations.

FIG. 42, Panels A–C: Show stability of exemplary virus storage formulations with differing EDTA concentrations.

FIG. 43: Displays stability of unpurified virus harvest formulations with different virus strains over 9 months.

FIG. 44: Illustrates initial potency loss of formulations associated with phosphate buffer.

FIG. 45: Gives a global picture of stability slopes of various formulations at 6 months.

FIG. 46: Gives a global picture of stability slopes of various formulations at 6 months.

FIG. 47: Shows stability of various formulations with gelatin and PVP/EDTA.

FIG. 48: Shows stability of various formulations with histidine at different pH.

FIG. 49: Shows stability of various formulations with different amounts of sucrose.

FIG. 50: Histogram derived from plotting the absorbance readings from the wells, versus the frequency of the values (number of wells read at that absorbance value).

FIG. 51: Histogram derived from plotting absorbance readings versus frequency of values.

FIG. 52: Shows a generic process for generating 6:2 influenza reassortants.

DETAILED DESCRIPTION

The present invention includes methods and compositions to increase throughput and output of viruses and virus composition productions suitable for vaccine production/use. Included are methods and compositions for, e.g., selecting for desired reassortants in virus production, temperature conditioning/filtration, rocking, antibody selection, potency assays, and many additional features as described in more detail herein.

It will be appreciated by those skilled in the art that the various steps herein are not required to be all performed or exist in the same production series. Thus, while in some preferred embodiments, all steps and/or compositions herein are performed or exist, e.g., as outlined in Table 1, in other embodiments, one or more steps are optionally, e.g., omitted, changed (in scope, order, placement, etc.) or the like.

The basic overview of the methods and compositions for virus production herein are outlined in Table 1. Once again, as is to be emphasized throughout, the individual steps of the invention, such as those listed in Table 1 are not necessarily mutually dependent. For example, in some embodiments, eggs containing an appropriate reasserted virus solution are rocked during incubation (see below), while in other embodiments they are not; heating and filtration in Step 10 is independent of use of universal reagents in Step 13, etc. The presence of any one step/method/composition in the invention is not dependent upon the necessary presence of any other step/method/composition in the invention. Therefore, various embodiments of the current invention can include only one of the steps, all of the steps, or any and all various combinations of the steps.

It will also be appreciated by those skilled in the art that typical embodiments comprise steps/methods/compositions that are known in the art, e.g., candling of virus containing eggs, inoculation of eggs with viruses, etc. Therefore, those skilled in the art are easily able to determine appropriate conditions, sub-steps, step details, etc., for such known steps to produce the appropriate viruses, virus solutions, compositions, etc. The individual steps are described in greater detail below. See Table 1 for listing of major steps involved in example embodiment.

For ease in discussion and description, the various steps of the current invention, e.g., the various methods and compositions, can be thought of as comprising or falling into four broad groups. The first group comprises such aspects as co-infection, reassortment, selection of reassortants, and cloning of reassortants (e.g., thereby roughly corresponding to Steps 1 through 3 in Table 1). The second group comprises such aspects as purification and expansion of reassortants and can be thought of as roughly corresponding to Steps 4 through 6 in Table 1. The third group comprises further expansion of reassortants in eggs, along with harvesting and purification of such harvested virus solutions (e.g., roughly corresponding to Steps 7 through 11 in Table 1). The fourth group comprises stabilization of harvested virus solutions and potency/sterility assays of the virus solutions (e.g., roughly corresponding to Steps 12 through 15 in Table 1). It is to be understood, however, that division of the aspects of the invention into the above four general categories is solely for explanatory/organizational purposes and no inference of interdependence of steps, etc. should be made.

DETAILED DESCRIPTION OF STEPS

As mentioned above, for ease in discussion and description, the various steps of the current invention can be thought of as comprising four broad groups. The first group comprises such aspects as co-infection, reassortment, selection of reassortants, and cloning of reassortants (e.g., thereby roughly corresponding to Steps 1 through 3 in Table 1). The second group comprises such aspects as purification and expansion of reassortants and can be thought of as roughly corresponding to Steps 4 through 6 in Table 1. The third group comprises further expansion of reassortants in eggs, along with harvesting and purification of such harvested virus solutions (e.g., roughly corresponding to Steps 7 through 11 in Table 1). The fourth group comprises stabilization of harvested virus solutions and potency/sterility assays of the virus solutions (e.g., roughly corresponding to Steps 12 through 15 in Table 1). It is to be emphasized, however, that division of the aspects of the invention into the above four general categories is solely for explanatory/organizational purposes and no inference of interdependence of steps, etc. should be made.

Group 1

Figure 1:
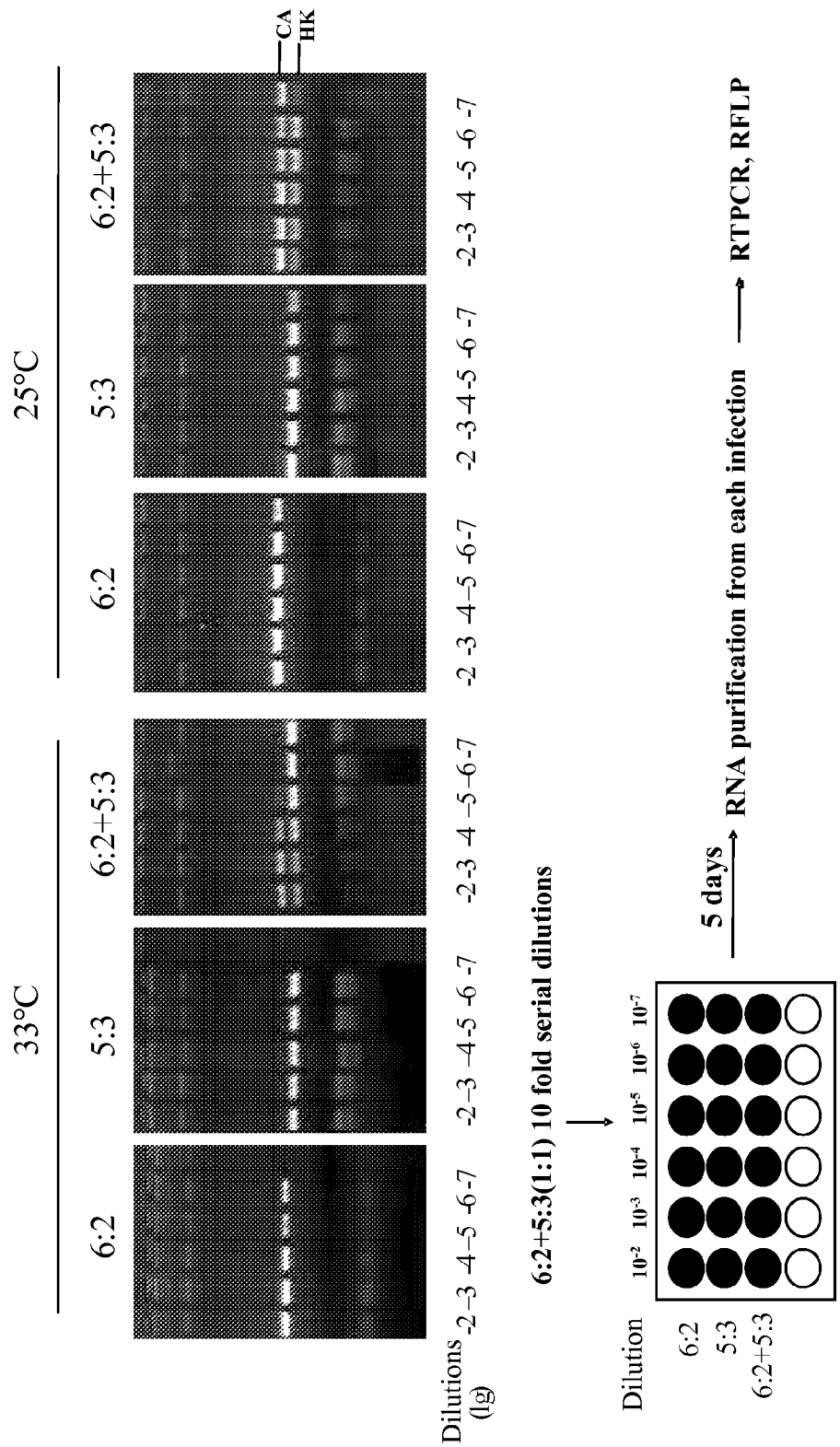
FIG. 1: Displays M Genotyping after infection at 33° C. and 25° C. in DEK TC-24.
Figure 2:
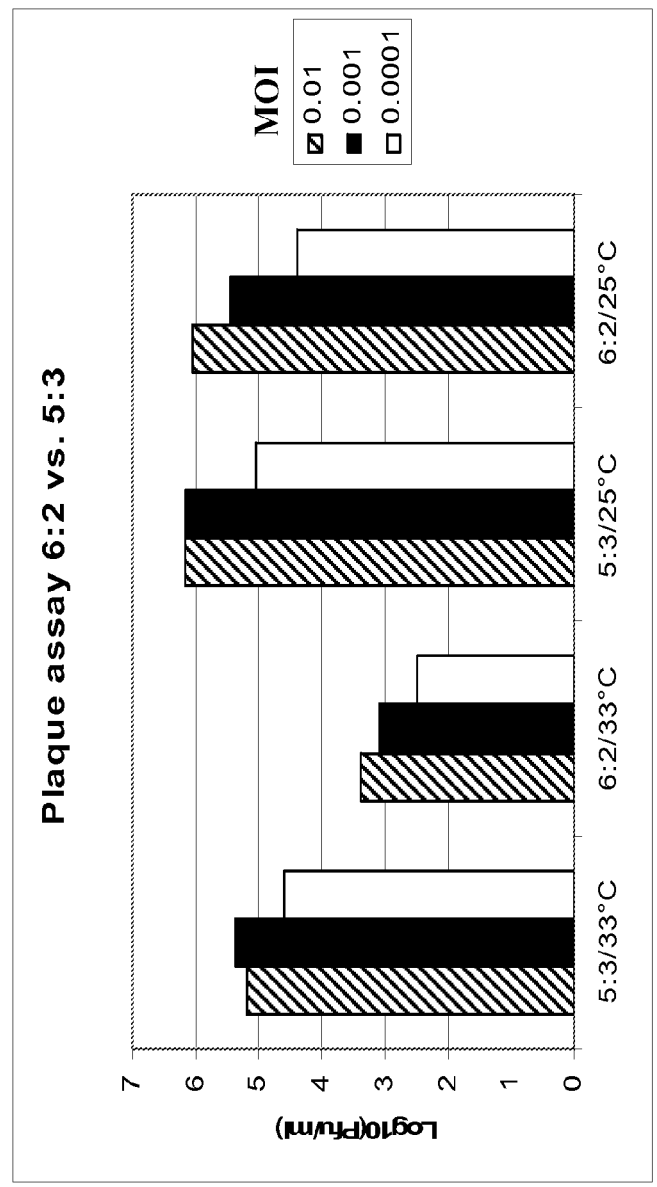
FIG. 2: Displays a plaque assay, and data, showing the different titers of 5:3 and 6:2 at 33° C.
Figure 3:
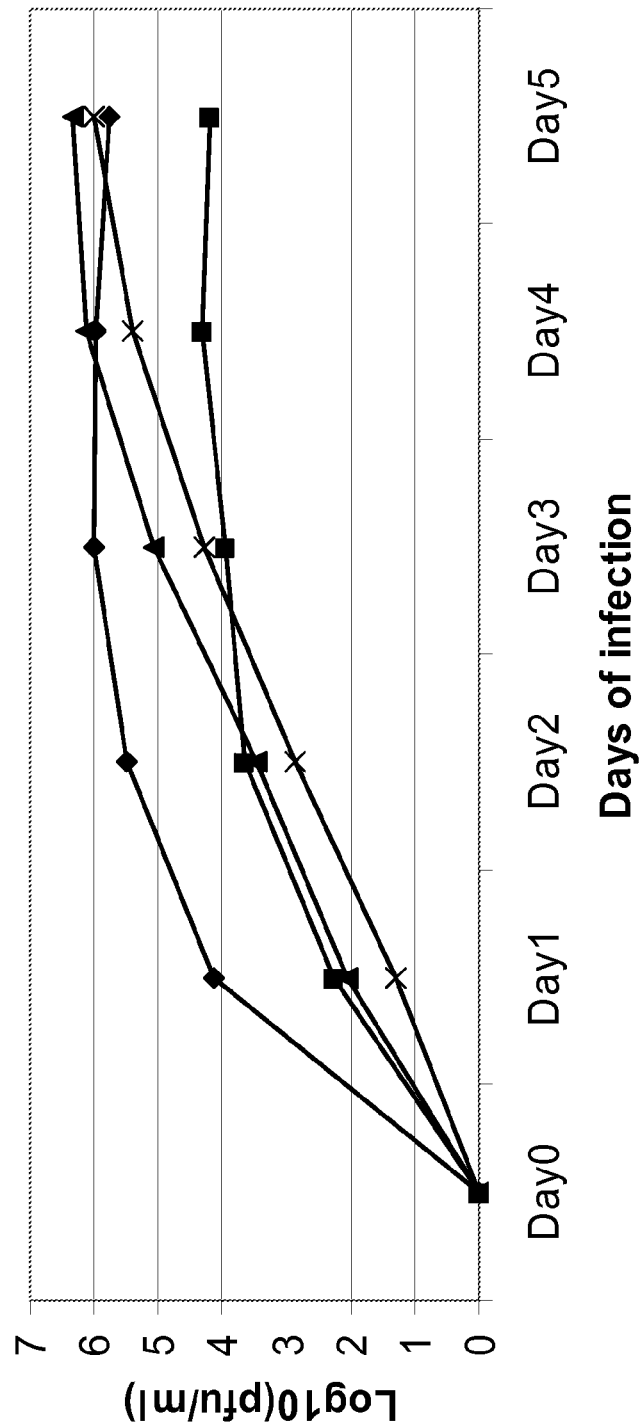
FIG. 3: Displays growth curves of 6:2 vs. 5:3 reassortants.

The aspects of the current invention which are broadly classified herein as belonging to Group 1, comprise methods and compositions related to optimization of co-infection of cell culture lines, e.g., with a master donor virus and one or more wild-type viruses in order to produce specifically desired reasserted viruses; selection of appropriate reassorted viruses; and cloning of the selected reassorted viruses. Reassortment of influenza virus strains is well known to those of skill in the art. Reassortment of both influenza A virus and influenza B virus has been used both in cell culture and in eggs to produce reasserted virus strains. See, e.g., Tannock et al., *Preparation and characterisation of attenuated cold-adapted influenza A reassortants derived from the A/Leningrad/134/17/57 donor strain, Vaccine* (2002) 20:2082–2090. Reassortment of influenza strains has also been shown with plasmid constructs. See, "Multi-Plasmid System for the Production of Influenza Virus," cited above.

Reassortment, in brief, generally comprises mixing (e.g., in eggs or cell culture) of gene segments from different viruses. For example, the typical 8 segments of influenza B virus strains can be mixed between, e.g., a wild-type strain having an epitope of interest and a "donor" strain, e.g., comprising a cold-adapted strain. Reassortment between the two virus types can produce, inter alia, viruses comprising the wild-type epitope strain for one segment, and the cold-adapted strain for the other segments. Unfortunately, to create the desired reassortants, a sometimes large number of reassortments need to be done. After being reasserted, the viruses can also be selected (e.g., to find the desired reassortants). The desired reassortants can then be cloned (e.g., expanded in number). Steps to decrease the time required for construction of reassortants and to enhance creation of desired reassortants are, thus, highly desirable.

Traditional optimization, selection, and cloning of desired reassortants for influenza B virus, typically occurs by co-infection of virus strains into a cell culture (e.g., CEK cells) followed by selection with appropriate antibodies, e.g., against material from one of the parent virus, (usually done in eggs), and cloning or expanding of virus, etc. which is typically done in cell culture. However, such traditional reassortment presents drawbacks in that thousands of reassortments are needed to create the desired segment mix. When such reassortments are done, it is apparent that truly random reassortments are not the end result. In other words, pressures that bias the process exist in the systems. For influenza A strains, however, such processes do not appear to have such bias. For A strains, co-infection of strains (typically into cell culture such as CEK cells) is followed by selection and cloning at the same time, again, typically in cell culture.

Thus, as detailed herein, various embodiments of the invention comprise steps to reduce the reassortment bias. Namely, cloning of reassortants is done in eggs (e.g., at 33° C.) rather than in cell lines, or is done in cell lines, but at, e.g., 25° C.

Optimization of Reassortment

The current invention utilizes the steps in Group 1 to optimize the reassortment process in order to reduce the number of reassortments needed (and thus increase the throughput of the vaccine production process). The steps utilizing such optimization techniques are typically embodied with reassortment of influenza B strains and are typically done in cell culture, e.g., CEK cells.

Other methods of reassortment of influenza virus mix dilutions of a master donor virus (MDV) and a wild-type virus, e.g., a 1:5 dilution of each no matter the concentration of the respective solutions, which are then incubated for 24 and 48 hours at 25° C. and 33° C. However, while such an approach is often acceptable for influenza A strains, influenza B strains do not typically give positive results with such protocol. For example, to achieve the proper 6:2 assortment (i.e., 6 genes from the MDV and 2 genes, NA and HA from the wild-type virus) thousands of reassortments must often be done.

Thus, typical embodiments of the steps in Group 1 of the invention comprise determination of the MOI (multiplicity of infection) of the MDV strain and the wild-type strains (especially for influenza B strains used), followed by reassortments comprising those illustrated in Table 2. The incubations of such optimized reassortment mixtures is carried out at 33° C. for 24 hours in eggs. In embodiments like this, proper 6:2 reassortments are typically achieved by screening hundreds of reassortment mixes as opposed to thousands of reassortment mixes necessary in non-optimized systems.

Selection and Cloning of Reassortments

Figure 52:
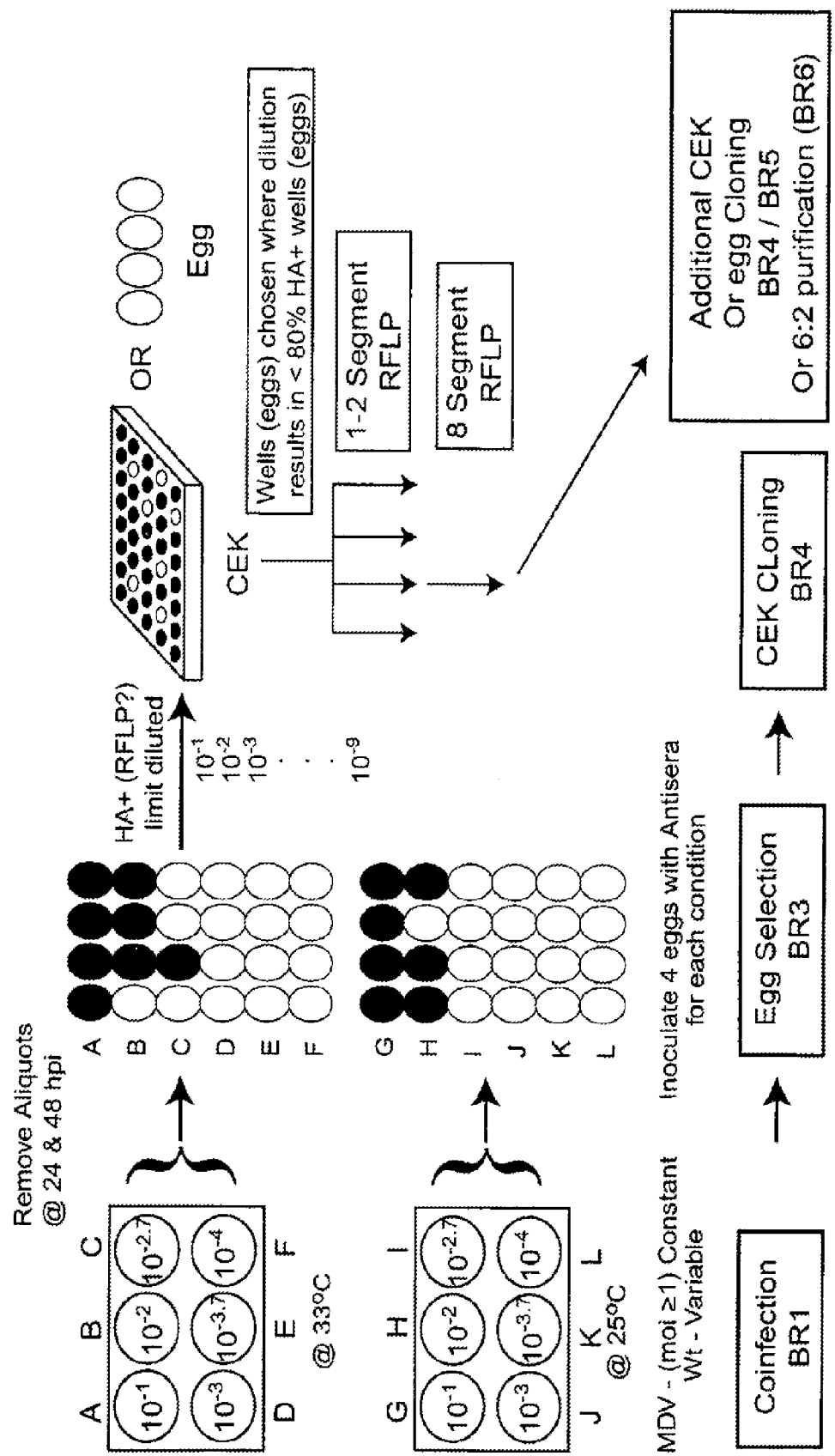

The steps in Group 1 also comprise selection of reasserted influenza viruses. The methods and compositions of the current invention are especially useful for (and are typically embodied for) selection of properly reasserted influenza B viruses. Reassorted influenza A strains are capable of selection in either cell culture (e.g., CEK cells) or in eggs. However, reasserted influenza B strains present problems when reasserted in cell culture (e.g., when selected for in CEK cells). It is believed that CEK cells interfere with the M gene in influenza B strains, thus reducing the overall production. See below. The current invention takes notice of such suppression by, in some embodiments, having selection of influenza B reassortments done in eggs (which are neutral in terms of selection pressure against the M gene in influenza B strains) at 33° C. or, alternatively, in CEK cells at 25° C. See FIG. 52.

Other embodiments of the invention in Group 1 include use of anti-HA (of the MDV) and anti-NA (of the MDV) antisera in the selection process, thus, achieving a stronger selection.

Yet other embodiments of the invention in Group 1 include cloning of the reassortments produced. As will be apparent from the previous discussion, cloning out of influenza B reassortments in CEK cell culture has proven problematic because of negative selection pressure. Thus, in some embodiments herein, B strain reassortments are cloned out in eggs at 33° C. A strain reassortments, on the other hand, are optionally cloned out and selected at the same time in CEK cell culture.

Even though some embodiments herein take advantage of the non-bias or non-suppression of eggs on reassortments (see above), other embodiments herein comprise selection/cloning of reassortments in cell culture, but at 25° C. Thus, some aspects of the current invention comprise embodiments which take advantage of the different properties of MDVB (master donor virus B) M gene and wild-type B virus M gene. For example, 6:2 and 5:3 co-infections are optionally done to produce the desired reassortments. Thus, for example, in the B/HongKong/330/01 MVS production process, the cloning from mixed wild-type and cold-adapted M viral RNAs by limiting dilution in CEK cells at 33° C., results in the dominant growth of wild-type M viral RNA. In both eggs and CEK cells, the wild-type M vRNA is dominant over MDV-derived M vRNA when 6:2 is coinfected with .5:3 (containing wild-type M gene) at 33° C., although the chance of getting wild-type M vRNA in eggs is higher. In contrast, both MDV-derived and wild-type M vRNAs are present in comparable amount when 6:2 and 5:3 are coinfected into CEK cells at 25° C. Therefore, in some embodiments herein 25° C. is used for 6:2 cloning in CEK cells in the MVS process. See, FIGS. 1 through 8. From the Figures it can be seen that plaque assays show that the titer of B virus 6:2 at 33° C. is at least 2 log10 lower than respective 5:3 at low MOI, while 6:2 grows to the same level as 5:3 at 25° C. The growth defect of 6:2 at 33° C. may account for the selection against 6:2 in MVS CEK cloning. The different growth properties of MDVB and 6:2 suggest the involvement of HA, NA in the M gene dominance. There are only two conservative amino acid differences between MDVB and wild-type B viruses. A single mutation of Valine to wild-type conservative Methionine on the 6:2 M1 gene is able to reverse the growth defect of 6:2 in CEK cells at 33° C.

Characterization of Reassortments

Yet other embodiments of the current invention utilize applications of a high throughput single strand conformation polymorphism/capillary electrophoresis (SSCP/CE) assay to determine the gene constellation of influenza viruses used herein. It should be appreciated that such characterization aspect can also be classified into other "Groups" herein, but is discussed here for organizational purposes. Influenza viruses contain 8 gene segments and, as described above, co-infection of a single cell with two different influenza strains can produce reassortant viruses with novel gene constellations distinct from either parent. Thus, some embodiments herein use a SSCP/CE assay to rapidly determine the gene segment constellation of a large number of influenza virus samples. The influenza viral gene segments are optionally amplified by RT-PCR using fluorescent-labeled primers specific for each of the eight segments. See, also, Arvin et al. (2000) *J. Clin. Micro.* 38(2):839–845 which is incorporated herein by reference for all purposes.

In order to reduce the number of RT-PCR reactions required to genotype all eight segments of the influenza genome, a multiplex reaction is optionally created in which multiple segments are simultaneously amplified in the same reaction. The RT-PCR products corresponding to each segment are differentiated by size, migration pattern and fluorescent color. The migration of a single strand DNA fragment in a non-denaturing matrix is determined not only by its size but also by its sequence content.

Cells are optionally co-infected with cold-adapted B/Ann Arbor/1/66 (MDV-B) or similar, and one of several wild-type influenza B strains. The progeny of the co-infection are cloned by limiting dilution and the nucleic acids amplified in multiplex reactions. Primers are selected and products separated by SSCP/CE at 18° C., which enhances the resolution between MDV B and wild-type strains' eight gene segments.

For example, to demonstrate the accuracy of the SSCP/CE assay, 400 gene segments from approximately 50 different reassortant viruses were analyzed and the SSCP/CE results were compared to those obtained by restriction fragment length polymorphism (RFLP). It was found that there was a high concordance (~98%) between the two sets of data, thereby validating the SSCP/CE assay. Furthermore, it was shown that the SSCP/CE assay was capable of detecting a single nucleotide substitution within the M gene segment of influenza B virus.

Prevention of Bacterial Contamination

Some embodiments of the current invention comprise steps to detect and/or prevent/detect microbial contamination of eggs in which influenza virus is produced. Such steps are useful in several areas as outlined in Table 1 and can be included in Groups 1, 2, and 3, but for organizational purposes are presented with the steps of Group 1. The microbial detection strategies of the invention are useful for rapid/high throughput microbial detection and, thus, as with many other steps herein, are useful for increasing throughput in virus/vaccine production.

Figure 9:
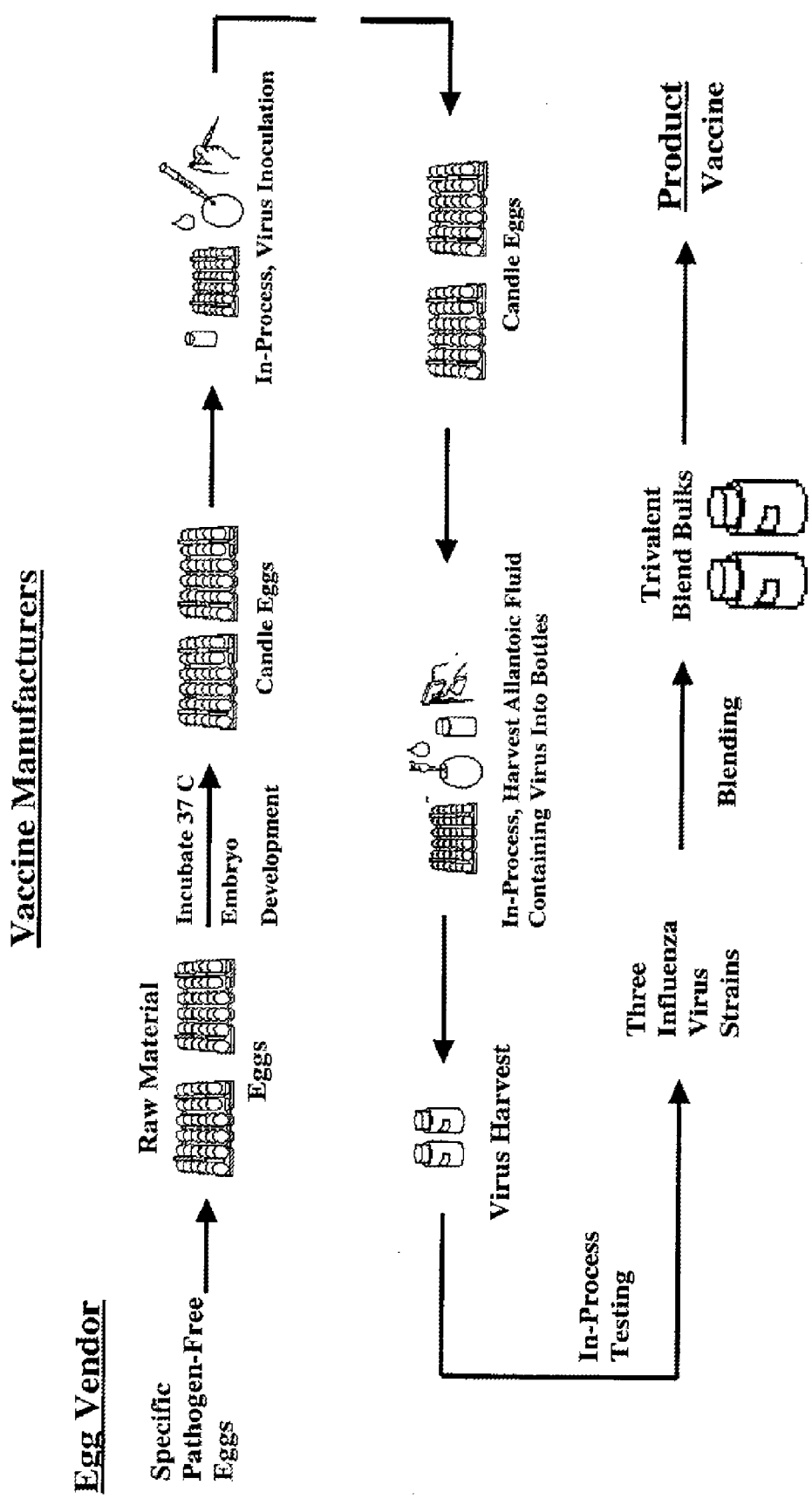
FIG. 9: Shows a flow chart of potential microbial contamination during vaccine production process.

Many current influenza vaccine production strategies, including some embodiments of the invention herein, use as a component, the traditional method for influenza virus expansion in specific-pathogen-free fertile chicken eggs. Possible microbial contamination can occur in several points in the production of virus in eggs. See, e.g., FIG. 9, which outlines one possible example of a virus production flowchart and possible areas of contamination therein. Unfortunately, the chicken eggs may have some microorganisms outside of their shells as part of their natural flora. It is also possible to have microorganisms enclosed within the shell of the egg during the development of the chicken embryo. Fertilized chicken eggs are incubated at 37° C. in high humidity for development of the embryo, which constitutes prime incubation conditions for many types of microbial contaminants as well. Another possible time of microbial contamination occurs when the shell is punctured to inoculate the egg. Even though prior to virus inoculation, the eggs are often sprayed with alcohol, there is still opportunity for microorganisms to enter into the egg.

After expansion of viruses for 2 to 3 days in the eggs, the top of the egg shell is typically removed for manual harvesting of the allantoic fluid containing virus within the egg. This harvesting is another point where microbial contamination may originate. Unfortunately eggs with such contaminating bioburden may escape detection, necessitating pooling into multiple bottles to minimize the rejection of the entire lot due to a failed MPA test. Since three influenza strains are typically used in vaccine production, blending of the three strains is required for the final bulk. In-process MPA (microbiological purity assay) testing is performed, e.g., at virus harvest (see FIG. 9) prior to use in the blending and filling to ensure microbial-free product.

After incubation, the "traditional" method of candling is used to identify infertile and dead eggs which are possibly dead due to natural causes or to microbial contamination (i.e., dead eggs may occur due to infectivity of the virus and/or expansion of microorganisms, both of which require detection and removal of such eggs). Candling comprises, e.g., the process of holding an egg in front of a light source in a darkened room to enable visualization of the developing embryo. Dead eggs are excluded from virus inoculation.

As can be seen from the above points, detection of microbial contamination can be needed at multiple steps during the manufacture of influenza vaccine. There is a need to eliminate or reduce avian and environmental microbes and a need to eliminate or reduce introduction of environmental and human microbes. Thus, a need for non-invasive and rapid methods of screening eggs to identify and remove infertile, dead, or microbially contaminated eggs exists. Such methods should preferably be non-invasive and rapid. Current methods for detection of contaminating microorganisms include, e.g., compendial methods (MPA and Bioburden). Current methods can include, e.g., egg candling during egg pre/post inoculation (which is typically done manually at a rate of about 500 eggs/hour/person); MPA and BioBurden tests which are typically manual and take about 14 days for MPA and about 3 days for BioBurden (which are done during virus harvest); mycoplasma testing; which is typically done manually and takes about 28 days (done during virus harvest); and mycobacterium testing which is typically manual and takes about 56 days (done during virus harvest). From such, it will be appreciated that there are opportunities for significant reduction in turn around times for the traditional methods. New methods are preferable, e.g., to reduce time to result from days to 24 hours or less (and preferably 4 hours or less for in-process testing) and from weeks to a few days for Release Testing. Other preferences include, e.g., to reduce to intermediate/inventory hold-time, to potentially expedite product release/approval, and to reduce cost/labor/overhead. In general, any method chosen to detect microbial contamination should consider, e.g., scientific requirements such as intended use, time to result, sample type, instrument capabilities, etc.; regulatory requirements such as FDA guidelines (e.g., the bioburden must be a measure of total viable organisms as required by the FDA), review, expectations/acceptability; compliance requirements such as vendor audits, vendor support (instrument IOPQ or instrumentally observed perspectival quality), software validation, and documentation; and business requirements such as industry trends, costs of implementation, cost per test, etc.

Figure 10:
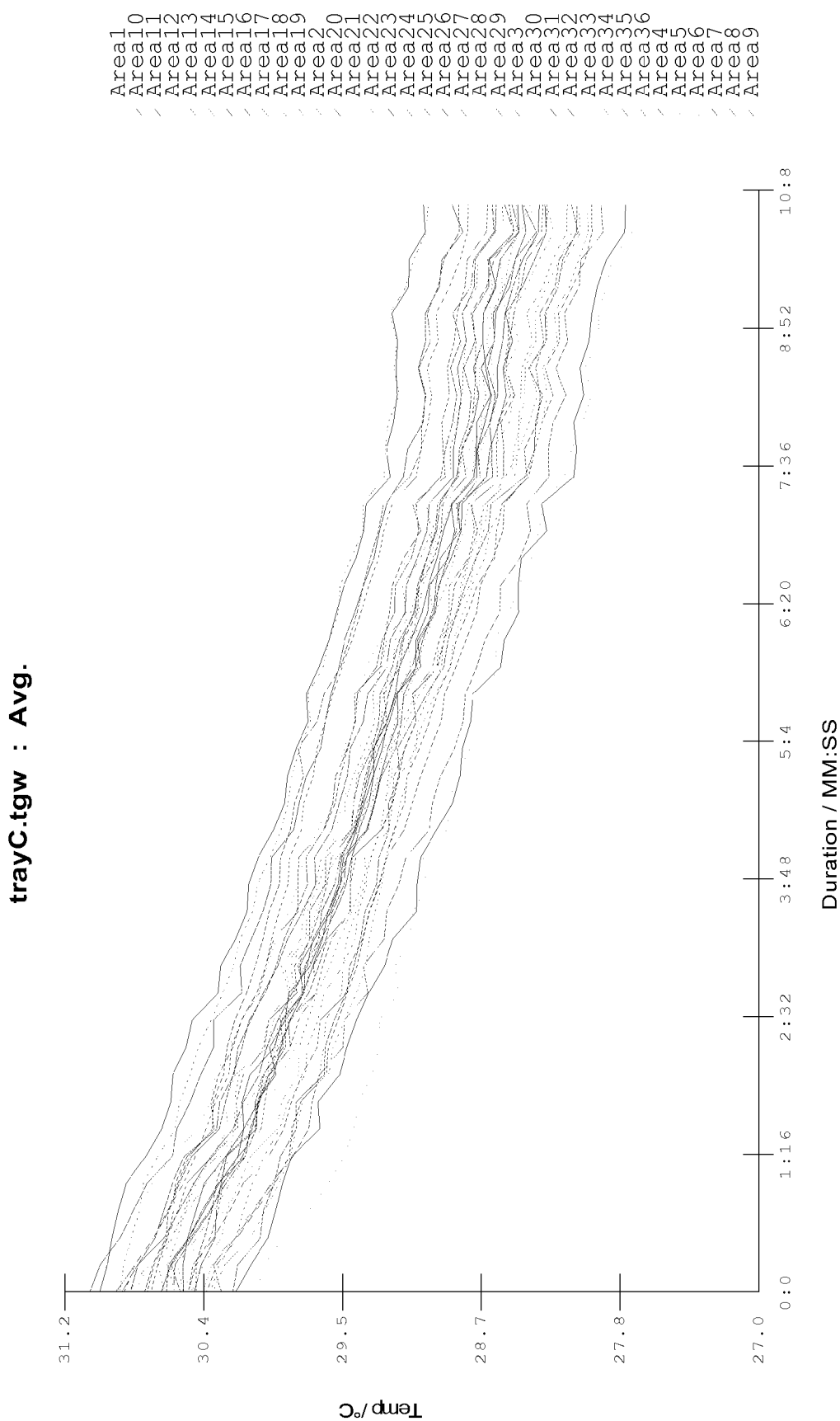
FIG. 10: Illustrates temperature decay rates of individual eggs via infra-red imaging.
Figure 11:
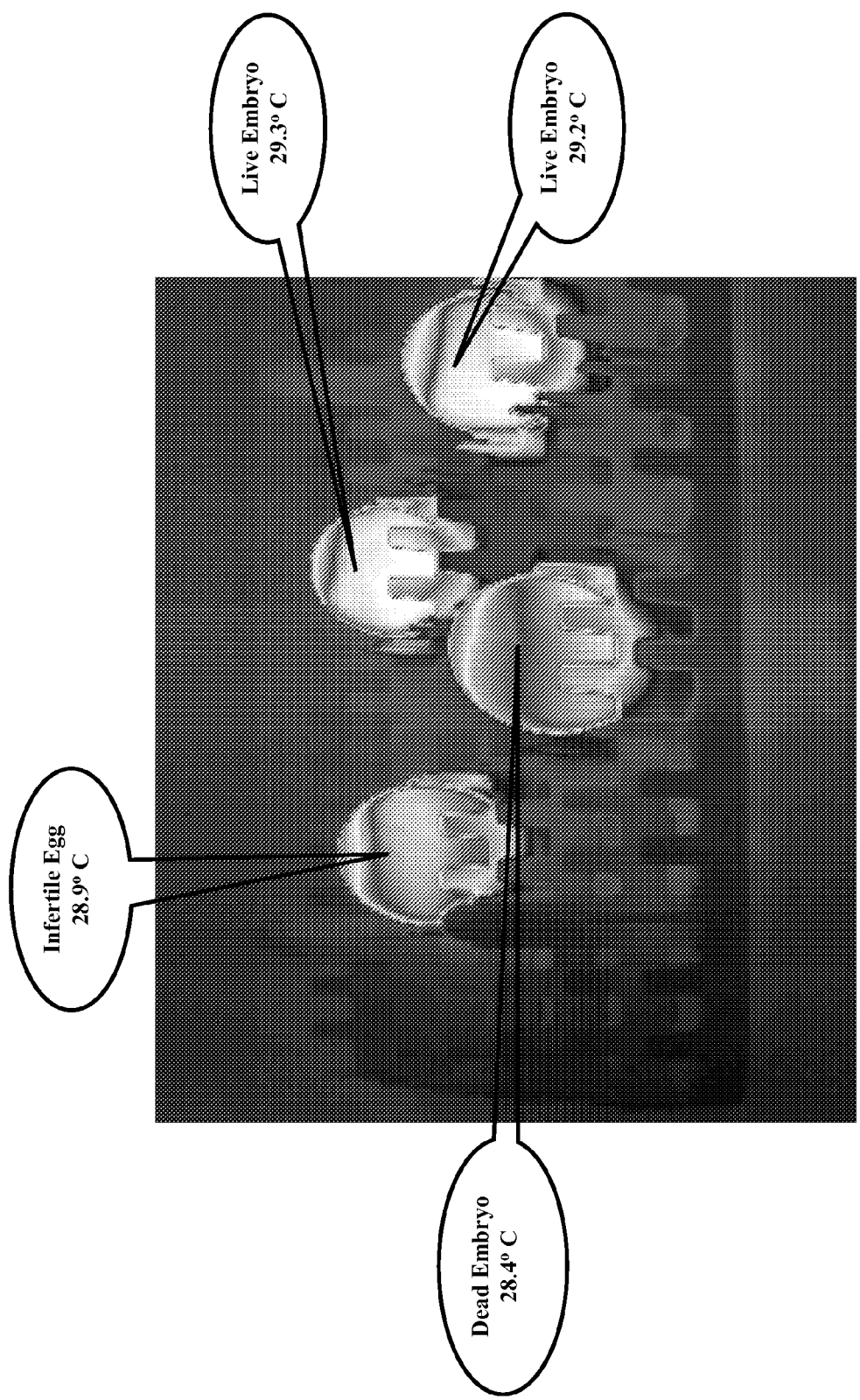
FIG. 11: Illustrates thermal imaging of live, infertile, and dead eggs.

A few potential alternative methods for detection of microbial contamination which are present within various embodiments of the invention are listed in Table 3. Thus, for example, an alternative to candling of eggs, and one embodiment of the current invention, comprises pre/post virus inoculation thermal imaging. In such embodiments, the infrared radiation emitted by incubated eggs is captured with an infrared camera. Using software, the captured images are converted into temperature readings for the eggs. The camera is able to capture differences in temperature less than or equal to 0.01° C. Metabolically active developing embryos lose heat slower than an infertile egg or a dead embryo, thus, resulting in a higher temperature differential. For example, to set up, as an alternative to candling of eggs, thermal imaging of pre/post virus inoculation, a tray of eggs can be thermally imaged (e.g., an infrared camera can be set below a tray-of eggs (e.g., a tray with open-bottomed cells)). Software can then be set up to measure the bottom temperature of each egg (or side, top, etc.). Temperature decay rates of each individual egg can be evaluated, thus, allowing identification of the time to show maximum temperature differential in problem eggs. Through such thermal imaging, temperature differentials between live embryos and infertile and dead eggs can be identified. See FIGS. 10 and 11.

In other embodiments herein, the current invention utilizes an alternative to bioburden test on virus harvest, namely, MPN or Most Probable Number, which is based upon *Bacteriological Analytical Manual Online, January 2001, Appendix 2, Most Probable Number from Serial Dilutions, FDA/CFSA-BAM*. For example, an MPN Test can involve a 3 replicate 96-well test, wherein 1:10 serial dilutions (e.g., 1:10, 1:100, 1:1K, 1:10K, 1:100K, and 1:1000K dilutions) can be run in triplicate for 3 different samples on a 96 well microtiter plate with negative controls. TSB can be added initially to all wells as a diluent and as an enriched media to the support the growth of microorganisms. Plates can be read visually or at 600 nm. MPN bioburden tests are quite useful in comparison to membrane filtration tests for detection of contamination. While membrane filtration tests can require (for 3 samples) 15 TSA plates, a large sample volume, intensive amounts of time and labor, can be difficult to automate and only sample at 1:10 and 1:100 dilutions, a 96-well MPN test can (for 3 samples) only require one 96-well microtiter plate (with controls), a small volume of sample, a few simple disposables and reagents, gives a dilution range from 1:10 to 1:100,000, and can also be visual read or automatably read with a 96-well plate reader. The results of testing 70 samples using conventional Bioburden and 96-well plate MPN were found in complete agreement with each other. Notably, for its intended purpose, the 96-well plate MPN provided comparable results with a higher throughput.

As an alternative to the traditional compendial Mycoplasma test for Virus Harvest, the current invention, in some embodiments, comprises use of universal commercial standardized rapid nucleic acid amplification-based kits (e.g., PCR). The current compendial method (direct and indirect) detects all strains of contamination (including avian *M. synoviae* and *M. gallisepticum* and human *M. pneumoniae*, i.e., all avian and human mycobacterium strains). The alternative PCR detection method comprises investigator-developed primer/probe sets for real-time PCR that specifically detect a mycoplasma panel, and possibly greater than 40 species based upon sequence homology of target gene (e.g., genus and/or species specific sequences on 16s and/or 23s rRNA) such as tubercle bacterial and non-tuberculous mycobacteria (e.g., *M. abscessus* and *M. avium*). Some embodiments herein utilize standardized nucleic acid amplification-based kits that rapidly detect tubercule bacteria and non-tuberculous mycobacteria, etc.

Group 2

Aspects of the current invention which fall into Group 2 include those corresponding to Step 4 through Step 6 in Table 1. After the process of correct reassortment and cloning of reassortants (i.e., the 6:2 viruses), such reassorted virus particles are further purified in embryonated hen eggs and the correct clones are expanded in quantity (again through growth in hen eggs) to generate a master virus strain (MVS) or master virus seed, which, in turn, is further expanded to generate a master working virus strain (MWVS) or manufacturer's working virus seed. Many aspects of purification of virus particles from eggs and use of such purified virus to inoculate more eggs in order to expand the quantity of virus particles are well known to those skilled in the art. Many such techniques are common in the current production of virus particles and have been used for at least 40 years. See, e.g., Reimer, et al. Influenza virus purification with the zonal ultracentrifuge, *Science* 1966, 152:1379–81. For example, common purification protocols can involve, e.g., ultracentrifugation in sucrose gradients (e.g., 10–40% sucrose), etc. Also, as noted herein, other procedures, etc. listed in other Groups are also optionally present within Group 2, e.g., prevention of microbial contamination, etc.

Group 3

Aspects of the current invention which fall under the heading of Group 3 include Step 7 through Step 11 in Table 1. These steps primarily deal with the conditioning of the embryonated eggs (e.g., specific handling and environmental conditions involved in the incubation of virus infected eggs) and the harvesting and clarification of influenza virus from the allantoic fluid of the eggs.

For example, the current invention comprises conditioning, washing, candling, and incubating eggs which contain the reasserted virus to be used in a vaccine; inoculation, sealing, etc. of such eggs; candling of such eggs; harvesting of the virus solution (e.g., the allantoic fluid) from the eggs; and clarification of the virus solution. Again, it should be noted that several techniques applicable to the steps in Groups 2 are equally applicable to the steps in Group 3 (e.g., candling, etc.). Several aspects of the invention which comprise Groups 3 are well known to those skilled in the art. Various aspects of candling of eggs in virus production, as well as inoculation of eggs with viruses and washing, incubating, etc. of such eggs are well known techniques in the production of virus/vaccines in eggs. Of course, it will be appreciated that such well-known techniques are used in conjunction with the unique and innovate aspects of the current invention.

Rocking

One drawback in culturing some types of influenza strains (e.g., especially influenza B strains such as Victoria/504/2000) is that they do not produce as high a titer as other strains when grown in eggs. For example, if a first strain (e.g., an influenza A strain) produces a titer of $10^8$ or $10^9$ log (i.e., $10^8$ or $10^9$ virus particles per milliliter) and a second strain (e.g., an influenza B strain) only produces $10^7$ virus particles per milliliter, then the second strain must be, e.g., grown in a greater quantity of eggs, or the first strain must be held until the second strain is grown in a second production, etc.

Thus, one aspect of the current invention is to rock or gently agitate the eggs in which the virus strains are incubated (i.e., after the eggs are inoculated with the virus). It should be noted that the exact mechanism used to achieve such rocking is not limiting. For example, the eggs are optionally rocked on a shaking platform or rocking platform (e.g., as is used to incubate bacterial culture flasks, as is used in egg incubators, etc.). In some embodiments, the eggs are rocked from about 1 cycle per minute or less to about 2 cycles per minute or more. In this context, "cycle" should be taken to mean the traveling of the eggs through a full range of motion. In yet other embodiments, the eggs are rocked from abut 0.5 cycles per minute or less to about 5 cycles per minute or more. In some embodiments, the eggs are rocked at about 1 cycle per minute. When rocking was added to the incubation steps in Group 3 (i.e., post inoculation) the titer of a B-Victoria influenza strain increased by 0.4 log over a control group of eggs which was not rocked.

Filtering and Warming

Yet another aspect of the invention that falls under Group 3 involves the effect of viral allantoic fluid (VAF) temperature on virus potency losses during sterile filtration (typically through 0.2 um filters). In various embodiments of the current invention, virus particles are harvested from allantoic fluid and then put through a process involving warming of the fluid followed by filtration of the fluid. See, e.g., Steps 10 and 11 in Table 1. Such steps are desirable for several reasons. For example, as pointed out herein, presence of allantoic fluid and debris in vaccine preparations can lead to allergic reactions. Also, quite importantly, filtration removes bioburden (bacteria) from the solutions. All VH (virus harvest) solutions containing bioburden must be discarded. This is also true in intranasal application of live-attenuated virus vaccines. Thus, the aspects of the current invention which allow filtration and clarification of live attenuated virus in order to remove and/or reduce the presence of such bioburden, etc. is quite desirable.

The effects of viral allantoic fluid (VAF) temperature and warming time necessary to filter a cold-adapted (ca) virus strain (e.g., A/Sydney/05/97, H3N2 type) with acceptable potency loss through sterilizing-grade filters is used as an example herein. Conditions to acceptably filter A/Sydney/05/97 are discussed, as well as the results of five additional cold adapted influenza strains (namely: 2×H1N1, 1×H3N2, 2×B) being filtered under similar conditions.

Three independent assays ($TCID_{50}$, neuraminidase, and hemagglutinin) were used to characterize viral allantoic fluid throughout the filtration process. The data demonstrate that the addition of a warming step (e.g., exposure to the temperature of 31±3° C. up to 60 minutes prior to filtration) to the filtration process reduced the potency losses to acceptable levels (0–0.3 $\log_{10}$ $TCID_{50}$) compared to the sterilizing-grade filtration performed without warming step for A/Sydney/05/97. In other embodiments, the warming temperature is optionally over 28° C., or from 28 to 36° C. for a period of time of at least 30 minutes, or, in other embodiments of from about 60 to 240 minutes. It will be appreciated that the warming process can, indeed, continue for long periods of time, but that after greater lengths of time, the loss in potency due to virus stability loss at such elevated temperatures becomes measurable and detrimental. The added warming step did not contribute to additional potency losses for other tested strains for the times tested, indicating the warming step is an acceptable process step for sterilizing-grade filtration of cold-adapted influenza viruses (CAIV).

As described herein, the current FluMist™ manufacturing process uses embryonated chicken eggs to generate master virus seeds (MVS), manufacturer's working virus seeds (MWVS) and virus harvests (VH). See Step 6 in Table 1. The seeds and viral harvest may contain bioburden (typically bacterial contamination), which would cause the seed or bulk virus product lots to be rejected in the vaccine production process. Through previous studies to evaluate the use of filtration for virus containing allantoic fluids, indication had been that bioburden can be reduced by the introduction of a filtration step in the process. However, based on previous work, such filtration is problematic with particular viral strains (e.g., A/Sydney/05/97). Based on such studies, design proposals have been made for filtration rigs comprised of a sterile plastic media bag connected to a pre-filter and 0.2 millimeter sterilizing-grade filter combination with various associated filling, dispensing and sampling lines (see below). Of course, it will be appreciated that specific listing or description of particular product types used, sizes, etc., is not to be considered limiting on the current invention unless specifically stated to be so.

As seen in such studies, the majority of tested cold-adapted (ca) viral strains can be filtered with minimal potency loss though a Sartorius Sartoclean CA pre-filter followed by a Sartorius Sartopore 2 as the sterilizing-grade filter. However, other filtration studies with A/Sydney/05/97 resulted in potency losses of between 0.7 to 1.4 $\log_{10}$ $TCID_{50}$/mL. Further studies revealed that this loss occurred across the Sartorius Sartopore 2 sterilizing-grade filter. Again, it should be noted that other filter brands and/or filter types are optionally used in such steps and that recitation of particular filter names/types should not be construed at limiting.

The purpose of the first set of experiments shown below was to test the effect of VAF temperature on virus potency loss during filtration. The second part of the study was designed to define the appropriate warming time of VAF prior to filtration. The cold-adapted (ca) A/Sydney/05/97 virus strain (H3N2 type) was used as a model strain to determine the warm-up conditions because, as stated previously, large potency losses have been observed during filtration of this strain.

The third part of this example evaluated the effect of warming the viral allantoic fluid (VAF) on potency losses caused by filtration for several other monovalent virus strains. Five CAIV strains (2×H1N1, 1×H3N2 and 2×B) were used in these runs. All experiments were performed at the CAIV seed-scale (MVS and MWVS) using 1.0–3.0 L of sucrose phosphate glutamate (SPG) stabilized VAF and appropriately scaled filters, i.e. approximately 1:30 to 1:10 of proposed maximum VH process scale, prior to removal of testing samples. Typical process scale is up to about 33 L of stabilized VH per filtration rig. Such volume typically works well with 50 L bags chosen for filtration rigs and has a reasonable safety margin for volume that can be filtered using standard 10″ filter capsules. However, such volume is often too large for development/exemplary work; thus, a $\frac{1}{10}^{th}$ scale filtration was performed (i.e., about 3 L).

Virus propagation for such temperature/filtration steps can be performed according to commonly known methods in the art, and/or using other aspects of the current invention (see, above and below) using cold-adapted (ca) influenza strains summarized in Table 4.

Samples from all stages of the experiment were assayed for potency by measuring the Tissue Culture Infectious Dose ($TCID_{50}$) in a manual assay (see below for other aspects of $TCID_{50}$ measurements). Neuraminidase activity (NA) and Hemagglutinin activity (HA) were also measured.

A series of filtrations through Sartorius Sartoclean CA/Sartorius Sartopore 2 filter combinations were performed in order to evaluate the effect of VAF temperature prior to filtration on: potency ($TCID_{50}$/mL), neuraminidase (NA) and hemagglutinin (HA) activity losses.

During the virus harvest, VAF was pooled into 1 L PETG bottles. Once the required volume of unstabilized VAF was collected and pooled, the filtrations were performed. The temperature (start-up temperature) of the unstabilized VAF at this stage was 15±3° C. The total warming time was defined as the time the VAF was in the 33±1° C. water bath and consisted of the warm-up time (from 15±3° C. to 28±3° C.) and warm-hold time (time greater than 28° C., e.g., at a set point).

The Part 1 VAF temperature effect studies (see below) were performed with the cold-adapted (ca) A/Sydney/05/97 virus strain (H3N2 type). Part 2 of the example focused on determination of the optional warm-hold time ("time at the temperature"). In part 3, the effect of the previously determined warm-hold time on five other strains (Table 5) was tested. In all parts of the example, 1.0–3.0 L of sucrose phosphate glutamate (SPG) stabilized VAF, typical virus seed-scale, and approximately 1:30–1:10 of proposed mVH process scale, were filtered through the rigs.

In the current typical manufacturing processes, after harvest, VH is centrifuged, stabilized and frozen for further transportation. In these examples, a sample of VAF withdrawn from the un-stabilized pool was centrifuged and stabilized with SPG, similarly to current manufacturing processes and this served as a control for filtered VAF in all parts of the current example.

Part 1: Temperature Effect on A/Sydney/05/97 Virus Titer Changes During Filtration In order to determine the effect of temperature on potency loss, two sets of filtration experiments at various temperatures were performed. Each set consisted of three parallel experiments performed on the same day with VAF collected from the same batch of eggs. In these experiments, after harvest, VAF was stabilized with SPG, split into three pools and exposed for 60 minutes prior to filtration to either 5±3° C. (refrigerator), 20±3° C. (bench top) or 31±3° C. (water bath). During this time, VAF in the bottle was mixed by inverting every 10 minutes. After the temperature treatment, it was filtered through Sartoclean CA and Sartopore 2 filters. In the control experiment, VAF was centrifuged and stabilized. $TCID_{50}$ results of filtration under different conditions were compared to each other and the control.

To determine the effect of VAF temperature on potency loss, VAF was exposed for 60 minutes prior to filtration to 5±3° C., 20±3° C or 31±3° C. The potency change, neuraminidase and hemagglutinin activity difference between centrifuged stabilized and post-filtration material with different temperate treatment is summarized in Tables 5–10. As can be seen, filtration of cold (5±3° C.) and room temperature (20±3° C.) VAF resulted in potency losses between 0.7 and 1.0 $\log_{10}$ $TCID_{50}$/mL (see, Tables 5 and 8). However, there was no post filtration titer loss (compared to the centrifuged stabilized VAF) when VAF was warmed up to 31±3° C. for 60 minutes (30 minutes warm up time +30 minutes warm-hold time at the set point temperature). See, Tables 5 and 8. Additionally, the post filtration neuraminidase activity levels were higher in the filtration performed after VAF was warmed up to 31±3° C. compared to the levels observed in cold and room temperature filtrations. See, Tables 6 and 9. Addition of the warm-up step also reduced hemagglutinin activity losses. See, Tables 7 and 10.

Part 2: Determination of the Warming Time Required for Acceptable Filtration Potency Losses of A/Sydney/05/97

In order to determine the necessary warming time, a series of experiments were conducted with VAF warmed to 31±3° C. prior to filtration in a water bath. In a control experiment, VAF was filtered immediately after stabilization with SPG. In all experiments, warming time was defined as the total time (warm up time plus warm-hold time) VAF was in the water bath (i.e., at 31±3° C.). VAF in the bottle was mixed by inverting every 10 minutes. After temperature treatment it was filtered through Sartoclean CA and Sartopore 2 filters. In the control experiment, representing the current manufacturing process, VAF was centrifuged and stabilized. $TCID_{50}$ results of filtration under different conditions were compared to each other and the control.

To determine the warming time prior to filtration that is required to filter ca A/Sydney/05/97 a series of experiments was conducted wherein VAF was warmed to 31±3° C. prior to filtration for 30, 90 or 180 minutes in one set of experiments and 30, 60 or 90 minutes in another set of experiments. In the control experiments, VAF was filtered without warming immediately after stabilization with SPG. The virus potency, neuraminidase and hemagglutinin levels between filtered VAF and control are summarized in Tables 11–16.

The data demonstrate that the exposure of VAF to 31±3° C. reduced post filtration virus potency losses and allowed partial recovery of neuraminidase and hemagglutinin activities. See, Tables 11–13. The temperature of un-stabilized VAF at the beginning of the experiments (post harvesting and prior to warming) was 15±2° C. The warm up time required for 1–1.5 L of VAF to reach 31±3° C. was about 20–30 minutes. Thus, a 30-minute total VAF warming time results in 0–10 minutes VAF warm hold time at 31±3° C.

The minimum warming time required to minimize filtration potency losses was determined in a second series of experiments. See, Tables 14–16 (first set) and Tables 17–19

(repeat set). The post filtration potency, HA and NA losses were observed in 0 and 30 minutes total warming time experiments. In 60 and 90 minute total warming time (warm-hold of 30–40 and 60–70 minutes at 31±3° C.) experiments, post filtration virus potency and HA and NA levels were similar to the control (centrifuged stabilized VAF) samples. See Tables 14–19.

Part 3: Effect of Warming on Other Strains

A series of experiments was conducted with 5 strains other than A/Sydney/05/97, i.e., 2×H1N1, 1×H3N2, and 2×B, in order to assess the effect of the warm up step on filtration of influenza virus strains other than A/Sydney/05/97. Each strain was tested twice. VAF was warmed to 31±3° C. for 60 minutes (30 minutes ramp up time+30 minutes time at the temperature) prior to filtration. After temperature treatment, it was filtered through Sartoclean CA and Sartopore 2 filters. In a control experiment, VAF was filtered immediately after stabilization with SPG at room temperature. $TCID_{50}$ results of filtration under different conditions were compared to each other and control experiments.

For the additional 5 cold-adapted influenza virus strains tested, a short exposure (total warming time of 60 minutes) to 31±3° C. (warm-hold time of 30–40 minutes at set point temperature) contributed to the reduction of post filtration potency losses compared to the experiments without temperature treatment for A/Sydney/05/97 and B/Victoria/504/2000 and did not impact potency for the other strains. The potency ($TCID_{50}$/mL), neuraminidase and hemagglutinin levels from these experiments are summarized in Tables 20–25, below.

As can be seen from the tables, the aspect of the current invention comprising warming to 31±3° C. or optionally even up to 36° C. (warm-hold time of 60 to 90 minutes for 1–1.5 L of VAF in bottles) of the stabilized viral harvest prior to filtration through Sartoclean CA pre filters and Sartopore 2 sterilizing grade filters resulted in acceptable reduction of virus potency (0–0.3 $\log_{10}$ $TCID_{50}$/ml) for A/Sydney/05/97. In the control experiments, when A/Sydney/05/97 stabilized viral harvest was filtered without warming, titer losses were up to 1.0 $\log_{10}$ $TCID_{50}$/ml.

As is also seen from such tables, for all 6 cold-adapted influenza virus strains tested, a short exposure (warm up and warm hold time of 60 minutes) at 31±3° C. (warm-hold of 30–40 minutes at 31±3° C.) either decreased the potency losses or did not contribute to additional potency losses during filtration. In all experiments, the post filtration titer loss was not higher than 0.3 log $TCID_{50}$/ml. The reduced activity losses of the viral surface proteins (neuraminidase and hemagglutinin) of warmed filtered VAF compared to not warmed, support the decreased potency loss data shown by $TCID_{50}$ assay.

Thus, the data verifies that some embodiments of the current invention which comprise a warming time required to filter CAIV (MVS, MWVS or VH) have acceptable potency losses of 60 minutes (time to warm up the VAF to 31±3° C. and warm hold (time at the set point temperature) for at least 30 minutes). Such warming tolerance is a novel and unexpected result, especially in light of other filtration attempts. See above. Again, as will be appreciated, the embodiments of the current invention comprising heating/filtration steps are not limited by the above examples. In other words, e.g., other filters and filter types, etc are optionally used, without deviating from the invention.

Group 4

Group 4 of the aspects of the current invention comprises, e.g., Steps 12–15 of Table 1. Such steps primarily concern stabilization (e.g., through addition of components, alterations in buffer/NAF ratios, etc.) and assays of potency/sterility of virus containing solutions. In some embodiments, the final viral solutions/vaccines comprising live viruses are stable in liquid form at 4° C. for a period of time sufficient to allow storage "in the field" (e.g., on sale and commercialization when refrigerated at 4° C., etc.) throughout an influenza vaccination season (e.g., typically from about September through March in the northern hemisphere). Thus, the virus/vaccine compositions are desired to retain their potency or to lose their potency at an acceptable rate over the storage period. For example, if a 0.3 log potency loss were acceptable and the storage period were 9 months, then an 0.05 log/month decrease in potency would be acceptable. Furthermore, use of FFA allows a greater latitude in terms of acceptable loss. For example, if a loss of up to 0.75 log were allowed, a rate of less than or equal to 0.09 log/month would be sufficient to allow stability of materials stored continuously at refrigerator temperature (e.g., 4° C.). In other embodiments, such solutions/vaccines are stable in liquid form at from about 2° C. to about 8° C. In yet other embodiments, the solutions/vaccines are stable at room temperature. Typical embodiments herein do not exhibit a decrease (or exhibit small decreases) in immunogenicity due to the NAF dilutions (see below).

Concentration/Diafiltration of Virus Harvests

In some embodiments herein, virus harvests are optionally concentrated using a appropriate column. Influenza virus solutions can be concentrated without loosing appreciable viral potency/activity. Such concentration without loss of potency is a quite surprising result because previous literature, etc. showed a loss of virus activity with concentration. Viral concentration can be done at a number of points in the purification/production process, e.g., as illustrated in Table 1, in order to enhance the viral particles and remove other proteins, RNA, etc. For example, concentration can be done prior to potency assaying, or even after potency assaying, etc., but in many embodiments is done within/amongst the steps categorized in Group 4. Concentration of virus particles can be useful for purification, vaccine preparation, and for analytical characterization. See, e.g., Methods and Techniques in Virology, Pierre Payment and Michel Trudel, Marcel Dekker, Inc., (1993). Due to the low amount of virus in some VAF samples, the direct analysis of the virus particles precludes some of the analytical techniques like Analytical Ultra Centrifugation (AUC), Disc Centrifuge, Matrix Assisted Laser Desertion Ionization (MALDI), and particle counting.

Figure 18A:
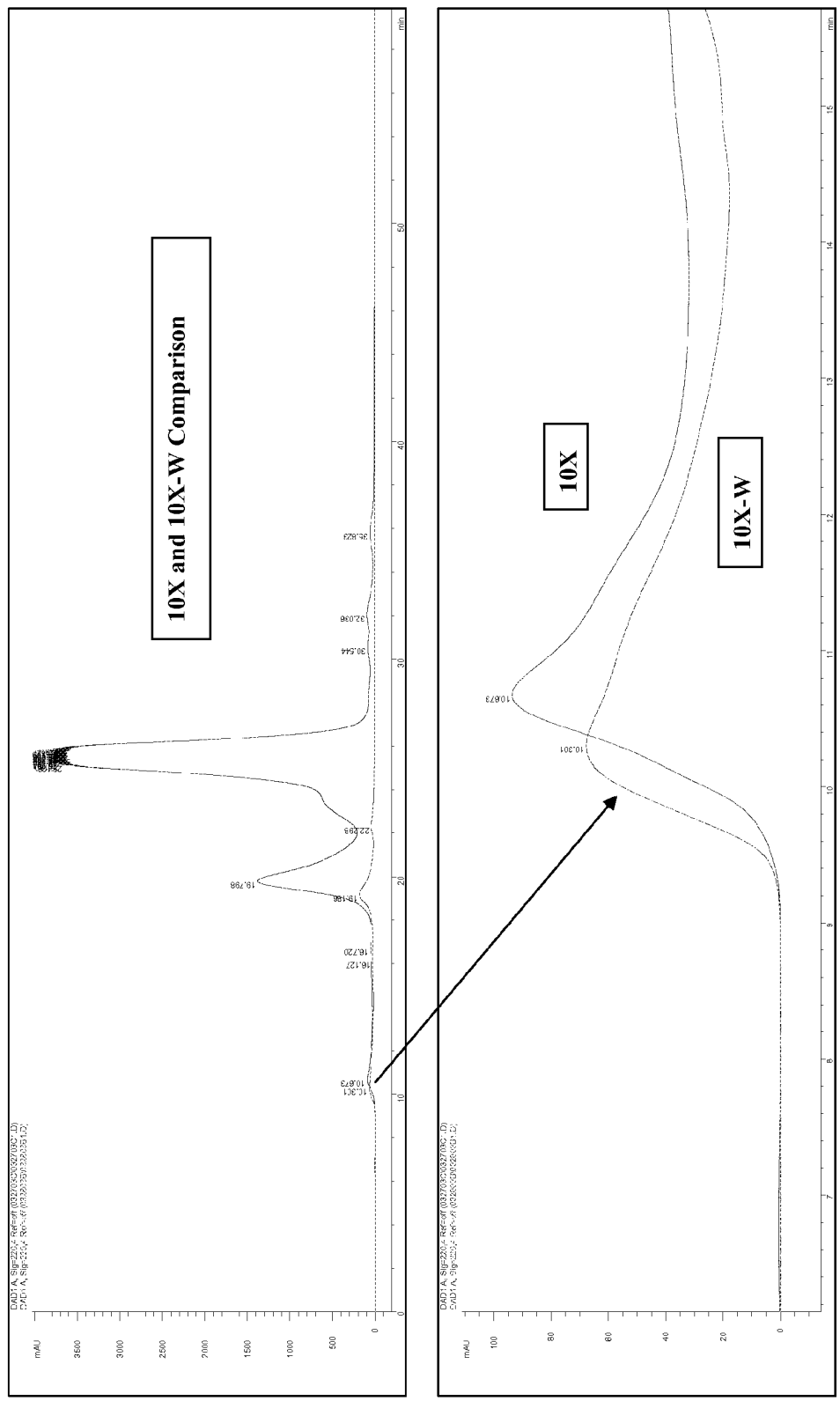
FIG. 18, Panels A–C: Display of 10× and 10×-W of A/New Caledonia/20/99; Permeate of A/New Caledonia/20/99; and 5 washes of A/New Caledonia/20/99.
Figure 18B:
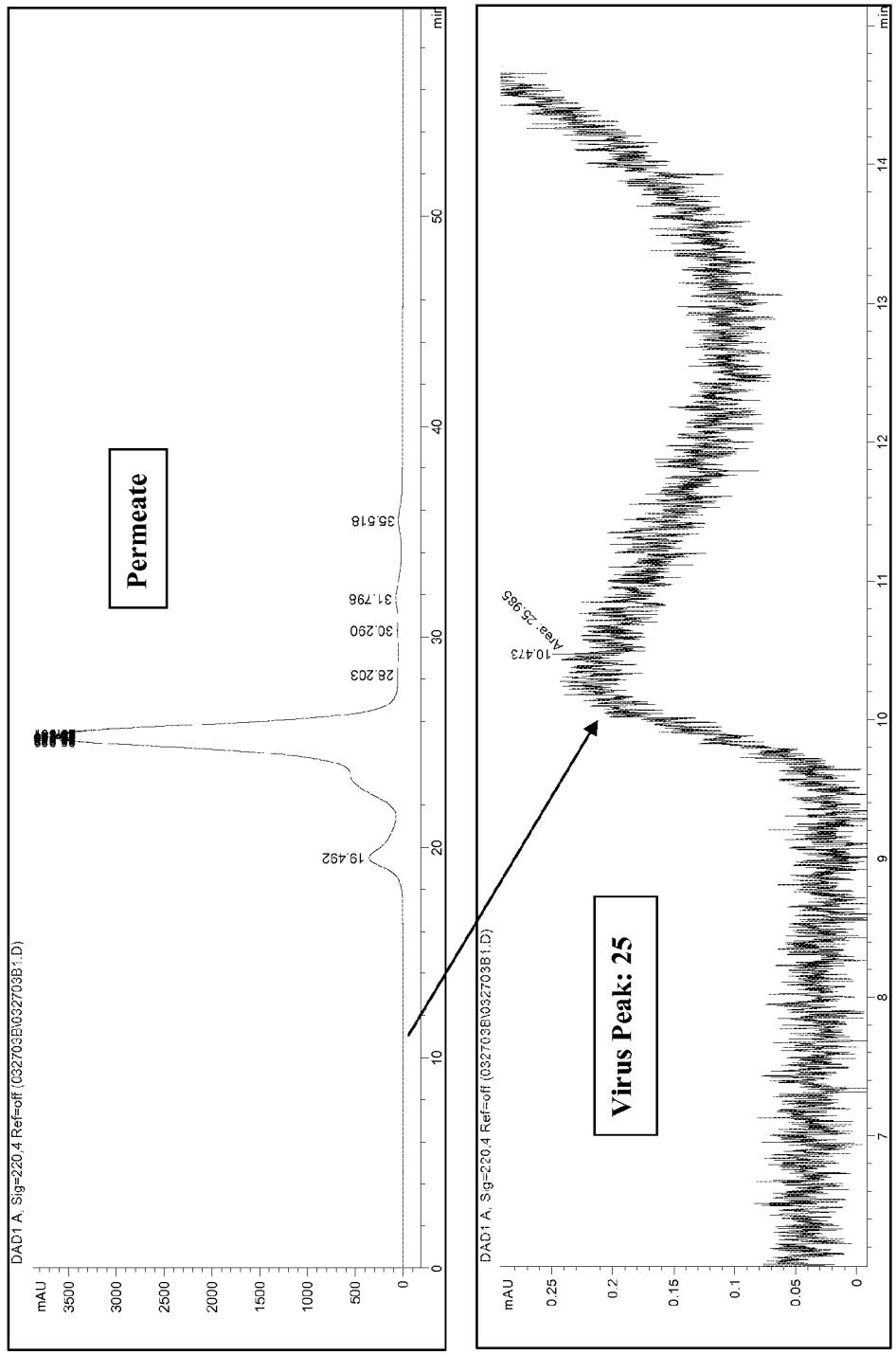
Figure 18C:
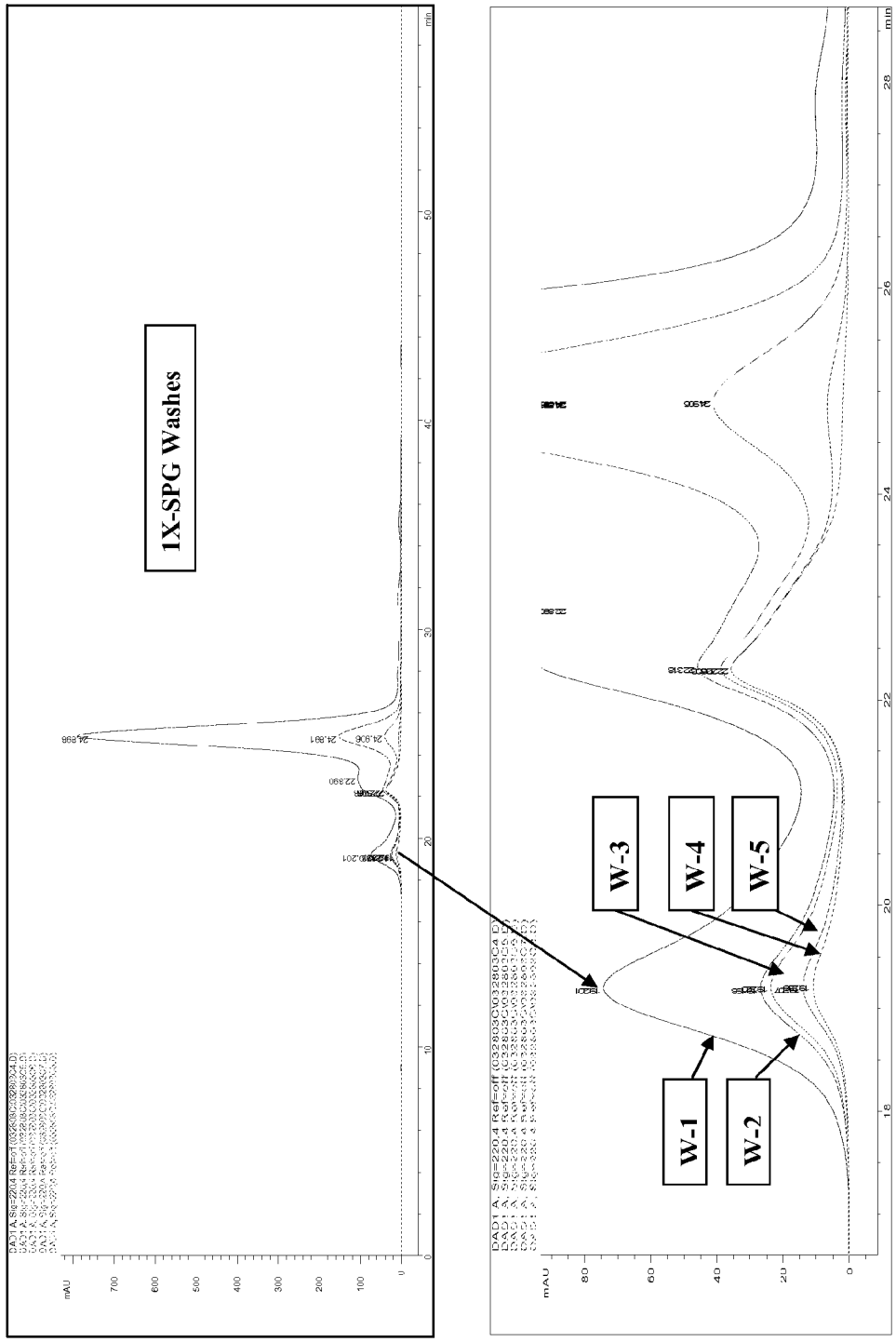

Prior traditional viral concentrations from egg NAF, etc. were done via gradient purification centrifugation. See, e.g., Concentration and Purification of Influenza Virus from Allantoic Fluid, Arora et al., *Analytical Biochemistry*, 144: 189–192 (1985). Embodiments herein, however, utilize size exclusion columns. Concentration can be used whether the virus is produced via egg production, cell culture production (e.g., Vero cells), plasmid rescue production, etc. Also, the concentration steps can be performed on a number of different viruses and/or virus strains (e.g., both influenza A and influenza B strains are amenable to such actions) as well as between different lots of one strain, e.g., to ensure product quality. Additionally, size exclusion column concentration can often be used as a track on the amount of virus particles within a harvest, e.g., within an egg, etc. Thus, for example, a peak area (i.e., of virus eluted from the column) can be used instead of, or in addition to, $TCID_{50}$ measurement of such solutions. Such tracking is especially useful for virus produced in eggs. Additionally, concentrated and purified virus material can optionally be a starting material for generating pure HA, NA and other viral components for further studies. Furthermore, SEC purified virus can provide a better insight into the virus structure and the binding mechanism with the host cells. Because in most of the VAF (virus/viral allantoic fluid) materials, virus particles are below the detection limit of UV, the concentration of the virus particles is quite helpful for further characterization.

In concentration of virus harvest, a size exclusion column, e.g., MidGee or QuixStand (Amersham) with hollow fiber filter under pressure can be used to remove impurities and/or unwanted buffers/fluids. The concentrated virus is, thus, also more easily suspended or stored in specific buffers/stabilizers. See below.

To illustrate the concentration of a virus harvest sample, an influenza harvest of A/New Caledonia was concentrated and analyzed from VAF by cross flow filtration. Of course, again, it is to be emphasized that the techniques, etc. of this section are not be limited to particular strains/types of viruses. Such concentration concentrated the virus particles, removed a majority of impurities and retained virus infectivity. As illustrated, the virus infectivity was checked by CELISA ($TCID_{50}$). Hemeagglutination by HA assay, neuraminidase activity, SEC analysis, NAF by RHPLC, and RNA by RTPCR were also done.

The virus concentration in the example below was achieved by using Amersham's Cross Flow Filtration Unit MidGee. MidGee is capable of concentrating 100 or 200 ml to 10 ml in 2–3 hours. Similarly, QuixStand can be used for concentrating the virus particles from 2 liters to 100 ml in 4 to 6 hours. Concentration of virus not only enhances the virus particle count, but also removes a majority of other impurities like egg proteins, RNA, and small molecules like uric acid.

The virus used in the following example was A/New Caledonia/20/99. NAF comprised cold adapted influenza virus. Chicken blood was from Colorado Serum Company (Denver, Colo.). The instrument used for concentration was from Amersham Biosciences (A/G Technology Corporation), and was a MidJet System with Peristaltic Pump (Watson Marlowe). The column used for concentration was from Amersham Biosciences (A/G Technology Corporation) and was a MidGee Hoop Cross Flow Filter with a nominal molecular weight cut-off of 750,000. Yet again, however, it is to be emphasized that use or recitation of particular models, producers, etc. of equipment are not to be construed as limiting upon the current invention. The buffer used for washing in this example was 1×-SPG.

For SEC, the instrument used was a Hewelt Packard HP 1100 HPLC system while the column was an Ultrahydrogel 1000 from Waters with a size of 7.8×300 mm. The buffer with the SEC was Dulbecco's Phosphate Buffered Saline from Hyclone Solvent. For the SEC, the method comprised an isocratic condition with a flow rate of 0.5 ml/min, monitored at 210 and 280 nm. For the RHPLC, the instrument was from Waters and the column was a YMC C4 (reverse phase), 2.1×250 mm, 5 um, 300 A. The method for the RHPLC was: Mobile Phase—A: 0.1% TFA in water, B: 95% CAN 0.09% TFA; Elution Conditions—Variable gradient, 13–100% B ; Flow Rate: 0.2 ml/min; Column Temp, −45 C; Injection Volume—50 ul; and Detection—214 nm.

As shown in FIG. 12, Step 1, 150 ml of A/New Caledonia/20/99 was concentrated by a MidJet instrument in a cold room. The pressure between the inlet and outlet was maintained between 5 to 10 PSI. After circulating through the cross filter for two hours, 150 ml of the 1× sample was reduced to 15 ml of 10× concentrated sample (Step 2). The permeate was collected separately and stored for further analysis. For analytical characterization, 4 ml of the 10× sample was removed (Step 3). The remaining 11 ml of the 10× sample was diluted to 110 ml with 1×-SPG, and was further concentrated down to 11 ml by removing the 1×-SPG as a permeate. The permeate carries most of the impurities from the retentate. This step was repeated five times with 1×-SPG as shown in Step 4 and Step 5. The washed permeate was saved for further analysis. The first and second wash showed yellow coloration. This is thought to be due to the removal of egg proteins and other small molecule impurities. The yellow color in the permeate disappeared after the 3rd and 4th wash. Following the 5th wash, the sample was diluted with 1×-SPG to 110 ml to bring the concentration back to 1×. At step 6, 10 ml of the 1×-W was reserved for the assay. The remaining 100 ml of the 1×-W was further concentrated down to 10×-W (Step 7). This concentrated sample was aliquoted into 1 ml quantities for further analysis.

All the samples were analyzed by SEC chromatography. The Ultrahydrogel 100 column was used for the analysis with DPBS as a solvent. Even though the data was collected at 220, 260 and 280 nm, for discussion purpose, the comparison was done with the 220 nm peak areas. The chromatogram peaks were classified into three major groups: one for virus (retention time around 10.6 min), one for impurities group-1(retention time 18 to 21 min), and one for impurities group-2 (retention time 21 to 27 min). Three NAF proteins Ovalbumin, Conalbumin and Ovomucoid elute around retention time 18–21 min. See FIG. 13. Lysozyme elutes around 27.0 min. It is thought that Group-2 impurities consist of small molecules such as uric acid and other uncharacterized materials. All the washes were checked by analytical SEC chromatogram under identical condition as the virus analysis. The CELISA, HA assay, NA assay, and RTPCR were carried out by different groups.

SEC Analysis and CELISA

The neat sample, 1× showed the virus peak at 11.1 minutes with a peak area 1,221. See FIG. 14. However, the concentrated 10× sample showed a peak area 11,192, see, FIG. 15, and the increment in the peak are was about 9.16 times compared to 1×. See Table 26, 11,192/1221. This is based on the previous experiments showing linearity between the peak area and the amount of virus sample injected. During the concentration, without any washes, some impurities have been removed but not significantly. See Table 26, FIG. 16*a*–*b*. The impurities group-1 and group-2 showed increment in the peak size between 1× and 10× (Table 26). Correspondingly the $TCID_{50}$ was increased from log 9.1 to log 10.0 (Table 27). During this step, 95.9% of the infectivity was retained. This data indicates that concentrating the 1× sample to 10× sample retained the infectivity quite well.

After the 5th wash with 1×-SPG, the virus peak area of the sample 1×-W, retained as 1005 compared to 1221 before the wash (Table 26). Recovery by peak area between 1× and 1×-W was about 82% (1005/1221). By comparing the 1× and 1×-W chromatogram (see FIG. 17), it shows that impurities group-1 and group-2 were significantly reduced (Table 26). The 1×-W showed a small decrease $TCID_{50}$ value (Table 27, 1×: 9.1, 1×-W: log 8.9). The recovery of infectivity was about 98.99% between 1× and 1×-W (log 8.9/log 9.1). The washing step improved the quality of the virus material by removing NAF proteins and other components.

Similarly, by comparing the 10× and 10×-W, the impurities group-1 and group-2 was removed to a great extent (Table 26, FIG. 18). By going through the 5 washes, the virus peak area of 10×: 11,192 was reduced to 10×-W: 10,282 (Table 26, 91.86% by peak area). The $TCID_{50}$ was changed from log 10.0 (10×) to log 9.9(10×-W) with the recovery of 99.56% (Table 27).

By comparing the 1×-W and 10×-W chromatogram, the peak area increased by 10 times. See Table 26, 1×-W: Peak Area: 1005 and 10×-W: 10,282. The $TCID_{50}$ value also increased one log (Table 27, 1×-W: log 8.9 and 10×-W: log 9.9). Since, the 10×-W was concentrated from 1×-W in one step, no loss in either activity or in the peak area was seen (10×-W: Peak area 10282 and 1×-W Peak Area 1005).

The permeate showed virus peak at 10.4 min with the peak area 25. This could be due to the loss of a very small amount of virus particles or some other proteins eluting along with the virus in 1× sample. Most of the impurities were eluting in group-1 and group-2. See Table 26. The CELISA values showed the infectivity was below the limitation of detection. This shows that there was not many virus particles eluting through the membrane during the concentration procedure.

Figure 19:
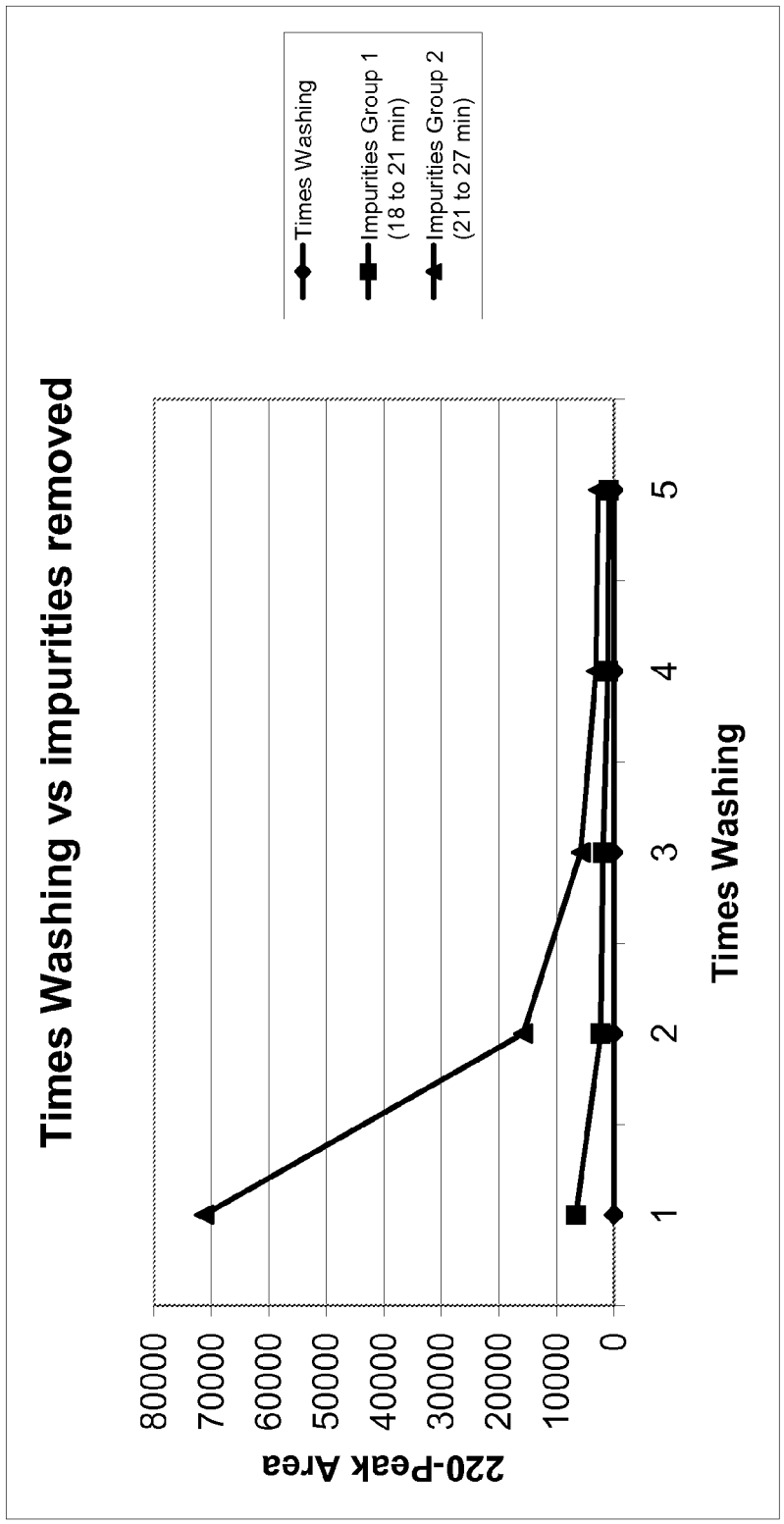
FIG. 19: Shows an analysis by SEC comparing times washed and impurities removed.
Figure 20:
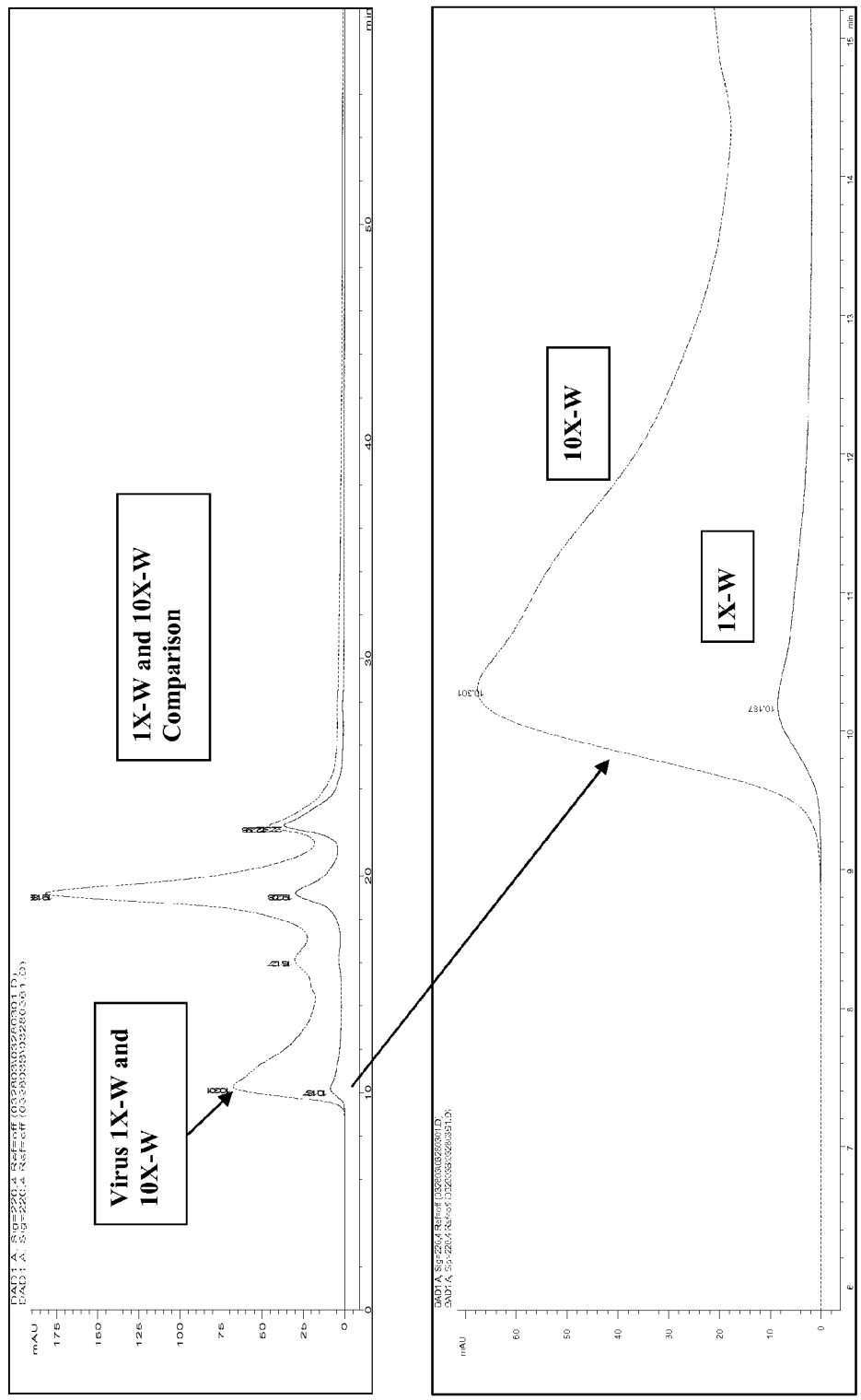
FIG. 20: Displays 1×W and 10×-W comparison of A/New Caledonia/20/99.

The five washes improved the quality of the virus by removing most of the impurities of group-1 and group-2. This is illustrated in the Table 26 and FIG. 19. Group-1 and group-2 impurities were significantly removed after the 2nd wash. After the 5th wash the curves reached a plateau. Even after the 5th wash, the samples 1×-W and 10×-W showed impurities group-i and group-2 in a very low amount. See FIG. 20. The identity of the peak at 19.208 min was confirmed as ovalbumin by isolating from the 10×-W sample. SDS-PAGE also confirmed the result.

HA Assay

Figure 12:
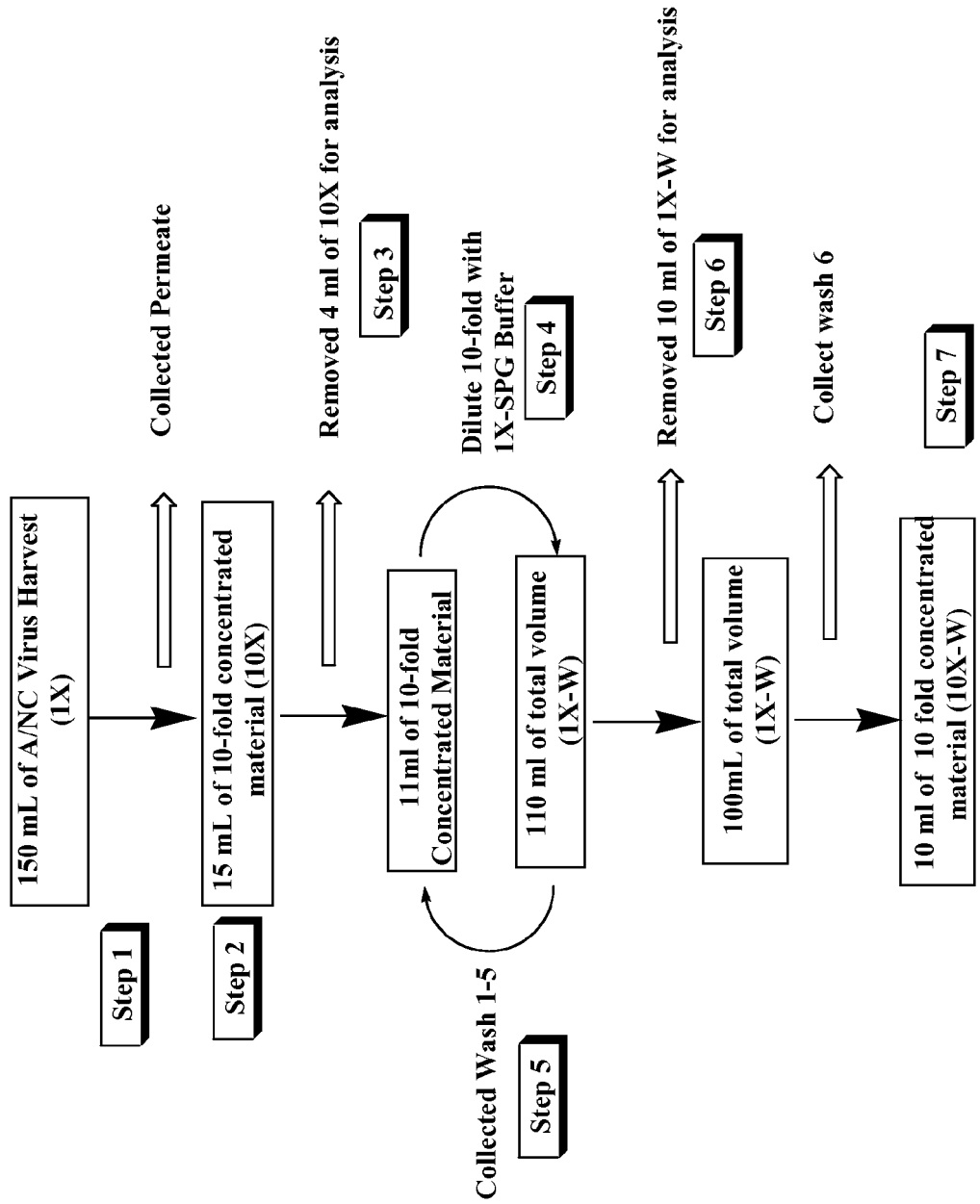
FIG. 12: Illustrates a schematic flowchart of virus harvest concentration.
Figure 13:
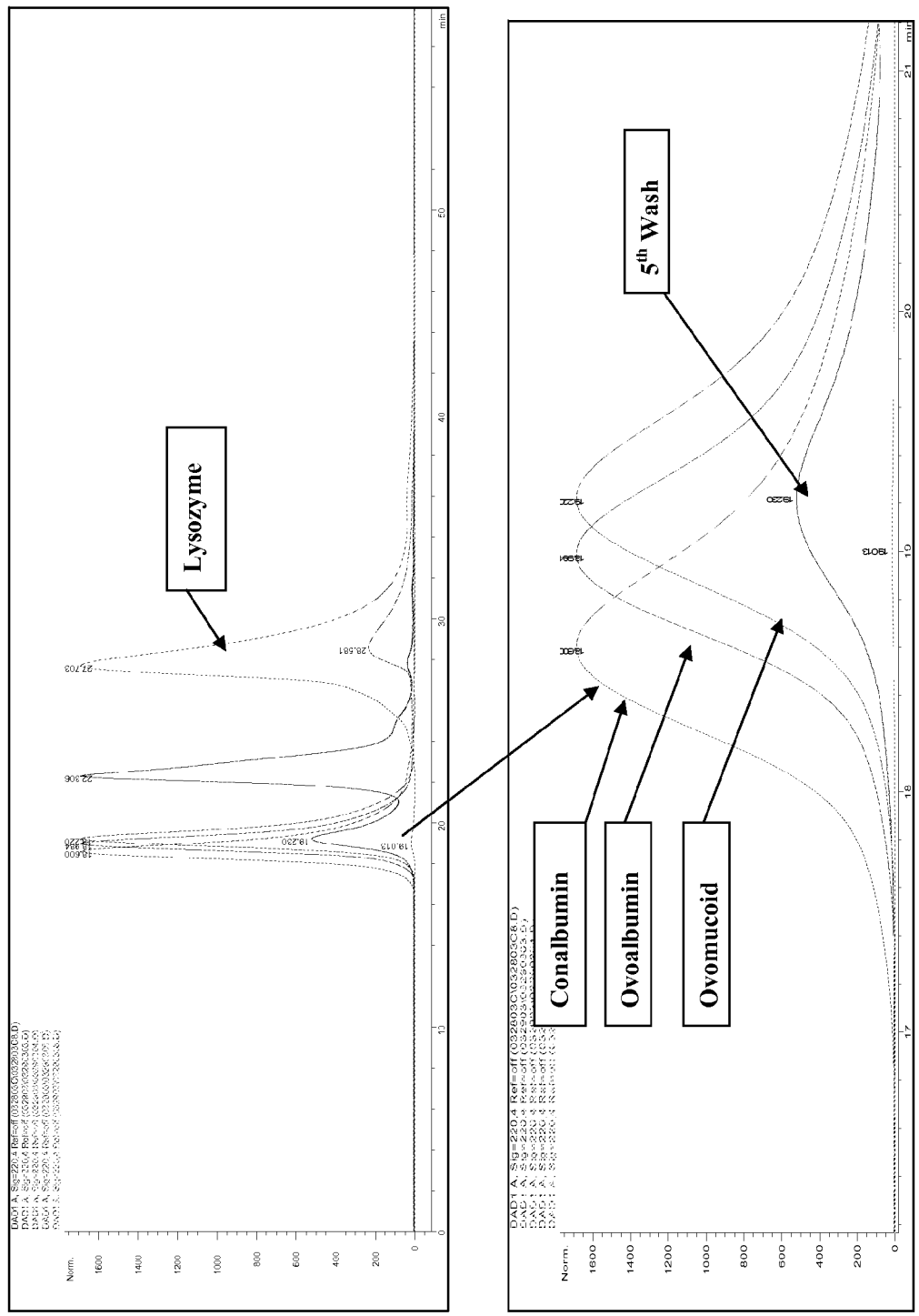
FIG. 13: Displays comparison of the $5^{th}$ wash with NAF proteins.
Figure 14:
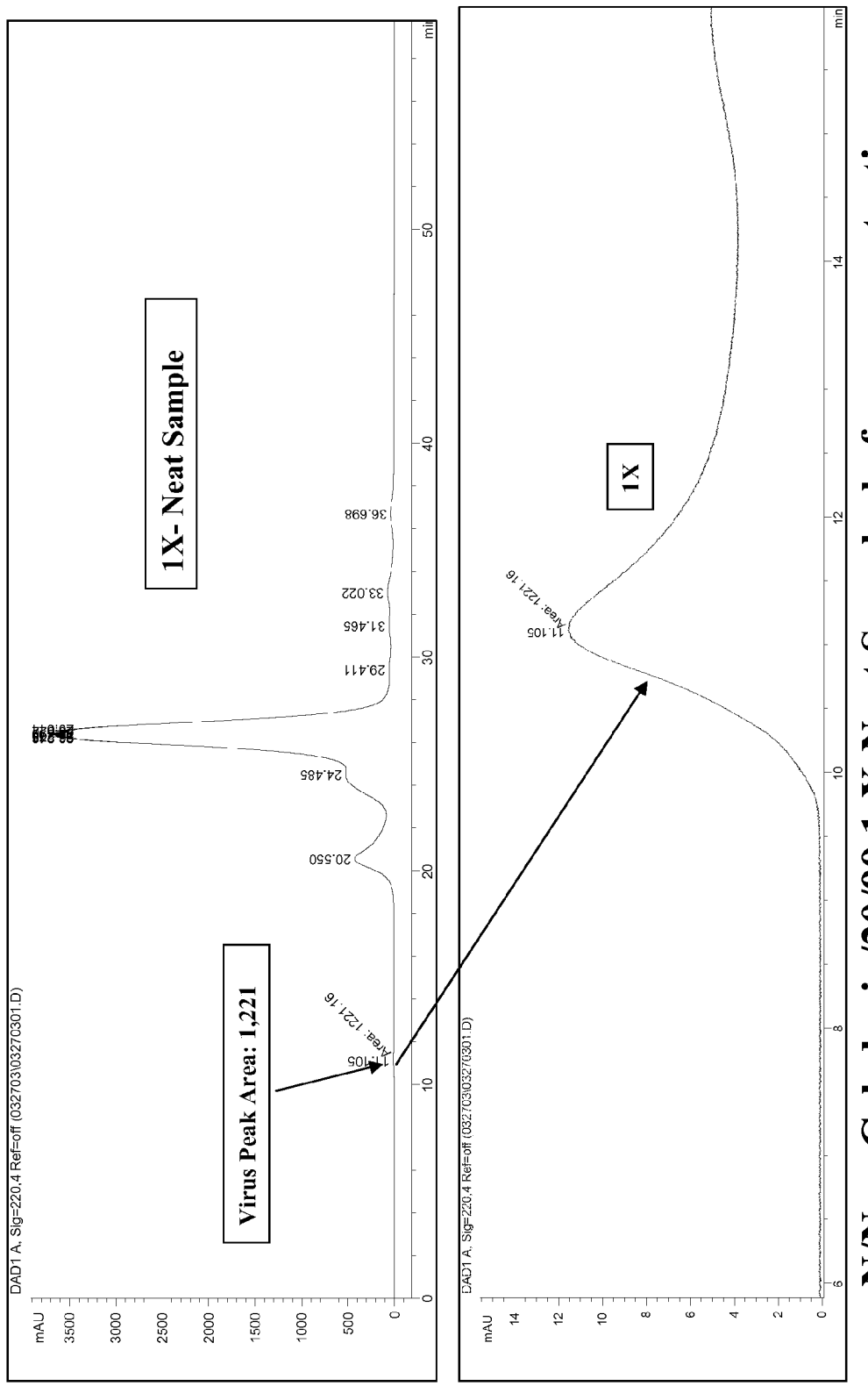
FIG. 14: Displays an assay of an N/New Caledonia/20/99 1-×-Neat sample before concentration.
Figure 15:
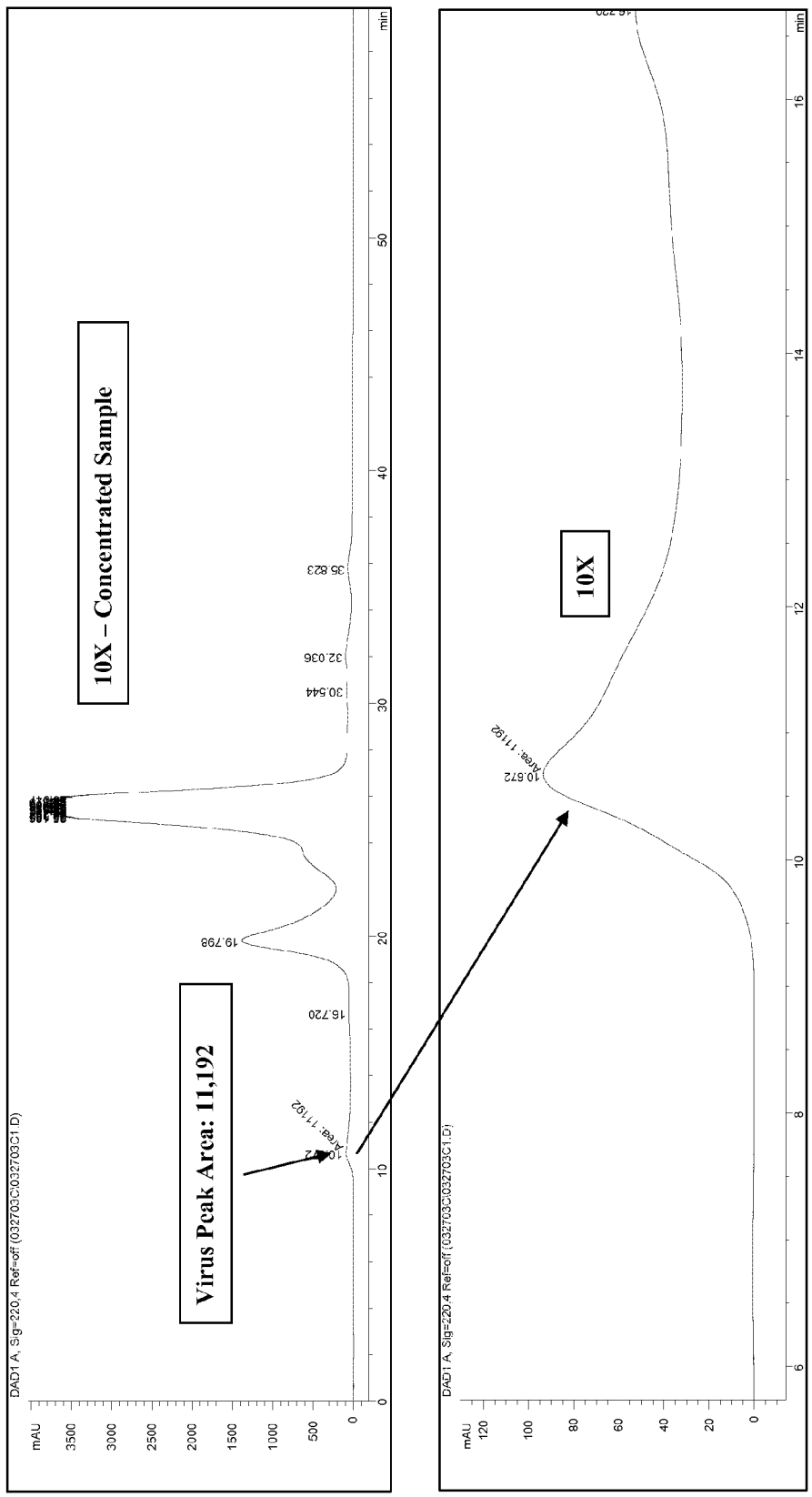
FIG. 15: Displays an assay of an A/New Caledonia/20/99 10× concentrated sample.
Figure 16A:
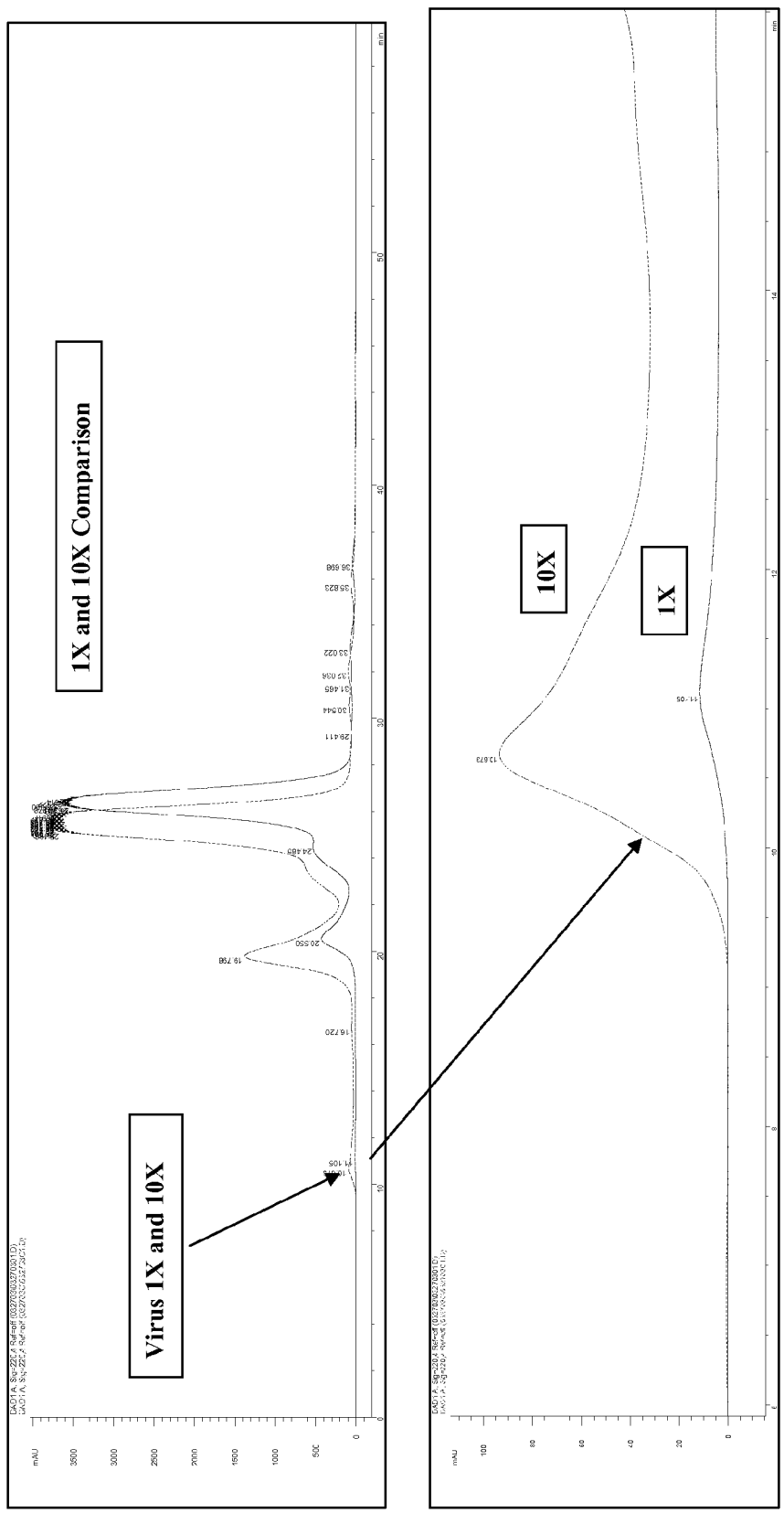
FIG. 16, Panels A–B: Display a comparison of 1× and 10× of A/New Caledonia/20/99; and 1×-W sample after 5 washes.
Figure 16B:
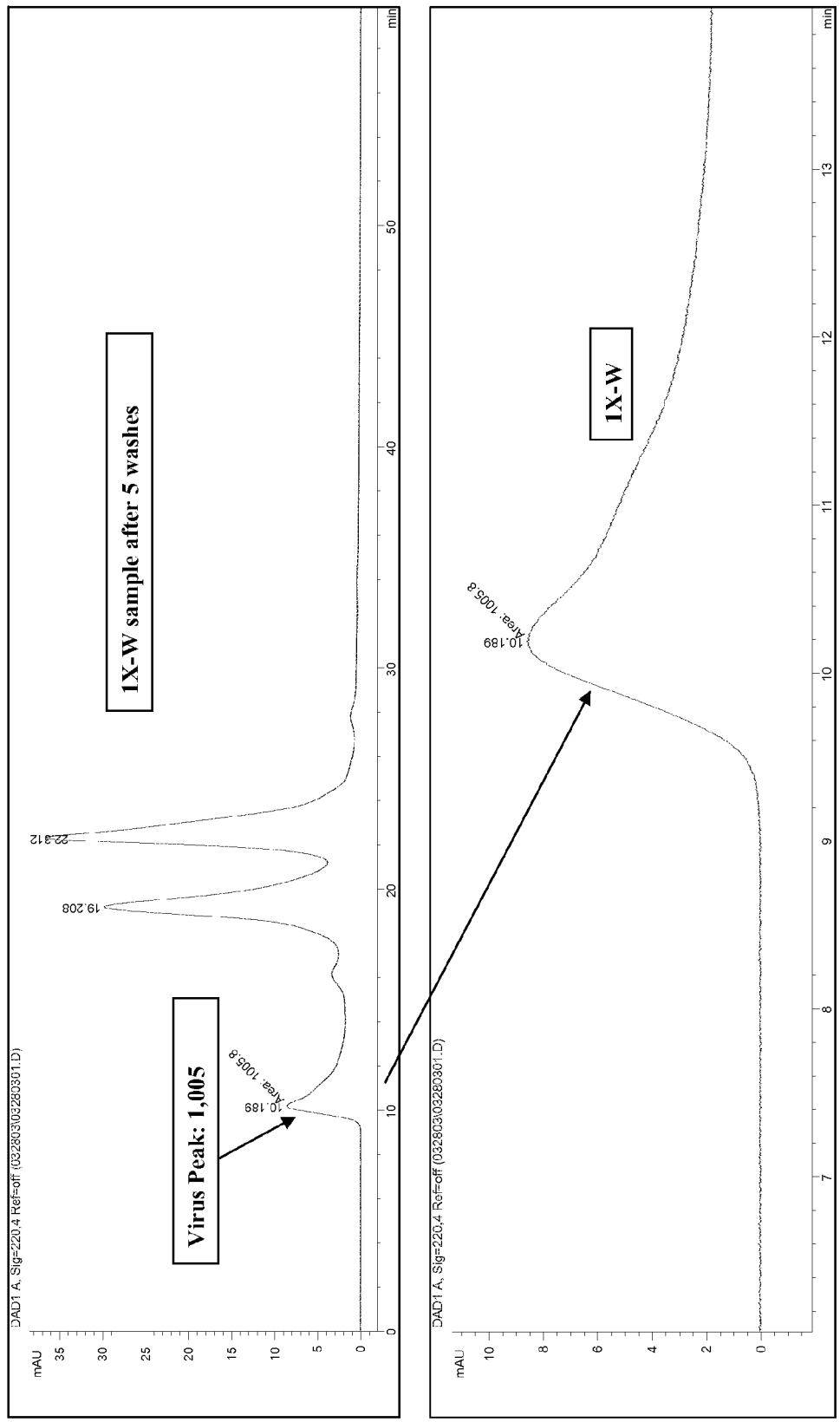
Figure 17:
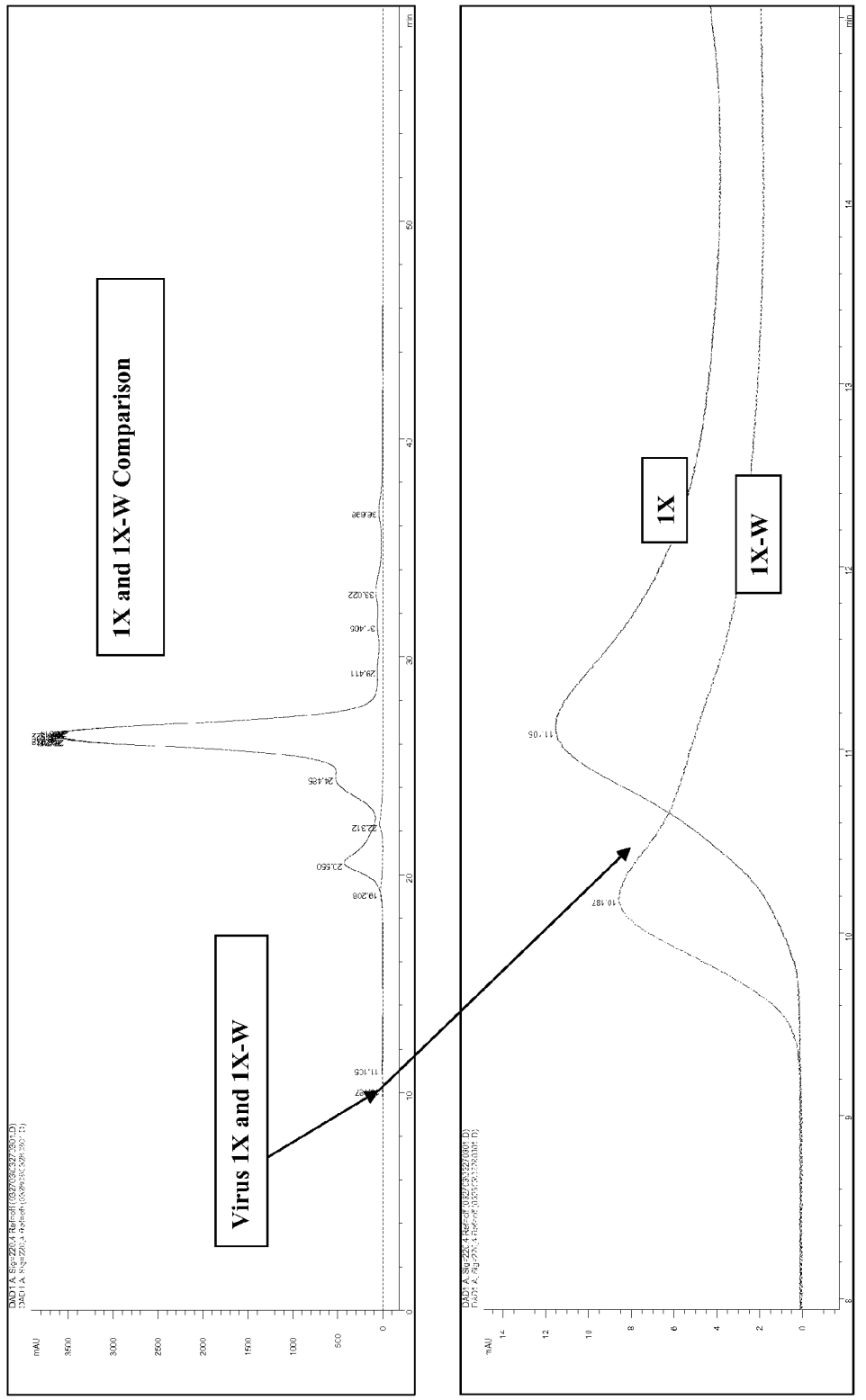
FIG. 17: Displays a comparison of A/New Caledonia/20/99 1× and 1×-W samples.
Figure 21:
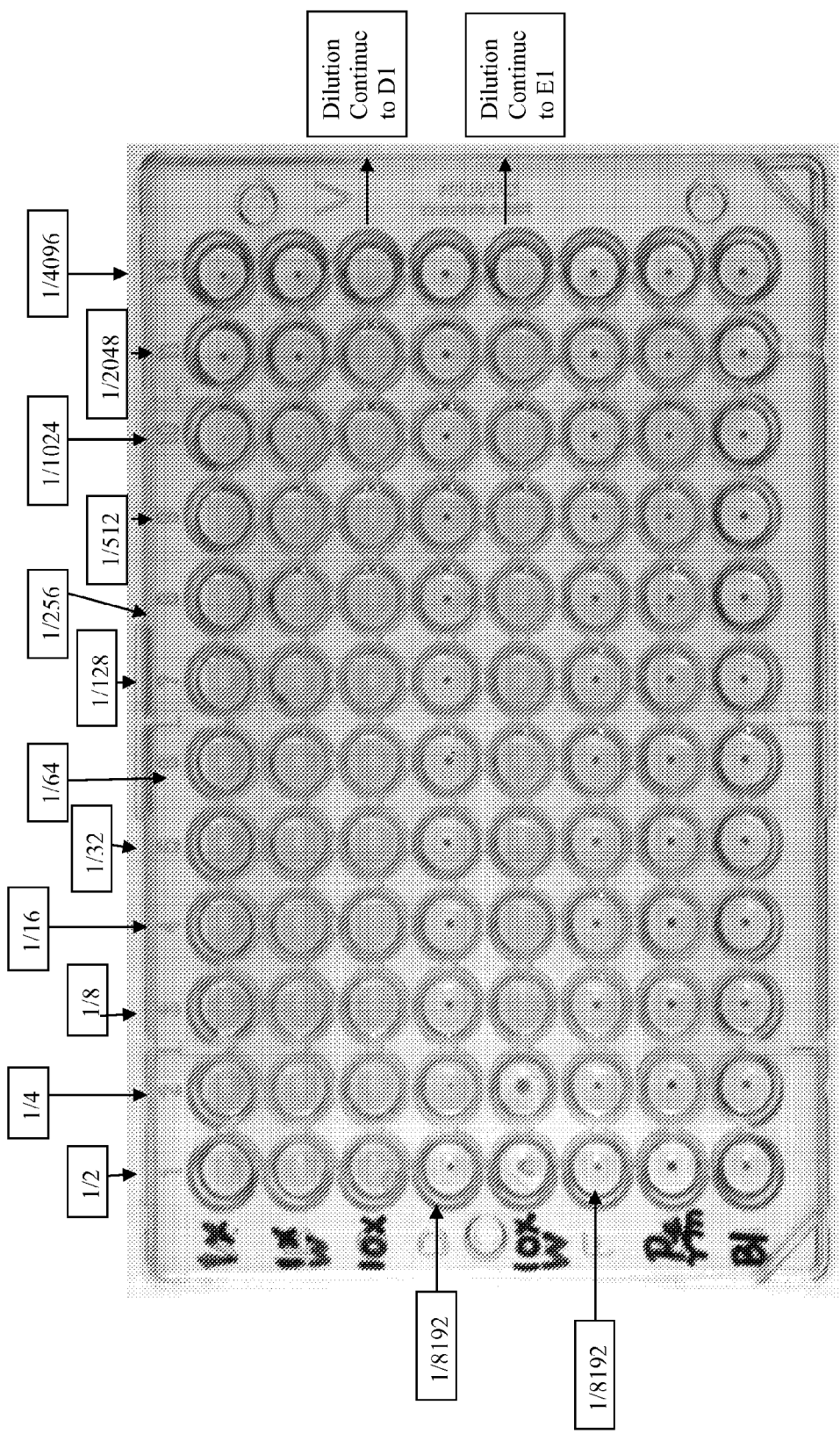
FIG. 21: Shows a 96-well plate assay of A/New Caledonia/20/99.

The sample 1× and 1×-W showed HAU 1024. See FIG. 21. The concentrated, but not washed, 10× showed at HAU 8192. However, 10×-W showed a false negative at HAU 2 and 4. This may be due to the large amount of virus compared to the chicken RBC. High amounts of neuraminidase reverse the hemeagglutination process. See, Virus cultivation, Detection, and Genetics, S. J. Flint, L. W. Enquist, R. M. Krug, V. R. Racaniello and A. M. Skalka, "Principles of Virology," ASM Press, Washington, p 34, (2000). The absence of HAU in the permeate shows that there was not much virus eluting in the step 1. See FIG. 12.

NA Assay

Figure 22:
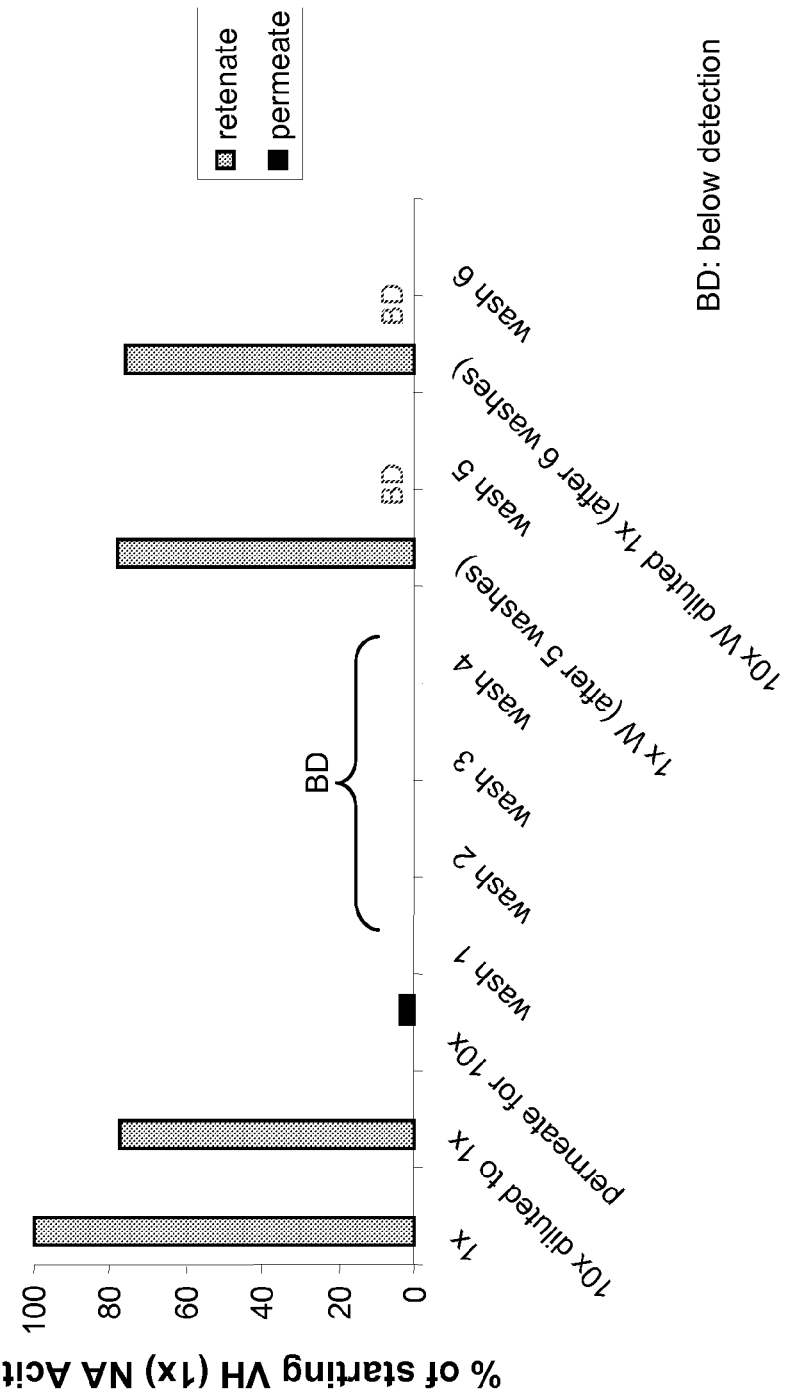
FIG. 22: Shows a graph neuraminidase activity/virus purification in retentate and permeate.

The neuraminidase assay illustrated that 10× diluted back to 1× shows some decrease in activity in comparison with 1×. See FIG. 22. This was thought to be due to the loss of free NA protein from the VAF material. This was supported by a small amount of NA in the permeate. Samples 1×-W and 10×-W diluted back to 1×-W retained the activity at the same level. This was because the sample 10×-W was concentrated directly from 1×-W. All the washes have the activity below the detection level.

RHPLC

Figure 23:
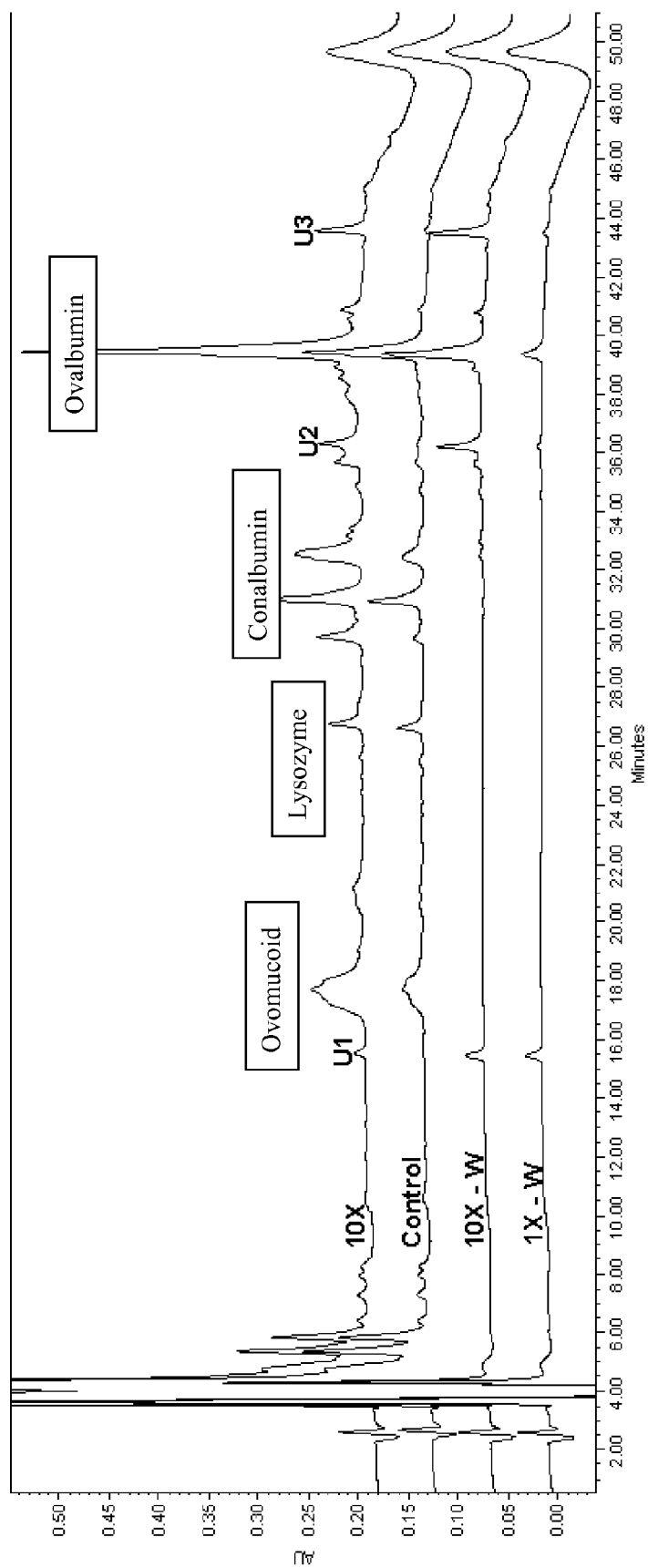
FIG. 23: Displays RHPLC of Control, 10×, 10×-W, and 1×-W.
Figure 24:
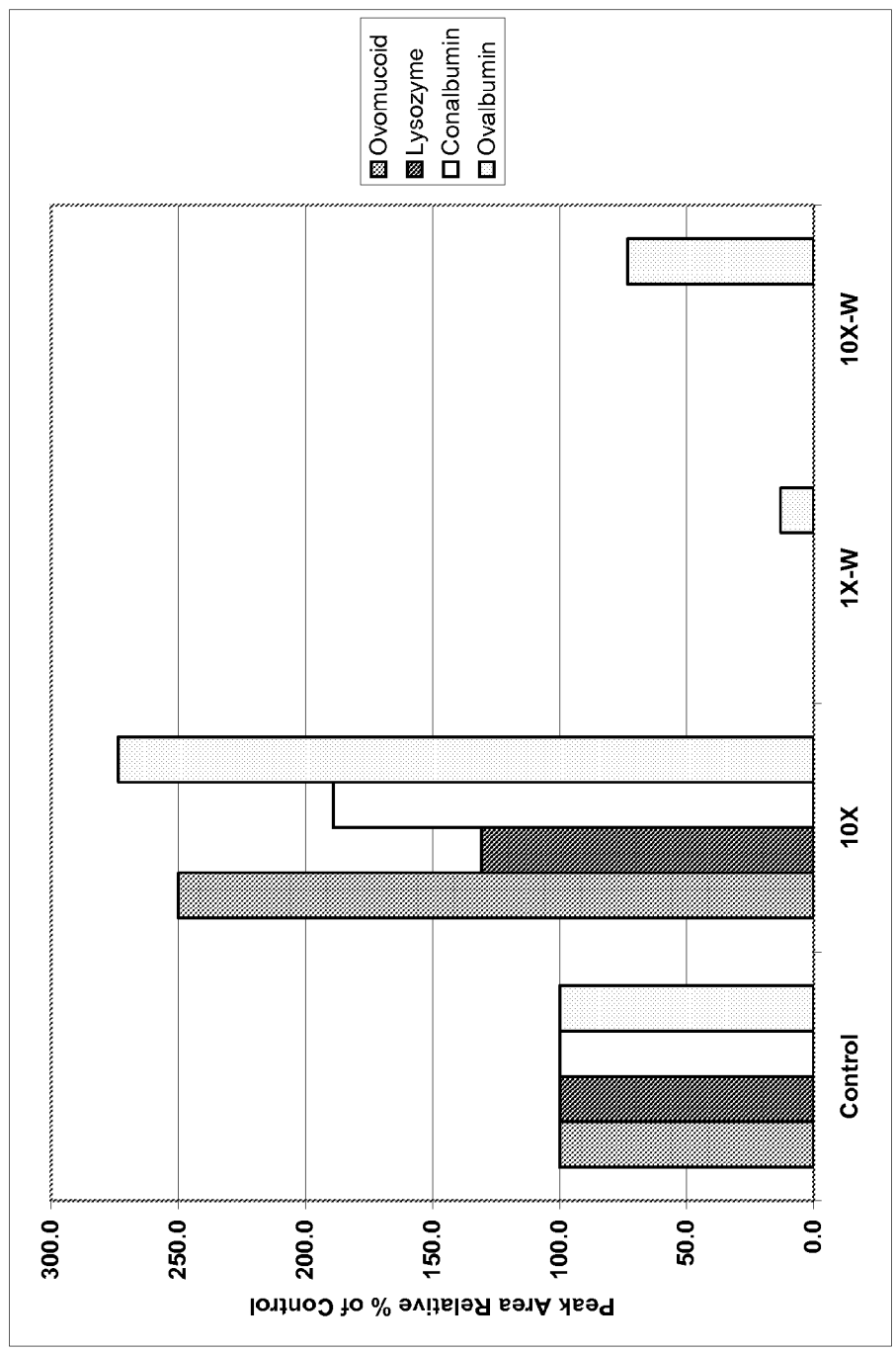
FIG. 24: Shows a graph of Control, 10×, 1×-W and 10×-w samples.

Egg protein analysis had been optimized previously by RHPLC, therefore, all the present materials in the example were analyzed under identical condition, e.g., C4 column with 0.1% TFA/Acetonitrile gradient and monitored by 214 nm. The elution pattern of the ovomucoid, lysozyme, conalbumin and ovalbumin is shown in FIG. 23. The 10-× sample, before any wash, showed all the egg proteins. This matches the retention time of the control sample. Also 10× showed unidentified viral protein peaks labeled as U1, U2 and U3. Completely washed samples 10×-W and 1×-W retained the viral proteins U1, U2 and U3. The 10× and 10×-W samples contained the same amount of U1, U2 and U3 proteins. Because the ratio of these proteins was the same, the proteins might be generated from the virus particles during the exposure to acetonitrile. However, the ovomucoid, lysozyme and conalbumin have been completely removed from 10× by washing with 1×-SPG for five times. Notably, in contrast, the most obvious protein peak is ovalbumin, which is still eluting along with 10×-W and 1×-W samples. Even though 10×-W and 1×-W have gone 6 and 5 washes, still ovalbumin bound to the virus. This may be due to the strong interaction between HA proteins and ovalbumin. This data also presented in the bar graph form as in FIG. 24.

Figure 25:
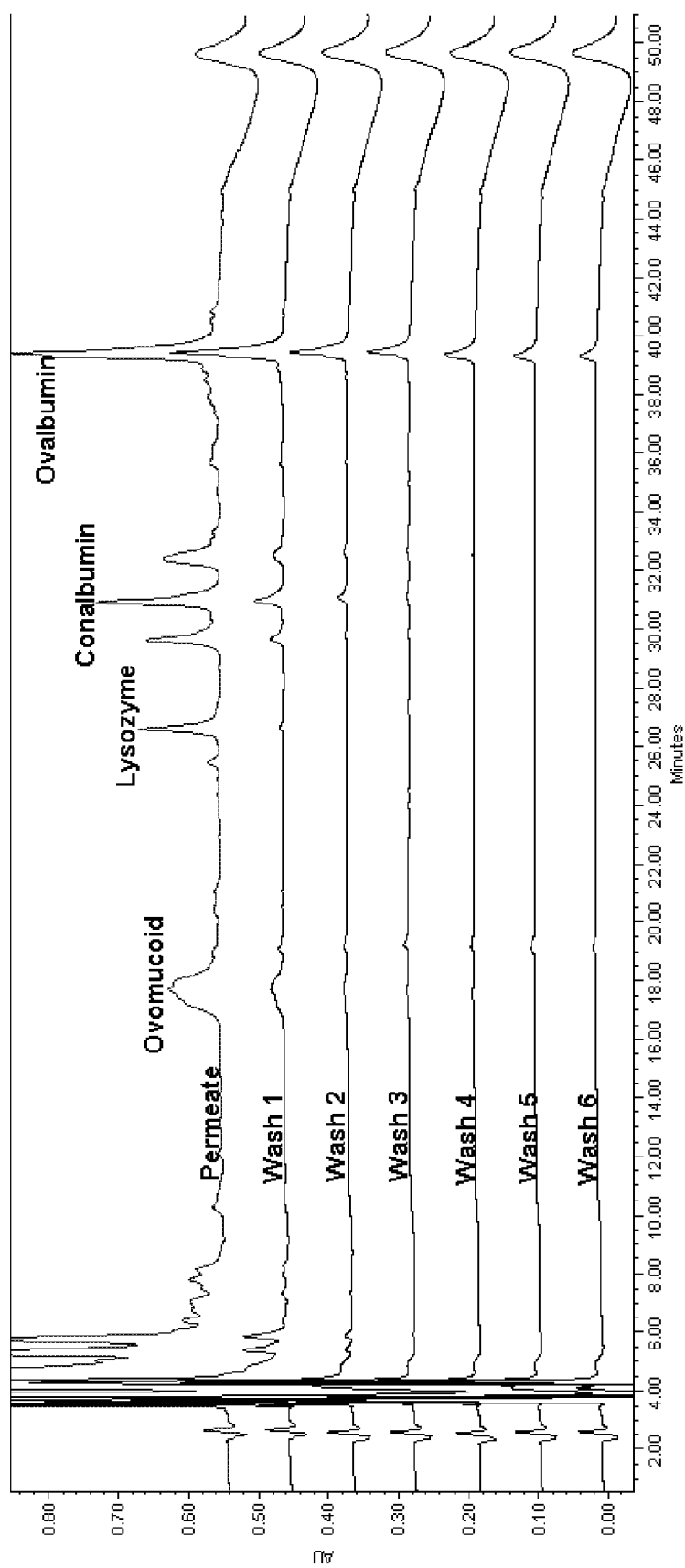
FIG. 25: Displays RHPLC of permeate and washes 1 to 6.
Figure 26:
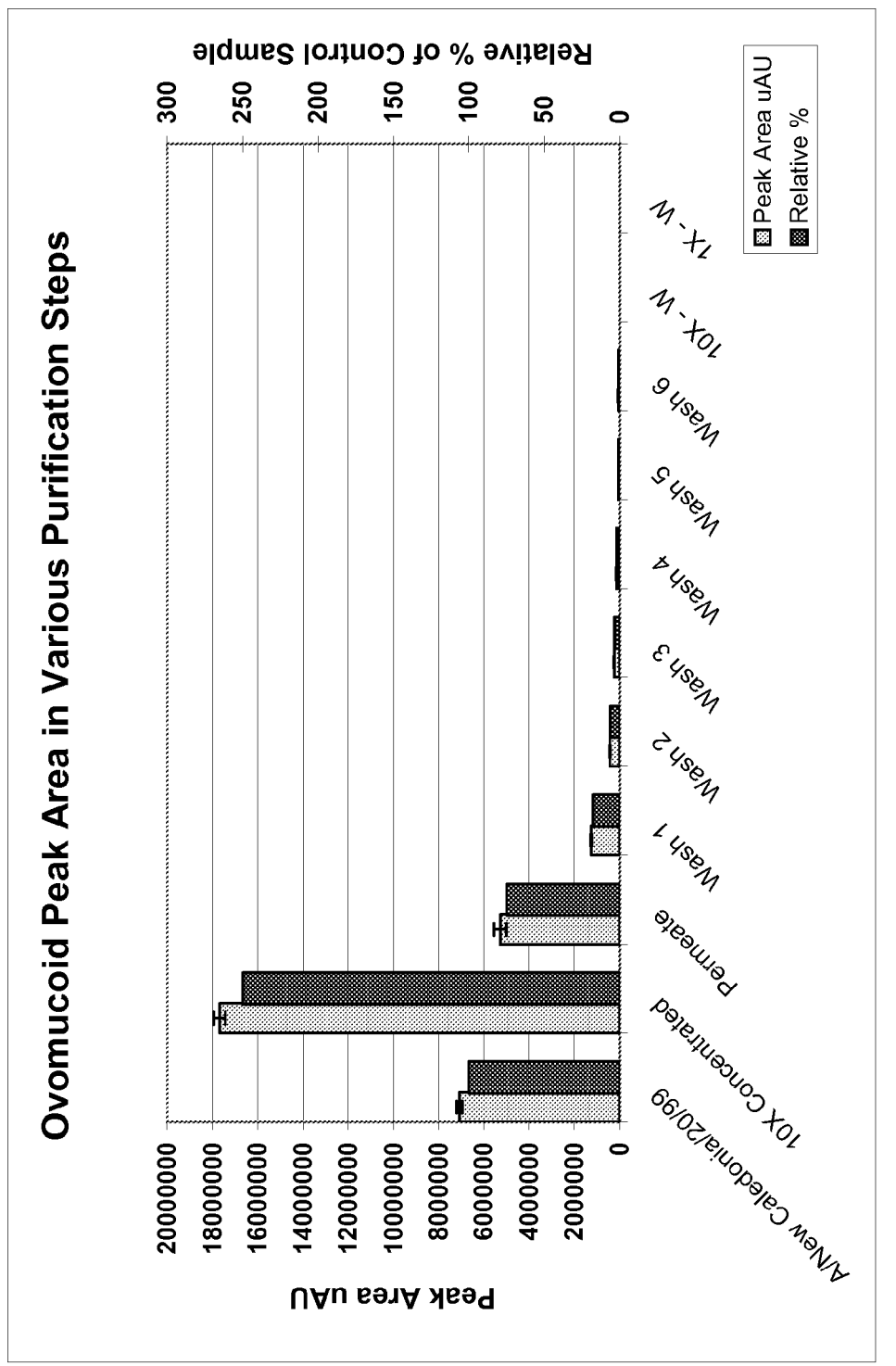
FIG. 26: Shows a graph of RHPLC ovomucoid removal (peak area).
Figure 27:
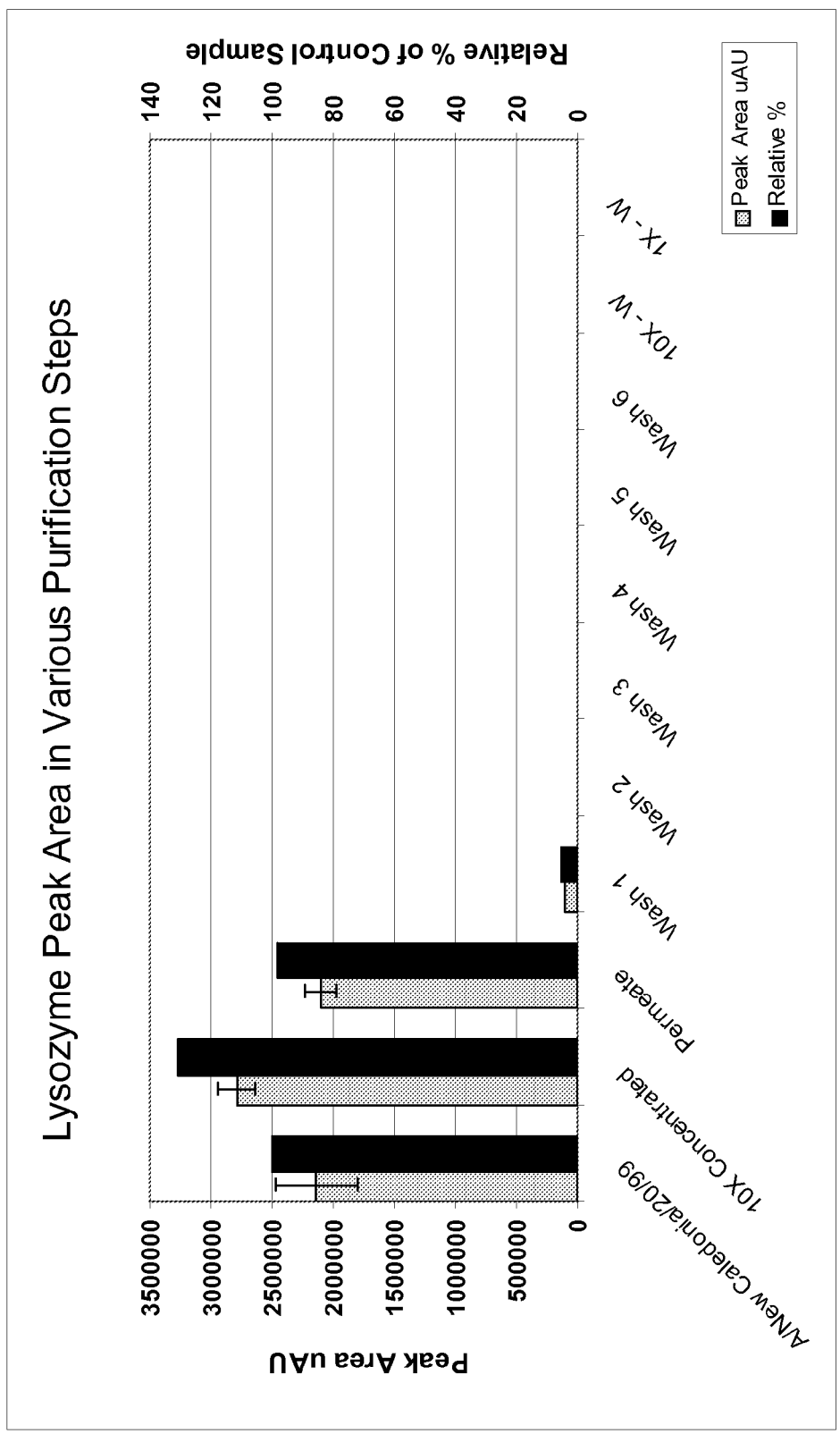
FIG. 27: Shows a graph of RHPLC of lysozyme removal (peak area).
Figure 28:
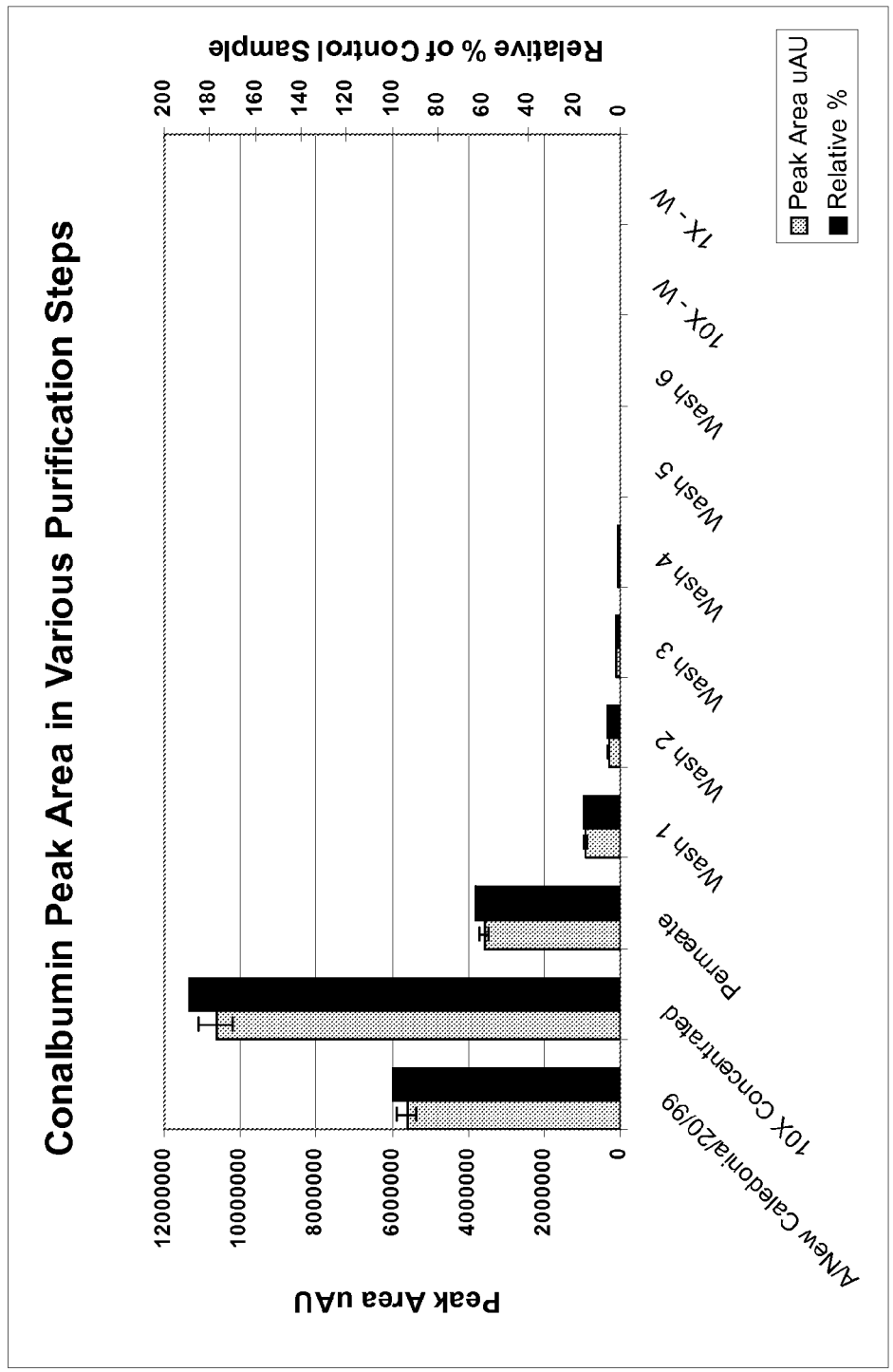
FIG. 28: Shows a graph of RHPLC of conalbumin removal (peak area).
Figure 29:
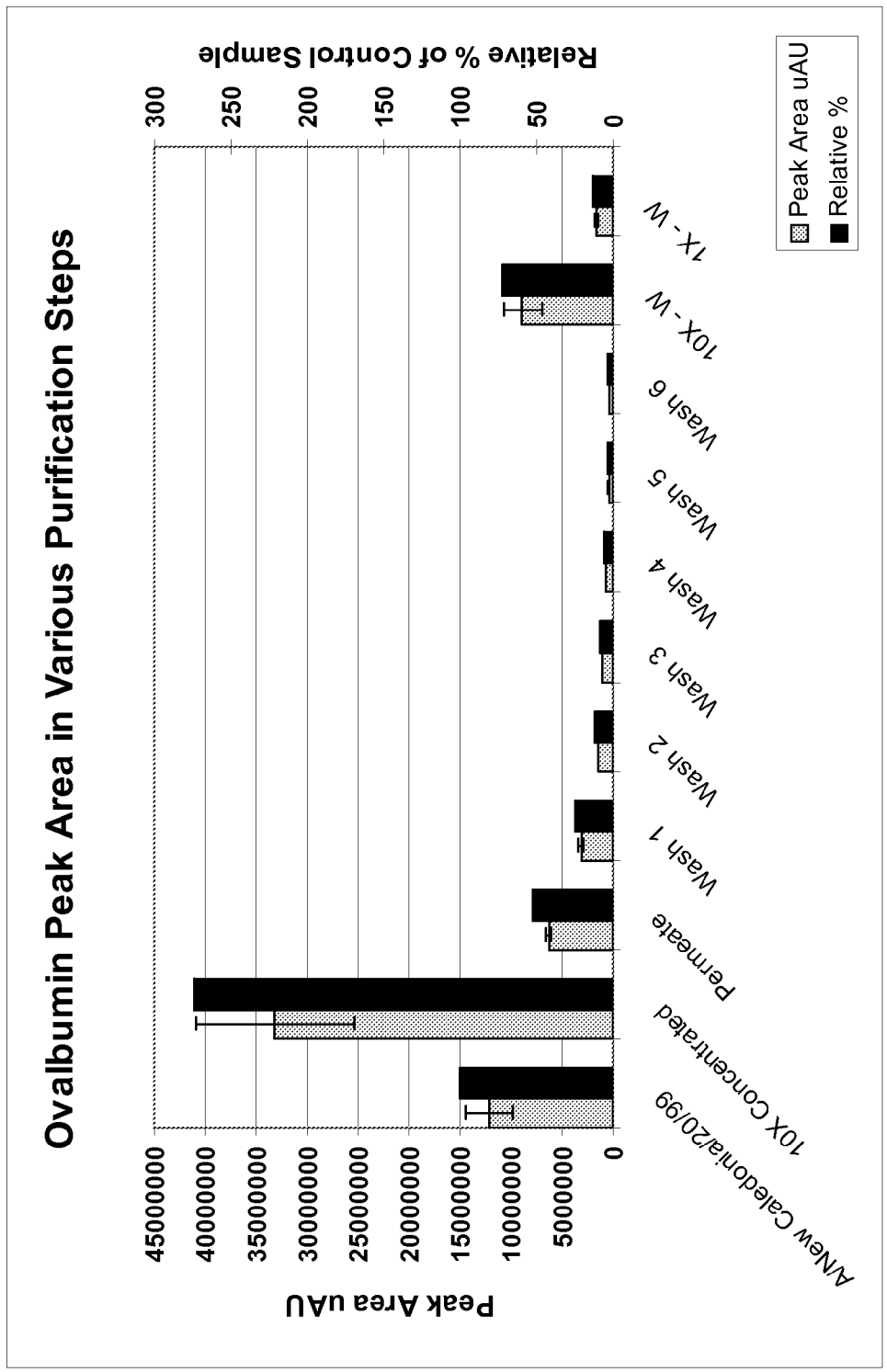
FIG. 29: Shows a graph of RHPLC of ovalbumin removal (by peak area).

The permeate and all the washes were checked by RHPLC. See FIG. 25. The permeate contains all the NAF proteins and other unidentified peaks. Ovomucoid was removed by two washes (see FIG. 26); lysozyme by 2 washes (see FIG. 27); conalbumin by two washes (see FIG. 28); and ovalbumin was depleted gradually, but about 5% remained even after wash number. 6. See FIG. 29.

Agilent Bioanalyzer

Figure 30:
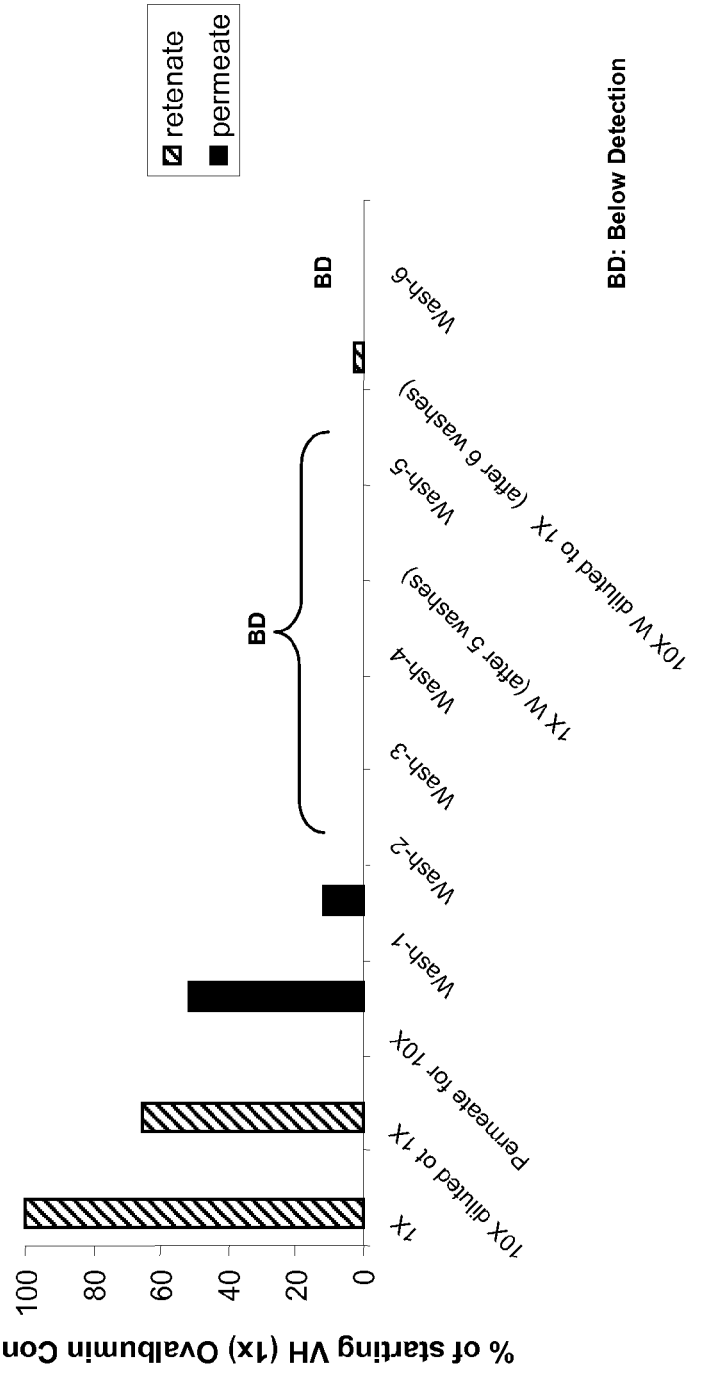
FIG. 30: Shows a graph of ovalbumin analysis by Agilent 2100.

Simultaneously, ovalbumin was estimated by Agilent Bioanalyzer as shown in FIG. 30. Just by the concentration, without any washing step, ovalbumin was considerably removed from 1× to 10×. The first permeate carried most of the ovalbumin. RHPLC showed ovalbumin in all the washes, but in the Bioanalyzer analysis it reached below the detection limit. The 10×-W sample was diluted ten times to reach the concentration close to 1×-W sample, and it showed a small amount of ovalbumin. Based on this data, 95% of the egg proteins were removed by the concentration and washing steps.

SDS-PAGE and Western Blot

Figure 31:
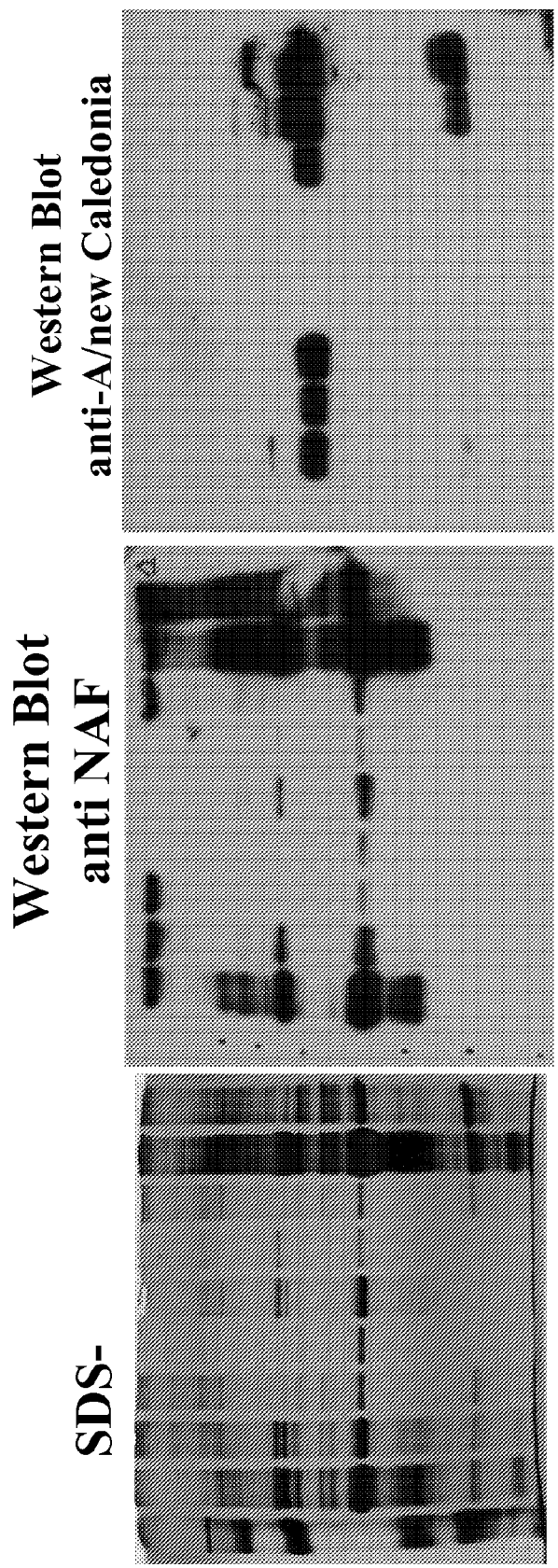
FIG. 31: Is a Western blot SDS-PAGE gel of anti-A/New Caledonia.
Figure 32:
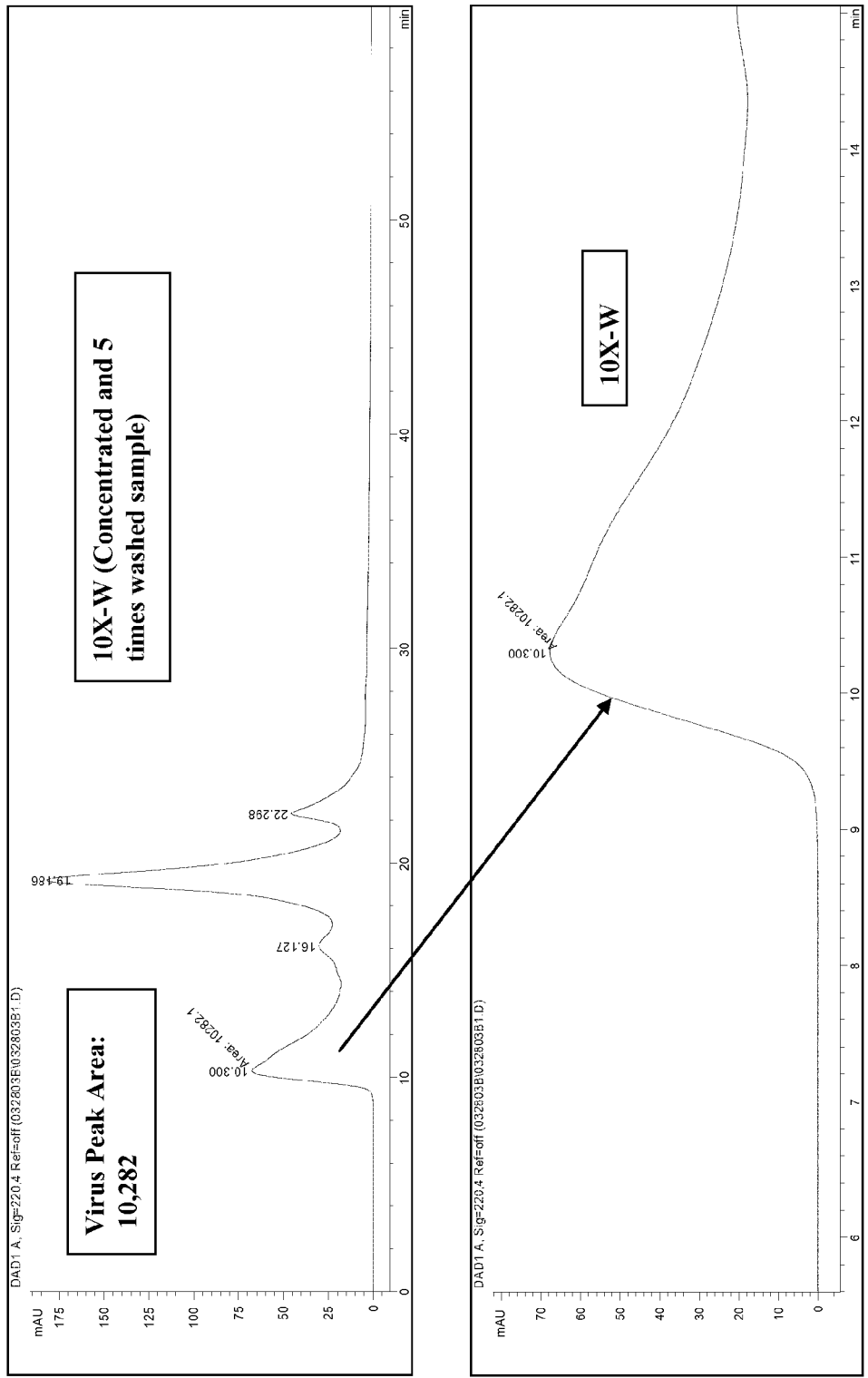
FIG. 32: Displays assays of 10×-W, sample after 5 washes of A/New Caledonia/20/99.

In comparison to 1× (lane 2), 10× (lane 9) contains more intense multiple silver stain bands. See FIG. 31. 10×-W (lane 10) showed fewer number of bands compared to 10×. This was due to the removal of NAF proteins and other impurities. Similarly 1×-W (lane 8) appears cleaner than 1×. Samples 1×, 10× diluted to 1× (3rd Lane), and 10×W diluted to 1×-W (4th lane) contain the same quantity of virus except different degrees of improvement in the removal of impurities. Obviously, 10×-W diluted to 1×-W shows clearer viral protein bands. However, this sample still contained an ovalbumin band. This is compared with NAF proteins in lane 6. The 10×-W sample was further purified by analytical SEC column and the fractions were collected. See FIG. 32. The fraction collected at 19.1 min was checked by SDS-PAGE, and this fraction contains mostly ovalbumin protein (lane 5). This lit up in the Western Blot against anti-NAF. This is additional evidence to show that ovalbumin strongly binds to the virus even after 6 washes. The anti-NAF gel was stripped and probed with chicken anti-A/New Caledonia. Distinct bands were observed representing the viral proteins, $HA_0$ and $HA_2$ or M protein. See FIG. 31.

RTPCR

Figure 33:
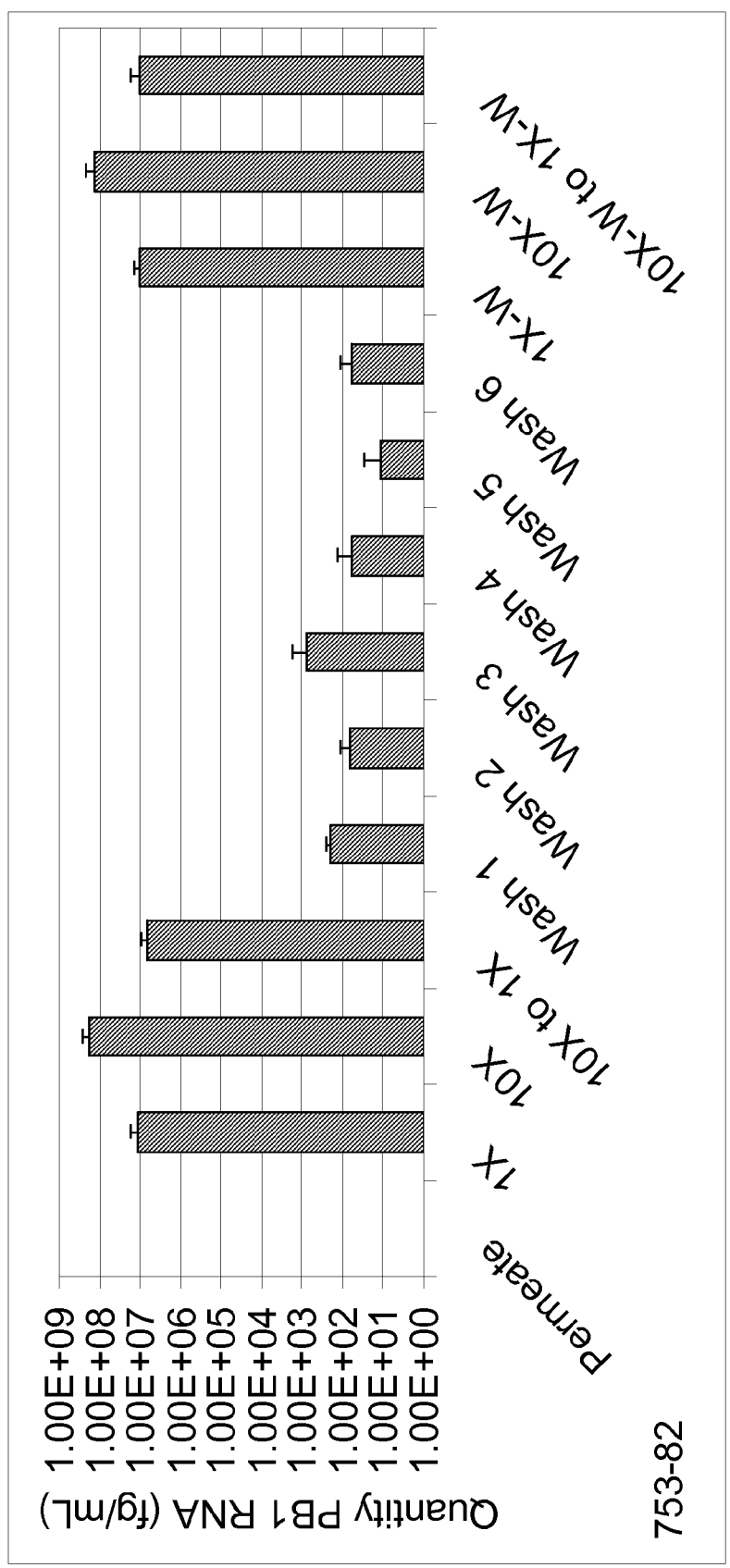
FIG. 33: Shows a graph of RNA analysis by RTPCR.
Figure 34:
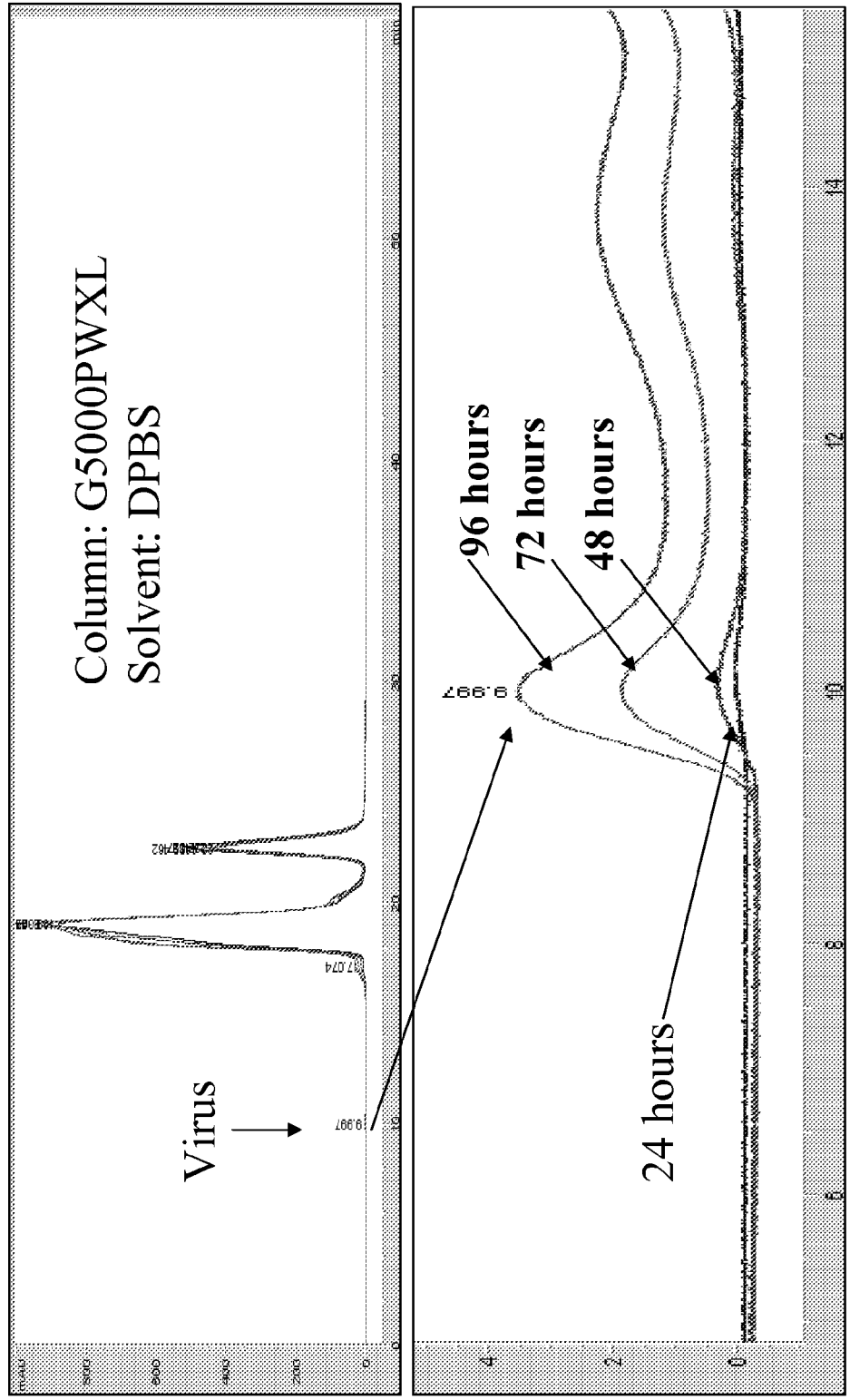
FIG. 34: Shows monitoring of A/Beijing—cell culture propagation by SEC.
Figure 36:
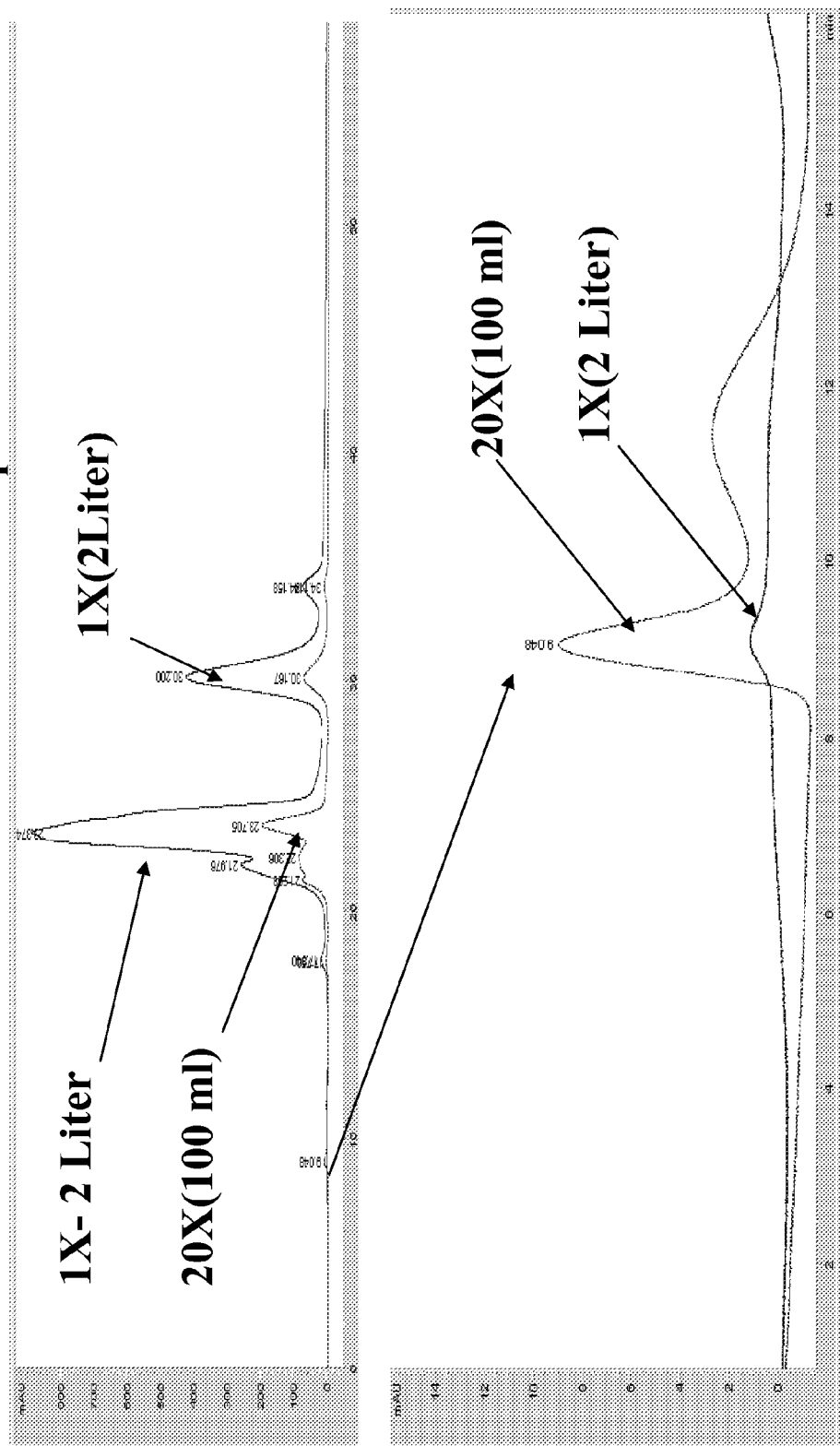
FIG. 36: Shows concentration of 2 liters of A/Panama cell culture.
Figure 37:
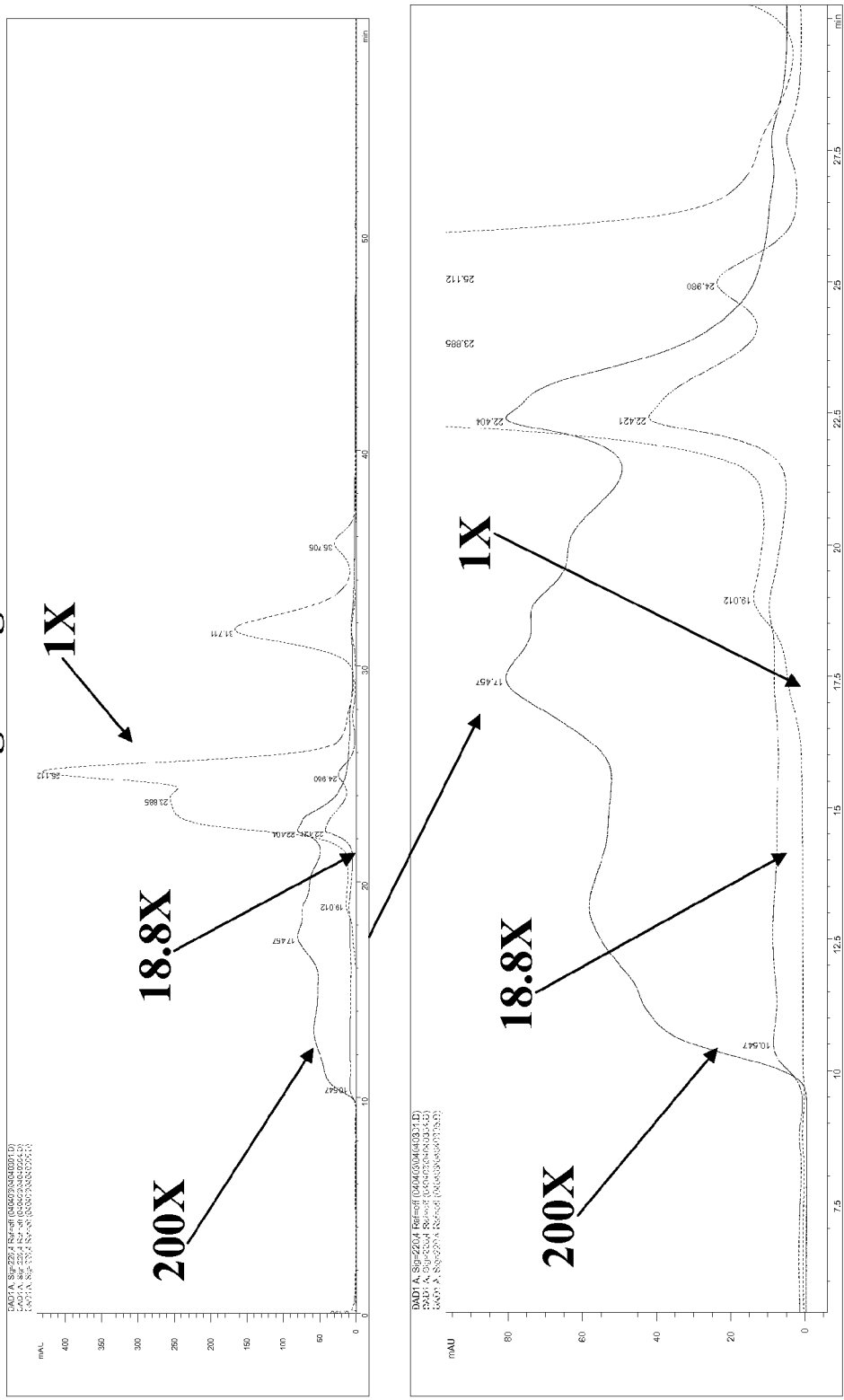
FIG. 37: Shows concentration of 2 liters of B/Hong Kong cell culture down to 10 ml.

RTPCR showed that the RNA was about a log higher between 1× and 10×. See FIG. 33. Similarly, there was about a ten-fold increase in the viral RNA between 1×-W and 10×-W. This indicated that most of the virus was retained during the concentrations step. Permeate does not have any detectable viral RNA, but the 1×-SPG washes showed a very small amount of RNA. This may be due to small amount of virus undergoing shearing during the circulation or some viral RNA bound to the filtrate and released latter slowly during the washing cycles.

In summary, the concentration of the A/New Caledonia/20/99 was achieved by using a cross-flow-filtration device. The infectivity of the virus particles was retained during this procedure, and it was confirmed by CELISA assay. Washing the concentrated material by 1×-SPG improved the quality of the virus by removing other impurities. Even after the 5th wash a small amount of ovalbumin was strongly bound to the virus. This may be due to the strong interaction between ovalbumin and the HA or NA protein. RHPLC and SDS-PAGE and Western Blot support this protein-protein view. The increase in the quantity of RNA between the neat and concentrated sample indicates that the majority of the virus is recovered by this procedure.

Similar techniques are also applicable for use with virus samples from cell culture, e.g., influenza samples grown in cells such as Vero cells, etc. To illustrate such, three viruses were grown in Vero cell culture, namely, A/Beijing (A/H1N1) used as is; A/Panama (A/H3N2) concentrated from 2L to 100 ml or 20×; and B/Hong Kong concentrated from 2 L to 10 ml or 200×. It will be appreciated that since virus yields from Vero cells are typically lower, the embodiments of the current section can optionally be used to concentrate the virus samples. Similar to the above illustration an Amersham MidGee and a QuixStand Instrument were used for the virus concentration FIGS. 34–35 show monitoring of A/Beijing cell culture propagation by SEC (FIG. 34) and A/Beijing Vero cell culture harvest (FIG. 35). As can be seen SEC is an efficient technique for monitoring the virus propagation in a short time. The amount required for such monitoring is also typically small (e.g., 100 ul). FIG. 36 illustrates concentration of a 2 liter sample of an A/Panama cell culture sample. Two liters of virus harvest were concentrated down to 100 ml by QuixStand. See above. The $TCID_{50}$ of the 1× mixture was non detectable, but the $TCID_{50}$ of the 20× mixture was 4.4. There was a peak area ratio of 20× to 1×. The concentration of the Panama cell culture sample illustrates the advantages of cross-flow filtration, e.g., virus particles can be efficiently enhanced, low molecular weight impurities can be removed from the solution and diafiltration can be done for further "clean-up" of the solution. FIG. 37 shows concentration of 2 liters down to 10 ml of a Vero cell grown culture of B/Hong Kong. At 1× the log10 $TCID_50$/ml was 4.7, while at 18.8× it was 5.8 (the theoretical for such being 5.95) and at 200× it was 6.95 (the theoretical of which being 7.00).

From the above figures it can be seen that SEC is a useful technique for monitoring virus growth in cell culture samples; very low titer virus can be assayed after concentration of virus samples; and low titer virus can be assayed after concentration.

Stabilizers/Buffers

The invention comprises compositions of virus solution and methods of creating the same. Such compositions optionally comprise various dilutions of NAF (typically unfractionated NAF) comprising the virus of interest and combinations of, e.g., sucrose, arginine, gelatin, EDTA, etc. as detailed herein. As will be noted, various compositions herein comprise from 10% to 60% NAF. NAF can possibly contain various enzymes such as nucleases lysozymes, etc. which could adversely affect the stability of virus compositions. Such methods and compositions are preferably stable (i.e., do not show unacceptable losses in potency) over selected time periods (typically at least 6 months, at least 9 months, at least 12 months, at least 15 months, at least 18 months, at least 24 months, etc.) at desired temperatures (e.g., typically 4° C., 5° C., 8° C., from about 2° C. to about 8° C. or greater than 2° C., etc.). Preferred embodiments show no decrease in potency over the desired storage period. Other embodiments show less than 10% decrease, less than 5%, less than 4%, less than 3%, less than 2%, or less than 1% decrease. The potency of virus compositions herein was measured in FFU or fluorescent focus units (see below in description of FFA assay). A target FFU value is typically set based upon the virus concentration at a time zero (e.g., due to dilution of the NAF, etc.). Preferred embodiments, thus, show little or no decrease from the starting value. In various compositions herein, the virus solutions comprise from about 5% to about 10% sucrose, from about 1% to about 4% arginine, and from about 1% to about 4% gelatin. Some preferred embodiments comprise about 7–10% sucrose, about 2% arginine, and about 2% gelatin. In some embodiments, the stability is measured after storage of the virus formulation at the desired temperature in a FluMist® applicator/accuspray device or other similar device.

In some embodiments, the invention comprises compositions comprising stabilizer of, e.g., arginine (of pH from about 7.0 to about 7.2), either in combination with, or in place of gelatin or gelatin related and/or derived products (e.g., gelatin hydrosylate). See, Steps 12 and 15 in Table 1. However, current regulatory concerns regarding the potential of unintentional contamination from animal and animal-derived products such as gelatin, collagen, etc. (e.g., by such problems as prions, mycoplasma, or host-derived viruses), as well as concerns regarding the potential for allergenicity of animal derived products, has lead to the need for non-animal based stabilizers. Arginine used either alone or in combination with additional excipients such as metal ion chelators (e.g. ethylenediaminetetraacetic (EDTA) and/or its salts) or other amino acids (e.g. Histidine and/or its salts) offers the potential of stabilization of cold-adapted influenza virus preparations with a non-animal derived excipient.

In various embodiments, the arginine optionally comprises either a salt with an inorganic acid or a salt with an organic acid. Of course, the salt typically comprises a pharmaceutically acceptable salt since it is to be used as a vaccine component. Typical preferable salts comprise, e.g., hydrochloride, citrate, and sulfate. The amount of such stabilizing agent used is not limited to specific particular ranges, however, typical amounts used range from about 5 mg to about 60 mg per 1 mL of the virus solution. The amount used may preferably be from about 10 mg to about 50 mg, and more preferably, from about 10 mg to about 25 mg per 1 mL of the virus solution. In other embodiments, the amount used may range from about 1%; from about 1.5%; from about 2%, from about 3%, or from about 4% to about 5% arginine solution of the virus solution. The amount used can vary in different embodiments of the invention. In yet other embodiments of the invention, the virus solution/vaccine solutions optionally comprise potassium phosphate. In some embodiments, the solutions comprise about 11 mM potassium phosphate. In other embodiments, the solutions comprise from about 10 mM to about 12 mM potassium phosphate. The formulated composition can optionally contain substantial amounts of egg allantoic fluid components (e.g. proteins and metabolites) and/or a buffer diluent. Additionally, acceptable compositions of vaccine can contain a buffer salt, such as a mixture of monobasic and dibasic sodium or potassium salts of phosphate at concentrations ranging from, e.g., 5 to 200 millimolar or histidine and/or its salts at concentrations ranging from, e.g., 25 to 100 millimolar. In preferred embodiments, sucrose is present at a concentration ranging from about 100 millimolar to 350 millimolar.

In many virus solutions/vaccine solutions a base solution of SPG (sucrose, potassium phosphate and monosodium glutamate) is optionally utilized. However, in some embodiments of the current invention, MSG is not part of the virus/vaccine solution. In yet other embodiments, levels of MSG are reduced. The amount of sucrose that is usable in the embodiments herein is variable over a wide range. Approximately 0.2 M sucrose is utilized (7% W/V) in typical embodiments, however, compositions comprising up to ca. 20% sucrose can present no detrimental effect on virus activity/potency. Surfactants in various embodiments of the compositions can comprise, e.g., Poloxamer 188 (polyoxy-ethylene-Polyoxypropylene block copoloymer, e.g. Pluronic F68) and Tween 20 (polyoxyethylene sorbitan monolaurate) at concentrations in the range of ca. 0.01 to 0.1% (W/V%). In some embodiments, the combination of Poloxamer, gelatin hydrolysate and arginine is superior to any solution containing only one of the components, each solution in turn being more stable than a solution containing none of the added components.

In yet other embodiments, steps in Group 4 (e.g., Step 15 of Table 1) comprise replacing all or part of the normal allantoic fluid (NAF) in which the viruses are suspended with a buffer of sucrose, potassium phosphate and monosodium glutamate (SPG) or other simple solutions, e.g., those with reduced MSG, etc. The use of SPG in place of some or all of the NAF diluent results in greater stability of the viruses in solution. Such stability is also a novel and unexpected benefit of the embodiments of the current invention. Representative formulations embodying some or all of the formulation attributes described above were prepared and the stability of the component cold-adapted viruses was evaluated. Compositions of representative formulations are shown in Table 28. The stability of the formulations at 5° C. is shown in Table 29.

Figure 38:
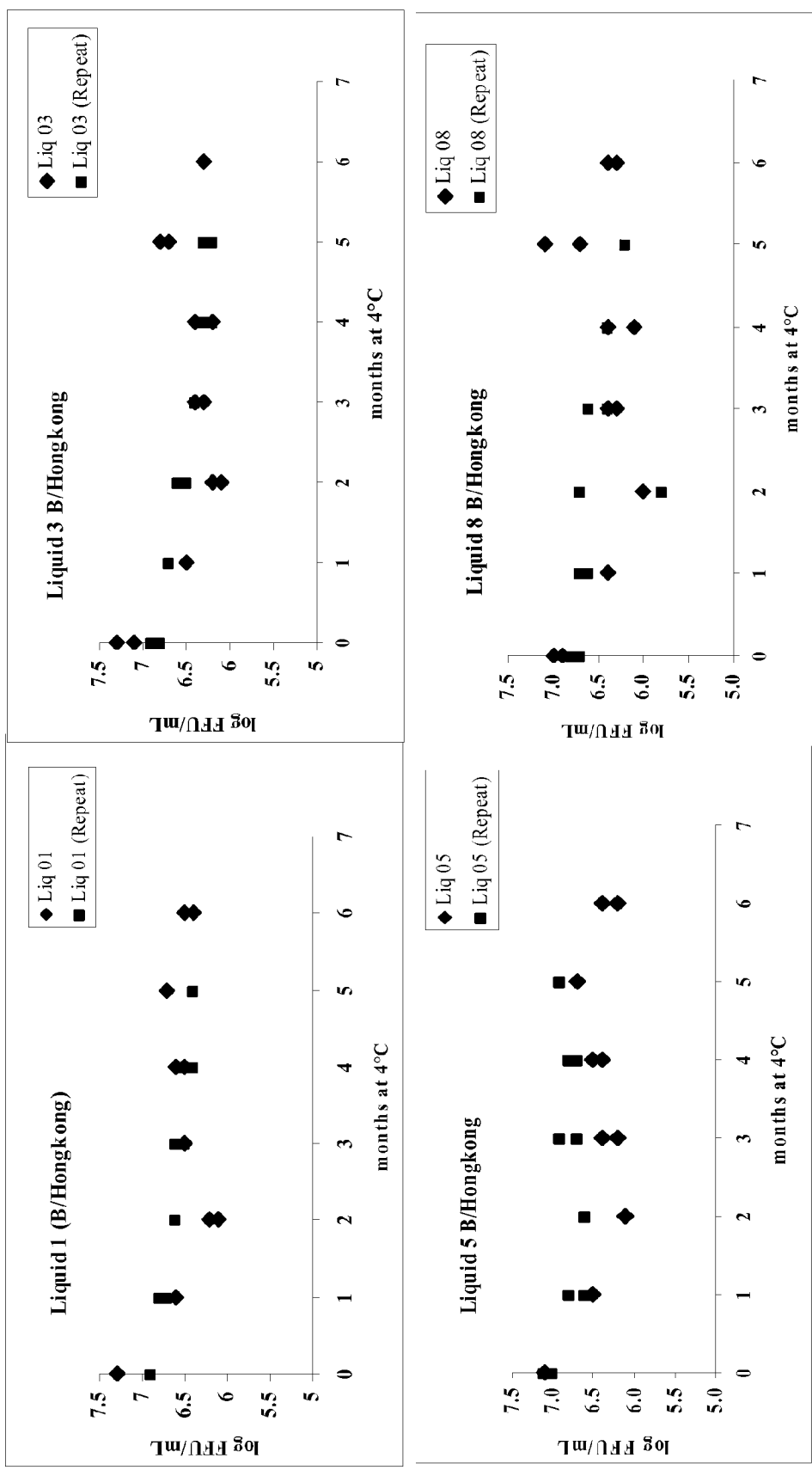
FIG. 38: Shows 4 graphs of stability of exemplary virus storage formulations.
Figure 39:
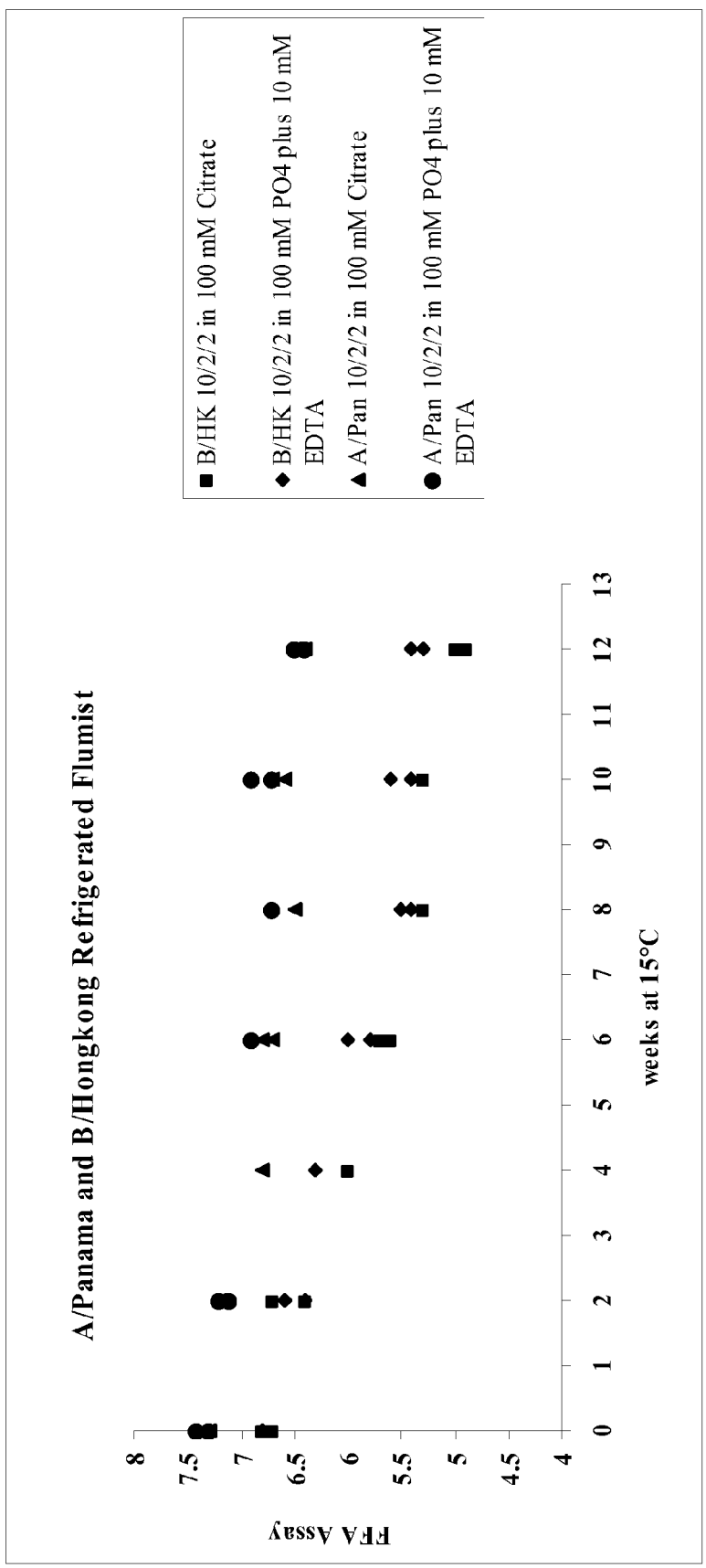
FIG. 39: Shows a graph of stability of exemplary virus storage formulations with various virus strains.
Figure 40:
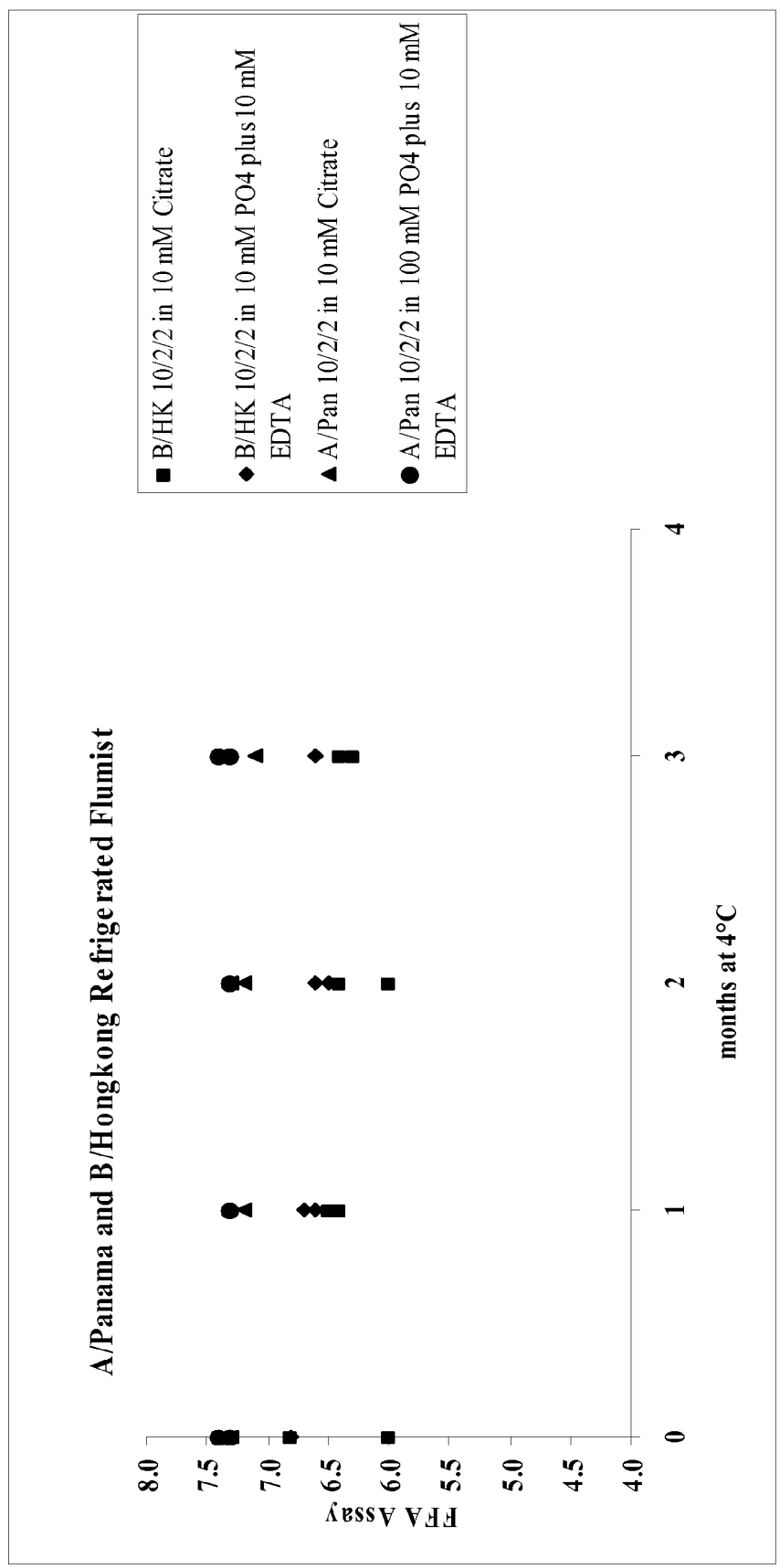
FIG. 40: Shows a graph of stability of exemplary virus storage formulations with various virus strains.

Various formulations of the invention were tested for their stability over a variety of months and temperatures. For example, Table 30 illustrates 12 different formulations. Formulations 10 and 11 were based upon formulations used for dried virus preparations. The formulations in such tables covered a range of various components, e.g., sucrose and gelatin. Tables 31–34 show the stability of such preparations comprising 4 different virus strains over six months (two sample points for each). FIG. 38 graphs the results of 4 exemplary formulations with the B/Hong Kong strain used. Table 35 shows compositions of additional formulations. The compositions in Table 35 examine addition of various compounds to the basic composition (i.e., typically 10/2/2 meaning about 10% sucrose, about 2% arginine, and about 2% gelatin) to help potentially inhibit adverse components present in the NAF such as lysozyme, etc. The stability results of the formulations in Table 35 are seen in Tables 36 through 39 and in FIGS. 39 and 40. Tables 40 and 41 and FIG. 41a–c look at varying concentrations of citrate in the formulations (here a base formulation of about 10% sucrose, about 1% gelatin, and about 2% arginine). Formulations with citrate showed a precipitate at about 7–8 months of storage. Tables 42 and 43 and FIG. 42a–c show a similar analysis, but with varying concentrations of EDTA. Exemplary formulations from the above examples were subjected to further testing which is shown in Table 44 and 45a–d. Additional formulations with varying concentrations of sucrose, gelatin, arginine, and EDTA, etc. are shown in Tables 46 through 48.

Figure 43:
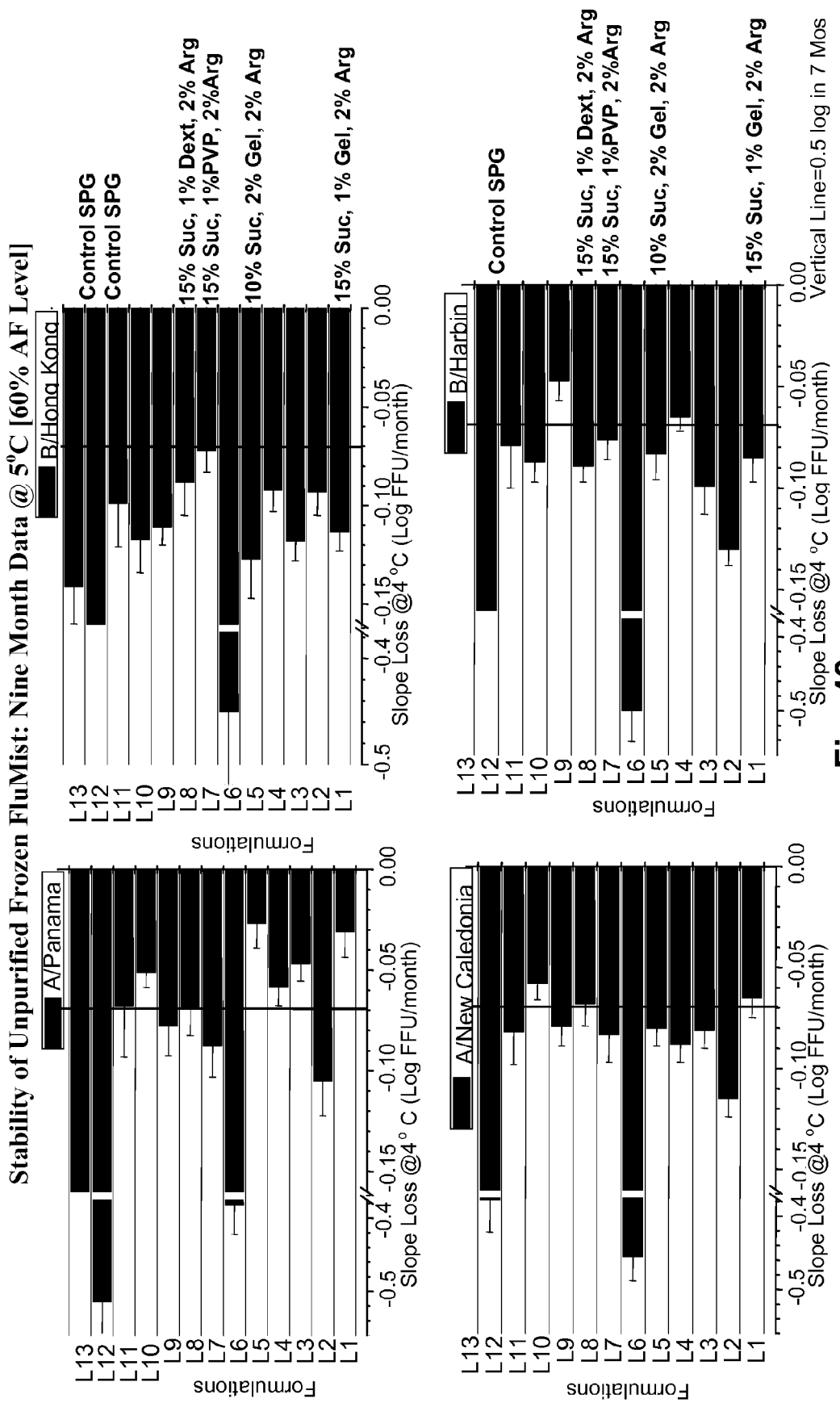

To further illustrate the stability of several monovalent formulations herein, compositions comprising 60% allantoic fluid were tested for stability. Samples were stored at 5° C. and examined with FFA analysis. Biweekly sampling was done for the first two months, then monthly sampling was done to 9 months. A concentration of 60% AF will allow a high probability of producing VH at the necessary potency even in years with low titer strains. Some formulations utilizing unpurified VH exhibited sufficient stability for all strains test to almost consistently meet a criterion of 0.5 log loss in 7 months at 5° C. Influenza strain B/Hong Kong/330/01 appeared to be the most problematic of the strains tested for stability. See Table 30 which gives percent composition of sucrose, arginine, gelatin and other components for the 13 different formulations. FIG. 43 illustrates the stability of four virus strains in such formulations after 9 months. Exemplary formulations of unpurified virus composition formulations can comprise, e.g., VH, 10% sucrose, 2% arginine, 2% gelatin; VH, 10% sucrose, 2% arginine; VH, 10% sucrose, 2% arginine, 1% dextran; VH, 10% sucrose, 2% arginine, 0.5% PVP; VH, 10% sucrose, 2% arginine, 2% gelatin, 2.5 mM EDTA; VH, 10% sucrose, 2% arginine, 2% gelatin, citrate buffer; and, VH, 10% sucrose, 2% arginine, 2% gelatin, histidine buffer.

Other methods of virus/vaccine solution purification (e.g., for stabilization, etc.) involve such techniques as removal of all NAF through fractionization (along with addition of stabilizers) to give stability of the solutions. Various embodiments of the current invention, however, involve, e.g., dilution out of the NAF in which the virus/vaccine exists. For example, in various embodiments herein, the concentration of NAF optionally comprises from about 10% to about 60% of the solution. In other embodiments, NAF can optionally comprise from about 20% to about 50%, or from about 30% to about 40% of the solution. Such dilution of NAF concentrations allows for greater stability of the virus/vaccine solutions, especially at desired temperatures (e.g., 4° C., from about 2° C. to about 8° C., etc.) in liquid form. Additionally, some embodiments of the invention comprise reduced NAF concentrations in conjunction with use of arginine (see above). Various formulations of the current invention were compared in stability with virus compositions that were NAF free purified formulations or that were NAF reduced (but still NAF purified) formulations. Table 49 illustrates the formulation of a number of compositions of the invention as well a number of formulations wherein the VH was purified from the NAF various ways. It will be appreciated that the base formulations shown in Table 49 also typically comprise about 2% arginine, about 2% gelatin, about 1% PVP, about 1% dextran, about 2.7 mM EDTA, and about 100 mM histidine. The numbers in Table 49 correspond to the formulations displayed in FIGS. 44–46.

The diluted NAF embodiments of the current invention are in comparison to alternative stabilization methodologies, e.g., which end up with 10–25% fractionated NAF or even 5% fractionated NAF or less in their final formulations. However, those of skill in the art will appreciate that the NAF present in some current embodiments does not comprise such fractionated NAF, but is instead comprised of un-fractionated NAF. The formulations of the invention were compared against other current virus solutions that were made from purified NAF (e.g., fractionated NAF, etc.) in terms of stability. The goal in the comparison was to reach less than or equal to 1.0 log potency loss in 12 months or less than or equal to 0.080 log/month loss in potency when stored at between 2° C. and 8° C., e.g., 4° C. The other current virus formulations compared against the formulations of the invention were purified through, e.g., fractionation, diafiltration, etc. The different formulations were tested with 3 different influenza strains: a H1N1 strain (A/New Caledonia/20/99 or A/NC), a H3N2 strain (A/Panama/2007/99 or A/Pan or A/PA), and a B strain (B/HongKong/330/01 or B/HK) and were filled into Accusprayers (i.e., a delivery device for FluMist®). In order to mimic a likely manufacturing process, the samples were frozen at −25° C. for at least 6 days as an initial step.

In a first comparison, a NAF purified cold-adapted trivalent formulation was compared in stability with an unpurified NAF formulation of the invention. The formulations comprised 7% sucrose, 1% gelatin, 1% arginine (which are the standards for the comparing trivalent formula) and 60% AF (allantoic fluid) for the formulation of the invention. The formulation of the invention after six months showed −0.035±0.016 for A/NC, −0.079±0.035 for A/Pan, and −0.151±0.018 for B/HK. The measurements for the purified composition was −0.020±0.027 for A/NC, −0.011±0.020 for A/Pan, and −0.138±0.022 for B/HK. The units above are in log FFU/month. See Table 50. Table 51 shows a comparison between a purified formulation and a formulation of the invention when the invention formulation uses a 10/2/2 composition, see above. The high initial potency loss observed is though to be attributed to freeze-thaw and/or blending loss. Table 52 shows a similar comparison, but with histidine in the FluMist® formulation, which gave rise to a better stability with no initial potency loss observed.

Figure 44:
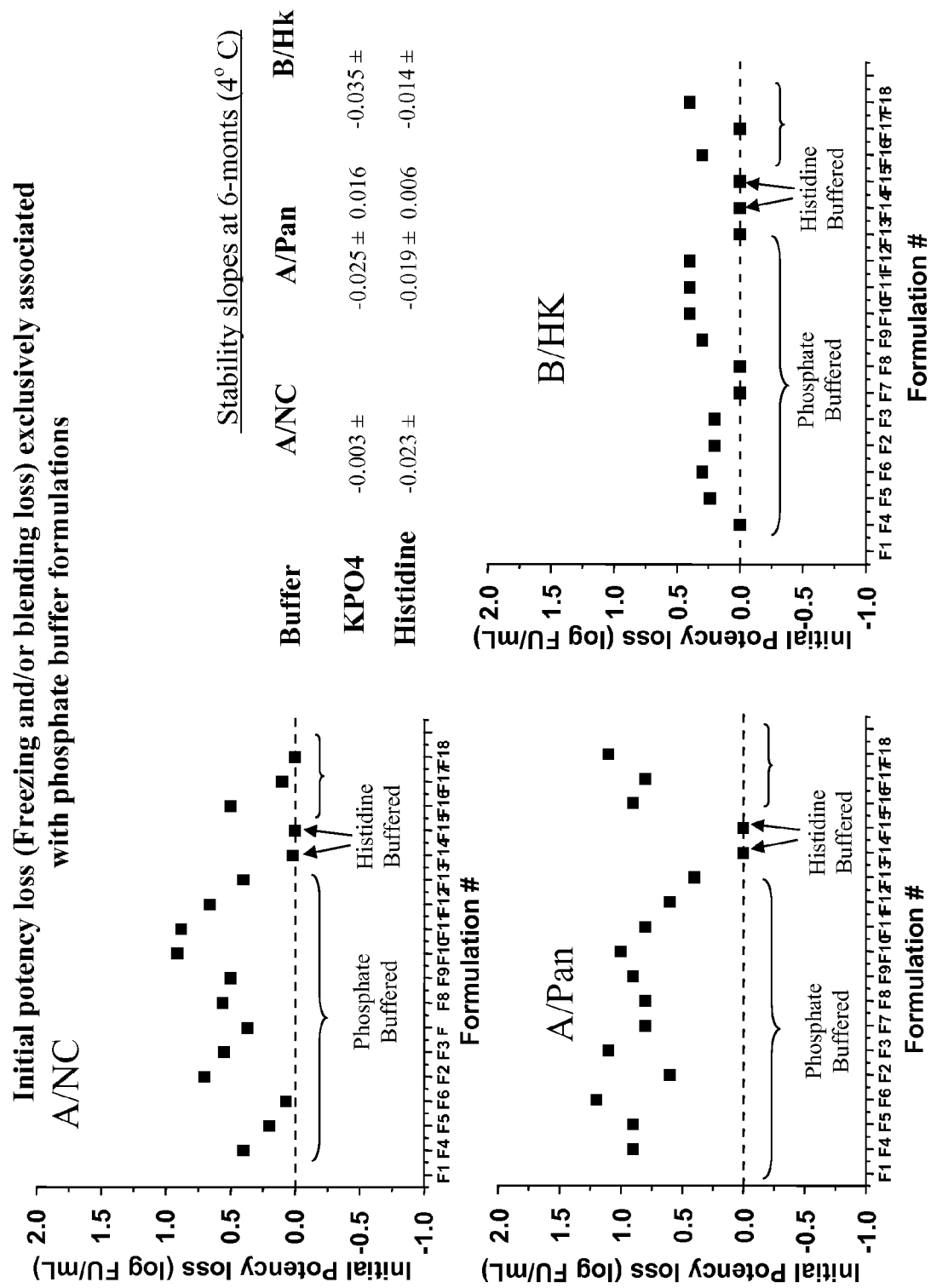
Figure 45:
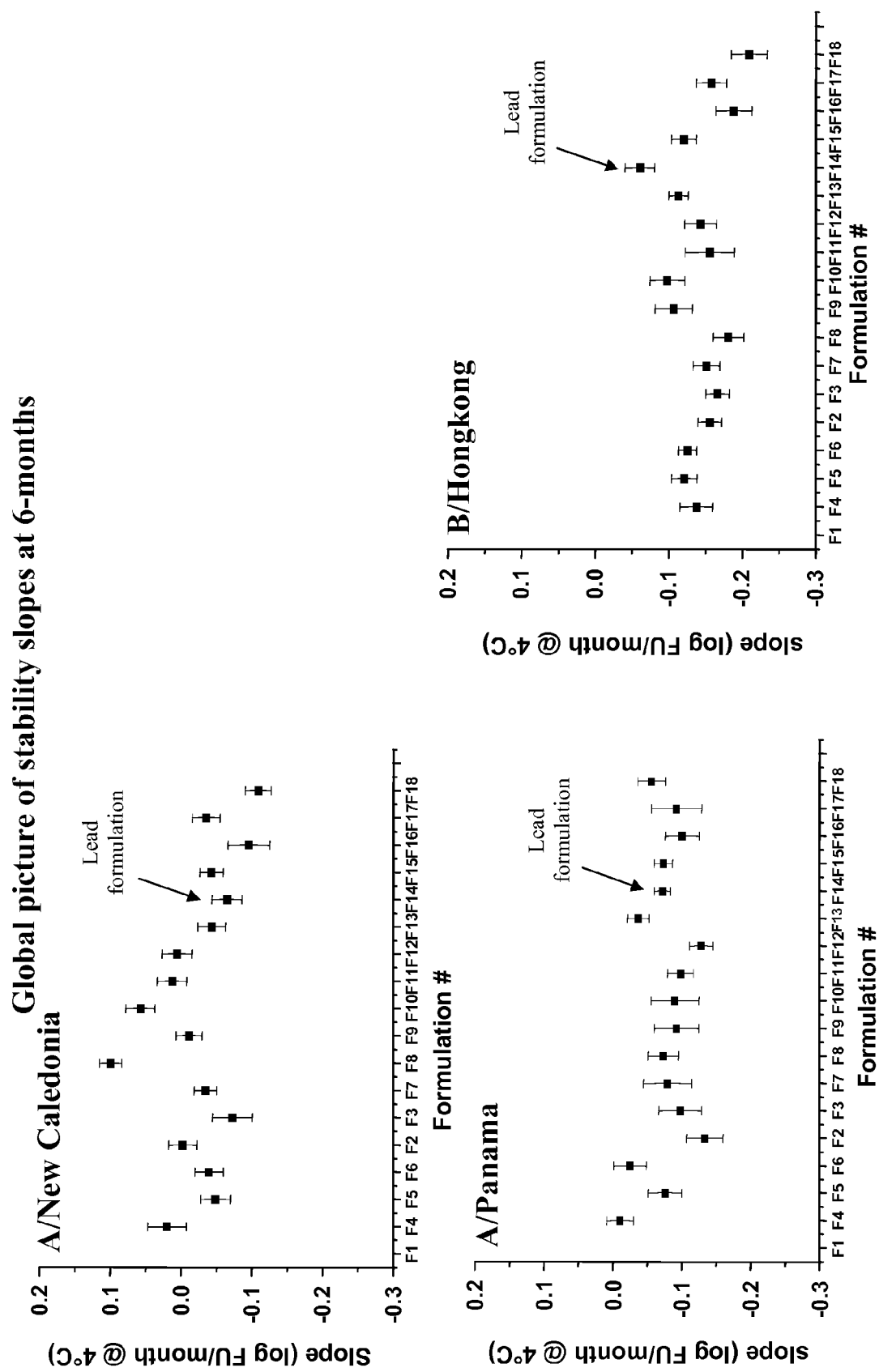
Figure 46:
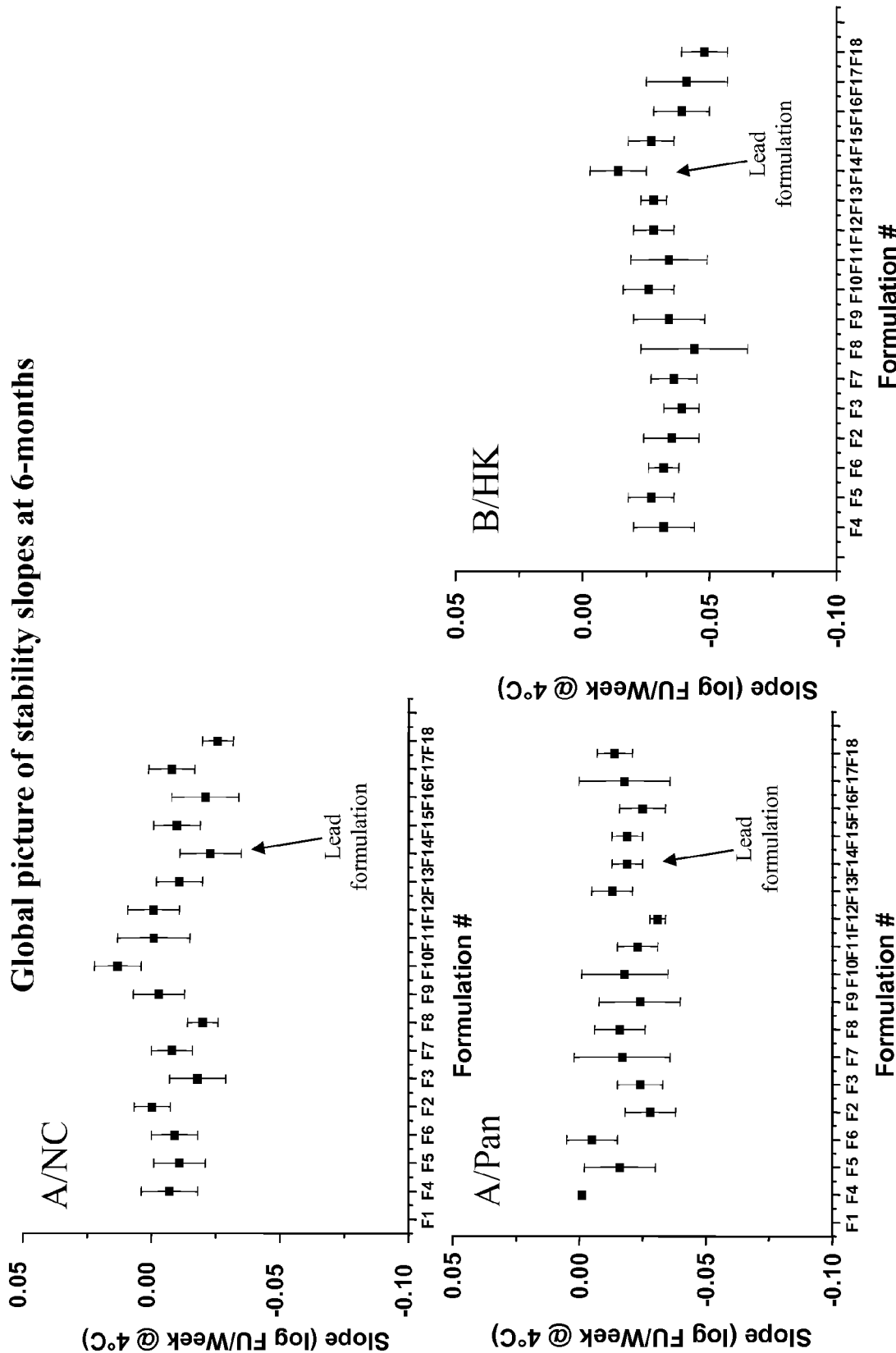
Figure 47:
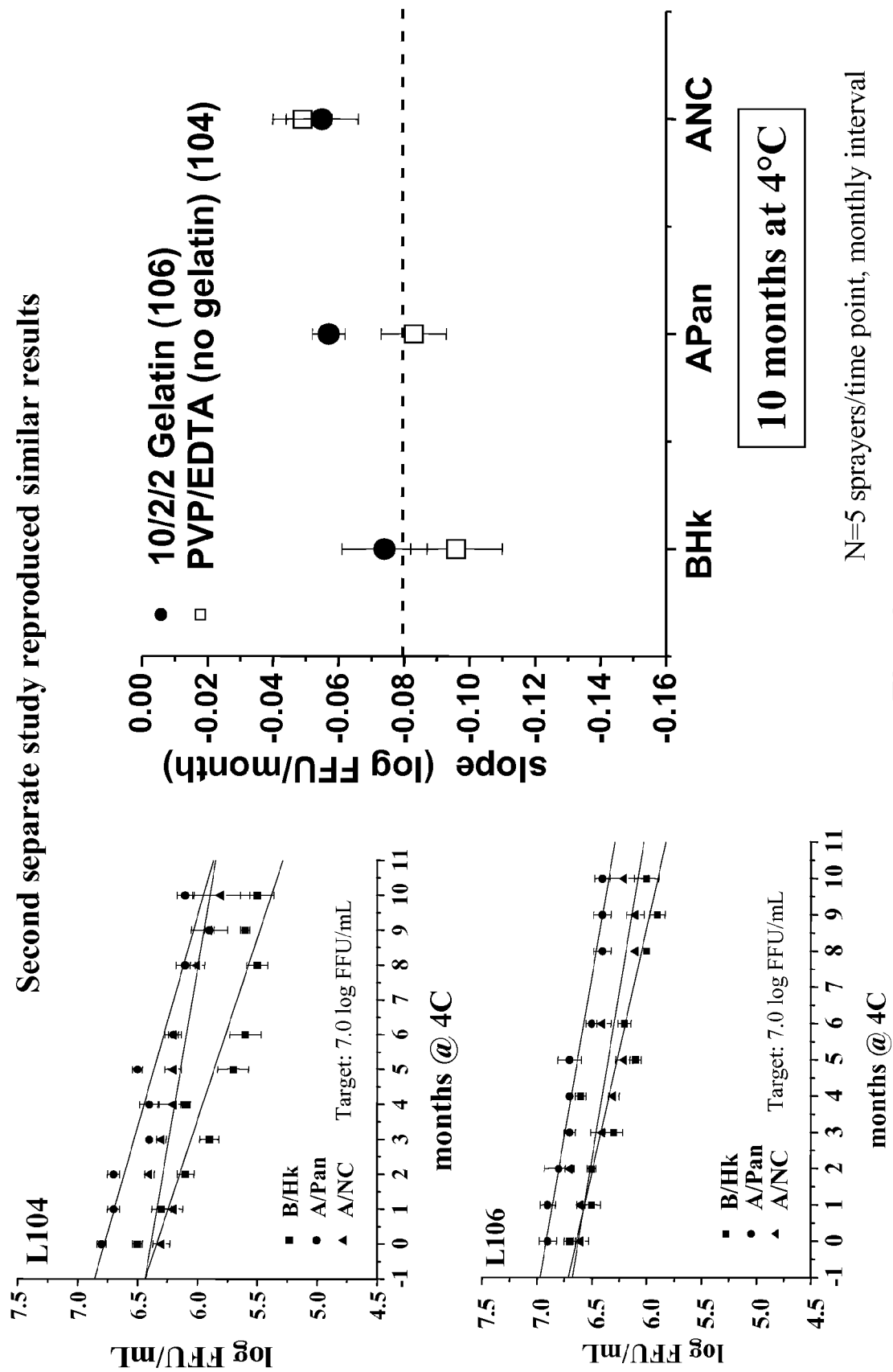
Figure 48:
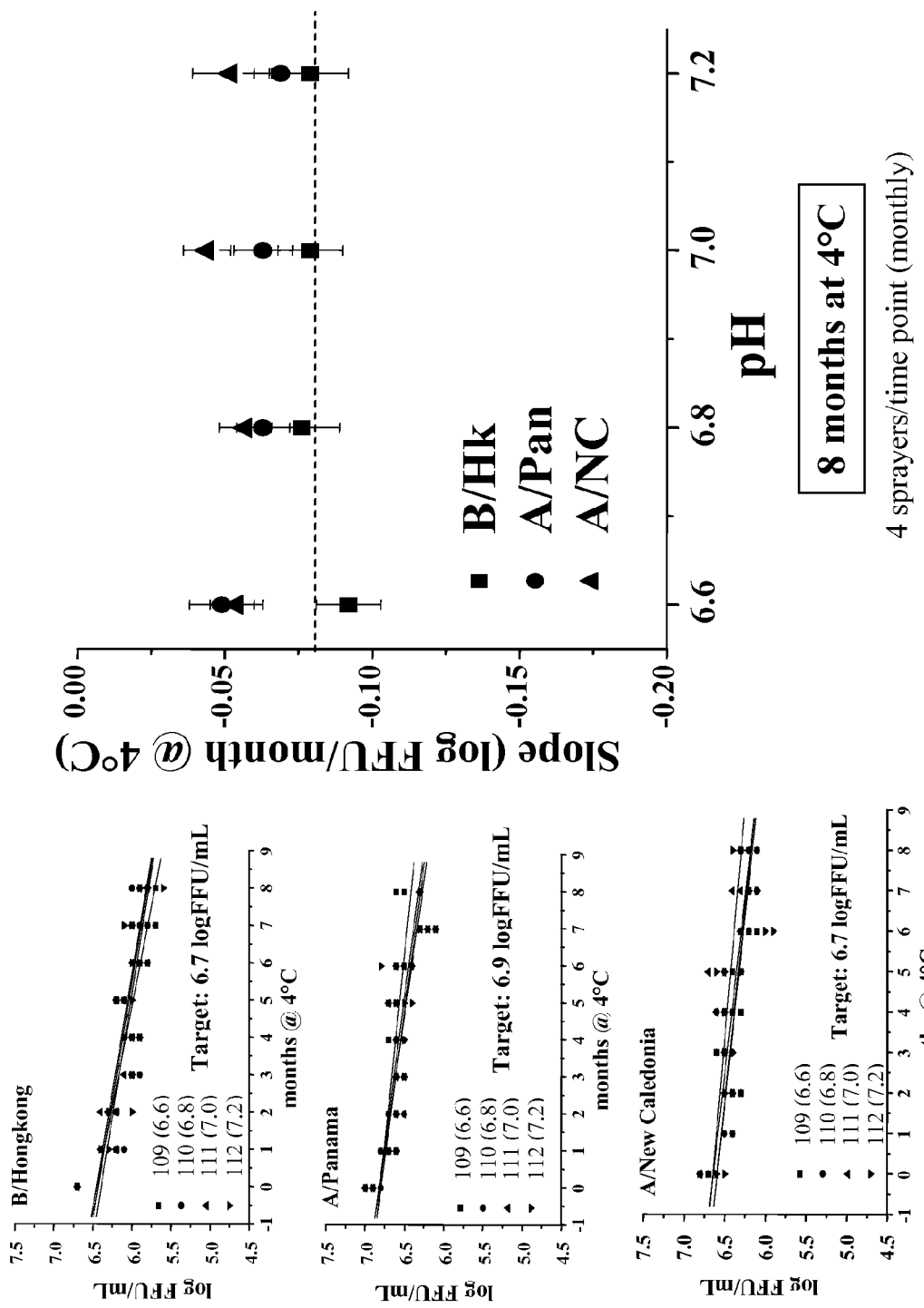
Figure 49:
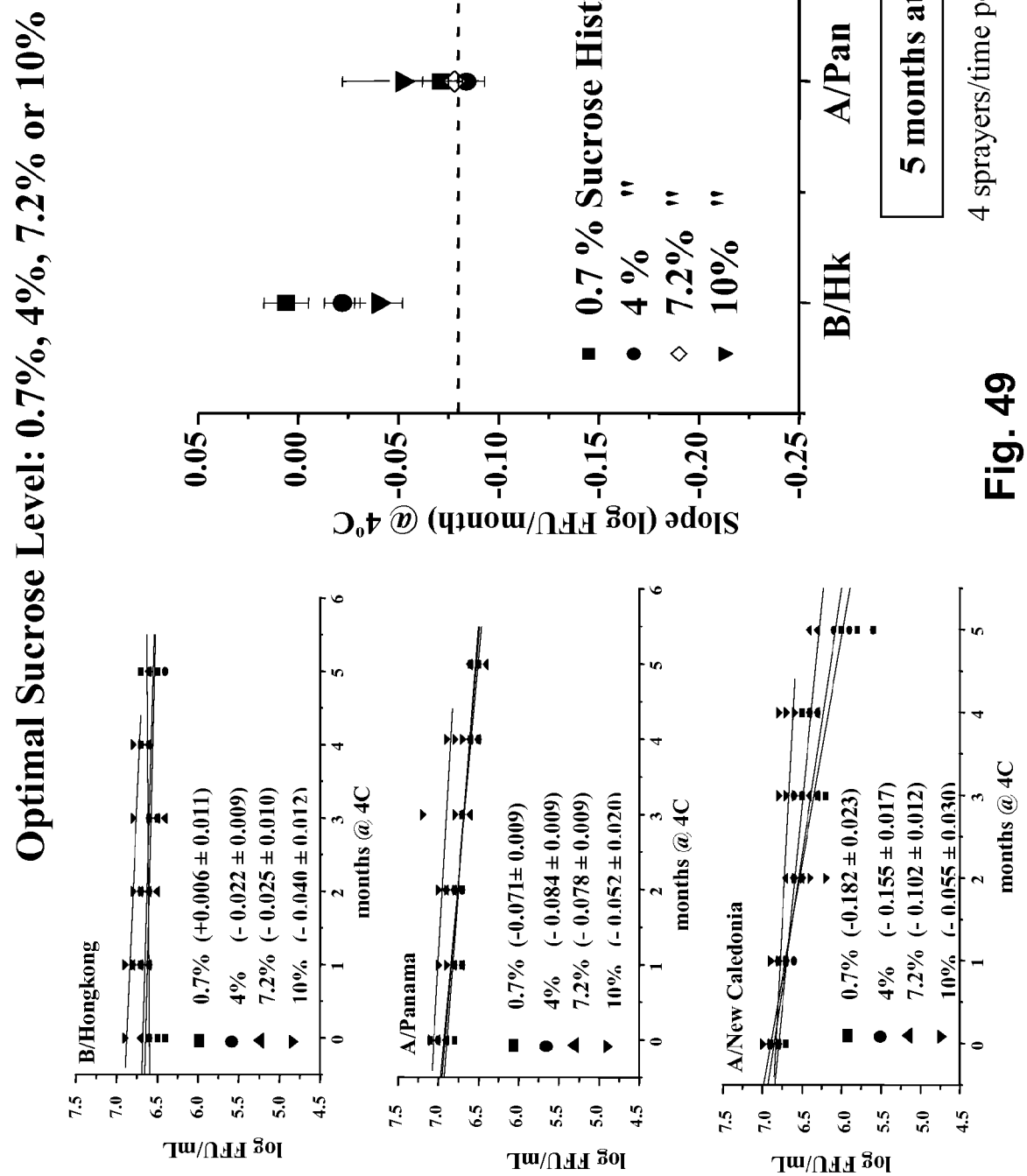

FIG. 44 illustrates the initial potency loss (freezing and/or blending loss) seen above is exclusively associated with phosphate buffered formulations. No initial potency loss was observed with histidine buffer, which exerted a positive impact on stability. The formulations shown in FIG. 44 are those listed in Table 49. FIG. 45 illustrates a "global" picture of the stability slopes of the formulations of Table 49 after 6 months. As can be seen the histidine buffered 10/2/2 formulation exhibited the best combination of stability and meeting the target goal. See above. FIG. 46 gives a different view of similar data (i.e., week rather than month). FIG. 47 illustrates a second study which produced results illustrating the stability of a 10/2/2+histidine formulation with either gelatin (L106) or PVP/EDTA (L104). As can be seen from the figure, the replacement of gelatin with PVP/EDTA produced stability almost as efficiently as the inclusion of gelatin. FIG. 48 examines the optimal pH of a histidine-based 10/2/2 formulation of the invention. As can be seen, pH 7.0 comprises a preferred embodiment. Ranges of pH from about 6.8 to about 7.2 for these 100 mM histidine 10/2/2 formulations are also included embodiments of the invention. FIG. 49 shows examination of preferred embodiments of sucrose concentration in embodiments of the invention. Some preferred embodiments comprise about 10% sucrose, while others comprise about 7%. The basic formulation in FIG. 49 comprises the 10/2/2 above, with the addition of sucrose histidine. In the various embodiments illustrated herein, some embodiments comprise histidine as a buffering additive and/or arginine as a stabilizer and/or dextran and/or PVP in place of gelatin.

Other embodiments of the current invention are optionally stabilized through use of ultrafiltration/concentration of the virus/vaccine solution. Such ultrafiltration is typically an alternate means of achieving solution stability as opposed to reductions/dilutions of NAF. For example, in some situations if the titer or potency of a particular strain/solution is low, then ultrafiltration can optionally be used in place of NAF dilution (which could act to further reduce the titer/potency of the solution). The ultrafiltration in Groups 4 steps is slightly different from the microfiltration as described above. In the earlier Group the filtration was for, e.g., sterility whereas in the current Group the filtration concerns stability, etc. and the viruses are kept during the filtration. See above.

Potency Assays

In some embodiments herein, the potency measurement for the virus/vaccine is performed by a cell-based ELISA (i.e., Cell-based ELISA, or CELISA, for Potency Measurement of FluMist-a live, attenuated influenza virus vaccine, or for other such vaccines). Such method is a simpler and faster alternative to the more traditional Median Tissue Culture Infective Dose ($TCID_{50}$) assay, for potency measurement of live virus. Briefly, confluent monolayers of Madin-Darby Canine Kidney (MDCK) cells in 96-well microtiter plates are infected with sample containing live virus, fixed with formalin 16–18 hours post-infection and reacted with influenza virus-specific monoclonal antibody (Mab). Virus antigen bound Mab is then detected using anti-mouse IgG~Peroxidase and peroxidase substrate to develop soluble colored product, the optical density (OD) of which is measured spectrophotometrically. Those of skill in the art will be familiar with epitopes/antigens shared by various subtypes of influenza strains (e.g., various HA, etc.). The potency of live virus in a sample is calculated from a standard curve generated using live influenza virus calibrators with known $log_{10}$ $TCID_{50}$ values obtained with a validated $TCID_{50}$ potency assay. CELISA is shown to be linear ($r^2$ greater than or equal to 9.95) in the range 4.9–6.7 $log_{10}$ $TCID_{50}$. Between-day, between-analyst, between-plate, within plate (residual) variability (Standard Deviation in $log_{10}TCID_{50}$) were 0.06, 0.02, 0.05 and 0.03 respectively. The potency of several vaccine and wild-type influenza A/H1N1, A/H3N2 and B strains measured by CELISA are comparable (±0.3 $log_{10}TCID_{50}$) to the potency measured in parallel by the validated $TCID_{50}$ potency assay. CELISA is capable of measuring potency of up to 10 samples/plate in 2 days in contrast to 2 samples/plate in 6 days for the validated $TCID_{50}$ potency assay. CELISA is optionally used in place of, or in addition to other methods of potency assay (e.g., FFA and $TCID_{50}$, see, below).

The Median Tissue Culture Infective (or Infectious) Dose 50% ($TCID_{50}$) assay (see, below for more details) is a widely used method for the potency measurement of live virus and live virus vaccines. However, in some embodiments herein, Cell-based ELISA (CELISA) is optionally used as a simpler and faster alternative to the traditional, long and labor intensive TCID assay to measure potency of influenza virus in FluMist, a live, attenuated vaccine (or in other similar vaccines).

In other typical embodiments, potency assays of the virus solutions optionally comprise fluorescent focus assays (FFA) as opposed to common $TCID_{50}$ assays which are used in the art. Such FFAs have the added benefit that they are more amenable to automation, thus, allowing higher throughput of vaccine production. $TCID_{50}$ assays usually measure the quantity of a virus suspension or solution that will infect 50% of a particular cell culture. The measurement gives accurate results, but is slower than FFA and thus can use up valuable time in the production of vaccines. FFA assays typically use type and/or subtype (or even universal antigen) specific anti-influenza antibodies (typically anti HA antibodies) to detect virus antigens in infected cells. In uses wherein the antibodies do not cross react with different types/subtypes of influenza they can be used to quantitate the separate virus types in multi-virus preparations (e.g., trivalent vaccine formulations). FFA assays can also be used as identity tests for specific strains. Those of skill in the art will be quite familiar with FFAs and their use in virus/vaccine testing.

Fluorescent focus assays, on the other hand, do not rely on the induction of cell death (either in the infected cells or the indicator cells). Instead, they use antibody staining methods to detect virus antigens within infected cells in a cell culture monolayer. These infected cells are then visualized and quantified using a fluorescent label on the virus-specific antibody. Typical FFAs of the current invention use, e.g., type and subtype specific anti-influenza HA antibodies to visualize virus antigens in infected cells.

In other embodiments, the FFAs (and optionally other assays herein) optionally use a universal reagent (or universal antigen) which is not specific for specific type/subtype influenza antigens, but is instead specific for a generalized influenza antigen. Therefore, the universal reagent is optionally useful for FFAs for myriad different screenings and type/subtype specific antibodies do not have to be developed and created each time a different virus is assayed.

Other embodiments herein comprise viral potency determination using a cell-based fluorometry assay (CFA). While FFA assays are quite useful in many embodiments, CFA assays are preferentially used in other embodiments. While the image processing and readout of FFA assays can be capped at about 20 plates/person/day (or about 5 plates/hour image processing), the image processing and readout from CFA assays can be up to about 4 times faster. Also, while FFA titers can differ from $TCID_{50}$ titers for influenza B strains, CFA titers have not shown significant differences from $TCID_{50}$ (or FFA) titers due to the use of assay standard or calibrators. In brief, the CFA assay measures infectious influenza viruses in MDCK cells grown in 96 well plates. As with FFA, CFA detects viral protein expression resulting from viral infection of MDCK cells during the first infection cycle. CFA assays utilize calibrator or assay standard for titer calculation. For CFA reagents, typical antibody reagents can comprise: primary antibodies specific to HA or A strains and B strains (for influenza) and secondary antibodies of, e.g., goat anti-mouse IgG conjugated with Alexa 488. Assay standards for CFA can include virus harvest of the same strain as the samples to be tested with a known FFA or TCID titer. Assay references for CFA can include, virus harvest with known FFA or TCID titer and known linear slope (does not have to be the same strain as the samples to be tested). Sample primary antibodies can include, e.g., those specific for A/H1N1 or A/H2N2 strains (from, e.g., Takara) at, e.g., a working dilution of 1:2000; those specific for A/H3N2 strains (from, e.g., Takara) at, e.g., a working dilution of 1:1000; and, those specific for B strains (from, e.g., Chemicon) at, e.g., a working dilution of 1:1000. A typical CFA assay procedure can comprise virus inoculation followed by 18 hours incubation at 33° C. followed by fixation and incubation at room temperature for 15 minutes. A primary antibody incubation for 60 minutes at 37° C. is then followed by a secondary antibody incubation for 60 minutes at 37° C. The plates are then read with a fluorometer and the data analyzed. In some embodiments of CFA, the infection level of a well, etc. is determined via protein expression (as opposed to typical FFA assays where the number of cells infected are measured). Those of skill in the art will be aware of typical FFA assays and fluorometry and similar concerns applicable to CFA assays.

Semi-Automated $TCID_{50}$ Assay

As stated above, some embodiments of the current invention comprise $TCID_{50}$ assays and various modifications, etc. thereof. For example, some embodiments comprise a semi-automated version such as illustrated by the following descriptions.

A comparison of Manual and Semi-Automated Median Tissue Culture Infective Dose ($TCID_{50}$) assays for Potency Measurement of a live, attenuated influenza virus vaccine, e.g., FluMist®, or other similar vaccines, is given in this section. The $TCID_{50}$ potency assay is optionally used for potency measurement of FluMist or other similar vaccines. A semi-automated $TCID_{50}$ potency assay is described in which two labor-intensive steps of the validated manual potency assay are improved. These are (i) use of an automated pipetting station for sample dilutions and infection of MDCK monolayers in place of multiple manual repeating dilution steps, and (ii) use, 6-days post-infection, of a 96-well plate reader to measure spectrophotometrically the product of MTT, a vital dye (3-(4,5-dimethylthiazol-2-yl)-2,5-diphenyltetrazolium bromide) widely used as an indicator of cell health/viability, in place of manual observation under a light microscope of each of the 96 wells of all assay plates in order to assess the presence of influenza virus induced cytopathic effect (CPE) in MDCK cells.

The semi-automated $TCID_{50}$ potency assay used in some embodiments herein was developed and validated to demonstrate precision (repeatability: <0.25 $\log_{10}TCID_{50}$; intermediate precision: $SD_{(Day)}$<0.3 $\log_{10}TCID_{50}$; $SD_{(Analyst)}$ and $SD_{(Instrument)}$<0.4 $\log_{10}TCID_{50}$; and reproducibility at the 90% Confidence Interval ±0.3 $\log_{10}TCID_{50}$), linearity, accuracy and range (Slope 1±0.1). The semi-automated $TCID_{50}$ potency assay using an automated pipetting station and MTT dye was shown to provide equivalent results to the validated manual $TCID_{50}$ potency assay (at the 90% Confidence Interval ±0.3 $\log_{10}TCID_{50}$). In brief, the results herein provide support for the use of a pipetting station and MTT dye to measure the potency of influenza virus in, e.g., FluMist® productions. These improvements also increase the testing throughput.

Infectivity/Potency (Monovalent) Assay Validation

A semi-automated version of the current manual method for potency determination of monovalent influenza strains is optionally used for manufacture of FluMist™ vaccine and other similar vaccines. The semi-automated potency assay incorporates automation of the plate washing and serial dilution steps, and an automated dye-based detection of the virus induced cytopathic effect (CPE) to replace the manual microscopic detection. Automation of the plate washing and serial dilution steps allows greater assay throughput, and reduces the risk of repetitive motion injuries for Quality Control analysts performing this assay. Automated dye-based detection of the virus induced CPE enhances assay consistency and throughput by elimination of the microscopic detection.

Some steps/aspects of the semi-automated assay are similar to more traditional $TCID_{50}$ assays, while other steps/aspects are quite different. The assay steps include preparation, incubation and washing of assay plates containing Madin-Darby canine kidney (MDCK) monolayers, infection and post-infection incubation of the assay plates, and calculation of the potency based on the number of CPE positive wells and sample testing configuration in both assays. The semi-automated potency assay has been validated and the performance of the assay demonstrated to be comparable to the current manual assay by the inventors and coworkers. This semi-automated assay optionally serves as the primary method for the infectivity/potency measurement of expanded wild-type influenza (eWT), Master Virus Seed (MVS), Manufacturer's Working Virus Seed (MWVS), and Virus Harvest (VH) samples. The manual assay is optionally used as a backup in a situation where the semi-automated assay cannot be performed; i.e. in the case of prolonged equipment downtime.

The traditional median tissue culture infectious dose ($TCID_{50}$) assay is a cell-based method that measures infectious cytocidal virions. MDCK cells are cultured in 96-well plates, and confluent monolayers are inoculated with serial dilutions of a virus sample. Replication of virus in the MDCK cells results in cell death. The progeny virus infects other cells, resulting in the eventual destruction of the monolayer. The CPE resulting from infection is allowed to develop during an incubation period of six days. The individual wells are read microscopically, to determine the presence of CPE in each well. Four individual determinations are performed on each of three days by this procedure, and the results of all 12 titrations are averaged in order to produce one test result. In addition to samples, each analyst analyzes one monovalent control, also with four replicate determinations on each, of three days.

The manual assay is labor intensive and has limited sample throughput. Each individual determination involves numerous cell washing and serial dilution steps, which are performed using a manual pipettor. Each well in the 96-well assay plate has to be microscopically scored for the presence or absence of CPE. Multiple plate washing and dilution steps pose a repetitive motion injury risk for analysts. In addition, the microscopic reading of each individual well in the 96-well plates is fatiguing, which limits the number of analyses that can be performed by each analyst to about 20 plates per day. One test result is obtained as an average of twelve determinations over a three-day test period, and each analyst performs one monovalent assay control in addition to samples. This limits the assay throughput to 9 samples per analyst per 3-day testing period (average of 3 samples per analyst per day). Because each individual sub-lot (about forty to fifty sub-lots per lot) of monovalent influenza vaccine harvest is tested by this assay, the limited throughput may limit capacity for full-scale commercialization of vaccines (e.g., FluMist™ vaccine, etc.).

Automation of the traditional assay, specifically the plate-washing and pipetting steps, and MTT (3-[4,5-Dimethylthiazol-2-yl]2,5-diphenyl-tetrazolium bromide) dye-based detection of CPE, results in development of a Semi-Automated $TCID_{50}$ Potency Assay for Influenza Virus Monovalent. The semi-automated assay uses the Skatron™ Cell Washer for the washing steps, where the debris and spent media are removed from the cell culture plates and replaced with fresh media. The Matrix SerialMate® multichannel pipetting station is used to perform the sequential 10-fold dilutions of the virus, and for transfer of the diluted samples onto the cell culture monolayers in 96-well assay plates. Of course, other devices which perform similar functions are optionally substituted herein and specific mention of particular brands or types of devices should not be construed as limiting unless specifically indicated to be so. After the six-day incubation period, the 96-well assay plates are then incubated for six hours with MTT dye, which is a widely accepted indicator of cell metabolism and viability. During the incubation period, intact and healthy cell monolayers process the dye to form the insoluble purple formazan product, which accumulates intracellularly. In wells where the cell monolayer is destroyed, no dye product is formed. A solubilizing solution of 0.01 N Hydrochloric Acid, containing 20% of the surfactant sodium dodecyl sulfate (SDS) is then added, and the plates incubated overnight to dissolve the insoluble dye product. The absorbance at 570 nm is measured to quantify the purple formazan dye product. The absorbance reading is processed using a Microsoft Excel™ Macro program (or other similar program), to identify and count the CPE positive or negative wells and calculate the $TCID_{50}$ titer. Wells containing intact cell monolayers show a higher absorbance when compared to a pre-determined cut-off value, and are identified as CPE negative, whereas CPE positive wells show absorbance readings below the cut-off value (see FIG. 50). The number of wells showing CPE at each dilution is then used to calculate the titer (log10 $TCID_{50}$/mL) based on the Karber modification of the Reed-Muench method. The automation of the cell washing, serial dilution and virus inoculation steps, and the MTT dye-based CPE detection are described in detail below.

Automation of Cell Washing Steps Using Skatron™ Cell Washer

In a manual assay, plates containing MDCK cell monolayers in 96-well plates are washed twice prior to inoculation with the diluted virus samples. Spent medium containing waste products and fetal bovine serum (FBS) from the four-day cell incubation is removed and replaced with fresh virus growth medium (VGM) without FBS. The cells are then incubated at 33±1° C. and 5±1% $CO_2$ for at least 10 minutes, then the VGM is removed and replaced with fresh VGM a second time. For each washing step, individual plates are inverted onto clean paper towels and gently blotted to remove media from the wells, and then each well is refilled with 200 µL of fresh VGM using a hand-held multichannel pipettor. This process is labor-intensive and time consuming when large numbers of plates are processed.

The Skatron™ Skanwasher (Series 300, Model 12010) is a microprocessor-controlled 96-channel cell washer, which performs these washing steps automatically. The Skanwasher is small enough to fit in a 6-foot laminar flow biosafety hood. Automation of cell plate washing steps using the Skatron™ Skanwasher, involves a wash program where the spent media are aspirated from the plates, then fresh VGM is dispensed into the empty wells. Individual plates are loaded into the Skanwasher, then removed to a 33±1° C. and 5±1% $CO_2$ incubator at the end of the wash cycle. The plates are incubated for a minimum of 10 minutes, then loaded onto the Skanwasher for the second wash, after which they are transferred back into the incubator. The performance of the Skatron™ Skanwasher in these wash steps is shown to be acceptable for use in the cell washing steps. The dispensing precision for the 200 µL volume is associated with a CV<10%, and the dispensing accuracy is within 10%. The residual volumes for the aspiration step are less than 1%. Thus the Skatron™ Skanwasher provides acceptable performance, while improving the ease of use and throughput efficiency of the cell-washing step. Again, it will be appreciated that similar devices capable of performance within the same standards are also optionally used herein.

Automated Serial Dilution and Virus Inoculation with Matrix SerialMate® Multichannel Pipetting Station The serial dilution and the virus inoculation steps of the traditional manual $TCID_{50}$ assay are carried out by hand-held multi-channel micropipettes. The serial dilutions are carried out in two steps. The first set of five serial dilutions is carried out in a 0.5 mL dilution block, and then the appropriate dilution from the first block is transferred to a 2 mL dilution block, for the final five serial dilutions. It is crucial that these serial dilutions be carefully executed, because pipetting errors at any one dilution may be propagated and magnified through the subsequent series. The subsequent virus inoculation step involves repetitive pipetting of diluted virus into multiple rows or columns of an assay plate containing confluent cell monolayers. Prolonged use of the hand-held multichannel micropipettes used to provide the necessary accuracy for these tasks can lead to severe muscle fatigue and tendonitis, which limits the number of plates each analyst can perform in one day and, thus, the throughput of the entire process.

Use of the Matrix SerialMate® pipetting station for the serial dilution and virus inoculation steps improves the ease of use and throughput of the assay, and reduces the occurrence of operator injuries, while providing the necessary precision and accuracy for these tasks. The Matrix SerialMate® pipetting station is a bench top liquid handling station equipped with a 12-channel nozzle head which can aspirate and dispense volumes in the range of 5 µL–225 µL. The unit is small enough to fit in a standard 4- or 6-foot biosafety cabinet and is easy to use. The Matrix SerialMate® provides precision better than 0.5 µL, and accuracy better than 1.0 µL for delivery volumes of 5 µL–225 µL. This corresponds to a precision better than ±1.7% and accuracy better than ±3.3% for the 30 µL delivery volume used in the serial dilution steps. The comparability of assay results obtained using the automated assay and the current manual assay is confirmed as described below. Again, it will be appreciated that similar devices capable of performance within the same standards are also optionally used herein.

Description of MTT Dye-Based Detection

The final step in a $TCID_{50}$ assay is the detection of CPE and quantitation of the virus. With the current (manual) $TCID_{50}$ assay, the individual wells are read microscopically, to look for signs of CPE in each well. These signs include areas of foci, partial or complete collapse of the cell monolayer, and the presence of rounded and darkened cells on top of the destroyed cell monolayer. It has been observed that significant eye strain sets in as the analyst counts large numbers of plates, setting the practical limit for the number of plates which may be counted by one operator to about 20 plates. This step is rate limiting to the throughput of the manual assay.

Tetrazolium dyes are widely used as cell viability indicators. The most commonly used dye is yellow MT dye. Viable cells, which possess active mitochondria, will reduce MT dye to an insoluble purple formazan product, which can be detected at 570 nm after a solubilization step. In CPE positive wells where the large majority of cells have been destroyed, little or no dye product is formed, and a much lower absorbance is observed.

In a semi-automated $TCID_{50}$ assay, after the infection and six-day incubation of the plates, the spent medium is removed, 100 µL of a solution of 0.5 mg/mL MTT dye in fresh virus growth medium is added to each well of the 96-well plates, and the cells are incubated at 37±1° C. and 5±1% $CO_2$ for six hours. The dye product is solubilized by overnight incubation at 37±1° C., following addition of 100 µL of a solubilizing reagent (20% SDS in 0.01 N HCl), then the absorbance at 570 nm due to the purple formazan dye product is measured with a plate reader. The absorbance data is transferred to a validated Microsoft Excel™ Macro (or other similar program) that converts the absorbance readings to a CPE count based a pre-established cut-off value. Wells containing intact cell monolayers yield a higher absorbance when compared to a pre-determined cut-off value, and are identified as CPE negative. CPE positive wells show absorbance readings below the cut-off value. The number of wells showing CPE at each dilution is then used to calculate the titer ($log10TCID_{50}/mL$) based on the Karber modification of the Reed-Muench method.

The automated dye-based detection enhances the consistency of the CPE readout and increases the assay throughput. The comparability of the dye-based detection to the manual microscopic CPE detection is ensured by extensive studies where the assay was run with different vaccine and wild type virus strains, and with plates prepared with different cell passage numbers and seeding densities. In these studies the plates were read first by manual microscopic examination, and then by dye-based absorbance detection. The results from these studies were analyzed to determine a universal absorbance cut-off, which provided comparable CPE counts by both detection methods. This universal cut-off value of 0.5254 for the absorbance at 570 nm was confirmed by a detailed study (see, below), in which 9 different analysts performed assays on three different instruments, over 6 assay days, using a total of 573 assay plates. The presence or absence of CPE in each well (80 virus inoculated wells per plate, for a total of 45,840 wells) was read first by manual microscopic examination, then by dye-based absorbance detection.

Figure 50:
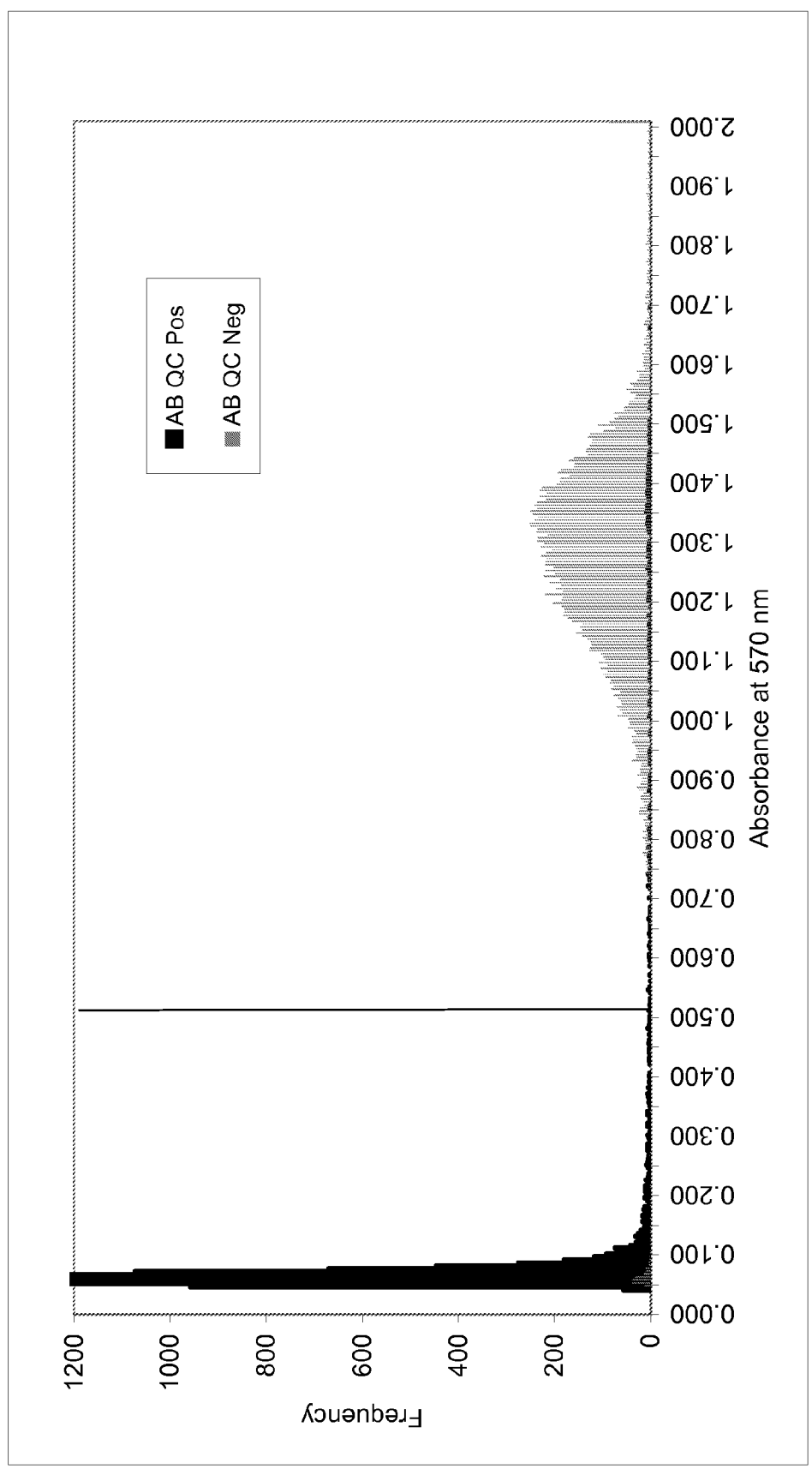

FIG. 50 shows a histogram derived from plotting the absorbance readings from the wells, versus the frequency of the values (number of wells read at that absorbance value). The frequency determination shows that the absorbance cut-off value of A570=0.5254 is located in the left-most tail (probability=0.007%) of the distribution of the CPE negative wells, and the right-most tail of the distribution of CPE positive wells (probability=0.02%). Comparison of the CPE detection of each well by both methods using this cut-off value, showed a one-to-one correspondence in most wells (45279 of 45840, 98.78%) for identification as either CPE positive or CPE negative, both by dye-based detection, and by microscopic examination.

Validation of Semi-Automated Potency Assay

The Semi-Automated median tissue culture infectious dose ($TCID_{50}$) potency assay for analysis of monovalent influenza vaccine virus is intended for the infectivity/potency measurement of expanded wild-type influenza (eWT), master virus seed (MVS), manufacturer's working virus seed (MWVS), and virus harvest (VH) samples. The assay was validated to demonstrate the precision (repeatability, intermediate precision and reproducibility), linearity, accuracy, and range of a Semi-Automated $TCID_{50}$ assay, and show that it provides comparable results to a manual $TCID_{50}$ assay. Validation tests were carried out with three different monovalent vaccine strains, chosen to include one Type A/H1N1, one Type A/H3N2 strain, and one Type B strain. The assay validation was carried out by two separate groups in different laboratories, to demonstrate laboratory-to-laboratory reproducibility. The precision (between-test variability), linearity, accuracy and range of a semi-automated assay are compared with those observed for a manual assay in Table 53.

The between-test standard deviation (SD) of the semi-automated assay, was evaluated from six tests performed on each of three vaccine strains, by the same analyst group, on the same pipetting station (each test result is obtained by averaging 12 determinations obtained over three days). The acceptance criterion for the between test variability of the semi-automated assay was 0.25 log10 $TCID_{50}$/ml, which is the half-width of the 95% confidence interval for a single test result based on the highest observed variability (0.11 log10 $TCID_{50}$units) of the manual assay. The actual SD values obtained with the semi-automated assay, for the three strains, ranged between 0.06–0.09 log10$TCID_{50}$/mL. These values are within the acceptance criterion of SD<0.25 log10 $TCID_{50}$ units and are comparable to the between-test variability (0.07 to 0.11 log10 $TCID_{50}$ units) observed for the manual $TCID_{50}$ assay, from nine repeat tests performed on three independent lots of each of three strains.

The assay was demonstrated to be linear over a 105-fold dilution range(titer range of 4.2–9.3 log10$TCID_{50}$/mL), by showing that the relationship of the calculated and measured $TCID_{50}$ titer passed a test for lack of fit to a linear model at the 1% significance level. The assay was accurate, with slopes of 1.00–1.02 for the three strains, which were all within the acceptance criterion of slope of 1±0.1. The linearity, accuracy and range of the semi-automated assay are comparable with the manual assay. See Table 53.

Intermediate precision of the semi-automated assay was demonstrated by fitting a random effects model to a set of 18 tests obtained by two analyst groups over nine different assay days, on one type A and one type B vaccine virus strain. The measured standard deviation ranges for the between day variability (SD(day)), between analyst group variability (SD(analyst)), and between instrument variability (SD(instrument)) were respectively 0.04–0.08, 0.14–0.16, and 0.000–0.03, which met the acceptance criteria of SD(day)<0.3, SD(analyst)<0.4, and SD(instrument)<0.4.

The inter-laboratory reproducibility of the assay was demonstrated by carrying out assays on one Type A/H1N1one TypeA/H3N2 and one Type B strain in two different laboratories. The acceptance criterion for laboratory-to-laboratory reproducibility required the two sided 90% confidence interval for the difference in the mean results from the two laboratories to be within ±0.3 log10TCID50/mL. This acceptance criterion was met, with the lower and upper bounds of the 90% confidence intervals of greater than −0.05 and less than +0.15, respectively, for all three strains.

A detailed statistical comparison was performed to demonstrate the comparability of the Manual and Semi-Automated assays. Two vaccine strains, one Type A/H1N1 (A/New Caledonia/20/99) and one Type B (B/Yamanashi/166/98), were assayed manually to obtain 18 test results on each strain. The data for all 18 test results obtained manually for each strain, were pooled and compared with the pooled test results from the precision and intermediate precision studies carried out for semi-automated test (18 test results per strain). The Proc Mixed method in SAS was used to estimate the between method mean difference and its 90% confidence interval (CI). The acceptance criterion was that the 90% CI must be within ±0.3 log10TCID$_{50}$/mL, i.e. the lower bound (LB) of the 90% CI must be greater than −0.3, and the upper bound (UB) must be less than 0.3. The results are presented in the assay validation report and summarized in Table 54, below. As may be seen from the results in, the two-sided 90% confidence intervals were within the acceptance criteria of ±0.3 log10TCID$_{50}$/mL for both strains, with actual estimates of the lower and upper bounds ranging between−0.05 and 0.10 log10TCID$_{50}$/mL.

Thus, in summary, while Manual TCID$_{50}$ Potency Assay for Influenza Virus Monovalent, is the traditional validated assay for the infectivity/potency measurement of monovalent influenza vaccine strains in expanded wild-type influenza (eWT) Master Virus Seed (MVS), Manufacturer's Working Virus Seed (MWVS), and Virus Harvest (VH) samples, it is a labor-intensive method involving numerous manual pipetting steps, which pose a repetitive motion injury hazard to analysts. In addition it uses a manual microscopic CPE readout, which limits the assay throughput to 3 tests per test day per analyst. Automation of the plate-washing and manual pipetting steps, and substitution of MTT dye-based detection of CPE for the manual microscopic readout can result in development of a Semi-Automated TCID$_{50}$ Potency Assay for Influenza Virus Monovalent. The implementation of the semi-automated assay, for testing of monovalent materials optionally increases the assay throughput 2–3 fold, and allows practical commercialization of vaccines such as FluMist™ Vaccine at the anticipated level of doses for market. An additional benefit is a lowered risk of repetitive motion injuries for Quality Control analysts.

The semi-automated assay has been validated to demonstrate repeatability, intermediate precision, linearity, and accuracy for assay of viral materials in the titer range of 4.2–9.3 log10TCID$_{50}$/mL in one group. The assay was also validated to demonstrate inter-laboratory reproducibility with another group.

A detailed statistical comparison of results obtained by using both the semi-automated assay and the manual assay, for repeated potency measurements of one Type A and one Type B influenza strains, also showed that the two assays yield comparable results. Thus, the semi-automated assay is demonstrated to be comparable to the manual assay for use in the potency measurement of expanded wild-type influenza, FluMist™ master virus seed (MVS), manufacturer's working virus seed (MWVS), and virus harvest (VH) samples.

Universal Cutoff Value of CPE in Semi-automated TCID$_{50}$ Assays

In yet other embodiments herein other variations and modifications of TCID$_{50}$ assays are employed to determine potency of vaccine/viruses. One such modification is the confirmation of the universal cutoff value for the assessment of CPE for the TCID$_{50}$ SemiAutomated Potency Assay for influenza virus monovalent. The "SemiAutomated TCID$_{50}$ Potency Assay for Influenza Virus Monovalent" (see above) uses the viable cell dye MTT (3-(4,5-dimethylthiazol-2-yl)-2,5-diphenyltetrazolium bromide) to score the cytopathic effect (CPE) in infected monolayers of MDCK cells. To reliably determine virus potency values using the MTT colorimetric endpoint to detect the number of CPE-positive wells, it is useful to establish an absorbance cutoff value that reproducibly distinguishes between CPE-positive and CPE-negative wells. As described in other work by the inventors, a "universal cutoff" absorbance (A570) value of 0.5254 has been determined. In the "SemiAutomated TCID$_{50}$ Assay for Influenza Virus Monovalent," a well is considered CPE-positive with an absorbance value of A570<0.5254; CPE-negative wells have absorbance values of A570>0.5254.

The data summarized in this section validates the universal cutoff value determined previously. The extensive testing of cold-adapted influenza strains, A/New Caledonia/20/99 (type A/H1N1), A/Sydney/05/97 (type A/H3N2), and B/Yamanashi/166/98 (type B) not only generate reinforcing data for the universal cutoff assignment, but allow comparisons among analysts and instruments. The data presented herein substantiate the robustness, reproducibility and reliability of the Semi-Automated TCID$_{50}$ assay and demonstrate comparability to the validated manual potency assay. Thus, illustrating the strength of embodiments comprising these measurements.

As explained above, the median tissue culture infectious dose (TCID$_{50}$) assay is a cell-based assay that measures the potency of infectious cytocidal virions. Serial dilutions of a virus sample are added to confluent monolayers of Madin-Darby canine kidney (MDCK) cells grown in 96-well plates. Replication of the virus in the MDCK cells affects cell metabolism, eventually resulting in the release of progeny virus into the culture supernatant and cell death. The progeny viruses in turn infect other cells, resulting in the eventual destruction of the monolayer. The cytopathic effect (CPE) resulting from the infection is allowed to develop during an incubation period of six days. After this period of time, MTT is used to detect the presence or absence of CPE in the cell monolayer. Vital dyes like MTT have been used extensively as indicators of cell health and viability in cell-based bioassays (see, e.g., Denizot et al., *J. Immun. Methods* (1986) 89:271–277; Gerlier et al., (1986) *J. Immuno. Methods* 94:57–63, Heeg, et al., *J. Immuno Methods* (1985) 77:237–246, Mooseman *J. Immuno. Methods* (1983) 65:55–63, Tada, et al., *J. Immuno. Methods* (1986) 93:147–165, and Vistica, *Cancer Research* (1991) 51: 2515–2520 ). Wells containing an intact monolayer of viable cells (CPE-negative) process the dye to a purple formazan dye product and yield a high absorbance value at 570 nm ($A_{570}$). In contrast, CPE-positive wells are marked by lower absorbance values due to the partial or complete monolayer destruction caused by the virus. To reliably determine virus potency values using a colorimetric endpoint to detect the number of CPE-positive wells, it is useful to establish an absorbance cutoff value that reproducibly distinguished between CPE-positive and CPE-negative wells. Used in conjunction with the universal cutoff value, absorbance values from virus test samples are scored CPE-positive or CPE-negative. The number of CPE-positive wells is used to calculate the virus titer (log10 $TCID_{50}$/mL).

Work by the inventors and coworkers provides an initial recommendation of the universal cutoff value based on two studies performed over several days by multiple analysts with three influenza virus strains. As described, a well was considered CPE-positive with an absorbance value of $A_{570}<0.5254$; CPE-negative wells had absorbance values of $A_{570}\geq0.5254$. The current section describes additional experiments designed to validate the absorbance cutoff value previously determined. Multiple analysts from two independent assay groups determined the potency of three reference virus strains using the SemiAutomated $TCID_{50}$ assay. As described, CPE assessed by the validated manual method of microscopic examination was considered the "gold standard" and compared to the CPE determined by MTT. The extensive testing of A/New Caledonia/20/99 (type A/H1N1), A/Sydney/05/97 (type A/H3N2), and B/Yamanashi/166/98 (type B) not only generated reinforcing data for the universal cutoff assignment, but allowed comparisons among analysts and instruments. The data presented herein substantiate the robustness, reproducibility and reliability of the SemiAutomated $TCID_{50}$ assay demonstrating comparability to the validated manual potency assay.

The development of the SemiAutomated potency assay required the use of reference virus strains with known potency values previously determined using a validated manual potency assay. The reference cold-adapted virus strains were as follows: A/New Caledonia/20/99, a type A/H1N1 virus; A/Sydney/05/97, a type A/H3N2 virus; and B/Yamanashi/166/98, a type B virus. The cold-adapted control virus strain A/Sydney/05/97, was used to confirm system suitability.

The method for the SemiAutomated $TCID_{50}$ Potency Assay for Influenza Monovalent has been developed by the inventors and coworkers as well as the overall assay configuration for half-plate replicates, as well as the visual CPE scoring method. See above. Briefly, confluent monolayers of MDCK cells in 96-well plates are washed twice with virus growth medium (VGM) using a Skatron™ Cell Washer. Serial ten-fold dilutions of virus samples are prepared in VGM containing TPCK-trypsin using a Matrix™ SerialMate Pipetting Station and 96-well dilution blocks. The last five serial dilutions (10-5 to 10-9) are transferred to MDCK cell plates to achieve final virus concentrations ranging from 10-6 to 10-10 relative to the initial starting titer. This format derives two potency data points from each plate. Since each sample is assayed on two plates, four replicate potency values are obtained. The 16 control wells (plate columns 6 and 7) receive virus-free VGM and serve as cell controls. After a 6-day incubation ($33\pm1°$ C. with $5\pm1\%$ $CO_2$) all wells are examined using a microscope and were scored for the presence or absence of CPE. Thus, a well is scored CPE-positive if the monolayer contained any evidence of virus destruction. Conversely, the monolayer in a CPE-negative well was completely intact.

After visually scoring the monolayers on the plates for CPE, the media is discarded and MTT (0.5 mg/mL), (US Biochemical Corporation, Cleveland, Ohio), prepared in phosphate buffered saline is dispensed to each well (100 μL/well). The monolayers are incubated with MTT for $6\pm0.5$ hours at $37\pm1°$ C. with $5\pm1\%$ $CO_2$. Solubilization buffer (100 μL of 20% SDS in 0.01N HCl) is added to each well and the plates are incubated for 16 to 20 hours at $37\pm1°$ C. in an environment of $5\pm1\%$ $CO_2$. The absorbance values at 570 nm are determined using a PerkinElmer-Wallac 1420 Multilabel Counter Spectrophotometer and were exported into a Microsoft™ Excel macro; a program used to calculate virus titer ($\log_{10}$ $TCID_{50}$/mL) from the number of CPE-positive wells.

Acceptance criteria are applied to the embodiment within this section. Accordingly, a plate was considered valid if not more than one of the sixteen cell control wells on each plate showed visual evidence of CPE, cell toxicity, or microbial contamination. In addition, for each half-plate to be valid, no less than 5 and no more than 36 wells had to be scored CPE-positive. Finally, both the mean and standard deviation (SD) of the four replicate $TCID_{50}$ titer values obtained for the monovalent virus control sample (A/Sydney/05/97) had to be within the qualified range reported in the qualified control certificate.

Estimates of sensitivity and specificity were calculated based on the relationship between the "gold standard" CPE and MT-assessed CPE shown below. TP denotes "true positive", FP is "false positive," FN is "false negative," and TN is "true negative." Therefore, "all positives" would be the sum of TP+FN, and "All negatives" would be the sum of FP+TN. See Table 55. The calculations are: Sensitivity for each replicate=(TP)/(All CPE positive) and Specificity for each replicate=(TN)/(All CPE negative)

In order to perform an instrument to instrument comparison, potency values were determined for three reference virus samples by six analysts in a first group using the SemiAutomated $TCID_{50}$ assay. Two sets of lab instruments AZ-039 and AZ-040 were used over three days. A second groups of testers used one instrument system, AZ-036. Three analysts from that group performed the SemiAutomated $TCID_{50}$ assay on three days using the three reference virus samples.

In order to perform an analyst to analyst comparison, each analyst in the testing (Analyst # 1–6) in Group 1 performed a SemiAutomated $TCID_{50}$ potency assay on the three reference strains using instrument AZ-039 over three days. In the second group, each of the three analysts (Analyst # 7–9) performed the SemiAutomated $TCID_{50}$ potency assay with the same three reference virus strains over three days using instrument AZ-036.

To reliably distinguish between CPE-positive and CPE-negative wells in the SemiAutomated $TCID_{50}$ potency assay using Mu, a universal cutoff value was statistically determined. In an effort to validate the use of this cutoff value, further independent evaluation by the two groups generated an additional 45,840 absorbance values. The results are presented below.

Sensitivity and specificity measurements were calculated using the manual microscopic method as the reference standard. The combined data from the two groups (n=45,840) are shown in Table 56. Using the recommended cutoff value of 0.5254 resulted in a sensitivity of 98.45% and a specificity of 99.12%. In addition, the data from the second group for sensitivity and specificity determinations were 99.15% and 99.99%, respectively. Likewise, the data from the first groups, for sensitivity and specificity were 98.13% and 98.71%, respectively. All data above (>95% sensitivity and >95% specificity) correlates with the data determined wherein a sensitivity of 99.05% and a specificity of 99.99% were determined.

Figure 51:
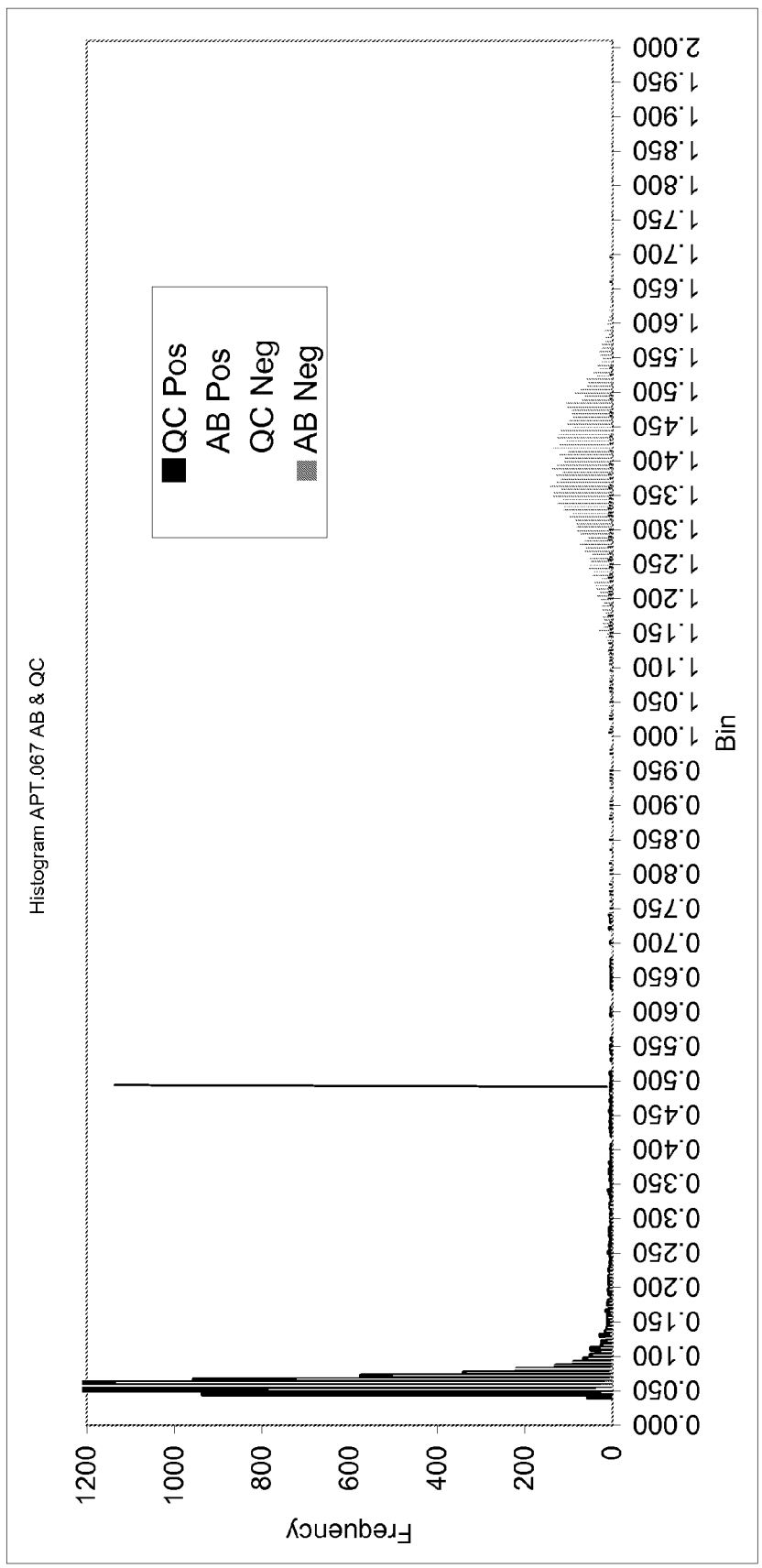

FIG. 51 shows a histogram derived from plotting the absorbance readings versus the frequency of the values (N=45,840). In agreement with the previous information, the combined data from the two groups indicate that the universal cutoff value of 0.5254 lies near the midpoint between the distribution of CPE-positive and CPE-negative wells. The frequency distribution shows that the recommended cutoff value resides in the left-most tail of the distribution of the control wells, corresponding to a probability of 0.007% in the tail extending towards the left. The cutoff value, 0.5254, also corresponds to a tail probability of 0.02%, when cutoff values were estimated using absorbance values from all CPE-positive wells. Furthermore, the distribution profiles evident in FIG. 51 highlight that absorbance values for CPE-positive wells are widely separated from absorbance values for CPE-negative wells A Comparison of the Mean Absorbance Values Obtained for CPE-Negative Control Wells Generated estimated a cutoff value of 0.5254 based on absorbance values from 6720 control wells was previously done. A mean absorbance value of 1.261 from the control wells was obtained with a standard deviation of 0.15. As shown in Table 57, the present study generated an additional 9168 control wells; 2880 were obtained from the second group and 6288 from the first group. Mean absorbance values of 1.226 and 1.235 were obtained from the second and first groups, respectively, with an overall mean absorbance value of 1.231. The difference between the combined mean absorbance value and that previously reported was only 0.03 absorbance values (see Table 57). This is a very small difference given that the data were generated over a 6-month period. The studies described previously were conducted over two consecutive months, while the studies described herein were conducted in second groups four months prior to that done by the first group.

Table 58 summarizes the potency values obtained for the three reference virus strains using the different instruments in the two groups in order to perform an instrument to instrument comparison. Six analysts from the first group performed the SemiAutomated $TCID_{50}$ Assay using two sets of instruments (designated AZ-039 and AZ-040). For A/New Caledonia/20/99 the overall mean ranged from 9.2 to 9.3 $log10TCID_{50}$/mL and the titer did not vary more than 0.09 $log10TCID_{50}$/mL between AZ-039 and AZ-040 (see Table 58). For A/Sydney/05/97 the overall mean ranged from 8.5 to 8.6 $log10TCID_{50}$/mL and did not vary more than 0.02 $log10TCID_{50}$/mL between AZ-039 and AZ-040. For B/Yamanashi/166/98 the overall mean ranged from 8.3 to 8.4 $log10TCID_{50}$/mL and did not vary more than 0.12 $log10TCID_{50}$/mL between AZ-039 and AZ-040. The second group produced results using one instrument system (AZ-036). Three analysts performed the SemiAutomated $TCID_{50}$ assay on three days with the three reference virus samples. The results of the mean difference between instruments in the second group and Quality Control Laboratory did not vary more than 0.09 $log10TCID_{50}$/mL for A/New Caledonia/20/99, 0.08 $log10TCID_{50}$/mL for A/Sydney/05/97 and 0.12 $log10TCID_{50}$/mL for B/Yamanashi/166/98. The mean difference data was calculated between the two instruments in the first group (AZ-039 and AZ-040) and between the first and second groups (AZ-036).

In order to do an analyst to analyst comparison, in the first group each analyst (Analyst 1 through 6) performed a SemiAutomated $TCID_{50}$ potency assay for A/New Caledonia/20/99, A/New Sydney/05/97, and B/Yamanashi/166/98 on Instrument AZ-039 over three days. In the second group, each of three analysts (Analyst 7 through 9) performed the SemiAutomated $TCID_{50}$ potency assay with the same virus strains over three days on Instrument AZ-036. The potency values were calculated for each virus and are shown in Table 59. The variability among the first group's results was less than or equal to 0.3 log10TCID50/mL for the three virus samples tested. Similarly, the variability among the second group's potency values was less than or equal to 0.2 $log10TCID_{50}$/mL. An overall comparison between the two groups of analysts was less than ±0.3 log10TCID50/mL for the three reference virus samples. The standard deviations (SD) for the test results (four replicates tested over three days) ranged between 0.11 and 0.27. Because the SD values were less than the acceptance criterion value of $0._{50}$, all were valid.

The results provided in this section validate a "universal cutoff" absorbance value (0.5254). There is a high level of confidence in the universal cutoff value because the studies produce strongly concordant data despite being generated by multiple analysts in independent assay groups over a relatively long timeframe. To summarize, control (CPE-negative) absorbance values generated by the two groups not only agreed with each other, but were virtually the same as the mean value reported previously (see, Table 57). The sensitivity and specificity values were very similar between the two groups; and agreed with previous work (see FIG. 51 and Table 57). In the two groups, the "universal cutoff" for the SemiAutomated $TCID_{50}$ potency assay, using MTT to assess CPE, produced potency values that were comparable to each other and to those obtained by the validated manual $TCID_{50}$ potency assay. Finally, the SemiAutomated system has several procedural advantages over the manual method. The use of instrumentation to replace the labor-intensive steps of manually pipetting and microscopically examining assay plates increases capacity and allows for a higher throughput. In addition, the spectrophotometric CPE readout and subsequent automated potency calculations provide a printout and/or an electronic record of the results.

Definitions

Unless defined otherwise, all scientific and technical terms are understood to have the same meaning as commonly used in the art to which they pertain. For the purpose of the present invention the following terms are defined below.

The terms "nucleic acid," "polynucleotide," "polynucleotide sequence" and "nucleic acid sequence" refer to single-stranded or double-stranded deoxyribonucleotide or ribonucleotide polymers, or chimeras or analogues thereof. As used herein, the term optionally includes polymers of analogs of naturally occurring nucleotides having the essential nature of natural nucleotides in that they hybridize to single-stranded nucleic acids in a manner similar to naturally occurring nucleotides (e.g., peptide nucleic acids). Unless otherwise indicated, a particular nucleic acid sequence optionally encompasses complementary sequences, in addition to the sequence explicitly indicated.

The term "gene" is used broadly to refer to any nucleic acid associated with a biological function. Thus, genes include coding sequences and/or the regulatory sequences required for their expression. The term "gene" applies to a specific genomic sequence, as well as to a cDNA or an mRNA encoded by that genomic sequence.

Genes also include non-expressed nucleic acid segments that, for example, form recognition sequences for other proteins. Non-expressed regulatory sequences include "promoters" and "enhancers," to which regulatory proteins such as transcription factors bind, resulting in transcription of adjacent or nearby sequences. A "tissue specific" promoter or enhancer is one which regulates transcription in a specific tissue type or cell type, or types.

The term "vector" refers to the means by which a nucleic acid can be propagated and/or transferred between organisms, cells, or cellular components. Vectors include plasmids, viruses, bacteriophage, pro-viruses, phagemids, transposons, and artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not autonomously replicating. Most commonly, the vectors of herein refer to plasmids.

An "expression vector" is a vector, such as a plasmid that is capable of promoting expression, as well as replication of, a nucleic acid incorporated therein. Typically, the nucleic acid to be expressed is "operably linked" to a promoter and/or enhancer, and is subject to transcription regulatory control by the promoter and/or enhancer.

A "bi-directional expression vector" is characterized by two alternative promoters oriented in the opposite direction relative to a nucleic acid situated between the two promoters, such that expression can be initiated in both orientations resulting in, e.g., transcription of both plus (+) or sense strand, and negative (−) or antisense strand RNAs.

In the context of the invention, the term "isolated" refers to a biological material, such as a nucleic acid or a protein, which is substantially free from components that normally accompany or interact with it in its naturally occurring environment. The isolated material optionally comprises material not found with the material in its natural environment, e.g., a cell. For example, if the material is in its natural environment, such as a cell, the material has been placed at a location in the cell (e.g., genome or genetic element) not native to a material found in that environment. For example, a naturally occurring nucleic acid (e.g., a coding sequence, a promoter, an enhancer, etc.) becomes isolated if it is introduced by non-naturally occurring means to a locus of the genome (e.g., a vector, such as a plasmid or virus vector, or amplicon) not native to that nucleic acid. Such nucleic acids are also referred to as "heterologous" nucleic acids.

The term "recombinant" indicates that the material (e.g., a nucleic acid or protein) has been artificially or synthetically (non-naturally) altered. The alteration can be performed on the material within, or removed from, its natural environment or state. Specifically, when referring to a virus, e.g., an influenza virus, is recombinant when it is produced by the expression of a recombinant nucleic acid.

The term "reassortant," when referring to a virus, indicates that the virus includes genetic and/or polypeptide components derived from more than one parental viral strain or source. For example, a 7:1 reassortant includes 7 viral genomic segments (or gene segments) derived from a first parental virus, and a single complementary viral genomic segment, e.g., encoding hemagglutinin or neuraminidase, from a second parental virus. A 6:2 reassortant includes 6 genomic segments, most commonly the 6 internal genes from a first parental virus, and two complementary segments, e.g., hemagglutinin and neuraminidase, from a different parental virus.

The term "introduced" when referring to a heterologous or isolated nucleic acid refers to the incorporation of a nucleic acid into a eukaryotic or prokaryotic cell where the nucleic acid can be incorporated into the genome of the cell (e.g., chromosome, plasmid, plastid or mitochondrial DNA), converted into an autonomous replicon, or transiently expressed (e.g., transfected mRNA). The term includes such methods as "infection," "transfection," "transformation," and "transduction." In the context of the invention, a variety of methods can be employed to introduce nucleic acids into prokaryotic cells, including electroporation, calcium phosphate precipitation, lipid mediated transfection (lipofection), etc.

The term "host cell" means a cell that contains a heterologous nucleic acid, such as a vector, and supports the replication and/or expression of the nucleic acid. Host cells can be prokaryotic cells such as *E. coli*, or eukaryotic cells such as yeast, insect, amphibian, avian or mammalian cells, including human cells. Exemplary host cells in the context of the invention include Vero (African green monkey kidney) cells, BHK (baby hamster kidney) cells, primary chick kidney (PCK) cells, Madin-Darby Canine Kidney (MDCK) cells, Madin-Darby Bovine Kidney (MDBK) cells, 293 cells (e.g., 293T cells), and COS cells (e.g., COS1, COS7 cells).

Influenza Virus

The compositions and methods herein are primarily concerned with production of influenza viruses for vaccines. Influenza viruses are made up of an internal ribonucleoprotein core containing a segmented single-stranded RNA genome and an outer lipoprotein envelope lined by a matrix protein. Influenza A and influenza B viruses each contain eight segments of single stranded negative sense RNA. The influenza A genome encodes eleven polypeptides. Segments 1–3 encode three polypeptides, making up a RNA-dependent RNA polymerase. Segment 1 encodes the polymerase complex protein PB2. The remaining polymerase proteins PB1 and PA are encoded by segment 2 and segment 3, respectively. In addition, segment 1 of some influenza strains encodes a small protein, PB1-F2, produced from an alternative reading frame within the PB 1 coding region. Segment 4 encodes the hemagglutinin (HA) surface glycoprotein involved in cell attachment and entry during infection. Segment 5 encodes the nucleocapsid nucleoprotein (NP) polypeptide, the major structural component associated with viral RNA. Segment 6 encodes a neuraminidase (NA) envelope glycoprotein. Segment 7 encodes two matrix proteins, designated M1 and M2, which are translated from differentially spliced mRNAs. Segment 8 encodes NS1 and NS2, two nonstructural proteins, which are translated from alternatively spliced mRNA variants.

The eight genome segments of influenza B encode 11 proteins. The three largest genes code for components of the RNA polymerase, PB1, PB2 and PA. Segment 4 encodes the HA protein. Segment 5 encodes NP. Segment 6 encodes the NA protein and the NB protein. Both proteins, NB and NA, are translated from overlapping reading frames of a biscistronic mRNA. Segment 7 of influenza B also encodes two proteins: M1 and BM2. The smallest segment encodes two products, NS1 which is translated from the full length RNA, and NS2 which is translated from a spliced mRNA variant.

Influenza Virus Vaccine

Historically, influenza virus vaccines have primarily been produced in embryonated hen eggs using strains of virus selected based on empirical predictions of relevant strains. More recently, reassortant viruses have been produced that incorporate selected hemagglutinin and neuraminidase antigens in the context of an approved attenuated, temperature sensitive master strain. Following culture of the virus through multiple passages in hen eggs, influenza viruses are recovered and, optionally, inactivated, e.g., using formaldehyde and/or β-propiolactone (or alternatively used in live attenuated vaccines).

However, production of influenza vaccine in this manner has several significant concerns. For example, contaminants remaining from the hen eggs can be highly antigenic and/or pyrogenic, and can frequently result in significant side effects upon administration. Thus, as described herein, one aspect of the current invention involves replacement of some percentage of egg components with animal free media. More importantly, virus strains designated for vaccine production must be selected and distributed, typically months in advance of the next flu season to allow time for production and inactivation of influenza vaccine. Again, any improvements in production time, e.g., as through use of the methods and compositions of the current invention, are thus quite desirable.

Attempts at producing recombinant and reassortant vaccines in cell culture have been hampered by the inability of some of the strains approved for vaccine production to grow efficiently under standard cell culture conditions. Thus, prior work by the inventors and their coworkers provided a vector system, and methods for producing recombinant and reassortant viruses in culture, thus, making it possible to rapidly produce vaccines corresponding to one or many selected antigenic strains of virus. See, Multi-Plasmid System for the production of Influenza virus, cited above. Of course, such reassortments are optionally further amplified in hen eggs. Typically, the cultures are maintained in a system, such as a cell culture incubator, under controlled humidity and $CO_2$, at constant temperature using a temperature regulator, such as a thermostat to insure that the temperature does not exceed 35 ° C. Such pioneering work, as well as other vaccine production, can be further optimized and streamlined through use of the current invention in whole or part.

Reassortant influenza viruses can be readily obtained by introducing a subset of vectors corresponding to genomic segments of a master influenza virus, in combination with complementary segments derived from strains of interest (e.g., antigenic variants of interest). Typically, the master strains are selected on the basis of desirable properties relevant to vaccine administration. For example, for vaccine production, e.g., for production of a live attenuated vaccine, the master donor virus strain may be selected for an attenuated phenotype, cold adaptation and/or temperature sensitivity.

FluMist™

As mentioned previously, numerous examples and types of influenza vaccine exist. An exemplary influenza vaccine is FluMist™ which is a live, attenuated vaccine that protects children and adults from influenza illness (Belshe et al. (1998) The efficacy of live attenuated, cold-adapted, trivalent, intranasal influenza virus vaccine in children *N. Engl. J. Med.* 338:1405–12; Nichol et al. (1999) Effectiveness of live, attenuated intranasal influenza virus vaccine in healthy, working adults: a randomized controlled trial *JAMA* 282: 137–44). In typical embodiments, the methods and compositions of the current invention are preferably adapted to, or used with, production of FluMist™ vaccine. However, it will be appreciated by those skilled in the art that the steps/compositions herein are also adaptable to production of similar or even different viral vaccines.

FluMist™ vaccine strains contain, e.g., HA and NA gene segments derived from the wild-type strains to which the vaccine is addressed along with six gene segments, PB1, PB2, PA, NP, M and NS, from a common master donor virus (MDV). The MDV for influenza A strains of FluMist (MDV-A), was created by serial passage of the wild-type A/Ann Arbor/6/60 (A/AA/6160) strain in primary chicken kidney tissue culture at successively lower temperatures (Maassab (1967) Adaptation and growth characteristics of influenza virus at 25 degrees C. *Nature* 213:612–4). MDV-A replicates efficiently at 25° C. (ca, cold adapted), but its growth is restricted at 38 and 39° C. (ts, temperature sensitive). Additionally, this virus does not replicate in the lungs of infected ferrets (att, attenuation). The ts phenotype is believed to contribute to the attenuation of the vaccine in humans by restricting its replication in all but the coolest regions of the respiratory tract. The stability of this property has been demonstrated in animal models and clinical studies. In contrast to the ts phenotype of influenza strains created by chemical mutagenesis, the ts property of MDV-A does not revert following passage through infected hamsters or in shed isolates from children (for a recent review, see Murphy & Coelingh (2002) Principles underlying the development and use of live attenuated cold-adapted influenza A and B virus vaccines *Viral Immunol.* 15:295–323).

Clinical studies in over 20,000 adults and children involving 12 separate 6:2 reassortant strains have shown that these vaccines are attenuated, safe and efficacious (Belshe et al. (1998) The efficacy of live attenuated, cold-adapted, trivalent, intranasal influenza virus vaccine in children *N. Engl. J. Med.* 338:1405–12; Boyce et al. (2000) Safety and immunogenicity of adjuvanted and unadjuvanted subunit influenza vaccines administered intranasally to healthy adults *Vaccine* 19:217–26; Edwards et al. (1994) A randomized controlled trial of cold adapted and inactivated vaccines for the prevention of influenza A disease *J. Infect. Dis.* 169: 68–76 ; Nichol et al. (1999) Effectiveness of live, attenuated intranasal influenza virus vaccine in healthy, working adults: a randomized controlled trial *JAMA* 282:137–44). Reassortants carrying the six internal genes of MDV-A and the two HA and NA gene segments of a wild-type virus (i.e., a 6:2 reassortant) consistently maintain ca, ts and att phenotypes (Maassab et al. (1982) Evaluation of a cold-recombinant influenza virus vaccine in ferrets *J. Infect. Dis.* 146:780–900). Production of such reassorted virus using B strains of influenza are is more difficult, however.

Recent work, see, Multi-Plasmid System for the Production of Influenza Virus, cited above, has shown an eight plasmid system for the generation of influenza B virus entirely from cloned cDNA, and methods for the production of attenuated live influenza A and B virus suitable for vaccine formulations, such as live virus vaccine formulations useful for intranasal administration.

The system and methods described previously are useful for the rapid production in cell culture of recombinant and reassortant influenza A and B viruses, including viruses suitable for use as vaccines, including live attenuated vaccines, such as vaccines suitable for intranasal administration such as FluMist®. The methods of the current invention herein, are optionally used in conjunction with or in combination with such previous work involving, e.g., reassorted influenza viruses for vaccine production to produce viruses for vaccines in a more stable, consistent and productive manner.

Cell Culture

As previously stated, influenza virus optionally can be grown in cell culture. Typically, propagation of the virus is accomplished in the media compositions in which the host cell is commonly cultured. Suitable host cells for the replication of influenza virus include, e.g., Vero cells, BHK cells, MDCK cells, 293 cells and COS cells, including 293T cells, COS7 cells. Commonly, co-cultures including two of the above cell lines, e.g., MDCK cells and either 293T or COS cells are employed at a ratio, e.g., of 1:1, to improve replication efficiency. Typically, cells are cultured in a standard commercial culture medium, such as Dulbecco's modified Eagle's medium supplemented with serum (e.g., 10% fetal bovine serum), or in serum free medium, under controlled humidity and $CO_2$ concentration suitable for maintaining neutral buffered pH (e.g., at pH between 7.0 and 7.2). Optionally, the medium contains antibiotics to prevent bacterial growth, e.g., penicillin, streptomycin, etc., and/or additional nutrients, such as L-glutamine, sodium pyruvate, non-essential amino acids, additional supplements to promote favorable growth characteristics, e.g., trypsin, β-mercaptoethanol, and the like.

Procedures for maintaining mammalian cells in culture have been extensively reported, and are well known to those of skill in the art. General protocols are provided, e.g., in Freshney (1983) *Culture of Animal Cells: Manual of Basic Technique*, Alan R. Liss, New York; Paul (1975) *Cell and Tissue Culture*, 5$^{th}$ ed., Livingston, Edinburgh; Adams (1980) *Laboratory Techniques in Biochemistry and Molecular Biology-Cell Culture for Biochemists*, Work and Burdon (eds.) Elsevier, Amsterdam. Additional details regarding tissue culture procedures of particular interest in the production of influenza virus in vitro include, e.g., Merten et al. (1996) Production of influenza virus in cell cultures for vaccine preparation in Cohen and Shafferman (eds.) *Novel Strategies in Design and Production of Vaccines*, which is incorporated herein in its entirety for all purposes. Additionally, variations in such procedures adapted to the present invention are readily determined through routine experimentation and will be familiar to those skilled in the art.

Cells for production of influenza virus can be cultured in serum-containing or serum free medium. In some case, e.g., for the preparation of purified viruses, it is typically desirable to grow the host cells in serum free conditions. Cells can be cultured in small scale, e.g., less than 25 ml medium, culture tubes or flasks or in large flasks with agitation, in rotator bottles, or on microcarrier beads (e.g., DEAE-Dextran microcarrier beads, such as Dormacell, Pfeifer & Langen; Superbead, Flow Laboratories; styrene copolymer-trimethylamine beads, such as Hillex, SoloHill, Ann Arbor) in flasks, bottles or reactor cultures. Microcarrier beads are small spheres (in the range of 100–200 microns in diameter) that provide a large surface area for adherent cell growth per volume of cell culture. For example a single liter of medium can include more than 20 million microcarrier beads providing greater than 8000 square centimeters of growth surface. For commercial production of viruses, e.g., for vaccine production, it is often desirable to culture the cells in a bioreactor or fermenter. Bioreactors are available in volumes from under 1 liter to in excess of 100 liters, e.g., Cyto3 Bioreactor (Osmonics, Minnetonka, Minn.); NBS bioreactors (New Brunswick Scientific, Edison, N.J.); laboratory and commercial scale bioreactors from B. Braun Biotech International (B. Braun Biotech, Melsungen, Germany).

Regardless of the culture volume, in many desired aspects of the current invention, it is important that the cultures be maintained at an appropriate temperature, to insure efficient recovery of recombinant and/or reassortant influenza virus using temperature dependent multi plasmid systems (see, e.g., Multi-Plasmid System for the Production of Influenza Virus, cited above), heating of virus solutions for filtration, etc. Typically, a regulator, e.g., a thermostat, or other device for sensing and maintaining the temperature of the cell culture system and/or other solution, is employed to insure that the temperature is at the correct level during the appropriate period (e.g., virus replication, etc.).

In some embodiments herein (e.g., wherein reasserted viruses are to be produced from segments on vectors) vectors comprising influenza genome segments are introduced (e.g., transfected) into host cells according to methods well known in the art for introducing heterologous nucleic acids into eukaryotic cells, including, e.g., calcium phosphate co-precipitation, electroporation, microinjection, lipofection, and transfection employing polyamine transfection reagents. For example, vectors, e.g., plasmids, can be transfected into host cells, such as COS cells, 293T cells or combinations of COS or 293T cells and MDCK cells, using the polyamine transfection reagent TransIT-LT1 (Mirus) according to the manufacturer's instructions in order to produce reasserted viruses, etc. Approximately 1 μg of each vector to be introduced into the population of host cells with approximately 2 μl of TransIT-LT1 diluted in 160 μl medium, preferably serum-free medium, in a total volume of 200 μl. The DNA:transfection reagent mixtures are incubated at room temperature for 45 minutes followed by addition of 800 μl of medium. The transfection mixture is added to the host cells, and the cells are cultured as described above or via other methods well known to those skilled in the art. Accordingly, for the production of recombinant or reassortant viruses in cell culture, vectors incorporating each of the 8 genome segments, (PB2, PB1, PA, NP, M, NS, HA and NA) are mixed with approximately 20 μl TransIT-LT1 and transfected into host cells. Optionally, serum-containing medium is replaced prior to transfection with serum-free medium, e.g., Opti-MEM I, and incubated for 4–6 hours.

Alternatively, electroporation can be employed to introduce such vectors incorporating influenza genome segments into host cells. For example, plasmid vectors incorporating an influenza A or influenza B virus are favorably introduced into Vero cells using electroporation according to the following procedure. In brief, approximately $5 \times 10^6$ Vero cells, e.g., grown in Modified Eagle's Medium (MEM) supplemented with 10% Fetal Bovine Serum (FBS) are resuspended in 0.4 ml OptiMEM and placed in an electroporation cuvette. Twenty micrograms of DNA in a volume of up to 25 μl is added to the cells in the cuvette, which is then mixed gently by tapping. Electroporation is performed according to the manufacturer's instructions (e.g., BioRad Gene Pulser II with Capacitance Extender Plus connected) at 300 volts, 950 microFarads with a time constant of between 28–33 msec. The cells are remixed by gently tapping and, approximately 1–2 minutes following electroporation, 0.7 ml MEM with 10% FBS is added directly to the cuvette. The cells are then transferred to two wells of a standard 6 well tissue culture dish containing 2 ml MEM, 10% FBS. The cuvette is washed to recover any remaining cells and the wash suspension is divided between the two wells. Final volume is approximately 3.5 mL. The cells are then incubated under conditions permissive for viral growth, e.g., at approximately 33° C. for cold adapted strains.

Kits

To facilitate use of the methods and compositions of the invention, any of the vaccine components and/or compositions, e.g., reasserted virus in allantoic fluid, and various formulations, etc., and additional components, such as, buffer, cells, culture medium, useful for packaging and infection of influenza viruses for experimental or therapeutic vaccine purposes, can be packaged in the form of a kit. Typically, the kit contains, in addition to the above components, additional materials which can include, e.g., instructions for performing the methods of the invention, packaging material, and a container.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

TABLE 1

| | Description of Step | Detail of Step |
|---|---|---|
| Step 1. | Co-infection of master donor virus (MDV) and WT virus in CEK cells. | |
| Step 2. | Selection of reassorted viruses. | Depending on virus strain, can be done in eggs or in CEK cells. Select for MDV NA and/or HA. |
| Step 3. | Cloning of reassorted viruses. | |
| Step 4. | Purification of reassorted viruses in eggs. | |
| Step 5. | Expansion of reassorted viruses in eggs to generate a master viral strain (MVS). | |
| Step 6. | Expansion of MVS to produce a master working viral strain (MWVS). | |
| Step 7. | Conditioning, washing, primary incubation of the eggs, and inoculation. | Eggs containing the reassorted virus are optionally rocked during incubation. |
| Step 8. | Candling, inoculation, sealing, secondary incubation, etc., of eggs. | |
| Step 9. | Candling of the eggs and chilling. | |
| Step 10. | Harvesting of virus solution from the eggs. | Virus containing solutions are optionally warmed and sterile filtered to remove impurities/contaminants (bioburden). |
| Step 11. | Clarification of the virus solution. | The solution is also optionally ultrafiltered to, e.g., remove uric acid and other animal derived impurities and to stabilize the solution. |
| Step 12. | Stabilization of the virus solution. | Arginine is optionally added either in addition to or in place of gelatin or gelatin hydrolysate at pH 6.6 to 8.0 to stabilize the solution. Use of arginine exclusively avoids the introduction of additional animal products. |

TABLE 1-continued

| | Description of Step | Detail of Step |
|---|---|---|
| Step 13. | Potency assay of the virus solutions. | Optional use of a "universal reagent" and field focus assays as opposed to, e.g., TCID50 to determine potency. |
| Step 14. | Sterility assay of the virus solutions. | |
| Step 15. | NAF adjustment of the virus solutions. | NAF is optionally reduced/ replaced with buffer, e.g., to increase stability. |

TABLE 2

| Tube/Well of cell culture | MOI of MDV | MOI of wild-type | Target incubation time in hours |
|---|---|---|---|
| 1 | 5.0 | 1.0 | 24 |
| 2 | 5.0 | 0.2 | 24 |
| 3 | 1.0 | 1.0 | 24 |
| 4 | 1.0 | 0.2 | 24 |
| 5 | 1.0 | 0.04 | 24 |
| 6 | n/a | n/a | 24 |

TABLE 3

| Manufacture Process | Detection | Type/Assay Time | Potential Alternatives |
|---|---|---|---|
| Egg pre/post inoculation | Egg Candling | Manual/hours | Automated candling of eggs or thermal imaging of eggs |
| Virus harvest | MPA<br>Bioburden | Manual/14 days<br>Manual/3 days | Bioluminence based detection or MPN |
| Virus Harvest | Mycoplasma growth | Manual/28 days | PCR |
| Virus harvest | Mycobacterium growth | Manual/56 days | PCR or clinical diagnostic systems |

TABLE 4

| Virus Type | Strain and Isolate Number |
|---|---|
| A H1N1 | ca A/Beijing/262/95 |
| A H1N1 | ca A/New Caledonia/20/99 |
| A H3N2 | ca A/Sydney/05/97 |
| A H3N2 | ca A/Panama/2007/99 |
| B | ca B/Victoria/504/2000 |
| B | ca B/Yamanashi/166/98 |

TABLE 5

A/Sydney/05/97 Virus potency [$\log_{10}$ $TCID_{50}$/mL].

| | Temperature | | |
|---|---|---|---|
| Process step | 5 ± 3° C. | 20 ± 3° C. | 31 ± 3° C. |
| Stabilized VAF (before treatment) | 8.7 ± 0.3 | 8.6 ± 0.2 | 8.8 ± 0.2 |
| Stabilized VAF (after treatment) | 9.0 ± 0.2 | 8.8 ± 0.2 | 8.8 ± 0.2 |
| Filtered VAF (pool) | 7.6 ± 0.2 | 7.7 ± 0.1 | 8.7 ± 0.1 |
| Centrifuged Stabilized VAF (control) | 8.4 ± 0.3 | 8.6 ± 0.2 | 8.7 ± 0.2 |
| Gain/Loss Filtered vs. Control | −0.8 | −0.7 | 0.0 |

NA = not assayed

All filtrations in Table 5 were performed from the same day harvest. Prior to filtration through Sartoclean CA and Sartopore 2 filters VAF was exposed for 60 minutes to 5 ± 3° C., 20 ± 3° C. and 31 ± 3° C.

TABLE 6

A/Sydney/05/97 neuraminidase activity [μU/mL].

| Process step | Temperature | | |
|---|---|---|---|
| | 5 ± 3° C. | 20 ± 3° C. | 31 ± 3° C. |
| Stabilized VAF (before treatment) | 34.4 | 36.4 | 38.4 |
| Stabilized VAF (after treatment) | 43.7 | 38.7 | 39.1 |
| Filtered VAF (pool) | BD | BD | 22.1 |
| Centrifuged Stabilized VAF (control) | 28.2 | 27.5 | 27.0 |
| Gain/Loss Filtered vs. Control | −28.2 | −27.5 | −4.9 |

BD = below detection (less than 5 μU/mL)
All filtrations in Table 6 were performed from the same day harvest. Prior to filtration through Sartoclean CA and Sartopore 2 filters VAF was exposed for 60 minutes to 5 ± 3° C., 20 ± 3° C. and 31 ± 3° C.

TABLE 7

A/Sydney/05/97 hemagglutinin activity [HA titer].

| Process step | Temperature | | |
|---|---|---|---|
| | 5 ± 3° C. | 20 ± 3° C. | 31 ± 3° C. |
| Stabilized VAF (before treatment) | 128 | 128 | 256 |
| Stabilized VAF (after treatment) | 128 | 256 | 128 |
| Filtered VAF (pool) | 4 | 16 | 64 |
| Centrifuged Stabilized VAF (control) | 128 | 64 | 256 |

All filtrations in Table 7 were performed from the same day harvest. Prior to filtration through Sartoclean CA and Sartopore 2 filters VAF was exposed for 60 minutes to 5 ± 3° C., 20 ± 3° C. and 31 ± 3° C.

TABLE 8

A/Sydney/05/97 Virus potency [$\log_{10}$ TCID$_{50}$/mL].

| Process step | Temperature | | |
|---|---|---|---|
| | 5 ± 3° C. | 20 ± 3° C. | 31 ± 3° C. |
| Stabilized VAF (before treatment) | 8.7 ± 0.1 | 8.5 ± 0.2 | 8.8 ± 0.1 |
| Stabilized VAF (after treatment) | 8.9 ± 0.2 | 8.9 ± 0.2 | 8.7 ± 0.2 |
| Filtered VAF (pool) | 7.6 ± 0.2 | 7.5 ± 0.2 | 8.7 ± 0.2 |
| Centrifuged Stabilized VAF (control) | 8.5 ± 0.2 | 8.5 ± 0.1 | 8.7 ± 0.1 |
| Gain/Loss Filtered vs. Control | −0.9 | −1.0 | 0.0 |

All filtrations in Table 8 were performed from the same day harvest. Prior to filtration through Sartoclean CA and Sartopore 2 filters VAF was exposed for 60 minutes to 5 ± 3° C., 20 ± 3° C. and 31 ± 3° C.*

TABLE 9

A/Sydney/05/97 neuraminidase activity [μU/mL].

| Process step | Temperature | | |
|---|---|---|---|
| | 5 ± 3° C. | 20 ± 3° C. | 31 ± 3° C. |
| Stabilized VAF (before treatment) | 29.8 | 26.1 | 27.0 |
| Stabilized VAF (after treatment) | 29.3 | 26.1 | 27.3 |
| Filtered VAF (pool) | BD | BD | 15.4 |
| Centrifuged Stabilized VAF (control) | 21.3 | 16.1 | 20.3 |
| Gain/Loss Filtered vs. Control | −21.3 | −16.1 | −4.9 |

BD = below detection (less than 5 μU/mL)
All filtrations were performed from the same day harvest. Prior to filtration through Sartoclean CA and Sartopore 2 filters VAF was exposed for 60 minutes to 5 ± 3° C., 20 ± 3° C. and 31 ± 3° C.*

TABLE 10

A/Sydney/05/97 hemagglutinin activity [HA titer].

| Process step | Temperature | | |
|---|---|---|---|
| | 5 ± 3° C. | 20 ± 3° C. | 31 ± 3° C. |
| Stabilized VAF (before treatment) | 256 | 128 | 256 |
| Stabilized VAF (after treatment) | 256 | 256 | 128 |
| Filtered VAF (pool) | 16 | 32 | 128 |
| Centrifuged Stabilized VAF (control) | 128 | 128 | 128 |

*10% of PBS was added to all experiments to adjust volume
All filtrations in Table 10 were performed from the same day harvest. Prior to filtration through Sartoclean CA and Sartopore 2 filters VAF was exposed for 60 minutes to 5 ± 3° C., 20 ± 3° C. and 31 ± 3° C.*

TABLE 11

A/Sydney/05/97 virus potency [$\log_{10}$ TCID$_{50}$/mL].

| Process step | Warming time | | |
|---|---|---|---|
| | 30 min | 90 min | 180 min |
| Stabilized VAF (before warming)* | 8.7 ± 0.2 | 8.7 ± 0.2 | 8.7 ± 0.2 |
| Stabilized VAF (warmed up) | 8.9 ± 0.2 | 8.9 ± 0.2 | 8.7 ± 0.2 |
| Filtered VAF (pool) | 8.5 ± 0.2 | 8.5 ± 0.2 | 8.9 ± 0.3 |
| Centrifuged Stabilized VAF (control)* | 8.9 ± 0.3 | 8.9 ± 0.3 | 8.9 ± 0.3 |
| Gain/Loss Filtered vs. Control | −0.4 | −0.4 | 0.0 |

All filtrations were performed from the same day harvest. Prior to filtration through Sartoclean CA and Sartopore 2 filters VAF was exposed to 31 ± 3° C. for 30, 90 or 180 minutes.

TABLE 12

A/Sydney/05/97 neuraminidase activity [μU/mL].

| Process step | Warming time | | |
|---|---|---|---|
| | 30 min | 90 min | 180 min |
| Stabilized VAF (before warming)* | 35.0 | 35.0 | 35.0 |
| Stabilized VAF (warmed up) | 38.0 | 35.2 | 36.0 |
| Filtered VAF (pool) | 17.8 | 22.9 | 23.1 |
| Centrifuged Stabilized VAF (control)* | 27.9 | 27.9 | 27.9 |
| Gain/loss Filtered vs. Control | −10.1 | −5.0 | −4.8 |

All filtrations were performed from the same day harvest. Prior to filtration through Sartoclean CA and Sartopore 2 filters VAF was exposed to 31 ± 3° C. for 30, 90 or 180 minutes.

TABLE 13

A/Sydney/05/97 hemagglutinin activity [HA titer].

| Process step | Warming time | | |
|---|---|---|---|
| | 30 min | 90 min | 180 min |
| Stabilized VAF (before warming)* | 256 | 256 | 256 |
| Stabilized VAF (warmed up) | 128 | 256 | 256 |
| Filtered VAF (pool) | 128 | 128 | 128 |
| Centrifuged Stabilized VAF (control)* | NA | NA | NA |

*Stabilized VAF and Centrifuged Stabilized VAF (control) samples were taken from the pool before VAF was divided into 4 individual experiments (0, 30, 60 or 90 minutes temperature treatment).
NA = not available
All filtrations were performed from the same day harvest. Prior to filtration through Sartoclean CA and Sartopore 2 filters, VAF was exposed to 31 ± 3° C. for 30, 90 or 180 minutes.

TABLE 14

A/Sydney/05/97 virus potency [$\log_{10}$ TCID$_{50}$/mL].

| Process step | Warming time | | | |
|---|---|---|---|---|
| | 0 min | 30 min | 60 min | 90 min |
| Stabilized VAF (before warming)* | 8.8 ± 0.3 | 8.8 ± 0.3 | 8.8 ± 0.3 | 8.8 ± 0.3 |
| Stabilized VAF (warmed up) | — | 8.7 ± 0.2 | 8.6 ± 0.1 | 8.6 ± 0.1 |
| Filtered VAF (pool) | 7.7 ± 0.1 | 8.3 ± 0.2 | 8.4 ± 0.2 | 8.6 ± 0.1 |
| Centrifuged Stabilized VAF (control)* | 8.6 ± 0.1 | 8.6 ± 0.1 | 8.6 ± 0.1 | 8.6 ± 0.1 |
| Gain/loss Filtered vs. Control | −0.9 | −0.3 | −0.2 | 0.0 |

All filtrations were performed from the same day harvest. Prior to filtration through Sartoclean CA and Sartopore 2 filters, VAF was exposed to 31 ± 3° C. for 0, 30, 60 or 90 minutes.

TABLE 15

A/Sydney/05/97 neuraminidase activity [µU/mL].

| Process step | Warming time | | | |
|---|---|---|---|---|
| | 0 min | 30 min | 60 min | 90 min |
| Stabilized VAF (before warming)* | 44.5 | 44.5 | 44.5 | 44.5 |
| Stabilized VAF (warmed up) | — | 44.5 | 41.0 | 47.5 |
| Filtered VAF (pool) | 6.0 | 17.5 | 26.0 | 30.0 |
| Centrifuged Stabilized VAF (control)* | 33.0 | 33.0 | 33.0 | 33.0 |
| Gain/loss Filtered vs. Control | −27.0 | −15.5 | −7.0 | −3.0 |

All filtrations were performed from the same day harvest. Prior to filtration through Sartoclean CA and Sartopore 2 filters, VAF was exposed to 31 ± 3° C. for 0, 30, 60 or 90 minutes.

TABLE 16

A/Sydney/05/97 hemagglutinin activity [HA titer].

| Process step | Warming time | | | |
|---|---|---|---|---|
| | 0 min | 30 min | 60 min | 90 min |
| Stabilized VAF (before warming)* | 64 | 64 | 64 | 64 |
| Stabilized VAF (warmed up) | — | 128 | 128 | 128 |
| Filtered VAF (pool) | 16 | 64 | 128 | 128 |
| Centrifuged Stabilized VAF (control)* | 64 | 64 | 64 | 64 |

*Stabilized VAF and Centrifuged Stabilized VAF (control) samples were taken from the pool before VAF was divided into 4 individual experiments (0, 30, 60 or 90 minutes temperature treatment).
All filtrations were performed from the same day harvest. Prior to filtration through Sartoclean CA and Sartopore 2 filters, VAF was exposed to 31 ± 3° C. for 0, 30, 60 or 90 minutes.

TABLE 17

Virus potency [$\log_{10}$ TCID$_{50}$/mL].

| Process step | Warming time | | | |
|---|---|---|---|---|
| | 0 min | 30 min | 60 min | 90 min |
| Stabilized VAF (before warming)* | 8.6 ± 0.2 | 8.6 ± 0.2 | 8.6 ± 0.2 | 8.6 ± 0.2 |
| Stabilized VAF (warmed up) | — | 8.6 ± 0.2 | 8.6 ± 0.2 | 8.5 ± 0.3 |
| Filtered VAF (pool) | 8.1 ± 0.2 | 8.1 ± 0.2 | 8.5 ± 0.2 | 8.5 ± 0.3 |
| Centrifuged Stabilized VAF (control)* | 8.6 ± 0.2 | 8.6 ± 0.2 | 8.6 ± 0.2 | 8.6 ± 0.2 |
| Gain/Loss Filtered vs. Control | −0.5 | −0.5 | −0.1 | −0.1 |

All filtrations were performed from the same day harvest. Prior to filtration through Sartoclean CA and Sartopore 2 filters, VAF was exposed to 31 ± 3° C. for 0 30, 60 or 90 minutes.

TABLE 18

Neuraminidase activity µU/mL.

| Process step | Warming time | | | |
|---|---|---|---|---|
| | 0 min | 30 min | 60 min | 90 min |
| Stabilized VAF (before warming)* | 35.5 | 35.5 | 35.5 | 35.5 |
| Stabilized VAF (warmed up) | — | 36.5 | 36.0 | 34.5 |
| Filtered VAF (pool) | 7.0 | 9.0 | 14.5 | 19.5 |
| Centrifuged Stabilized VAF (control)* | 23.0 | 23.0 | 23.0 | 23.0 |
| Gain/Loss Filtered vs. Control | −16 | −14 | −8.5 | −3.5 |

All filtrations were performed from the same day harvest. Before filtration through Sartoclean CA Sartopore 2 filters, VAF was exposed to 31 ± 3° C. for 0 30, 60 or 90 minutes.

TABLE 19

Hemagglutinin activity.

| Process step | Warming time | | | |
|---|---|---|---|---|
| | 0 min | 30 min | 60 min | 90 min |
| Stabilized VAF (before warming)* | 64 | 64 | 64 | 64 |
| Stabilized VAF (warmed up) | — | 64 | 64 | 128 |
| Filtered VAF (pool) | 16 | 32 | 64 | 64 |
| Centrifuged Stabilized VAF (control)* | 64 | 64 | 64 | 64 |

*Stabilized VAF and Centrifuged Stabilized VAF (control) samples were taken from the pool before VAF was divided into 4 individual experiments (0, 30, 60 or 90 minutes temperature treatment).
All filtrations were performed from the same day harvest. Before filtration through Sartoclean CA Sartopore2 filters VAF was exposed to 31 ± 3° C. for 0 30, 60 or 90 minutes.

TABLE 20

Virus potency [$\log_{10}$ TCID$_{50}$/mL] of six influenza strains.

| | Process step | | | |
|---|---|---|---|---|
| Influenza strain | Stabilized VAF* | Filtered VAF | Centrifuged Stabilized VAF* | Potency Gain/Loss |
| A/Beijing/262/95 RT** | 9.7 ± 0.1 | 9.6 ± 0.2 | 9.6 ± 0.3 | 0.0 |
| A/Beijing/262/95 31 ± 3° C. | 9.7 ± 0.1 | 9.4 ± 0.3 | 9.6 ± 0.3 | −0.2 |
| A/New Caledonia/20/99 RT** | 9.6 ± 0.2 | 9.3 ± 0.2 | 9.5 ± 0.2 | −0.2 |
| A/New Caledonia/20/99 31 ± 3° C. | 9.6 ± 0.2 | 9.3 ± 0.2 | 9.5 ± 0.2 | −0.2 |
| A/Sydney/05/97 RT | 8.8 ± 0.3 | 7.7 ± 0.1 | 8.6 ± 0.1 | −0.9 |
| A/Sydney/05/97 31 ± 3° C. | 8.8 ± 0.3 | 8.4 ± 0.2 | 8.6 ± 0.1 | −0.2 |
| A/Panama/2007/99 RT** | 8.5 ± 0.2 | 8.2 ± 0.1 | 8.5 ± 0.3 | −0.3 |
| A/Panama/2007/99 31 ± 3° C. | 8.5 ± 0.2 | 8.6 ± 0.2 | 8.5 ± 0.3 | 0.1 |
| B/Victoria/504/2000 RT** | 8.3 ± 0.2 | 7.8 ± 0.2 | 8.4 ± 0.2 | −0.6 |
| B/Victoria/504/2000 31 ± 3° C. | 8.3 ± 0.2 | 8.4 ± 0.2 | 8.4 ± 0.2 | 0.0 |
| B/Yamanashi/166/98 RT** | 8.4 ± 0.2 | 8.3 ± 0.2 | 8.6 ± 0.2 | −0.3 |
| B/Yamanashi/166/98 31 ± 3° C. | 8.4 ± 0.2 | 8.4 ± 0.2 | 8.6 ± 0.2 | −0.2 |

*Stabilized VAF and Centrifuged Stabilized VAF (control) samples were taken from the pool before VAF was divided into individual experiments (RT and 31 ± 3° C.).
**RT room temperature
Both filtrations for the same strain were performed from the same day harvest. Prior to filtration through Sartoclean CA and Sartopore 2 filters, VAF was exposed to 31 ± 3° C. for 0 (RT) or 60 minutes.

TABLE 21

Neuraminidase activity [µU/mL] of six influenza strains.

| | Process step | | | |
|---|---|---|---|---|
| Influenza train | Stabilized VAF | Filtered VAF | Centrifuged Stabilized VAF | Activity Gain/Loss |
| A/Beijing/262/95 RT** | 55.5 | 47.5 | 52.0 | −4.5 |
| A/Beijing/262/95 31 ± 3° C. | 55.5 | 51.5 | 52.0 | −0.5 |
| A/New Caledonia/20/99 RT** | 49.5 | 47.5 | 48.5 | −1.0 |
| A/New Caledonia/20/99 31 ± 3° C. | 49.5 | 48.5 | 48.5 | 0.0 |
| A/Sydney/05/97 RT** | 44.5 | 6.0 | 33.0 | −27.0 |
| A/Sydney/05/97 31 ± 3° C. | 44.5 | 26.0 | 33.0 | −7.0 |
| A/Panama/2007/99 RT** | 61.0 | 16.5 | 48.0 | −31.5 |
| A/Panama/2007/99 31 ± 3° C. | 61.0 | 40.0 | 48.0 | −8.0 |
| B/Victoria/504/2000 RT** | 58.5 | 20.5 | 44.0 | −23.5 |
| B/Victoria/504/2000 31 ± 3° C. | 58.5 | 37.0 | 44.0 | −7.0 |

TABLE 21-continued

Neuraminidase activity [μU/mL] of six influenza strains.

| Influenza train | Process step | | | |
|---|---|---|---|---|
| | Stabilized VAF | Filtered VAF | Centrifuged Stabilized VAF | Activity Gain/Loss |
| B/Yamanashi/166/98 RT** | 66.5 | 51.0 | 55.5 | −4.5 |
| B/Yamanashi/166/98 31 ± 3° C. | 66.5 | 53.0 | 55.5 | −2.5 |

*Stabilized VAF and Centrifuged Stabilized VAF (control) samples were taken from the pool before VAF was divided into individual experiments (RT and 31 ± 3° C.).
**RT = room temperature
Both filtrations for the same strain were performed from the same day harvest. Prior to filtration through Sartoclean and CA Sartopore 2 filters, VAF was exposed to 31 ± 3° C. for 0 (RT) or 60 minutes.

TABLE 22

Hemagglutinin activity [HA titer] of six influenza strains.

| Influenza train | Process step | | | |
|---|---|---|---|---|
| | Stabilized VAF* | Stabilized Warmed up VAF | Filtered VAF | Centrifuged Stabilized VAF* |
| A/Beijing/262/95 RT** | 1024 | — | 128 | 1024 |
| A/Beijing/262/95 31 ± 3° C. | 1024 | 512 | 512 | 1024 |
| A/New Caledonia/20/99 RT** | 32 | — | 32 | 64 |
| A/New Caledonia/20/99 31 ± 3° C. | 32 | 32 | 32 | 64 |
| A/Sydney/05/97 RT** | 64 | — | 16 | 64 |
| A/Sydney/05/97 31 ± 3° C. | 64 | 128 | 128 | 64 |
| A/Panama/2007/99 RT** | 128 | — | 32 | 128 |
| A/Panama/2007/99 31 ± 3° C. | 128 | 128 | 64 | 128 |
| B/Victoria/504/2000 RT** | 128 | — | 32 | 128 |
| B/Victoria/504/2000 31 ± 3° C. | 128 | 64 | 64 | 128 |
| B/Yamanashi/166/98 RT** | 512 | — | 16 | 32 |
| B/Yamanashi/166/98 31 ± 3° C. | 512 | 32 | 32 | 32 |

*Stabilized VAF and Centrifuged Stabilized VAF (control) samples were taken from the pool before VAF was divided into individual experiments (RT and 31 ± 3° C.).
**RT = room temperature
Both filtrations for the same strain were performed from the same day harvest. Prior to filtration through Sartoclean and CA Sartopore 2 filters, VAF was exposed to 31 ± 3° C. for 0 (RT) or 60 minutes.

TABLE 23

Virus potency [$\log_{10}TCID_{50}$/mL] of six influenza strains.

| Influenza strain | Process step | | | |
|---|---|---|---|---|
| | Stabilized VAF* | Filtered VAF | Centrifuged Stabilized VAF* | Potency Gain/Loss |
| A/Beijing/262/95 RT** | 9.6 ± 0.1 | 9.4 ± 0.2 | 9.6 ± 0.1 | −0.2 |
| A/Beijing/262/95 31 ± 3° C. | 9.6 ± 0.1 | 9.5 ± 0.2 | 9.6 ± 0.1 | −0.1 |
| A/New Caledonia/20/99 RT** | 9.1 ± 0.2 | 9.5 ± 0.2 | 9.2 ± 0.2 | 0.3 |
| A/New Caledonia/20/99 31 ± 3° C. | 9.1 ± 0.2 | 9.2 ± 0.3 | 9.2 ± 0.2 | 0.0 |
| A/Sydney/05/97 RT** | 8.6 ± 0.2 | 8.1 ± 0.2 | 8.6 ± 0.2 | −0.5 |
| A/Sydney/05/97 31 ± 3° C. | 8.6 ± 0.2 | 8.5 ± 0.2 | 8.6 ± 0.2 | −0.1 |
| A/Panama/2007/99 RT** | 8.9 ± 0.2 | 8.3 ± 0.2 | 8.5 ± 0.2 | −0.2 |
| A/Panama/2007/99 31 ± 3° C. | 8.9 ± 0.2 | 8.6 ± 0.1 | 8.5 ± 0.2 | 0.1 |
| B/Victoria/504/2000 RT** | 7.6 ± 0.2 | 7.7 ± 0.2 | 7.9 ± 0.2 | −0.2 |
| B/Victoria/504/2000 31 ± 3° C. | 7.6 ± 0.2 | 7.7 ± 0.1 | 7.9 ± 0.2 | −0.2 |
| B/Yamanashi/166/98 RT** | 8.4 ± 0.1 | 8.2 ± 0.2 | 8.3 ± 0.3 | −0.1 |
| B/Yamanashi/166/98 31 ± 3° C. | 8.4 ± 0.1 | 8.3 ± 0.2 | 8.3 ± 0.3 | 0.0 |

*Stabilized VAF and Centrifuged Stabilized VAF (control) samples were taken from the pool before VAF was divided into individual experiments (RT and 31 ± 3° C.).
**RT = room temperature
Both filtrations for the same strain were performed from the same day harvest. Prior to filtration through Sartoclean CA and Sartopore2 filters, VAF was exposed to 31 ± 3° C. for 0 (RT) or 60 minutes.

TABLE 24

Neuraminidase activity [μU/mL] of six influenza strains.

| Influenza strain | Process step Stabilized VAF | Filtered VAF | Centrifuged Stabilized VAF* | Activity Gain/Loss |
|---|---|---|---|---|
| A/Beijing/262/95 RT** | 56.5 | 47.5 | 54.5 | −7.0 |
| A/Beijing/262/95 31 ± 3° C. | 64.5 | 56.0 | 58.5 | −1.5 |
| A/New Caledonia/20/99 RT** | 46.0 | 38.5 | 40.0 | −1.5 |
| A/New Caledonia/20/99 31 ± 3° C. | 46.0 | 43.0 | 40.0 | 3.0 |
| A/Sydney/05/97 RT** | 35.5 | 7.0 | 23.0 | −16.0 |
| A/Sydney/05/97 31 ± 3° C. | 35.5 | 14.5 | 23.0 | −8.5 |
| A/Panama/2007/99 RT** | 55.5 | 15.0 | 34.5 | −19.5 |
| A/Panama/2007/99 31 ± 3° C. | 60.5 | 42.5 | 39.0 | 3.5 |
| B/Victoria/504/2000 RT** | 35.0 | 21.0 | 28.5 | −7.5 |
| B/Victoria/504/2000 31 ± 3° C. | 39.0 | 25.5 | 31.5 | −6.0 |
| B/Yamanashi/166/98 RT** | 29.0 | 26.0 | 28.5 | −2.5 |
| B/Yamanashi/166/98 31 ± 3° C. | 33.5 | 27.5 | 29.5 | −2.0 |

*Stabilized VAF and Centrifuged Stabilized VAF (control) samples were taken from the pool before VAF was divided into individual experiments (RT and 31 ± 3° C.).
**RT = room temperature.
Both filtrations for the same strain were performed from the same day harvest. Prior to filtration through Sartoclean CA and Sartopore 2 filters, VAF was exposed to 31 ± 3° C. for 0 (RT) or 60 minutes.

TABLE 25

Hemagglutinin activity [HA titer] of six influenza strains.

| Influenza strain | Process step Stabilized VAF* | Stabilized Warmed up VAF | Filtered VAF | Centrifuged Stabilized VAF* |
|---|---|---|---|---|
| A/Beijing/262/95 RT** | 256 | — | 1024 | 512 |
| A/Beijing/262/95 31 ± 32° C. | 256 | 1024 | 2048 | 512 |
| A/New Caledonia/20/99 RT** | 512 | — | 512 | 512 |
| A/New Caledonia/20/99 31 ± 3° C. | 512 | 512 | 512 | 512 |
| A/Sydney/05/97 RT** | 64 | — | 16 | 64 |
| A/Sydney/05/97 31 ± 3° C. | 64 | 64 | 64 | 64 |
| A/Panama/2007/99 RT** | 256 | — | 64 | 256 |
| A/Panama/2007/99 31 ± 3° C. | 256 | 512 | 512 | 256 |
| B/Victoria/504/2000 RT** | 64 | — | 128 | 128 |
| B/Victoria/504/2000 31 ± 3° C. | 64 | 64 | 64 | 128 |
| B/Yamanashi/166/98 RT** | 128 | — | 32 | 128 |
| B/Yamanashi/166/98 31 ± 3° C. | 128 | 64 | 64 | 128 |

*Stabilized VAF and Centrifuged Stabilized VAF (control) samples were taken from the pool before VAF was divided into individual experiments (RT and 31 ± 3° C.).
**RT = room temperature. Both filtrations for the same strain were performed from the same day harvest. Prior to filtration through Sartoclean CA and Sartopore 2 filters, VAF was exposed to 31 ± 3° C. for 0 (RT) or 60 minutes.

TABLE 26

Analysis by SEC - Peak Area Comparison

| Sample Details | Sample ID | Peak Area at 220 Virus Peak ~(10.5 min) | Impurities Group 1 (18 to 21 min) | Impurities Group 2 (21 to 27 min) |
|---|---|---|---|---|
| Neat (VH) | 1X | 1221 | 31785 | 339528 |
| 10 times concentrated sample | 10X | 11192 | 126849 | 435652 |
| 1 × Washed 5 times with 1X-SPG | 1X-W | 1005 | 2131 | 2510 |
| 10 × washed with 1X-SPG 5 times | 10X-W | 10282 | 15858 | 2194 |
| Permeate or filtrate | Permeate | 25 | 33837 | 360812 |
| Wash-1 | W-1 | | 6626 | 71260 |
| Wash-2 | W-2 | | 2296 | 15773 |
| Wash-3 | W-3 | | 1879 | 5765 |
| Wash-4 | W-4 | | 1046 | 3110 |
| Wash-5 | W-5 | | 876 | 2769 |

TABLE 27

A/New Caledonia - CELISA Values

| Sample Details | Sample ID | Replicate (N) | Mean +/− SD (CELISA) |
|---|---|---|---|
| Neat (VH) | 1X | 4 | 9.1 +/− 0.02 |
| 10 times concentrated sample | 10X | 4 | 10.0 +/− 0.05 |
| 1 × Washed 5 times with 1X-SPG | 1X-W | 4 | 8.9 +/− 0.03 |
| 10 × washed with 1X-SPG 5 times | 10X-W | 4 | 9.9 +/− 0.04 |
| Permeate or filtrate | Permeate | 4 | <LOQ |
| 10X diluted back to 1X with 1X-SPG | 10X to 1X | 4 | 9.0 +/− 0.08 |
| 10X-W diluted back to 1X-W with 1X-SPG | 10X-W to 1X-w | 4 | 8.9 +/− 0.02 |

TABLE 28

Composition of Representative Formulations

| Formulation Number | Composition |
|---|---|
| 1 | 10% Allantoic fluid in 100 millimolar phosphate buffer, 7% Sucrose, no added excipients |
| 2 | 60% Allantoic fluid in 100 millimolar phosphate buffer, 7% Sucrose, no added excipients |
| 3 | 10% Allantoic fluid in 100 millimiolar phosphate buffer, 7% sucrose [2] with 1% gelatin hydrolysate and 1% arginine |
| 4 | 60% Allantoic fluid in 100 millimolar phosphate buffer, 7% sucrose [3] with 1% gelatin hydrolysate and 1% arginine |
| 5 | 60% Allantoic fluid in 100 millimolar phosphate buffer, 10% sucrose, 2% arginine, 2% gelatin hydrolysate |
| 6 | 60% Allantoic fluid in 100 millimolar phosphate buffer, 10% sucrose, 2% arginine |
| 7 | 60% Allantoic fluid in 100 millimolar phosphate buffer, 10% sucrose, 2% arginine, 2% gelatin hydrolysate, 2.5 mM EDTA |
| 8 | 60% Allantoic fluid in 50 millimolar histidine buffer, 10% sucrose, 2% arginine, 2% gelatin hydrolysate |
| 9 | 60% Allantoic fluid in 50 millimolar histidine buffer, 10% sucrose, 2% arginine, 2% gelatin hydrolysate, 2.5 mM EDTA |

TABLE 29

Stability of Virus in Representative Formulations (loss of titer in $\log_{10}$/mL/month)

| Formulation Number | A/New Caledonia20/99 | A/Panama/ 2007/99 | B/Hong Kong/ 330/01 |
|---|---|---|---|
| 1 | 0.030 | 0.133 | 0.156 |
| 2 | 0.040 | 0.098 | 0.166 |
| 3 | 0.042 | 0.080 | 0.151 |
| 4 | 0.087 | 0.073 | 0.181 |
| 5 | 0.021 | 0.093 | 0.107 |
| 6 | No loss observed | 0.090 | 0.097 |
| 7 | 0.046 | 0.037 | 0.113 |
| 8 | 0.068 | 0.072 | 0.061 |
| 9 | 0.034 | 0.073 | 0.121 |

TABLE 30

| INGREDIENTS | Liq01 | Liq02 | Liq03 | Liq04 | Liq05 | Liq06 | Liq07 | Liq08 | Liq09 | avs43 Liq10 | avs53 Liq11 | Liq12 |
|---|---|---|---|---|---|---|---|---|---|---|---|---|
| KPO4 PH 7.2 | 100 mM | 100 mM | 100 mM | 100 mM | 100 mM |  | 100 mM | 100 mM | 100 mM | 100 mM | 100 mM |  |
| HEPES |  |  |  |  |  | 100 mM |  |  |  |  |  |  |
| Sucrose | 15% | 15% | 15% | 15% | 10% | 15% | 15% | 15% | 20% | 20% | 20% |  |
| Gelatin | 1% | 1% | 1% | 2% | 2% | 1% |  |  | 2% | 2% | 2% |  |
| Arginine | 2% |  |  | 2% | 2% | 2% | 2% | 2% | 2% |  |  |  |
| Glycine |  | 1% |  |  |  |  |  |  |  |  |  |  |
| Methionine |  |  |  |  |  |  |  |  |  | 0.15% |  |  |
| PVP |  |  |  |  |  |  | 1% |  |  |  |  |  |
| Dextran |  |  |  |  |  |  |  | 1% |  |  |  |  |
| Pluronic |  |  |  |  |  |  |  |  |  | 0.02% | 0.02% |  |
| CAIV Monovalent (added) | 10% | 10% | 10% | 10% | 10% | 10% | 10% | 10% | 10% | 10% | 10% | 10% |
| NAF (added) | 50% | 50% | 50% | 50% | 50% | 50% | 50% | 50% | 50% | 50% | 50% | 50% |
| Purified Water | q.s. | q.s. | q.s. | q.s. | q.s. | q.s. | q.s. | q.s. | q.s. | q.s. | q.s. | q.s. |

TABLE 31

B/Hongkong (in SPG) Target: 6.9 4° C. (Monthly)

| Formulation | 0 | 0 | 1 | 1 | 2 | 2 | 3 | 3 | 4 | 4 | 5 | 5 | 6 | 6 | Formulation |
|---|---|---|---|---|---|---|---|---|---|---|---|---|---|---|---|
| Liq 01 | 7.3 | 7.3 | 6.6 | 6.6 | 6.1 | 6.2 | 6.5 | 6.5 | 6.5 | 6.6 | 6.7 | 6.7 | 6.5 | 6.4 | 15Suc/1Gel/2Arg |
| Liq 01 (Repeat) | 6.9 |  | 6.8 | 6.7 | 6.6 | 6.6 | 6.5 | 6.6 | 6.5 | 6.4 | 6.4 | 6.4 |  |  | 15Suc/1Gel/2Arg |
| Liq 02 | 7.3 | 7.3 | 6.6 | 6.4 | 6.3 | 6.4 | 6.3 | 6.3 | 6.4 | 6.4 | 6.6 | 6.7 | 6.1 | 6.3 | 15Suc/1Gel/1Glyc |
| Liq 02 (Repeat) | 6.7 | 6.6 | 6.3 | 6.6 | 6.5 | 6.6 | 6.4 | 6.3 | 6.4 | 6.3 | 6.2 | 6.2 |  |  | 15Suc/1Gel/1Glyc |
| Liq 03 | 7.3 | 7.1 | 6.5 | 6.5 | 6.2 | 6.1 | 6.4 | 6.3 | 6.4 | 6.2 | 6.7 | 6.8 | 6.3 |  | 15Suc/1Gel |
| Liq 03 (Repeat) | 6.8 | 6.9 | 6.7 | 6.7 | 6.5 | 6.6 | 6.4 | 6.4 | 6.3 | 6.2 | 6.3 | 6.2 |  |  | 15Suc/1Gel |
| Liq 04 | 7.2 | 7.2 | 6.3 | 6.5 | 6.1 | 6.1 | 6.2 | 6.4 | 6.4 | 6.4 | 6.7 | 6.8 | 6.5 | 6.3 | 15Suc/2Gel/2Arg |
| Liq 04 (Repeat) | 6.8 | 6.8 | 6.7 | 6.7 | 6.5 | 6.5 | 6.4 | 6.4 | 6.4 | 6.4 | 6.3 | 6.2 |  |  | 15Suc/2Gel/2Arg |
| Liq 05 | 7.1 | 7.1 | 6.5 | 6.5 | 6.1 | 6.1 | 6.4 | 6.2 | 6.4 | 6.5 | 6.7 | 6.7 | 6.4 | 6.2 | 10Suc/2Gel/2Arg |
| Liq 05 (Repeat) | 7.0 | 7.1 | 6.8 | 6.6 | 6.6 | 6.6 | 6.7 | 6.9 | 6.7 | 6.8 | 6.9 | 6.9 |  |  | 10Suc/2Gel/2Arg |
| Liq 06 | 7.1 | 7.0 | 5.8 | 5.7 | 5.4 | 5.3 | 5.1 | 5.3 | 4.6 | 4.1 | 4.4 | 3.6 | 3.7 | 5.0 | 15Suc/1Gel/2Arg, HEPES |
| Liq 07 | 7.0 | 7.1 | 6.3 | 6.3 | 5.9 | 5.9 | 6.3 | 6.3 | 6.2 | 6.2 | 6.5 | 6.6 | 6.4 | 6.4 | 15Suc/1PVP/2Arg |
| Liq 07 (Repeat) | 6.7 | 6.6 | 6.4 | 6.5 | 6.3 | 6.4 | 6.4 | 6.3 | 6.3 | 6.2 | 6.1 | 6.2 |  |  | 15Suc/1PVP/2Arg |
| Liq 08 | 7.0 | 6.9 | 6.4 | 6.4 | 6.0 | 6.0 | 6.3 | 6.4 | 6.4 | 6.1 | 7.1 | 6.7 | 6.4 | 6.3 | 15Suc/1Dextran/2Arg |
| Liq 08 (Repeat) | 6.7 | 6.8 | 6.6 | 6.7 | 5.8 | 6.7 | 6.4 | 6.6 | 6.4 | 6.4 | 6.2 | 6.2 |  |  | 15Suc/1Dextran/2Arg |
| Liq 09 | 6.9 | 7.0 | 6.5 | 6.4 | 6.0 | 6.0 | 6.3 | 6.3 | 6.0 | 6.2 | 6.7 | 6.6 | 6.3 | 6.4 | 20Suc/2Gel/2Arg |
| Liq 09 (Repeat) | 6.9 | 6.9 | 6.7 | 6.8 | 6.6 | 6.6 | 6.6 | 6.5 | 6.3 | 6.4 | 6.4 | 6.3 |  |  | 20Suc/2Gel/2Arg |
| Liq 10 | 6.9 | 7.0 | 6 | 6.3 | 5.7 | 6.0 | 6.2 | 6.3 | 5.9 | 6.2 | 6.7 | 6.5 | 6.2 | 6.3 | 20Suc/2 Ge//0.15 Meth/0.02Plur |
| Liq 10 (Repeat) | 6.9 | 6.9 | 6.5 | 6.5 | 6.5 | 6.3 | 6.3 | 6 | 6.2 | 6.2 | 6.2 | 6 |  |  | 20Suc/2 Ge//0.15 Meth/0.02Plur |
| Liq 11 | 7.0 | 7.0 | 6.3 | 6.3 | 6.0 | 5.9 | 6.2 | 6.4 | 6.0 | 6.0 | 6.4 | 6.6 | 6.1 | 6.1 | 20Suc/2Ge//0.02Plur |
| Liq 12 | 6.9 | 7.0 | 6.3 | 6.5 | 6.4 | 6.4 | 6.1 | 6.1 | 5.8 | 5.3 | 5.1 | 5.3 | 5.6 | 5.3 | NAF only (60%) |

TABLE 32

B/Harbin (in SPG) Target: 7.0 4° C. (Monthly)

| Formulation | 0 | 0 | 1 | 1 | 2 | 2 | 3 | 3 | 4 | 4 | 5 | 5 | 6 | 6 | Formulation |
|---|---|---|---|---|---|---|---|---|---|---|---|---|---|---|---|
| Liq 01 | 7.1 | 7.2 | 6.6 | 6.7 | 6.2 | 6.4 | 6.6 | 6.6 | 6.8 | 6.8 | 6.7 | 6.8 | 6.2 | 6.1 | 15Suc/1Gel/2Arg |
| Liq 01 (Repeat) | 6.9 | 6.9 | 6.7 | 6.8 | 6.7 | 6.6 | 6.6 | 6.6 | 6.6 | 6.4 | 6.4 | 6.5 |  |  | 15Suc/1Gel/2Arg |
| Liq 02 | 7.1 | 7.1 | 6.7 | 6.6 | 6.2 | 6.0 | 6.5 | 6.5 | 6.5 | 6.7 | 6.7 | 6.7 | 6.0 | 6.0 | 15Suc/1Gel/1Glyc |
| Liq 02 (Repeat) | 6.9 | 7 | 6.8 | 6.7 | 6.5 | 6.6 | 6.5 | 6.5 | 6.3 | 6.4 | 6.3 | 6.2 |  |  | 15Suc/1Gel/1Glyc |
| Liq 03 | 7.1 | 7.0 | 6.5 | 6.7 | 6.1 | 6.0 | 6.5 | 6.5 | 6.7 | 6.5 | 6.7 | 7.1 | 6.2 | 6.3 | 15Suc/1Gel |
| Liq 03 (Repeat) | 6.9 | 6.9 | 6.7 | 6.7 | 6.5 | 6.5 | 6.6 | 6.5 | 6.5 | 6.4 | 6.4 | 6.4 |  |  | 15Suc/1Gel |
| Liq 04 | 7.0 | 7.0 | 6.5 | 6.8 | 6.1 | 6.2 | 6.5 | 6.6 | 7.0 | 6.9 | 7.3 | 7.1 | 6.4 | 6.5 | 15Suc/2Gel/2Arg |
| Liq 04 (repeat) | 6.8 | 6.8 | 6.7 | 6.7 | 6.7 | 6.6 | 6.5 | 6.5 | 6.4 | 6.5 | 6.4 | 6.5 |  |  | 15Suc/2Gel/2Arg |
| Liq 05 | 7.1 | 7.2 | 6.8 | 6.7 | 6.2 | 6.1 | 6.6 | 6.7 | 6.9 | 6.7 | 6.9 | 6.9 | 6.4 | 6.3 | 10Suc/2Gel/2Arg |
| Liq 05 (Repeat) | 7.0 | 7.0 | 6.6 | 6.5 | 6.7 | 6.8 | 6.8 | 6.8 | 6.7 | 6.8 | 6.7 | 6.6 |  |  | 10Suc/2Gel/2Arg |
| Liq 06 | 7.1 | 7.1 | 6.4 | 6.3 | 5.4 | 5.4 | 5.4 | 5.3 | 5.4 | 5.2 | 4.3 | 4.3 | 3.8 | ud | 15Suc/1Gel/2Arg, HEPES |
| Liq 07 | 7.0 | 7.1 | 6.7 | 6.8 | 6 | 6.2 | 6.4 | 6.4 | 6.5 | 6.6 | 6.4 | 6.7 | 6.4 | 6.5 | 15Suc/1PVP/2Arg |
| Liq 07 (Repeat) | 6.9 | 6.8 | 6.6 | 6.5 | 6.5 | 6.6 | 6.4 | 6.4 | 6.3 | 6.2 | 6.4 | 6.4 |  |  | 15Suc/1PVP/2Arg |
| Liq 08 | 7.1 | 6.9 | 6.6 | 6.9 | 5.9 | 6.1 | 6.4 | 6.4 | 6.6 | 6.9 | 6.7 | 6.7 | 6.2 | 6.4 | 15Suc/1Dextran/2Arg |
| Liq 08 (Repeat) | 6.8 | 6.9 | 6.7 | 6.6 | 6.6 | 6.6 | 6.4 | 6.4 | 6.2 | 6.4 | 6.4 | 6.3 |  |  | 15Suc/1Dextran/2Arg |
| Liq 09 | 6.9 | 7.0 | 6.8 | 6.9 | 6.1 | 6.2 | 6.5 | 6.5 | 6.8 | 6.8 | 6.6 | 6.9 | 6.4 | 6.4 | 20Suc/2Gel/2Arg |
| Liq 09 (Repeat) | 6.7 | 6.7 | 6.6 | 6.5 | 6.4 | 6.4 | 6.3 | 6.2 | 6.4 | 6.2 | 6.5 | 6.6 |  |  | 20Suc/2Gel/2Arg |
| Liq 10 | 7.0 | 7.0 | ud | ud | 6.1 | 6.2 | 6.4 | 6.4 | 6.7 | 6.8 | 6.5 | 6.6 | 6.6 | 6.4 | 20Suc/2 Ge//0.15 Meth/0.02Plur |
| Liq 10 (Repeat) | 6.8 | 6.7 | 6.7 | 6.7 | 6.6 | 6.5 | 6.5 | 6.3 | 6.4 | 6.4 | 6.3 | 6.3 |  |  | 20Suc/2 Ge//0.15 Meth/0.02Plur |
| Liq 11 | 6.9 | 6.9 | ud | ud | 6 | 6.1 | 6.4 | 6.5 | 6.6 | 6.7 | 6.6 | 6.3 | 6.5 | 6.4 | 20Suc/2Ge//0.02Plur |
| Liq 12 | 6.9 | 6.9 | 6.5 | 6.5 | 6.3 | 6.1 | 6.0 | 6.1 | 6.1 | 6.1 | 5.8 | 5.7 | 5.9 | 5.9 | NAF only (60%) |

TABLE 33

A/New Caledonia (in SPG) Target: 6.8 4° C. (Monthly)

| Formulation | 0 | 0 | 1 | 1 | 2 | 2 | 3 | 3 | 4 | 4 | 5 | 5 | 6 | 6 | Formulation |
|---|---|---|---|---|---|---|---|---|---|---|---|---|---|---|---|
| Liq 01 | 7.1 | 7.0 | 7.0 | 7.0 | 6.6 | 6.8 | 6.5 | 6.6 | 6.7 |  | 6.8 | 6.9 | 6.8 | 6.5 | 6.6 | 15Suc/1Gel/2Arg |
| Liq 01 (Repeat) | 7.0 | 7.0 | 6.9 | 6.7 | 6.7 | 6.6 | 6.5 | 6.5 | 6.6 |  | 6.7 | 6.6 | 6.6 |  |  | 15Suc/1Gel/2Arg |
| Liq 02 | 7.0 | 7.0 | 6.9 | 7.0 | 6.7 | 6.6 | 6.6 | 6.4 | 6.5 |  | 6.6 | 6.9 | 6.8 | 6.3 | 6.4 | 15Suc/1Gel/1Glyc |
| Liq 02 (Repeat) | 7.1 | 7.1 | 6.9 | 6.9 | 6.9 | 6.7 | 6.8 | 6.7 | 6.7 |  | 6.8 | 6.7 | 6.4 |  |  | 15Suc/1Gel/1Glyc |
| Liq 03 | 7.0 | 7.2 | 6.8 | 6.9 | 6.4 | 6.5 | 6.5 | 6.5 | 6.5 |  | 6.5 | 6.9 | 6.9 | 6.4 | 6.4 | 15Suc/1Gel |
| Liq 03 (Repeat) | 6.8 | 6.9 | 6.7 | 6.7 | 6.6 | 6.6 | 6.5 | 6.6 | 6.6 |  | 6.6 | 6.6 | 6.5 |  |  | 15Suc/1Gel |
| Liq 04 | 7.2 | 7.2 | 6.8 | 7.0 | 6.7 | 6.4 | 6.5 | 6.5 | 6.5 |  | 6.7 | 7.0 | 7.1 | 6.5 | 6.5 | 15Suc/2Gel/2Arg |
| Liq 04 (Repeat) | 6.9 | 7.0 | 6.8 | 6.9 | 6.8 | 6.9 | 6.8 | 6.8 | 6.7 |  | 6.6 | 6.5 | 6.4 |  |  | 15Suc/2Gel/2Arg |
| Liq 05 | 7.2 | 7.1 | 7.0 | 7.0 | 6.7 | 6.6 | 6.5 | 6.6 | 6.6 |  | 6.7 | 7.0 | 7.1 | 6.7 | 6.6 | 10Suc/2Gel/2Arg |
| Liq 05 (repeat) | 6.9 |  | 6.9 | 6.9 | 6.8 | 6.8 | 6.8 | 6.8 | 6.6 |  | 6.7 | 6.6 | 6.6 |  |  | 10Suc/2Gel/2Arg |
| Liq 06 | 6.9 | 6.9 | 6.4 | 6.3 | 5.5 | 5.5 | 5.4 | 5.0 | UD |  | UD | 4.7 | 4.7 | 3.8 | 4.1 | 15Suc/1Gel/2Arg, HEPES |
| Liq 07 | 7.1 | 7.1 | 6.5 | 6.6 | 6 | 6.1 | 6.3 | 6.3 | 6.3 |  | 6.3 | 6.8 | 6.6 | 6.4 | 6.2 | 15Suc/1PVP/2Arg |
| Liq 07 (Repeat) | 6.9 | 7.0 | 6.4 | 6.5 | 6.3 | 6.4 | 6.6 | 6.5 | 6.4 |  | 6.3 | 6.5 | 6.2 |  |  | 15Suc/1PVP/2Arg |
| Liq 08 | 7.1 | 6.9 | 6.8 | 6.9 | 6.3 | 6.4 | 6.4 | 6.4 | 6.5 |  | 6.5 | 6.8 | 7.3 | 6.4 | 6.4 | 15Suc/1Dextran/2Arg |

TABLE 33-continued

A/New Caledonia (in SPG) Target: 6.8 4° C. (Monthly)

| Formulation | 0 | 0 | 1 | 1 | 2 | 2 | 3 | 3 | 4 | 4 | 5 | 5 | 6 | 6 | Formulation |
|---|---|---|---|---|---|---|---|---|---|---|---|---|---|---|---|
| Liq 08 (Repeat) | 6.7 | 6.7 | 6.6 | 6.5 | 6.5 | 6.5 | 6.5 | 6.6 | 6.3 | | 6.5 | 6.5 | 6.3 | | 15Suc/1Dextran/2Arg |
| Liq 09 | 6.8 | 6.9 | 7.0 | 6.8 | 6.5 | 5.7 | 6.5 | 6.5 | 6.4 | | 6.5 | 7.1 | 7.2 | 6.4 | 6.3 20Suc/2Gel/2Arg |
| Liq 09 (Repeat) | 6.8 | 6.9 | 6.8 | 6.7 | 6.6 | 6.6 | 6.7 | 6.6 | 6.5 | | 6.6 | 6.6 | 6.3 | | 20Suc/2Gel/2Arg |
| Liq 10 | 6.7 | 6.9 | 6.8 | 6.8 | 6.6 | 6.5 | 6.4 | 6.3 | 6.2 | | 6.2 | 6.9 | 7.0 | 6.3 | 6.3 20Suc/2 Ge//0.15 Meth/0.02Plur |
| Liq 10 (Repeat) | 6.6 | 6.6 | 6.5 | 6.5 | 6.4 | 6.4 | 6.3 | 6.3 | 6.5 | | 6.3 | 6.2 | 6.2 | | 20Suc/2 Ge//0.15 Meth/0.02Plur |
| Liq 11 | 6.8 | 6.7 | 6.8 | 6.7 | 6.7 | 6.6 | 6.3 | 6.4 | 6.3 | | 6.2 | 6.7 | 6.8 | 6.4 | 6.3 20Suc/2Gel//0.02Plur |
| Liq 12 | 6.9 | 7.0 | 5.7 | 5.6 | 5.5 | 5.3 | 5.1 | 5.3 | 4.7 | | 4.6 | 4.5 | 4.5 | 4.4 | 4.5 NAF only (60%) |

TABLE 34

A/Panama (in SPG) Target: 7.4 4° C. (Monthly)

| Formulation | 0 | 0 | 1 | 1 | 2 | 2 | 3 | 3 | 4 | 4 | 5 | 5 | 6 | 6 | Formulation |
|---|---|---|---|---|---|---|---|---|---|---|---|---|---|---|---|
| Liq 01 | 7.6 | 7.6 | 7.4 | 7.3 | 6.9 | 7.1 | 6.6 | 6.6 | 6.8 | 7.1 | 7.4 | 7.4 | 6.6 | 6.7 | 15Suc/1Gel/2Arg |
| Liq 01 (Repeat) | 6.8 | 6.8 | 6.8 | 6.6 | 6.6 | 6.7 | 6.7 | 6.8 | 6.6 | 6.6 | 6.7 | 6.7 | | | 15Suc/1Gel/2Arg |
| Liq 02 | 7.6 | 7.6 | 7.3 | 7.3 | 6.9 | 6.4 | 6.6 | 6.6 | 6.9 | 6.8 | 7.3 | 7.4 | 6.6 | 6.6 | 15Suc/1Gel/1Glyc |
| Liq 02 (Repeat) | 7.3 | 7.0 | 7.3 | 7.1 | 7.1 | 7.4 | 7.3 | 7.2 | 7.2 | | 6.7 | 6.7 | | | 15Suc/1Gel/1Glyc |
| Liq 03 | 7.2 | 7.8 | 7.2 | 7.3 | 6.8 | 6.7 | 6.6 | 6.7 | 6.6 | 7.1 | 7.3 | 7.4 | 6.6 | 6.8 | 15Suc/1Gel |
| Liq 03 (Repeat) | 6.8 | 6.8 | 6.9 | 6.8 | 6.7 | 6.8 | 6.8 | 6.8 | 6.7 | 6.8 | 6.8 | 6.6 | | | 15Suc/1Gel |
| Liq 04 | 7.8 | 7.8 | 7.4 | 7.4 | 7.1 | 7.1 | 6.5 | 6.6 | 6.9 | 6.9 | 7.5 | 7.4 | 6.6 | 6.7 | 15Suc/2Gel/2Arg |
| Liq 04 (Repeat) | 7.0 | 7.1 | 6.9 | 6.9 | 6.8 | 6.9 | 6.6 | 6.8 | 6.7 | 6.6 | 6.7 | 6.8 | | | 15Suc/2Gel/2Arg |
| Liq 05 | 7.8 | 7.8 | 7.5 | 7.4 | 6.8 | 6.8 | 6.7 | 6.7 | 7.0 | 7.0 | 7.4 | 7.3 | 6.7 | 6.7 | 10Suc/2Gel/2Arg |
| Liq 05 (repeat) | 7.0 | 7.0 | 6.6 | 6.5 | 6.7 | 6.8 | 6.8 | 6.8 | 6.7 | 6.8 | 6.7 | 6.6 | | | 10Suc/2Gel/2Arg |
| Liq 06 | 7.7 | 7.6 | 6.9 | 7.0 | 6.3 | 6.4 | 6.2 | 5.9 | 5.8 | 5.8 | 6.0 | 6.0 | 5.0 | 4.8 | 15Suc/1Gel/2Arg, HEPES |
| Liq 07 | 7.2 | 7.1 | 7.4 | 7.0 | 7.0 | 6.6 | 6.7 | 6.5 | 7.0 | 7.1 | 7.2 | 7.3 | 6.6 | 6.3 | 15Suc/1PVP/2Arg |
| Liq 07 (Repeat) | 7.2 | 7.2 | 7.2 | 6.9 | 7.2 | 6.9 | 6.8 | 6.6 | 6.6 | 6.7 | 6.8 | 6.9 | | | 15Suc/1PVP/2Arg |
| Liq 08 | 7.1 | 7.2 | 7.1 | 7.2 | 6.6 | 6.8 | 6.7 | 6.8 | 6.9 | 6.9 | 7.2 | 7.2 | 6.5 | 6.6 | 15Suc/1Dextran/2Arg |
| Liq 08 (Repeat) | 7.2 | 6.8 | 7.0 | 6.8 | 6.9 | 6.9 | 6.9 | 6.5 | 6.8 | 6.9 | 6.9 | 6.7 | | | 15Suc/1Dextran/2Arg |
| Liq 09 | 7.4 | 7.3 | 6.9 | 6.9 | 6.7 | 7.0 | 6.3 | 6.8 | 6.7 | 7.0 | 7.3 | 7.3 | 6.5 | 6.5 | 20Suc/2Gel/2Arg |
| Liq 09 (Repeat) | 7.2 | 7.2 | 7.0 | 6.7 | 6.8 | 7.0 | 6.9 | 6.9 | 6.7 | 7.0 | 6.8 | 6.7 | | | 20Suc/2Gel/2Arg |
| Liq 10 | 7.2 | 7.1 | 7.1 | 7.1 | 6.8 | 6.6 | 6.6 | 6.4 | 6.7 | 6.7 | 7.3 | 7.2 | 6.5 | 6.6 | 20Suc/2 Ge//0.15 Meth/0.02Plur |
| Liq 10 (Repeat) | 7.0 | 6.7 | 6.7 | 6.7 | 6.7 | 6.7 | 6.6 | 6.6 | 6.6 | 6.6 | 6.6 | 6.5 | | | 20Suc/2 Ge//0.15 Meth/0.02Plur |
| Liq 11 | 7.1 | 6.9 | 7.1 | 7.2 | 6.5 | 6.6 | 6.7 | 6.5 | 6.6 | 6.9 | 7.2 | 7.3 | 6.6 | 6.4 | 20Suc/2Gel/0.02Plur |
| Liq 12 | 7.2 | 7.3 | 6 | 6.4 | 6.3 | 5.9 | 4.9 | 5.0 | 5.1 | 4.5 | 4.6 | 4.6 | 3.8 | 4.1 | NAF only (60%) |

TABLE 35

| Ingredients | Control Liq13a | Liq14 | Liq15 | Liq15 (degassed) | Liq16 | Liq17 | Liq18 | Liq19 | Liq20 |
|---|---|---|---|---|---|---|---|---|---|
| KPO4 buffer, pH 7.2 (1.1 mM from virus included) | 1.1 mM | | 100 mM | 100 mM | 100 mM | 100 mM | 100 mM | 100 mM | 100 mM |
| Citrate buffer, pH 7.2 | | 100 mM | | | | | | | |
| Sucrose (0.7% from virus included) | 7% | 10% | 10% | 10% | 10% | 10% | 10% | 10% | 10% |
| Gelatin | | 2% | 2% | 2% | 2% | 2% | 2% | 2% | 2% |
| Arginine | | 2% | 2% | 2% | 2% | 2% | 2% | 2% | 2% |
| Aprotinin (PI) | | | | | 0.02% | | | | |
| Leupeptin hemisulfate (PI) | | | | | | 0.02% | | | |
| Lysozyme Inhibitor | | | | | | | 0.1% | | |
| Protease Inhibitor Cocktail | | | | | | | | (0.6% DMSO) 0.5%* | |
| PMSF | | | | | | | | | 1 mM |
| Cytidine 2' monophosphate | | | | | | | | | |
| NAF (from virus) | 10% | 10% | 10% | 10% | 10% | 10% | 10% | 10% | 10% |
| NAF (added) | 50% | 50% | 50% | 50% | 50% | 50% | 50% | 50% | 50% |
| 1N KOH or 1N HCl to pH 7.2 | pH 7.2 | pH 7.0 | to pH 7.2 | to pH 7.2 | to pH 7.2 | to pH 7.2 | to pH 7.2 | to pH 7.2 | to pH 7.2 |
| Purified Water | None added | q.s. | q.s. | q.s. | q.s. | q.s. | q.s. | q.s. | q.s. |

TABLE 35-continued

| Ingredients | Liq21 | Liq22 | Liq23 | Liq31 | Liq24 | Liq25 | Liq26 | Liq27 |
|---|---|---|---|---|---|---|---|---|
| KPO4 buffer, pH 7.2 (1.1 mM from virus included) | 100 mM | 100 mM | 100 mM | 100 mM | 100 mM | 100 mM | 100 mM | 100 mM |
| Sucrose (0.7% from virus included) | | 10% | 10% | 10% | 10% | 10% | 10% | 9.3% |
| Gelatin | 10% | 2% | 2% | 2% | 2% | 2% | 2% | 2% |
| Arginine | 2% | 2% | 2% | 2% | 2% | 2% | 2% | 2% |
| L-Ascorbic Acid | 2% | 0.05% | | | | | | |
| Ascorbic Acid 6 Palmitate | | | 0.005% | 0.001% | | | | |
| Arbutin | | | | | 0.05% | | | |
| Propyll Gallate | | | | | | 0.05% | | |
| EDTA | | | | | | | 10 mM | |
| RNAse Inhibitor, SuperAse In | | | | | | | | (0.05% Glyc) 2.0 U/μL |
| NAF (from virus) | 5 mM | 10% | 10% | 10% | 10% | 10% | 10% | 10% |
| NAF (added) | 10% | 50% | 50% | 50% | 50% | 50% | 50% | 50% |
| 1N KOH or 1N HCl to pH 7.2 | 50% | titrate to pH 7.2 | titrate to pH 7.2 | titrate to pH 7.2 | titrate to pH 7.2 | titrate to pH 7.2 | titrate to pH 7.2 | titrate to pH 7.2 |
| Purified Water | to pH 7.2 q.s. | q.s. | q.s. | q.s. | q.s. | q.s. | q.s. | q.s. |

TABLE 36

SP stabilized B/Hongkong Target: 6.9 15° C. (weekly)

| | 0 | 0 | 2 | 2 | 4 | 4 | 6 | 6 | 8 | 8 | 10 | 10 | 12 | 12 | 14 | 14 | |
|---|---|---|---|---|---|---|---|---|---|---|---|---|---|---|---|---|---|
| Liq 13a | 6.6 | 6.7 | 6.3 | 6.3 | 5.8 | 5.8 | 5.7 | 5.6 | 5.5 | 5.0 | 5.1 | 5.2 | 5.5 | 5.1 | 4.4 | 4.7 | no excipient (60% NAF), equil. at 15° C. |
| Liq 13b | 6.6 | 6.6 | 6.4 | 6.4 | 6.0 | 5.8 | 5.6 | 5.5 | 5.0 | 5.3 | 4.8 | 4.9 | ud | 4.6 | ud | 5.2 | no excipient (60% NAF), equil. at 33° C. |
| Liq 13c | 6.5 | 6.7 | 6.1 | 6.3 | 5.7 | 5.8 | 5.5 | 5.6 | 5.3 | 5.2 | 5.1 | 4.7 | 4.7 | 4.5 | 4.7 | 4.5 | no excipient (60% NAF), equil. at 45° C. |
| Liq 14 | 6.7 | 6.8 | 6.4 | 6.7 | 6.0 | 6.0 | 5.7 | 6.0 | 5.3 | 5.3 | 5.3 | 5.3 | 5.0 | 4.9 | 4.8 | 4.8 | Citr., 10Suc/2Gel/2Arg, equil. at 15° C. |
| Liq 15a | 6.9 | 6.7 | 6.6 | 6.5 | 6.2 | 6.2 | 6.0 | 5.9 | 5.6 | 5.8 | 5.5 | 5.5 | 5.4 | 5.1 | 5.0 | 5.4 | 10Suc/2Gel/2Arg, equil. at 15° C. |
| Liq 15b | 6.7 | 6.9 | 6.6 | 6.5 | 6.1 | 6.1 | 6.0 | 6.0 | 5.4 | 5.3 | 4.8 | 5.7 | 5.1 | 5.2 | 5.0 | 4.7 | 10Suc/2Gel/2Arg, equil. at 33° C. |
| Liq 15c | 6.7 | 6.8 | 6.4 | 6.4 | 5.9 | 6.0 | 5.7 | 5.8 | 4.8 | 5.3 | 5.2 | ud | | 5.0 | 4.5 | 4.7 | 10Suc/2Gel/2Arg, equil. at 45° C. |
| Liq 15d | 7.0 | 7.0 | 6.2 | 6.3 | 5.7 | 5.9 | 5.8 | 5.8 | disc. | | | | | | | | 10Suc/2Gel/2Arg (Degassed) |
| Liq 16 | 6.8 | 6.9 | 6.2 | 6.2 | 5.8 | 5.8 | 5.8 | 5.5 | 5.6 | 5.6 | 5.6 | 5.2 | disc. | | | | 10Suc/2Gel/2Arg/0.02Aprotinin(PI) |
| Liq 17 | 6.8 | 6.9 | 6.1 | 6.1 | 5.8 | 5.8 | 5.6 | 5.9 | 5.6 | 5.7 | 5.6 | 5.5 | disc. | | | | 10Suc/2Gel/2Arg/0.02Leup.Hemisulfate(PI) |
| Lip 18 | 7.0 | 7.1 | 6.3 | 6.3 | 6.2 | 6.0 | 5.9 | 5.9 | disc. | | | | | | | | 10Suc/2Gel/2Arg/0.1Lysozyme Inhib. |
| Liq 19 | 6.6 | 6.6 | 6.2 | 6.2 | 5.9 | 5.6 | 5.7 | 5.6 | 5.7 | 5.4 | 5.3 | 5.2 | disc. | | | | 10Suc/2Gel/2Arg/0.5Prot.Inhib.Cocktail |
| Liq 20 | ud | 4.8 | ud | ud | ud | ud | dsic. | | | | | | | | | | 10Suc/2Gel/2Arg/1 mM PMSF |
| Liq 21 | 6.7 | 6.5 | 6.3 | 6.3 | 5.9 | 5.9 | 5.9 | 5.8 | 6.3 | 6.3 | 5.8 | 5.4 | disc. | | | | 10Suc/2Gel/2Arg/1 mM Cytid.2'Monophos. |
| Liq 22 | 6.8 | 6.7 | 5.8 | 5.6 | 5.6 | 5.7 | ud | ud | ud | ud | disc. | | | | | | 10Suc/2Gel/2Arg/0.05L-Ascorbic Acid |
| Liq 22a (deg) | 6.5 | 6.5 | 5.2 | 5.9 | disc. | | | | | | | | | | | | 10Suc/2Gel/2Arg/0.05L-Ascorbic Acid |
| Liq 23 | 4.5 | 4.9 | ud | ud | ud | ud | disc | | | | | | | | | | 10Suc/2Gel/2Arg/0.005AscorbAcidPalmitate |
| Liq 24 | 6.8 | 6.7 | 6.4 | 6.5 | 6.3 | 5.9 | 5.8 | 5.7 | 5.3 | 5.5 | 5.8 | 5.3 | 5.1 | 5.1 | 4.8 | 4.8 | 10Suc/2Gel/2Arg/0.05Arbutin |
| Liq 24 (deg) | 6.7 | 6.6 | 6.2 | 6.3 | 6.0 | 5.0 | disc. | | | | | | | | | | 10Suc/2Gel/2Arg/0.05Arbutin |
| Liq 25 | 6.6 | 6.7 | 5.1 | 6.2 | 5.1 | ud | ud | ud | ud | disc. | | | | | | | 10Suc/2Gel/2Arg/0.05PropyllGallate |
| Liq 25 (deg) | 6.4 | 6.4 | 4.8 | 4.7 | disc. | | | | | | | | | | | | 10Suc/2Gel/2Arg/0.05PropyllGallate |
| Liq 26 | 6.8 | 6.8 | 6.6 | 6.4 | 6.3 | 6.3 | 5.8 | 6.0 | 5.4 | 5.5 | 5.4 | 5.6 | 5.3 | 5.4 | 5.3 | 5.3 | 10Suc/2Gel/2Arg/10 mM EDTA |
| Liq 26a (deg) | 6.8 | 6.7 | 6.5 | 6.5 | 6.5 | 6.3 | | | | | | | | | | | 10Suc/2Gel/2Arg/10 mM EDTA |
| Liq 27 | 6.6 | 6.7 | | | ud | ud | | | | | | | | | | | 10Suc/2Gel/2Arg/RNAse Inhibt. 2 U/μL |
| Liq 31 | ud | 5.9 | ud | ud | ud | ud | disc | | | | | | | | | | 10Suc/2Gel/2Arg/0.001 AscorbAcidPalmitate |

TABLE 37

SP stabilized A/Panama Target: 7.5 15° C. (weekly)

| | 0 | 0 | 2 | 2 | 4 | 4 | 6 | 6 | 8 | 8 | 10 | 10 | 12 | 12 | 14 | 14 | 16 | 16 | |
|---|---|---|---|---|---|---|---|---|---|---|---|---|---|---|---|---|---|---|---|
| Liq 13a | 7.0 | 6.9 | 6.4 | 6.4 | 5.3 | | 5.5 | 5.4 | 5.3 | 5.3 | 4.7 | 5.1 | 4.8 | 4.5 | 4.6 | 4.2 | 3.8 | | no excipient (60% NAF), equil. at 15° C. |
| Liq 13b | 6.9 | 6.9 | 6.4 | 6.3 | 5.4 | | 5.6 | 5.4 | 5.6 | 5.2 | 4.8 | 4.9 | 5.0 | 4.8 | 4.6 | 4.3 | 4.6 | | no excipient (60% NAF), equil. at 33° C. |
| Liq 13c | 6.8 | 6.7 | 6.3 | 6.3 | 5.4 | | 5.6 | 5.3 | 5.0 | 5.1 | 4.7 | 4.5 | 4.7 | 4.7 | 4.9 | 4.5 | 4.2 | | no excipient (60% NAF), equil. at 45° C. |
| Liq 14 | 7.3 | 7.3 | 7.2 | 7.2 | 6.8 | | 6.8 | 6.7 | 6.8 | 6.5 | 6.5 | 6.7 | 6.6 | 6.4 | 6.5 | 6.1 | 6.2 | 6.5 | 6.5 Citr., 10Suc/2Gel/2Arg, equil. at 15° C. |
| Liq 15a | 7.2 | 7.2 | 6.9 | 7 | 6.6 | | 6.7 | 6.6 | 6.4 | 6.2 | 6.0 | 6.0 | 6.0 | 5.7 | 6.1 | 5.7 | 5.7 | 6.1 | 5.8 10Suc/2Gel/2Arg, equil. at 15° C. |

TABLE 37-continued

SP stabilized A/Panama Target: 7.5 15° C. (weekly)

| | 0 | 0 | 2 | 2 | 4 | 4 | 6 | 6 | 8 | 8 | 10 | 10 | 12 | 12 | 14 | 14 | 16 | 16 | |
|---|---|---|---|---|---|---|---|---|---|---|---|---|---|---|---|---|---|---|---|
| Liq 15b | 7.3 | 7.1 | 7.0 | 6.9 | 6.3 | 6.5 | 6.7 | 6.6 | 6.0 | 5.8 | 6.1 | 6.0 | 6.1 | 5.8 | 5.9 | 5.8 | 6.0 | 6.0 | 10Suc/2Gel/2Arg, equil. at 33° C. |
| Liq 15c | 7.1 | 6.9 | 6.8 | 6.8 | 6.3 | 6.0 | 6.3 | 6.5 | 5.8 | 5.8 | 6.1 | 6.1 | 5.8 | 5.8 | 5.8 | 5.8 | 5.9 | 5.9 | 10Suc/2Gel/2Arg, equil. at 45° C. |
| Liq 15d | 6.8 | 6.7 | 6.7 | 6.5 | 6.5 | 6.4 | 6.4 | 6.4 | 6.4 | 6.4 | | | | | | | | | 10Suc/2Gel/2Arg (Degassed) |
| Liq 16 | only for B/Hongkong | | | | | | | | | | | | | | | | | | 10Suc/2Gel/2Arg/0.02Aprotinin(PI) |
| Liq 17 | only for B/Hongkong | | | | | | | | | | | | | | | | | | 10Suc/2Gel/2Arg/0.02Leup.Hemisulfate(PI) |
| Liq 18 | 6.9 | 6.9 | 6.7 | 6.5 | 6.2 | 6.5 | 6.2 | 6.4 | 6.5 | 6.4 | | | | | | | | | 10Suc/2Gel/2Arg/0.1Lysozyme Inhib. |
| Liq 19 | 6.5 | 6.6 | 6.6 | 6.5 | 5.7 | 6.0 | 5.9 | ud | 5.4 | 5.4 | 5.5 | 5.8 | 5.8 | 5.8 | | | | | 10Suc/2Gel/2Arg/0.5Prot.Inhib.Cocktail |
| Liq 20 | 6.8 | 6.9 | 6.0 | 5.7 | ud | ud | ud | ud | disc. | | | | | | | | | | 10Suc/2Gel/2Arg/1 mM PMSF |
| Liq 21 | 6.9 | 6.7 | 6.2 | 6.3 | 6.5 | 6.6 | 6.9 | 7.1 | 5.8 | 5.9 | 6.1 | 6.0 | 5.9 | 5.7 | 6 | 6.1 | 5.8 | 5.6 | 10Suc/2Gel/2Arg/1 mM Cytid.2'Monophos. |
| Liq 22 | 7.1 | 7.2 | 6.0 | 6.0 | 5.9 | 5.8 | 5.1 | ud | 5.7 | ud | ud | 5.4 | ud | ud | disc. | | | | 10Suc/2Gel/2Arg/0.05L-Ascorbic Acid |
| Liq 22a (deg) | 6.7 | 6.7 | 6.2 | 5.9 | 6.0 | 5.9 | | | | | | | | | | | | | 10Suc/2Gel/2Arg/0.05L-Ascorbic Acid |
| Liq 23 | 5.6 | 5.5 | ud | ud | ud | | disc. | | | | | | | | | | | | 10Suc/2Gel/2Arg/0.005AscorbAcid6Palmitate |
| Liq 24 | 7.0 | 6.9 | 6.7 | 6.8 | 6.6 | 6.6 | 6.4 | 6.5 | 6.2 | 6.2 | 6 | 6.3 | 6.1 | 5.9 | 5.7 | 5.9 | 5.9 | 6.1 | 10Suc/2Gel/2Arg/0.05Arbutin |
| Liq 24a (deg) | 6.6 | 6.6 | 6.5 | 6.6 | | | | | | | | | | | | | | | 10Suc/2Gel/2Arg/0.05Arbutin |
| Liq 25 | 6.9 | 6.5 | 5.1 | 5.5 | ud | ud | ud | ud | ud | ud | disc | | | | | | | | 10Suc/2Gel/2Arg/0.05PropyllGallate |
| Liq 25a (deg) | ud | ud | ud | ud | disc | | | | | | | | | | | | | | 10Suc/2Gel/2Arg/0.05PropyllGallate |
| Liq 26 | 7.4 | 7.3 | 7.2 | 7.1 | ud(repd) | ud(repd) | 6.9 | 6.9 | 6.7 | 6.7 | 6.9 | 6.5 | 6.4 | 6.4 | 6.4 | | | | 10Suc/2Gel/2Arg/10 mM EDTA |
| Liq 26a (deg) | 7.1 | 7.2 | 7 | 7.1 | 6.9 | | | | | | | | | | | | | | 10Suc/2Gel/2Arg/10 mM EDTA |
| Liq 27 | only for B/Hongkong | | | | | | | | | | | | | | | | | | 10Suc/2Gel/2Arg/RNAse Inhibt. 2 U/μL |
| Liq 31 | ud | ud | ud | ud | 3.5 | 3.8 | disc. | | | | | | | | | | | | 10Suc/2Gel/2Arg/0.001AscorbAcid6Palmitate |

TABLE 38

SP stabilized B/Hongkong Target: 6.9 4° C. (Monthly)

| | 0 | 0 | 1 | 1 | 2 | 2 | 3 | 3 | 4 | 4 | |
|---|---|---|---|---|---|---|---|---|---|---|---|
| Liq 13a | 6.6 | 6.7 | 6.4 | 6.5 | 6.2 | 6.2 | 6.4 | 6.3 | 6.1 | 6.2 | no excipient (60% NAF), equil. at 15° C. |
| Liq 13b | 6.6 | 6.6 | 6.5 | 6.4 | 6.3 | 6.2 | 6.3 | 6.4 | 6.1 | 6.2 | no excipient (60% NAF), equil. at 33° C. |
| Liq 13c | 6.5 | 6.7 | 6.4 | 6.4 | 6.1 | 6.1 | 6.3 | 6.4 | 6 | 5.9 | no excipient (60% NAF), equil. at 45° C. |
| Liq 14 | 6.0 | 6.8 | 6.4 | 6.5 | 6.0 | 6.4 | 6.3 | 6.4 | 6.1 | 6.1 | Citr., 10Suc/2Gel/2Arg, equil. at 15° C. |
| Liq 15a | 6.9 | 6.7 | 6.7 | 6.8 | 6.4 | 6.3 | 6.7 | 6.7 | 6.5 | 6.5 | 10Suc/2Gel/2Arg, equil. at 15° C. |
| Liq 15b | 6.7 | 6.9 | 6.7 | 6.6 | 6.0 | 6.2 | 6.5 | 6.5 | 6.4 | 6.4 | 10Suc/2Gel/2Arg, equil. at 33° C. |
| Liq 15c | 6.7 | 6.8 | 6.6 | 6.6 | 6.1 | 6.2 | 6.5 | 6.4 | 6.4 | 6.4 | 10Suc/2Gel/2Arg, equil. at 45° C. |
| Liq 15d | 7.0 | 7.0 | 6.8 | 6.8 | 6.5 | 6.3 | | | | | 10Suc/2Gel/2Arg (Degassed) |
| Liq 16 | 6.8 | 6.9 | 6.4 | 6.7 | 6.6 | 6.5 | 6.1 | 6.3 | | | 10Suc/2Gel/2Arg/0.02Aprotinin(PI) |
| Liq 17 | 6.8 | 6.9 | 6.7 | 6.6 | 6.5 | 6.5 | 6.1 | 6.3 | | | 10Suc/2Gel/2Arg/0.02Leup.Hemisulfate(PI) |
| Liq 18 | 7.0 | 7.1 | 6.9 | 6.8 | 6.5 | 6.5 | | | | | 10Suc/2Gel/2Arg/0.1Lysozyme Inhib. |
| Liq 19 | 6.6 | 6.6 | 6.5 | 6.4 | 6.5 | 6.5 | | | | | 10Suc/2Gel/2Arg/0.5Prot.Inhib.Cocktail |
| Liq 20 | ud | 4.8 | ud | disc. | | | | | | | 10Suc/2Gel/2Arg/1 mM PMSF |
| Liq 21 | 6.7 | 6.5 | 6.6 | 6.6 | 7.0 | 7.0 | 6.6 | 6.6 | | | 10Suc/2Gel/2Arg/1 mM Cytid.2'Monophos. |
| Liq 22 | 6.8 | 6.7 | 5.9 | UD | UD | UD | 5.2 | 5.5 | | | 10Suc/2Gel/2Arg/0.05L-Ascorbic Acid |
| Liq 22a (deg) | 6.5 | 6.5 | 6 | 6.2 | | | | | | | 10Suc/2Gel/2Arg/0.05L-Ascorbic Acid |
| Liq 23 | 4.5 | 4.9 | ud | disc. | | | | | | | 10Suc/2Gel/2Arg/0.005AscorbAcid6Palmitate |
| Liq 24 | 6.8 | 6.7 | 6.7 | 6.6 | ud (rep) | ud (rep) | 6.4 | 6.3 | 6.3 | 6.2 | 10Suc/2Gel/2Arg/0.05Arbutin |
| Liq 24 (deg) | 6.7 | 6.6 | 7.0 | 7.0 | | | | | | | 10Suc/2Gel/2Arg/0.05Arbutin |
| Liq 25 | 6.6 | 6.7 | 6.2 | 6.3 | 5.2 | 5.2 | 5.4 | 5.3 | | | 10Suc/2Gel/2Arg/0.05PropyllGallate |
| Liq 25 (deg) | 6.4 | 6.4 | 5.8 | 5.9 | | | | | | | 10Suc/2Gel/2Arg/0.05PropyllGallate |
| Liq 26 | 6.8 | 6.8 | 6.5 | 6.7 | 6.6 | | 6.6 | 6.6 | 6.3 | | 10Suc/2Gel/2Arg/10 mM EDTA |
| Liq 26a (deg) | 6.8 | 6.7 | 6.9 | 6.9 | | | | | | | 10Suc/2Gel/2Arg/10 mM EDTA |
| Liq 27 | 6.6 | 6.7 | 6.6 | 6.4 | 6.6 | 6.5 | 6.3 | 6.3 | | | 10Suc/2Gel/2Arg/RNAse Inhibt. 2 U/μL |
| Liq 31 | ud | 5.9 | 5.1 | 4.9 | disc. | | | | | | 10Suc/2Gel/2Arg/0.001AscorbAcid6Palmitate |

TABLE 39

SP stabilized A/Panama Target: 7.5 4° C. (Monthly)

|  | 0 | 0 | 1 | 1 | 2 | 2 | 3 | 3 | 4 | 4 |  |
|---|---|---|---|---|---|---|---|---|---|---|---|
| Liq 13a | 7.0 | 6.9 | 6.2 | 6.2 | 6.0 | 6.1 | 5.8 | 5.9 | 5.8 | 5.6 | no excipient (60% NAF),equil. at 15° C. |
| Liq 13b | 6.9 | 6.9 | 5.9 | 6.0 | 6.0 | 6.0 | 5.9 | 5.7 | 5.9 | 6.0 | no excipient (60% NAF), equil. at 33° C. |
| Liq 13c | 6.8 | 6.7 | 6 | 6.1 | 5.8 | 6.1 | 5.9 | 5.7 | 5.8 | 5.6 | no excipient (60% NAF), equil. at 45° C. |
| Liq 14 | 7.3 | 7.3 | 7.2 | 7.2 | 7.3 | 7.2 | 7.1 | 7.1 | 6.8 | 7 | Citr., 10Suc/2Gel/2Arg, equil. at 15° C. |
| Liq 15a | 7.2 | 7.2 | 6.7 | 6.6 | 6.6 | 6.6 | 6.5 | 7.0 | 6.4 | 6.6 | 10Suc/2Gel/2Arg, equil. at 15° C. |
| big 15b | 7.3 | 7.1 | 6.7 | 6.7 | 6.7 | 6.6 | 6.9 | 6.8 | 6.4 | 6.6 | 10Suc/2Gel/2Arg, equil. at 33° C. |
| Liq 15c | 7.1 | 6.9 | 6.5 | 6.4 | 6.7 | 6.6 | 6.6 | 6.6 | 6.4 | 6.4 | 10Suc/2Gel/2Arg, equil. at 45° C. |
| Liq 15d | 6.8 | 6.7 | 6.9 | 6.8 | 6.4 | 6.4 |  |  |  |  | 10Suc/2Gel/2Arg (Degassed) |
| Liq 16 | only for B/ Hongkong |  |  |  |  |  |  |  |  |  | 10Suc/2Gel/2Arg/0.02Aprotinin(PI) |
| Liq 17 | only for B/ Hongkong |  |  |  |  |  |  |  |  |  | 10Suc/2Gel/2Arg/0.02Leup.Hemisulfate(PI) |
| Liq 18 | 6.9 | 6.9 | 6.9 | 6.8 | 6.4 | 6.3 |  |  |  |  | 10Suc/2Gel/2Arg/0.1Lysozyme Inhib. |
| Liq 19 | 6.5 | 6.6 | 6.2 | 6.4 | 6.3 | 6.6 | 6.3 | 6.3 |  |  | 10Suc/2Gel/2Arg/0.5Prot.Inhib.Cocktail |
| liq 20 | 6.8 | 6.9 | 6.9 | 7.0 | 7.1 | 7.2 | 6.9 | 6.7 |  |  | 10Suc/2Gel/2Arg/1 mM PMSF |
| Liq 21 | 6.9 | 6.7 | 6.7 | 6.8 | 6.7 | 6.8 | 7.0 | 7.1 |  |  | 10Suc/2Gel/2Arg/1 mM Cytid.2'Monophos. |
| Liq 22 | 7.1 | 7.2 | 6.2 | 6.0 | 6.3 | 5.8 | 6.0 | 5.9 | 6.1 | 6.1 | 10Suc/2Gel/2Arg/0.05L-Ascorbic Acid |
| Liq 22a (deg) | 6.7 | 6.7 | 6.7 | 6.6 |  |  |  |  |  |  | 10Suc/2Gel/2Arg/0.05L-Ascorbic Acid |
| Liq 23 | 5.6 | 5.5 | ud | ud | disc. |  |  |  |  |  | 10Suc/2Gel/2Arg/0.005AscorbAcid6Palmitate |
| Liq 24 | 7.0 | 6.9 | 6.5 | 6.7 | 6.4 | 6.3 | 6.8 | 6.7 | 6.4 | 6.5 | 10Suc/2Gel/2Arg/0.05Arbutin |
| Liq 24a (deg) | 6.7 | 6.6 | 6.2 | 6.2 |  |  |  |  |  |  | 10Suc/2Gel/2Arg/0.05Arbutin |
| Liq 25 | 6.9 | 6.5 | 5.1 | 7.2 | 5.1 | ud | disc. |  |  |  | 10Suc/2Gel/2Arg/0.05PropyllGallate |
| Liq 25a (deg) | 6 | 6.3 | rep | 6.4 |  |  |  |  |  |  | 10Suc/2Gel/2Arg/0.05PropyllGallate |
| Liq 26 | 7.4 | 7.3 | 7.3 | 7.3 | 7.3 | 7.3 | 7.4 | 7.3 | 7.0 | 7.1 | 10Suc/2Gel/2Arg/10 mM EDTA |
| Liq 26a (deg) | 7.1 | 7.2 | 7.4 | 7.5 | 7.1 | 7.0 |  |  |  |  | 10Suc/2Gel/2Arg/10 mM EDTA |
| Liq 27 | only for B/ Hongkong |  |  |  |  |  |  |  |  |  | 10Suc/2Gel/2Arg/RNAse Inhibt. 2 U/μL |
| Liq 31 | ud | ud | ud | ud | disc. |  |  |  |  |  | 10Suc/2Gel/2Arg/0.001AscorbAcid6Palmitate |

TABLE 40

| | Formulation | | | | |
|---|---|---|---|---|---|
| Ingredients | No Citrate | 20 mM Citrate | 50 mM Citrate | 100 mM Citrate | 200 mM Citrate |
| Citrate buffer pH 7.2 | 0 | 20 mM | 50 mM | 100 mM | 200 mM |
| KPO4 buffer (from virus material) | 1.1 mM | 1.1 mM | 1.1 mM | 1.1 mM | 1.1 mM |
| Sucrose (0.7% from virus included) | 10% | 10% | 10% | 10% | 10% |
| Gelatin | 1% | 1% | 1% | 1% | 1% |
| Arginine | 2% | 2% | 2% | 2% | 2% |
| NAF (from virus: B/Hongkong; A/Panama) | 10% | 10% | 10% | 10% | 10% |
| NAF (added) | 50% | 50% | 50% | 50% | 50% |
| 1N KOH or 1N HCl to pH 7.2 | titrate to pH 7.2 | titrate to pH 7.2 | titrate to pH 7.2 | titrate to pH 7.2 | titrate to pH 7.2 |
| Purified Water | q.s. | q.s. | q.s. | q.s. | q.s. |

Results: Potency by FFA Assay

TABLE 41

|  | A/Panama Aliquot 1 | A/Panama Aliquot 2 | B/Hongkong Aliquot 1 | B/Hongkong Aliquot 2 |
|---|---|---|---|---|
| A/Panama, Starting material | Ave. of 9 plates 8.1 ± 0.2 (8.5) |  | Ave. of 6 plates 7.9 ± 0.1 (7.9) |  |
| Pre-diluted Starting Material (1:10) | 8.0 ± 0.1 (8.0) | none | n/a | n/a |
| 0% Citrate | 6.7 ± 0.1 (7.0) | 6.9 ± 0.0 (7.0) | 6.7 ± 0.0 (6.9) | 6.8 ± 0.1 (6.9) |
| 20 mM Citrate | 6.7 ± 0.1 (7.0) | 6.7 ± 0.2 (7.0) | 6.9 ± 0.0 (6.9) | 6.8 ± 0.1 (6.9) |
| 50 mM Citrate | 6.7 ± 0.1 (7.0) | 6.7 ± 0.1 (7.0) | 6.9 ± 0.0 (6.9) | 6.8 ± 0.1 (6.9) |

TABLE 41-continued

|  | A/Panama Aliquot 1 | A/Panama Aliquot 2 | B/Hongkong Aliquot 1 | B/Hongkong Aliquot 2 |
|---|---|---|---|---|
| 100 mM Citrate | 6.8 ± 0.0 (7.0) | 6.8 ± 0.0 (7.0) | 6.8 ± 0.1 (6.9) | 6.9 ± 0.1 (6.9) |
| 200 mM Citrate | 6.8 ± 0.1 (7.0) | 6.8 ± 0.0 (7.0) | 6.7 ± 0.1 (6.9) | 6.6 ± 0.2 (6.9) |

Base Formulation: 60% NAF, 10% Sucrose, 1% Gelatin 2% Arginine

TABLE 42

| | Formulation | | | | | |
|---|---|---|---|---|---|---|
| Ingredients | No EDTA | 0.5 mM EDTA | 1.0 mM EDTA | 2.0 mM EDTA | 5.0 mM EDTA | 10 mM EDTA |
| KPO4 buffer, pH 7.2 (1.1 mM from virus included) | 100 mM | 100 mM | 100 mM | 100 mM | 100 mM | 100 mM |
| Sucrose (0.7% from virus included) | 10% | 10% | 10% | 10% | 10% | 10% |
| Gelatin | 1% | 1% | 1% | 1% | 1% | 1% |
| Arginine | 2% | 2% | 2% | 2% | 2% | 2% |
| EDTA | 0% | 0.0186% (0.5 mM) | 0.037% (1.0 mM) | 0.0744% (2.0 mM) | 0.186% (5.0 mM) | 0.372% (10 mM) |
| NAF (from virus: B/Hongkong; A/Panama) | 10% | 10% | 10% | 10% | 10% | 10% |
| NAF (added) | 50% | 50% | 50% | 50% | 50% | 50% |
| 1N KOH or 1N HCl to pH 7.2 | titrate to pH 7.2 | titrate to pH 7.2 | titrate to pH 7.2 | titrate to pH 7.2 | titrate to pH 7.2 | titrate to pH 7.2 |
| Purified Water | q.s. | q.s. | q.s. | q.s. | q.s. | q.s. |

TABLE 43

|  | A/Panama Aliquot 1 | A/Panama Aliquot 2 | B/Hongkong Aliquot 1 | B/Hongkong Aliquot 2 |
|---|---|---|---|---|
| A/Panama, Starting material | Ave. of 9 plates 8.1 ± 0.2 (8.5) |  | Ave. of 6 plates 7.9 ± 0.1 (7.9) |  |
| Pre-diluted Starting Material (1:10) | 8.0 ± 0.1 (8.0) | none | n/a | n/a |
| 0% EDTA | 6.1 ± 0.2 (7.0) | 6.1 ± 0.2 (7.0) | 6.7 ± 0.1 (6.9) | 6.7 ± 0.1 (6.9) |
| 0.5 mM EDTA | 6.3 ± 0.2 (7.0) | 6.3 ± 0.1 (7.0) | 6.7 ± 0.1 (6.9) | 6.6 ± 0.1 (6.9) |
| 1.0 mM EDTA | 6.5 ± 0.1 (7.0) | 6.5 ± 0.1 (7.0) | 6.8 ± 0.1 (6.9) | 6.6 ± 0.1 (6.9) |
| 2.0 mM EDTA | 6.6 ± 0.0 (7.0) | 6.8 ± 0.1 (7.0) | 6.6 ± (6.9) | 6.6 ± 0.1 (6.9) |
| 5.0 mM EDTA | 6.7 ± 0.0 (7.0) | 6.8 ± 0.1 (7.0) | 6.6 ± 0.1 (6.9) | 6.7 ± 0.2 (6.9) |
| 10 mM EDTA | 6.8 ± 0.1 (7.0) | 6.7 ± 0.1 (7.0) | 6.7 ± 0.1 (6.9) | 6.6 ± 0.2 (6.9) |

Base Formulation: 100 mM KPO4, 60% NAF, 10% Sucrose, 1% Gelatin 2% Arginine

TABLE 44

| Ingredients | Liq28 | Liq29 | Liq30 |
|---|---|---|---|
| KPO4 buffer, pH 7.2 (1.1 mM from virus included) | 100 mM | 100 mM |  |
| Citrate buffer, pH 7.2 | n/a | n/a | 100 mM |
| Sucrose (0.7% from virus included) | 10% | 10% | 10% |
| Gelatin | 2% | n/a | 2% |
| Arginine | 2% | 2% | 2% |
| EDTA | (5 mM) 0.186% | (10 mM) 0.372% | (10 mM) 0.372% |
| NAF (from virus) | 10% | 10% | 10% |
| NAF (added) | 50% | 50% | 50% |

TABLE 44-continued

| Ingredients | Liq28 | Liq29 | Liq30 |
|---|---|---|---|
| 1N HCl or 1N KOH to pH 7.2 | titrate to pH 7.2 | titrate to pH 7.2 | titrate to pH 7.2 |
| Purified Water | q.s. | q.s. | q.s. |

TABLE 45

A
SP stabilized B/Hongkong Target: 6.9 15° C. (weekly)

| | 0 | 0 | 2 | 2 | 4 | 4 | 6 | 6 | 8 | 8 | 10 | 10 | 12 | 12 | 14 | 14 | Formulation |
|---|---|---|---|---|---|---|---|---|---|---|---|---|---|---|---|---|---|
| Liq 26 | 6.8 | 6.8 | 6.6 | 6.4 | 6.3 | 6.3 | 5.8 | 6.0 | 5.4 | 5.5 | 5.4 | 5.6 | 5.3 | 5.4 | 5.3 | 5.3 | 10Suc/2Gel/2Arg/10 mM EDTA |
| Liq 26a (deg) | 6.8 | 6.7 | 6.5 | 6.5 | 6.5 | 6.3 | | | | | | | | | | | 10Suc/2Gel/2Arg/10 mM EDTA |
| Liq 28 | 6.2 | 5.9 | 5.8 | 5.9 | 6.2 | 6.0 | 5.4 | 5.3 | 5.1 | 5.1 | disc. | | | | | | 10Suc/2Gel/2Arg/5 mM EDTA |
| Liq 28a | 6.5 | 6.5 | 6.2 | 6.0 | 6.0 | 5.9 | 5.8 | 5.6 | disc. | | | | | | | | 10Suc/2Gel/2Arg/5 mM EDTA |
| Liq 29 | 4.9 | 4.9 | 4.8 | 4.7 | 5.0 | 4.8 | 4.2 | 4.0 | ud | 3.6 | disc. | | | | | | 10Suc/2Arg/10 mM EDTA |
| Liq 29a | 6.3 | 6.4 | 6.0 | 6.3 | 6.1 | 5.9 | 5.8 | 5.7 | disc. | | | | | | | | 10Suc/2Arg/10 mM EDTA |
| Liq 30 | 6.6 | 6.6 | 6.3 | 6.4 | 6.7 | 6.5 | 5.9 | 5.9 | 5.4 | 5.4 | disc. | | | | | | Citr./10Suc/2Gel/2Arg/10 mM EDTA |
| Liq 30a | 6.6 | 6.6 | 6.1 | 6.2 | 6.1 | 5.9 | 5.8 | 5.8 | disc. | | | | | | | | Citr./10Suc/2Gel/2Arg/10 mM EDTA |

B
SP stabilized B/Hongkong Target: 6.9 4° C. (Monthly)

| | 0 | 0 | 1 | 1 | 2 | 2 | 3 | 3 | 4 | 4 | Formulation |
|---|---|---|---|---|---|---|---|---|---|---|---|
| Liq 26 | 6.8 | 6.8 | 6.6 | 6.7 | 6.6 | 6.5 | 6.6 | 6.6 | 6.3 | | 10Suc/2Gel/2Arg/10 mM EDTA |
| Liq 26a (deg) | 6.8 | 6.7 | 6.9 | 6.9 | | | | | | | 10Suc/2Gel/2Arg/10 mM EDTA |
| Liq 28 | 6.2 | 5.9 | 6.6 | 6.4 | 6.6 | 6.5 | 5.8 | 5.8 | | | 10Suc/2Gel/2Arg/5 mM EDTA |
| Liq 28a | 6.5 | 6.5 | 6.7 | 6.8 | 6.5 | 6.6 | | | | | 10Suc/2Gel/2Arg/5 mM EDTA |
| Liq 29 | 4.9 | 4.9 | 5.1 | 5.1 | 4.9 | 4.9 | disc. | | | | 10Suc/2Arg/10 mMEDTA |
| Liq 29a | 6.3 | 6.4 | 6.4 | 6.5 | 6.3 | 6.4 | | | | | 10Suc/2Arg/10 mM EDTA |
| Liq 30 | 6.6 | 6.6 | 6.8 | 7.1 | 6.6 | 6.5 | 6.2 | 6.0 | | | Citr./10Suc/2Gel/2Arg/10 mM EDTA |
| Liq 30a | 6.6 | 6.6 | 6.9 | 6.7 | 6.4 | 6.0 | | | | | Citr./10Suc/2Gel/2Arg/10 mM EDTA |

C
SP stabilized A/Panama Target: 7.5 15° C. (weekly)

| | 0 | 0 | 2 | 2 | 4 | 4 | 6 | 6 | 8 | 8 | 10 | 10 | 12 | 12 | 14 | Formulation |
|---|---|---|---|---|---|---|---|---|---|---|---|---|---|---|---|---|
| Liq 26 | 7.4 | 7.3 | 7.2 | 7.1 | ud(repd) | ud(repd) | 6.9 | 6.9 | 6.7 | 6.7 | 6.7 | 6.9 | 6.5 | 6.4 | 6.4 | 10Suc/2Gel/2Arg/10 mM EDTA |
| Liq 26a (deg) | 7.1 | 7.2 | 7 | 7.1 | 7.1 | | 6.9 | | 6.4 | 6.8 | | | | | | 10Suc/2Gel/2Arg/10 mM EDTA |
| Liq 28 | 7.5 | 7.4 | 7.1 | 7.1 | 6.9 | | 7.0 | | 6.7 | 6.7 | 6.5 | 6.5 | 6.6 | 6.6 | 6.1 | 10Suc/2Gel/2Arg/5 mM EDTA |
| Liq 29 | 7.3 | 7.3 | 6.9 | 6.9 | 7.0 | | 7.0 | | 6.7 | 6.8 | 6.6 | 6.7 | 6.5 | 6.7 | 6.0 | 10Suc/2Arg/10 mM EDTA |
| Liq 30 | 7.4 | 7.3 | 7.0 | 7.0 | 6.8 | | 6.9 | | 6.3 | 6.3 | 6.1 | 6.3 | 6.2 | 6.1 | 5.8 | Citr./10Suc/2Gel/2Arg/10 mM EDTA |

D
SP stabilized A/Panama Target: 7.5 4° C. (Monthly)

| | 0 | 0 | 1 | 1 | 2 | 2 | 3 | 3 | 4 | 4 | Formulation |
|---|---|---|---|---|---|---|---|---|---|---|---|
| Liq 26 | 7.4 | 7.3 | 7.3 | 7.3 | 7.3 | 7.3 | 7.4 | 7.3 | 7.0 | 7.1 | 10Suc/2Gel/2Arg/10 mM EDTA |
| Liq 26a (deg) | 7.1 | 7.2 | 7.4 | 7.5 | 7.1 | 7.0 | | | | | 10Suc/2Gel/2Arg/10 mM EDTA |
| Liq 28 | 7.5 | 7.4 | 7.3 | 7.3 | | | 7.1 | 7.2 | | | 10Suc/2Gel/2Arg/5 mM EDTA |
| Liq 29 | 7.3 | 7.3 | 7.2 | 7.5 | | | 7.1 | 7.1 | | | 10Suc/2Arg/10 mM EDTA |
| Liq 30 | 7.4 | 7.3 | 7.3 | 7.4 | | | 7.0 | 7.2 | | | Citr./10Suc/2Gel/2Arg/10 mM EDTA |

TABLE 46

A

| Ingredients | Liq36 | Liq37 | Liq38 | Liq39 | Liq40 | Liq41 | Liq42 | Liq43 | Liq44 | Liq45 | Liq46 | Liq47 |
|---|---|---|---|---|---|---|---|---|---|---|---|---|
| KPO4 buffer, pH 7.2 (1.1 mM from virus included) | 50 mM | 50 mM | 50 mM | 50 mM | 50 mM | 50 mM | 50 mM | 50 mM | 50 mM | 50 mM | 50 mM | 50 mM |
| Sucrose (0.7% from virus included) | 0.0% | 7.5% | 7.5% | 7.5% | 7.5% | 7.5% | 7.5% | 10% | 10% | 10% | 10% | 10% |

TABLE 46-continued

| Ingredients | | | | | | | | | | | |
|---|---|---|---|---|---|---|---|---|---|---|---|
| Gelatin | 0% | 0% | 0% | 1% | 1% | 2% | 2% | 0% | 0% | 0% | 1% | 1% |
| Arginine | 2% | 2% | 4% | 0% | 4% | 0% | 2% | 4% | 2% | 4% | 2% | 2% |
| EDTA | 1 mM | 2.7 mM | 5 mM | 1 mM | 2.7 mM | 5 mM | 1 mM | 5 mM | 5 mM | 1 mM | 1 mM | 2.7 mM |
| NAF (from virus: B/Hongkong; A/Panama) | 10% | 10% | 10% | 10% | 10% | 10% | 10% | 10% | 10% | 10% | 10% | 10% |
| NAF (added) | 50% | 50% | 50% | 50% | 50% | 50% | 50% | 50% | 50% | 50% | 50% | 50% |
| 1N KOH or 1N HCl to pH 7.2 | titrate to pH 7.2 | titrate to pH 7.2 | titrate to pH 7.2 | titrate to pH 7.2 | titrate to pH 7.2 | titrate to pH 7.2 | titrate to pH 7.2 | titrate to pH 7.2 | titrate to pH 7.2 | titrate to pH 7.2 | titrate to pH 7.2 | titrate to pH 7.2 |
| Purified Water | q.s. | q.s | q.s | q.s | q.s | q.s | q.s | q.s | q.s | q.s | q.s | q.s |

B

| Ingredients | Liq48 | Liq49 | Liq50 | Liq51 | Liq52 | Liq53 | Liq54 | Liq55 | Liq56 | Liq57 | Liq58 | Liq59 |
|---|---|---|---|---|---|---|---|---|---|---|---|---|
| KPO4 buffer, pH 7.2 (1.1 mM from virus included) | 50 mM | 50 mM | 50 mM | 50 mM | 50 mM | 50 mM | 50 mM | 50 mM | 50 mM | 50 mM | 50 mM | 50 mM |
| Sucrose (0.7% from virus included) | 10% | 10% | 10% | 10% | 15% | 15% | 15% | 15% | 15% | 15% | 15% | 15% |
| Gelatin | 1% | 2% | 2% | 2% | 0% | 0% | 0% | 1% | 1% | 1% | 2% | 2% |
| Arginine | 4% | 0% | 0% | 4% | 2% | 2% | 4% | 0% | 0% | 4% | 2% | 4% |
| EDTA | 5 mM | 1 mM | 2.7 mM | 2.7 mM | 2.7 mM | 1 mM | 2.7 mM | 2.7 mM | 5 mM | 1 mM | 5 mM | 1 mM |
| NAF (from virus: B/Hongkong; A/Panama) | 10% | 10% | 10% | 10% | 10% | 10% | 10% | 10% | 10% | 10% | 10% | 10% |
| NAF (added) | 50% | 50% | 50% | 50% | 50% | 50% | 50% | 50% | 50% | 50% | 50% | 50% |
| 1N KOH or 1N HCl to pH 7.2 | titrate to pH 7.2 | titrate to pH 7.2 | titrate to pH 7.2 | titrate to pH 7.2 | titrate to pH 7.2 | titrate to pH 7.2 | titrate to pH 7.2 | titrate to pH 7.2 | titrate to pH 7.2 | titrate to pH 7.2 | titrate to pH 7.2 | titrate to pH 7.2 |
| Purified Water | q.s. | q.s | q.s | q.s | q.s | q.s | q.s | q.s | q.s | q.s | q.s | q.s |

TABLE 47

SP stabilized B/Hongkong Target: 6.9 4° C. (monthly)

| | 0 | 0 | 0 | 1 | 1 | 1 | 2 | 2 | 2 | 3 | 3 | 3 | 4 | 4 | 4 | 5 | 5 | 5 | |
|---|---|---|---|---|---|---|---|---|---|---|---|---|---|---|---|---|---|---|---|
| Liq 36 | 6.8 | 6.8 | 6.7 | | | | | | | | | | | | | | | | 50 mM KPO4/0Suc/0Gel/2Arg/1 mm EDTA |
| Liq 37 | 6.6 | 6.6 | 6.7 | | | | | | | | | | | | | | | | 50 mM KPO4/7.5Suc/0Gel/2Arg/2.7 mm EDTA |
| Liq 38 | 6.6 | 6.5 | 6.6 | | | | | | | | | | | | | | | | 50 mM KPO4/7.5Suc/0Gel/4Arg/5 mm EDTA |
| Liq 39 | 6.9 | 6.8 | 6.7 | | | | | | | | | | | | | | | | 50 mM KPO4/7.5Suc/1Gel/0Arg/1 mm EDTA |
| Liq 40 | 6.7 | 6.7 | 6.7 | | | | | | | | | | | | | | | | 50 mM KPO4/7.5Suc/1Gel/4Arg/2.7 mm EDTA |
| Liq 41 | 7.0 | 7.0 | 7.0 | | | | | | | | | | | | | | | | 50 mM KPO4/7.5Suc/2Gel/0Arg/5 mm EDTA |
| Liq 42 | 6.9 | 6.9 | 7.0 | | | | | | | | | | | | | | | | 50 mM KPO4/7.5Suc/2Gel/2Arg/1 mm EDTA |
| Liq 43 | 6.8 | 6.8 | 6.7 | | | | | | | | | | | | | | | | 50 mM KPO4/10Suc/0Gel/4Arg/5 mm EDTA |
| Liq 44 | 6.8 | 6.9 | 6.9 | | | | | | | | | | | | | | | | 50 mM KPO4/10Suc/0Gel/2Arg/5 mm EDTA |
| Liq 45 | 6.7 | 6.8 | 6.8 | | | | | | | | | | | | | | | | 50 mM KPO4/10Suc/0Gel/4Arg/1 mm EDTA |
| Liq 46 | 7.0 | 7.0 | 6.8 | | | | | | | | | | | | | | | | 50 mM KPO4/10Suc/1Gel/2Arg/1 mm EDTA |
| Liq 47 | 7.1 | 7.0 | 7.0 | | | | | | | | | | | | | | | | 50 mM KPO4/10Suc/1Gel/2Arg/2.7 mm EDTA |
| Liq 48 | 7.0 | 6.9 | 6.9 | | | | | | | | | | | | | | | | 50 mM KPO4/10Suc/1Gel/4Arg/5 mm EDTA |
| Liq 49 | 7.0 | 7.0 | 7.0 | | | | | | | | | | | | | | | | 50 mM KPO4/10Suc/2Gel/0Arg/1 mm EDTA |
| Liq 50 | 7.0 | 6.8 | 7.0 | | | | | | | | | | | | | | | | 50 mM KPO4/10Suc/2Gel/0Arg/2.7 mm EDTA |
| Liq 51 | 6.9 | 6.8 | 6.9 | | | | | | | | | | | | | | | | 50 mM KPO4/10Suc/2Gel/4Arg/5 mm EDTA |
| Liq 52 | 6.6 | 6.7 | 6.7 | | | | | | | | | | | | | | | | 50 mM KPO4/15Suc/0Gel/2Arg/2.7 mm EDTA |
| Liq 53 | 6.7 | 6.8 | 6.7 | | | | | | | | | | | | | | | | 50 mM KPO4/15Suc/0Gel/2Arg/1 mm EDTA |
| Liq 54 | 6.7 | 6.8 | 6.7 | | | | | | | | | | | | | | | | 50 mM KPO4/15Suc/0Gel/4Arg/2.7 mm EDTA |
| Liq 55 | 6.9 | 6.8 | 6.9 | | | | | | | | | | | | | | | | 50 mM KPO4/15Suc/1Gel/0Arg/2.7 mm EDTA |
| Liq 56 | 6.8 | 6.8 | 7 | | | | | | | | | | | | | | | | 50 mM KPO4/15Suc/1Gel/0Arg/5 mm EDTA |
| Liq 57 | 6.9 | 6.8 | 6.8 | | | | | | | | | | | | | | | | 50 mM KPO4/15Suc/1Gel/4Arg/1 mm EDTA |
| Liq 58 | 6.9 | 6.8 | 6.9 | | | | | | | | | | | | | | | | 50 mM KPO4/15Suc/2Gel/2Arg/5 mm EDTA |
| Liq 59 | | | | | | | | | | | | | | | | | | | 50 mM KPO4/15Suc/2Gel/4Arg/1 mm EDTA |

TABLE 48

SP stabilized A/Panama Target: 7.0 4° C. (monthly)

| | 0 | 0 | 0 | | | | | | | | | | | | | | | | |
|---|---|---|---|---|---|---|---|---|---|---|---|---|---|---|---|---|---|---|---|
| Liq 36 | 6.4 | 6.2 | 6.1 | | | | | | | | | | | | | | | | 50 mM KPO4/0Suc/0Gel/2Arg/1 mm EDTA |
| Liq 37 | 6.6 | 6.7 | 6.6 | | | | | | | | | | | | | | | | 50 mM KPO4/7.5Suc/0Gel/2Arg/2.7 mm EDTA |
| Liq 38 | 6.7 | 6.7 | 6.6 | | | | | | | | | | | | | | | | 50 mM KPO4/7.5Suc/0Gel/4Arg/5 mm EDTA |
| Liq 39 | 6.4 | 6.4 | 6.4 | | | | | | | | | | | | | | | | 50 mM KPO4/7.5Suc/1Gel/0Arg/1 mm EDTA |
| Liq 40 | 6.7 | 6.7 | 6.6 | | | | | | | | | | | | | | | | 50 mM KPO4/7.5Suc/1Gel/4Arg/2.7 mm EDTA |
| Liq 41 | 6.0 | 6.0 | 6.0 | | | | | | | | | | | | | | | | 50 mM KPO4/7.5Suc/2Gel/0Arg/5 mm EDTA |
| Liq 42 | 5.9 | 5.9 | 6.0 | | | | | | | | | | | | | | | | 50 mM KPO4/7.5Suc/2Gel/2Arg/1 mm EDTA |
| Liq 43 | 6.5 | 6.6 | 6.5 | | | | | | | | | | | | | | | | 50 mM KPO4/10Suc/0Gel/4Arg/5 mm EDTA |
| Liq 44 | 6.5 | 6.4 | 6.4 | | | | | | | | | | | | | | | | 50 mM KPO4/10Suc/0Gel/2Arg/5 mm EDTA |
| Liq 45 | 6.3 | 6.3 | 6.4 | | | | | | | | | | | | | | | | 50 mM KPO4/10Suc/0Gel/4Arg/1 mm EDTA |
| Liq 46 | 6.3 | 6.3 | 6.3 | | | | | | | | | | | | | | | | 50 mM KPO4/10Suc/1Gel/2Arg/1 mm EDTA |
| Liq 47 | 6.7 | 6.7 | 6.6 | | | | | | | | | | | | | | | | 50 mM KPO4/10Suc/1Gel/2Arg/2.7 mm EDTA |
| Liq 48 | 6.6 | 6.6 | 6.7 | | | | | | | | | | | | | | | | 50 mM KPO4/10Suc/1Gel/4Arg/5 mm EDTA |
| Liq 49 | 6.1 | 6.1 | 6.1 | | | | | | | | | | | | | | | | 50 mM KPO4/10Suc/2Gel/0Arg/1 mm EDTA |
| Liq 50 | 6.6 | 6.6 | 6.5 | | | | | | | | | | | | | | | | 50 mM KPO4/10Suc/2Gel/0Arg/2.7 mm EDTA |
| Liq 51 | 6.9 | 7.0 | 6.9 | | | | | | | | | | | | | | | | 50 mM KPO4/10Suc/2Gel/4Arg/2.7 mm EDTA |
| Liq 52 | 6.8 | 6.7 | 6.8 | | | | | | | | | | | | | | | | 50 mM KPO4/15Suc/0Gel/2Arg/2.7 mm EDTA |
| Liq 53 | 6.7 | 6.7 | 6.7 | | | | | | | | | | | | | | | | 50 mM KPO4/15Suc/0Gel/2Arg/1 mm EDTA |
| Liq 54 | 6.9 | 6.9 | 6.8 | | | | | | | | | | | | | | | | 50 mM KPO4/15Suc/0Gel/4Arg/2.7 mm EDTA |
| Liq 55 | 6.7 | 6.9 | 6.7 | | | | | | | | | | | | | | | | 50 mM KPO4/15Suc/1Gel/0Arg/2.7 mm EDTA |
| Liq 56 | 6.8 | 6.6 | 6.8 | | | | | | | | | | | | | | | | 50 mM KPO4/15Suc/1Gel/0Arg/5 mm EDTA |
| Liq 57 | 6.9 | 6.8 | 6.9 | | | | | | | | | | | | | | | | 50 mM KPO4/15Suc/1Gel/4Arg/1 mm EDTA |
| Liq 58 | 6.8 | 6.8 | 7.0 | | | | | | | | | | | | | | | | 50 mM KPO4/15Suc/2Gel/2Arg/5 mm EDTA |
| Liq 59 | 6.9 | 6.8 | 6.6 | | | | | | | | | | | | | | | | 50 mM KPO4/15Suc/2Gel/4Arg/1 mm EDTA |

TABLE 49

Formulations in the Comparison Study

| | Unpurified VH | | purified VH 1 | | | DiaFiltered VH 2 |
|---|---|---|---|---|---|---|
| | 10% AF | 60% AF | <1% AF | 10% AF | 60% AF | <1% AF |
| 7% SucrosePO$_4$ (base stabilizers) | 2 | 3 | 1 | | | 16 |
| Wyeth Clinical Formulation | 7 | 8 | 4 | 5 | 6 | |
| 7% SucrosePO$_4$ Arg | | | | | | 17 |
| 7% SucrosePO$_4$ Arg, Gel | | | | | | 18 |
| 10% SucrosePO$_4$, Arg, Gel | | 9 | | | | |
| 10% SucrosePO$_4$, Arg | | 10 | | | | |
| 10% SucrosePO$_4$, Arg, PVP | | 12 | | | | |
| 10% SucrosePO$_4$, Arg, Dextran | | 11 | | | | |
| 10% SucrosePO$_4$, Arg, Gel, EDTA | | 13 | | | | |
| 10% Sucrose, Arg, Gel, Histidine | | 14 | | | | |
| 10% Sucrose, Arg, Gel, Hist., EDTA | | 15 | | | | |

TABLE 50

Stability of Purified VH vs. Unpurified VH (FluMist): when both are stabilized by the purified formulation

| | Stability slope @40° C. (±SE), at six months | |
|---|---|---|
| | Purified formulation (Log FFU/month) | FluMist* (Log FFU/month) |
| A/NC | −0.020 ± 0.027 | −0.035 ± 0.016 |
| A/Pan | −0.011 ± 0.020 | −0.079 ± 0.035 |
| B/HK | −0.138 ± 0.022 | −0.151 ± 0.018 |

Formulation: 7% Sucrose, 1% gelatin, 1% arginine ['7/1/1' formulation]
*60% AF level

TABLE 51

Stability of purified VH vs. FluMist: When FluMist is stabilized by '10/2/2' formulation

| | Stability slope @4° C. (±SE), at six months [log FFU/month] | | Initial Potency loss (Log FFU)** | |
|---|---|---|---|---|
| | Purified VH | FluMist* | Purified VH | FluMist* |
| A/NC | −0.020 ± 0.027 | −0.011 ± 0.019 | 0.4 | 0.5 |
| A/Pan | −0.011 ± 0.020 | −0.093 ± 0.032 | 0.9 | 0.9 |
| B/HK | −0.138 ± .022 | −0.107 ± 0.025 | 0 | 0.3 |

Purified VH formulation: 7% Sucrose, 1% gelatin, 1% arginine ['7/1/1' formulation], no added AF
*FluMist formulation: 10% Sucrose, 2% gelatin, 2% arginine ['10/2/2' formulation], 60% AF level
**Based on linear regression

TABLE 52

Stability of purified VH formulaiton vs. FluMist: When FluMist is stabilized by '10/2/2 Histidine' formulation

| | Stability slope @40° C. (±SE), at six months [log FFU/month] | | Initial Potency loss** (log FFU) | |
|---|---|---|---|---|
| | Purified VH | FluMist* | Purified VH | FluMist* |
| A/NC | −0.020 ± 0.027 | −0.068 ± 0.014 | 0.4 | 0 |
| A/Pan | −0.011 ± 0.020 | −0.072 ± 0.012 | 0.9 | 0 |
| B/HK | −0.138 ± .022 | −0.061 ± 0.020 | 0 | 0 |

Purified VH formulation: 7% Sucrose, 1% gelatin, 1% arginine ['7/1/1' formulation], no added AF
*FluMist formulation: Histidine, 10% Sucrose, 2% gelatin, 2% arginine ['10/2/2 His' formulation], 60% AF level
**Based on linear regression

TABLE 53

Comparison of Method Performance

| | Method Performance | |
|---|---|---|
| Test Parameter | Manual | Semi-automated |
| Precision/Between Test Variability (SD)) | SD range from 0.07 to 0.11 log $TCID_{50}$ units[1] | SD range from 0.06–0.09 $log_{10}TCID_{50}/mL$[2,3] |
| Linearity | Passes test for lack of fit to a linear model at the 1% significance level. | Passes test for lack of fit to a linear model at the 1% significance level.[3] |
| Accuracy | Slope range 0.986–1.007. | Slopes range 1.00–1.02.[3] |
| Range | 4.7–9.5 $log_{10}TCID_{50}/mL$. | 4.2–9.3 $log_{10}TCID_{50}/mL$.[3] |

[1]Between-test SD from 9 tests on the same material (each test results is an average of 12 determinations over 3 days), by the same analyst group, on the same pipetting station. The materials tested include 3 independent manufacturing lots of each of three virus strains (H1N1, H3N2 and B).
[2]Between-test SD from 6 tests on the same material (each test results is an average of 12 determinations over 3 days), by the same analyst group, on the same pipetting station. The materials tested include one lot of each of three virus strains (H1N1, H3N2 and B).
[3]Validation Report for Semi-Automated TCID50 Potency Assay for Influenza Virus Monovalent.

TABLE 54

Inter-Assay Comparison

| | Mean Titer ($log_{10}TCID_{50}/mL$) | | | |
|---|---|---|---|---|
| Strain | Manual Assay | Semi-Automated Assay | Difference | 90% CI (LB, UB) |
| A/NewCaledonia/20/99 | 9.40 | 9.42 | −0.02 | (−0.05, 0.01) |
| B/Yamanashi/166/98 | 8.47 | 8.40 | 0.07 | (0.03, 0.10) |

TABLE 55

| SemiAutomated | Manual "gold standard" readout | |
|---|---|---|
| MTT readout | CPE-positive | CPE-negative |
| CPE-positive ($A_{570}$ ≦ cutoff) | TP | FP |
| CPE-negative ($A_{570}$ > cutoff) | FN | TN |
| | All positives | All negatives |

TABLE 56

SemiAutomated $TCID_{50}$ Potency Assay for Influenza Virus Monovalent: Sensitivity and Specificity Estimates Based on the "Gold Standard" Validated Manual CPE Readout and the MTT Assay A570 Cutoff Value of 0.5254

| | True positive | False negative | Sensitivity[a] | True negative | False positive | Specificity[b] |
|---|---|---|---|---|---|---|
| AB (N = 14,400) | 7,091 | 61 | 99.15% | 7,247 | 1 | 99.99% |
| QC (N = 31,440) | 15,835 | 301 | 98.13% | 15,106 | 198 | 98.71% |
| AB and QC (N = 45,840) | 22,926 | 362 | 98.45% | 22,353 | 199 | 99.12% |
| Control ATR.0126 | 17,248 | 167 | 99.05% | 15,882 | 3 | 99.99% |

[a]SENSITIVITY = (TRUE POSITIVE)/ALL POSITIVE
[b]SPECIFICITY = (TRUE NEGATIVE)/ALL NEGATIVE

TABLE 57

Control Well (CPE-negative) Absorbance Values Obtained by the two groups with previous Values Reported Shown for Comparison

| | 2nd group | 1st group | Combined (two groups) | (previous values) Control |
|---|---|---|---|---|
| Well count | 2880 | 6288 | 9168 | 6720 |
| $A_{570}$Average | 1.226 | 1.235 | 1.231 | 1.261 |
| SD | 0.17 | 0.20 | 0.19 | 0.15 |

TABLE 58

Instrument-to-Instrument Comparison: SemiAutomated $TCID_{50}$ Potency Values for Reference Virus Strains

| | Reference Virus Strain (Mean $log_{10}TCID_{50}/mL$ ± SD) | | |
|---|---|---|---|
| Instrument (group) | A/New Caledonia/ 20/99 | A/Sydney/ 05/97 | B/Yamanashi/ 166/98 |
| AZ-039 (1st)[1,2] | 9.2 ± 0.15 | 8.6 ± 0.09 | 8.4 ± 0.10 |
| AZ-040 (1st)[1,3] | 9.3 ± 0.08 | 8.6 ± 0.01 | 8.4 ± 0.10 |
| AZ-036 (2nd)[1] | 9.2 ± 0.08 | 8.5 ± 0.05 | 8.3 ± 0.06 |

[1]Number of tests (AZ-036, N = 9; AZ-039, N = 5; AZ-040, N = 2);
1st = first group,
2nd = second group.
[2]For AZ-039, one test result rejected due to failure of intra-day SD acceptance criteria
[3]For AZ-040, four test results rejected due to failure of intra-day SD acceptance criteria or mishandling of plates

TABLE 59

Analyst-to-Analyst Comparison: SemiAutomated $TCID_{50}$ Potency Values for Reference Virus Strains Using Instruments AZ-039 or AZ-036

| | Reference Virus Strain (Mean $log_{10}TCID_{50}/mL \pm SD$)[a] | | |
|---|---|---|---|
| | A/New Caledonia/20/99 | A/Sydney/05/97 | B/Yamanashi/166/98 |
| first group | AZ-039 | AZ-039 | AZ-039 |
| Analyst # 1 | 9.3 ± 0.19 | 8.5 ± 0.25 | 8.4 ± 0.26 |
| Analyst # 2 | 9.1 ± 0.17 | 8.5 ± 0.27 | 8.4 ± 0.16 |
| Analyst # 3 | 9.1 ± 0.16 | 8.5 ± 0.15 | 8.4 ± 0.19 |
| Analyst # 4 | 9.2 ± 0.24 | 8.6 ± 0.21 | 8.6 ± 0.24 |
| Analyst # 5 | 9.1 ± 0.21 | 8.6 ± 0.19 | 8.3 ± 0.23 |
| Analyst # 6 | 9.4 ± 0.21 | 8.7 ± 0.20 | 8.6 ± 0.21 |
| second group | AZ-036 | AZ-036 | AZ-036 |
| Analyst # 7 | 9.4 ± 0.16 | 8.5 ± 0.21 | 8.3 ± 0.18 |
| Analyst # 8 | 9.2 ± 0.21 | 8.5 ± 0.18 | 8.2 ± 0.15 |
| Analyst # 9 | 9.3 ± 0.16 | 8.5 ± 0.20 | 8.3 ± 0.16 |

[a]Mean potency values are derived from four replicates obtained over three test days (n = 12).

What is claimed is:

1. A method of making an influenza virus composition, the method comprising the steps of:
   a. passaging an influenza virus through eggs;
   b. chilling the eggs to a temperature of between about 2° C. to about 8° C.;
   c. harvesting the influenza virus;
   d. warming the influenza virus to a temperature from about 28° C. to 40° C.; and,
   e. filtering the influenza virus through a membrane; wherein warming occurs before and/or during filtering of the influenza virus.

2. The method of claim 1, wherein the influenza virus composition comprises one or more influenza A virus strain and/or one or more influenza B virus strain.

3. The method of claim 1, wherein the influenza virus is filtered through a microfilter, wherein the microfilter has a pore size of from about 0.2 micrometer to about 0.45 micrometer.

4. The method of claim 1, wherein the influenza virus is warmed to a temperature of about 31° C.

5. The method of claim 1, wherein the influenza virus is warmed to a temperature from about 28° C. to about 36° C.

6. The method of claim 1, wherein the influenza virus is warmed to a temperature from about 28° C. to about 34° C.

7. The method of claim 1, wherein the influenza virus is warmed to a temperature from about 30° C. to about 33° C.

8. The method of claim 1, wherein warming occurs before filtering of the influenza virus.

9. The method of claim 1, wherein warming occurs during the filtering of the influenza virus.

10. The method of claim 1, wherein warming occurs both before and during the filtering of the influenza virus.

11. The method of claim 1, wherein warming is performed for a duration of about 1 hour.

12. The method of claim 1, wherein warming is performed for a duration of from about 30 minutes to about 240 minutes.

13. The method of claim 12, wherein warming is performed for a duration of from about 45 minutes to about 200 minutes.

14. The method of claim 12, wherein warming is performed for a duration of from about 60 minutes to about 90 minutes.

15. The method of claim 1, wherein the eggs are rocked during said passage.

16. The method of claim 15, wherein rocking comprises tilting the eggs at rate of approximately 1 cycle per minute or less, about 5 cycles per minute or less, or about 10 cycles per minute or less.

17. The method of claim 15, wherein the eggs are rocked for approximately 12 hours.

18. The method of claim 15, wherein the eggs are rocked for approximately 24–48 hours.

19. The method of claim 15, further comprising a secondary incubation.

20. The method of claim 19, wherein the eggs are rocked during the secondary incubation.

21. The method of claim 15, wherein the influenza virus composition comprises one or more influenza A virus strain and/or one or more influenza B virus strain.

22. The method of claim 15, wherein a $TCID_{50}$ of the influenza virus passaged through rocked eggs is at least 0.4 log greater than a $TCID_{50}$ of the same influenza virus passaged through non-rocked eggs.

23. The method of claim 1, 2, 3, 4, 5, 6 or 7, wherein the influenza virus composition has a filtration potency loss of less than 0.3 log TCID/ml.

24. The method of claim 1, wherein the passaging an influenza virus through eggs takes place at a temperature less than or equal to 35° C.

25. The method of claim 1, 5, 6 or 7, wherein the influenza virus composition has a filtration potency loss of less than 0.2 log TCID/ml.

26. The method of claim 1, 5, 6 or 7, wherein the influenza virus composition has a filtration potency loss of less than 0.1 log TCID/ml.

27. The method of claim 1, 5, 6 or 7, wherein the influenza virus composition has no filtration potency loss.

* * * * *